United States Patent
Shi et al.

(10) Patent No.: US 8,080,708 B2
(45) Date of Patent: Dec. 20, 2011

(54) MAIZE MULTIDRUG RESISTANCE-ASSOCIATED PROTEIN POLYNUCLEOTIDES AND METHODS OF USE

(75) Inventors: Jinrui Shi, Johnston, IA (US); David Ertl, Waukee, IA (US); Hongyu Wang, Johnston, IA (US); Bailin Li, Hockessin, DE (US); Marianna Faller, Wilmington, DE (US); Kathleen Schellin, Johnston, IA (US)

(73) Assignees: Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 183 days.

(21) Appl. No.: 12/371,209

(22) Filed: Feb. 13, 2009

(65) Prior Publication Data

US 2010/0218276 A1  Aug. 26, 2010

Related U.S. Application Data

(63) Continuation of application No. 11/133,075, filed on May 19, 2005, now Pat. No. 7,511,198.

(60) Provisional application No. 60/572,704, filed on May 20, 2004.

(51) Int. Cl.
  *A01H 1/00* (2006.01)
  *C12N 15/82* (2006.01)
  *C12N 15/00* (2006.01)
(52) U.S. Cl. .................. 800/312; 800/285; 536/320.1
(58) Field of Classification Search .................. None
  See application file for complete search history.

(56) References Cited

U.S. PATENT DOCUMENTS

| | | | |
|---|---|---|---|
| 5,689,054 A | 11/1997 | Raboy | |
| 6,476,212 B1 | 11/2002 | Lalgudi et al. | |
| 6,677,502 B1 * | 1/2004 | Allen et al. | ............ 800/278 |
| 2004/0034888 A1 | 2/2004 | Liu et al. | |

FOREIGN PATENT DOCUMENTS

| | | |
|---|---|---|
| WO | WO 91/14782 A1 | 10/1991 |
| WO | WO 99/05298 A1 | 2/1999 |
| WO | WO 99/55879 A1 | 11/1999 |
| WO | WO 00/73473 A1 | 12/2000 |
| WO | WO 02/083911 A1 | 10/2002 |
| WO | WO 03/027243 A2 | 4/2003 |
| WO | WO 2005/113779 A2 | 12/2005 |

OTHER PUBLICATIONS

Wells, (Biochemistry 29:8509-8517, 1990).*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Nunes et al. (Planta 224:125-132; 2006).*
Guo et al. (PNAS, 101: 9205-9210, 2004).*
Grusak et al. (NCBI, GenBank Sequence Accession No. BQ 1245241, Published Apr. 2002).*
Bruening, *Proc. Natl. Acad. Sci.*, 1998, pp. 13349-13351, vol. 95.
Colliver, et al., *Plant Molecular Biology*, 1997, pp. 509-522, vol. 35.
Elomaa, et al., *Molecular Breeding*, 1996, pp. 41-50, vol. 2.
Emery, et al., *Current Biology*, 2003, pp. 1768-1774, vol. 13.
Guo, et al., *PNAS*, 2004, pp. 9205-9210, vol. 101.
Gutterson, *HortScience*, 1995, pp. 964-966, vol. 30.
Keskin, et al., *Protein Science*, 2004, pp. 1043-1055, vol. 13.
Kolukisaoglu, H.U., et al., "Family business: The Multidrug-Resistance Related Protein (MRP) ABC Transporter Genes in *Arabidopsis Thaliana*," *Planta*, 2002, pp. 107-119, vol. 216.
Larson, S., et al., "Isolation and Genetic Mapping of a Non-Lethal Rice (*Oryza sativa* L.) *low phytic acid 1* Mutation," *Crop Science*, Sep. 2000, pp. 1397-1405, vol. 40(5).
Larson, S., and V. Raboy, "Linkage Mapping of Maize and Barley myo-Inositol 1-Phosphate Synthase DNA Sequences: Correspondence with a *low phytic acid* Mutation," *Theoretical and Applied Genetics*, Jul. 1999,pp. 27-36, vol. 99(1/2).
Ngo, et al., "The Protein Folding Problem and Tertiary Structure Prediction," K. Merz., and S. Le Grand (eds.), 1994, pp. 492-495.
Nunes, et al., *Planta*, 2006, pp. 125-132, vol. 224.
Raboy, V., et al., "Genetics and Breeding of Seed Phosphorus and Phytic Acid," *J. Plant Physiol.*, 2001, pp. 489-497, vol. 158.
Raboy, V., "myo-Inositol-1,2,3,4,5,6-hexakisphosphate," *Phytochemistry*, Nov. 2003, pp. 1033-1043, vol. 64(6).
Raboy, V., et al., "Origin and Seed Phenotype of Maize *low phytic acid* 1-1 and *low phytic acid* 2-1," *Plant Physiol.*, Sep. 2000, pp. 355-368, vol. 124.
Shi, J., et al., "The Maize *low phytic acid* 3 Encodes a Myo-inositol Kinase That Plays a Role in Phytic Acid Biosynthesis in Developing Seeds," *The Plant Journal*, 2005, pp. 708-719, vol. 42.
Swarbreck, D., et al., "Isolation and Characterisation of Two Multidrug Resistance Associated Protein Genes from Maize," *Gene*, 2003, pp. 153-164. vol. 315.
Thorton, et al., *Nature Structural Biology*, Nov. 2000, Structural Genomics Supp.
Wells, *Biochemistry*, 1990, pp. 8509-8517, vol. 29.
EMBL Database Accession No. AK121451, Submitted Jan. 31, 2003 (XP-002347541).

* cited by examiner

*Primary Examiner* — Vinod Kumar
(74) *Attorney, Agent, or Firm* — Alston & Bird LLP

(57) ABSTRACT

Compositions and methods are provided for modulating the level of phytate in plants. More specifically, the invention relates to methods of modulating the level of phytate utilizing nucleic acids comprising multidrug resistance-associated protein (MRP) nucleotide sequences to modulate the expression of MRP(s) in a plant of interest. The compositions and methods of the invention find use in agriculture for improving the nutritional quality of food and feed by reducing the levels of phytate and/or increasing the levels of non-phytate phosphorus in food and feed. The invention also finds use in reducing the environmental impact of animal waste.

7 Claims, 13 Drawing Sheets

```
ABC_membrane: domain 1 of 2, from 311 to 583: score 99.2, E = 1e-26
                  *->lliaillllilagatalvt..fplllgrlldsgfplsdgnddhearss
                     ++ a + + +a+++ +v+   p+l+++++d   + +gn+   ++
      query    311    WREAAVNGTFAAVNTIVSyvGPYLISYFVD----YLSGNIA--FPHE  351 lislailsllavfvligllllqgsfyllagerlgqrlrkrlfrallrqilg
                     +++la + ++++ +l +l+++++++ +     ++g+++ + l + ++r+ l+
      query    352    GYILASI-FFVAKLLETLTARQWYLG--VDIMGIHVKSGLTAMVYRKGLR  398 lfdsffdtnsvGeltsRltnDvekirdglgeklgllfqslatvvgglivm
                     l+    ++ +++Ge+++ ++ Dv+++  d   +++   ++ ++l+++++++  i++
      query    399    LSNASRQSHTSGEIVNYMAVDVQRVGDYAWYFHDIWMLPLQIILALAILY  448 fyyswkLtLillailpllillsavlakklrklsrkeqkayakagsvaeEs
                     ++   +    l+ +++l i+ s+ +ak      +++k + + +++ + + E
      query    449    KNVGIAMVSTLV-ATVLSIAASVPVAKLQEHYQDKLMASKDERMRKTSEC  497 lsgirTVkafgrEeyelerfdkaledaekagikkaiiagllfgitqlisy
                     l ++r   k   ++E++ +    ++ ++ +e ++++ a+++ +   ++++    s+
      query    498    LKNMRILKLQAWEDRYRLQLEEMRN-VECRWLRWALYSQAAVTFVFWSSP  546 lsyalalwfGgylvasvisgglsvgtlfaflslgnqligpl<-*
                     + ++++++fG+       ++g+l+ g + ++l + +l+ pl
      query    547    I-FVAVITFGTCI---LLGGQLTAGGVLSALATFRILQEPL      583

ABC_tran: domain 1 of 2, from 657 to 828: score 137.0, E = 4.2e-38
                  *->GevlalvGpNGaGKSTLLklisGllppteGtilldGardlsdlsklk
                     G ++a+ G  G+GKS+LL  i+G++p    G +++ G
      query    657    GMRVAVCGVIGSGKSSLLSSILGEIPKLCGHVRISG-T---------  693 erlellrknigvvfQdptlfpnpeltvreniafglrlslglskdeqddrl
                              ++v+Q +    ++ ++eni+fg +      ++++++ +
      query    694    ---------AAYVPQTAWIQ---SGNIEENILFGSQM----DRQRYKRVI  727 kkagaeelLerlglgyddlldrrpgtLSGGqkQRvaiARaLltkpklLlL
                     + + + + Le l  g+ +++++++r+ +LSGGqkQRv +ARaL+++++++lL
      query    728    AACCLKKDLELLQYGDQTVIGDRGINLSGGQKQRVQLARALYQDADIYLL  777

DEPTagLDpasraqll.ellrelrqqggTvllvtHdldlldrlaDrilvl
                     D P+++ D+++ +l++e++    +  +Tv++vtH++++ + aD ilvl
      query    778    DDPFSAVDAHTGSELFKEYILTALA-TKTVIYVTHQVEF-LPAADLILVL  825 edG<-*
                     +dG
      query    826    KDG      828
```

FIG. 1A

```
ABC_membrane: domain 2 of 2, from 948 to 1218: score 74.7, E = 2.4e-19
              *->lliailllilagatalvtfplllgrlldsgfplsdgnddhearssli
                 +  ++il   +   ++ ++  +++++   +       ++g+ +    +  +++
    query   948    IPLIILAQTMFQVLQIA-SNWWMAWANP----QTEGDAP---KTDSV 986 slailslllavfvliglllqgsfyllagerlgqrlrkrlfrallrqilglf
                 l ++ ++ ++++ +l+ + ++ l        g  ++++lf ++lr +++++
    query   987 VLLVV-YMSLAFGSSLFVFMRSLL--VATFGLAAAQKLFIKMLRCVFRAP 1033 dsffdtnsvGeltsRltnDvekirdglgeklgllfqslatvvgglivmfy
                 +sffdt+++G++++R++ D + ++    ++++lg +     ++++g+++vm+
    query  1034 MSFFDTTPSGRILNRVSVDQSVVDLDIAFRLGGFASTTIQLLGIVAVMSK 1083 yswkLtLillailpllillsavlakklrklsrkeqkayakagsvaeEsls
                 + w+ +++++++ +  +++++++   +r+l+r  + + +++  ++ Es+
    query  1084 VTWQVLILIVPMAVACMWMQRYYIASSRELTRILSVQKSPVIHLFSESIA 1133 girTVkafgrEeyelerfdkaledaekagikkaiiagllfgitqlisyls
                 g  T++ fg E+++ +r     l+ + +   +  +++   +l  +++l+s+++
    query  1134 GAATIRGFGQEKRFMKRNLYLLDCFARPLFSSLAAIEWLCLRMELLSTFV 1183 yalalwfGgylvasvisgglsvgtlfaflslgnqligpl<-*
                 +a+++ + + +        g + + +  ++ ++g+ l++++
    query  1184 FAFCMAILVSF----PPGTIEPSMAGLAVTYGLNLNARM     1218

ABC_tran: domain 2 of 2, from 1294 to 1477: score 159.4, E = 7.4e-45
              *->GevlalvGpNGaGKSTLLklisGllppteGtilldGardlsdlsklk
                 G+++++vG+ G+GKSTL+ ++ +l++pt G+i +d+  d+s ++
    query  1294    GKKIGIVGRTGSGKSTLIQALFRLIEPTGGKIIIDN-IDISAIG--- 1336 erlellrknigvvfQdptlfpnpeltvreniafglrlslglskdeqddrl
                 l++lr +++  ++Qdptlf    e+t+r n++   l+      +++e++++l
    query  1337 --LHDLRSRLSIIPQDPTLF---EGTIRMNLDP-LEE---CTDQEIWEAL 1377 kkagaeelLerlglgyddlldrrpgtLSGGqkQRvaiARaLltkpklLlL
                 +k+++  e++++    + d+ + +  +++++ S  Gq+Q  +a+ RaLl+++++k+L+L
    query  1378 EKCQLGEVIRSKEEKLDSPVLENGDNWSVGQRQLIALGRALLKQAKILVL 1427

DEPTagLDpasraqllellrelrqqggTvllvtHdldlldrlaDrilvle
                 DE+Ta+ D a+     +++++r+   +  +Tv ++ H++       +D +lvl+
    query  1428 DEATASVDTATDNLIQKIIRSEFK-DCTVCTIAHRIPT-VIDSDLVLVLS 1475 dG<-*
                 dG
    query  1476 DG      1477
```

FIG. 1B

```
                    1                                                                    70
OsMRP 13 mRNA    (1) --------ACTCTTTCTCGCTCGACGAGGAGGTGAGGTGAGGTGGGAGA---------GCTAGCGAACAA
ZmMRP 3 mRNA     (1) CCTCTCTCTCCCCTCCTCGAACCAGGCGCAGGCGAGCGTCTCTGCCCGCCCGCCTGCTGCTACCGCCAAA
Consensus        (1)            C  C  T  CTCG   C  A  G  G  AGG GAG      TG   G       GCTA CG    AA
                    71                                                                   140
OsMRP 13 mRNA   (54) AGGCTTGGTTTGGTGCCATCTGGCGGCTCCGATGGCGTAACCCGCCGCCGCCCTCAGAGCTCGGCCTTTG
ZmMRP 3 mRNA    (71) ACGCCTCCTTTGTTGCCATC------CGCCGATGCCGTAATCCGCCGCC-----CAAAGCTCTTCCTTTT
Consensus       (71) A GC T  TTTG TGCCATC      C CCGATG CGTAA CCGCCGCC     CA AGCTC  CCTTT
                    141                                                                  210
OsMRP 13 mRNA  (124) CCTGCCTTGCCTGCCTTCTGCCCCGCCGCCCCTGCCCT--CTGCCGTGGCGTGGCGAGGCCCAATGCCT
ZmMRP 3 mRNA   (130) TCCCTCTCTCTCGCCCCGCGGCCGCACTCCCTGCCCCAGTGCCTGCCGTGGCGAGCCCAACCCCAATGCCT
Consensus     (141) C   CT  C  GCC   C GCC  C  CC   C  C  T   CTGCCGTGGCG G C A  CCCAATGCCT
                    211                                                                  280
OsMRP 13 mRNA  (192) TTTAAACCCCGCCCCGCTGCCATCCTGACGCCCCGATCCCCACCGCCTCCCAATGCCGCACT---TCCC
ZmMRP 3 mRNA   (200) TTTAAACCCCTCCCCGCTCCCTCACTGA---------TCCCCACCGCCTCCCAATGCCGCCCTCCTTCCC
Consensus     (211) TTTAAACCCC CCCCGCT CC   CTGA         TCCCCACCGCCTCCCAATGCCGC  CT    TCCC
                    281                                                                  350
OsMRP 13 mRNA  (259) GAACCTCCCGCTCCCGGAGGCTGCCGCCGCCGCGCACGCCGCGCTGCTCGCCCTCGCCCTGCTCCTG
ZmMRP 3 mRNA   (261) CTCCCTCCCGCTCCCGGAGGCCGTTGCCGCCACCGCCCACGCCGCGCTGCTCGCGCTCGCCGCACTCCTG
Consensus     (281)      CCTCCCGCTCCCGGAGGC  G   GCCGCC  CCGC  CACGCCGCGCTGCTCGC   CTCGCC    CTCCTG
                    351                                                                  420
OsMRP 13 mRNA  (329) CTCCTCCTCCGCTCCGCGCGCGCCCTCGCCTCGCGCTGCGCGTCATGCCTCAAGAC--CGCCCCGC-GCC
ZmMRP 3 mRNA   (331) CTCCTCCTCCGCGCCGCGCGCGCGCTCGCCTCCCGCTGCGCGTCATGCCTCAAGGCGCCGCGCCGCCGCG
Consensus     (351) CTCCTCCTCCGC  CCGCGCGCGC  CTCGCCTC   CGCTGCGCGTCATGCCTCAAG  C  CGC  CCGC  GC
                    421                                                                  490
OsMRP 13 mRNA  (396) GAGCCGCGGCGGTCGACGGGGGCTCGCCGCCG---------------CGTCGTCCGTGGGCGCGTGGTA
ZmMRP 3 mRNA   (401) GGGGCCCCGCCGTCGTCGTGGGCGACGGCGCCGGCGGCGCCCTCGCGGCGGCGACTGCCGGCGCCTGGCA
Consensus     (421) G  G  C  C   GC  GTCG  CG  GGG       CG   CGCCG              CG CG  C G   GGCGC TGG A
                    491                                                                  560
OsMRP 13 mRNA  (451) CAGGGCGGCGCTGGCGTGCTGCGGCTACGCCCTGCTGGCGCAGGTCGCCGCCCTGAGCTACGAGGTCGCG
ZmMRP 3 mRNA   (471) CAGGGCCGTGCTGGCGTCCTGCGCCTACGCCCTGCTCTCGCAGGTCGCCGTGCTGAGCTACGAGGTGGCC
Consensus     (491) CAGGGC  G  GCTGGCGT CTGCG  CTACGCCCTGCT   CGCAGGTCGCCG  CTGAGCTACGAGGT  GC
                    561                                                                  630
OsMRP 13 mRNA  (521) GTGGCCGGTTCTCATGTCGCCGTGGAGGCCCTGCTGCTGCCCGCGGTGCAGGCGCTGGCGTGGGCGGCGC
ZmMRP 3 mRNA   (541) GTCGCCGGCTCGCGCGTCTCGGCGCGGGCGCTGCTGCTGCCGGCCGTGCAGGCGGTGTCCTGGGCCGCGC
Consensus     (561) GT GCCGG TC C  GTC C G  GGC CTGCTGCTGCC GC GTGCAGGCG TG C TGGGC GCGC
                    631                                                                  700
OsMRP 13 mRNA  (591) TCCTGGCGCTCGCGATGCAGGCCCGGGCCGTCGGGTGGGCAGGTTCCCCGTACTGGTGCGCGTCTGGTG
ZmMRP 3 mRNA   (611) TGCTGGCGCTCGCGCTTCAGGCCCGCGCCGTCGGCTGGGCCAGGTTCCCTGCGCTGGTGCGGCTCTGGTG
Consensus     (631) T  CTGGCGCTCGCG  T CAGGCCCG  GCCGTCGG TGGG  CAGGTTCCC G   CTGGTGCG   TCTGGTG
                    701                                                                  770
OsMRP 13 mRNA  (661) GGTGGTCTCCTTCGTGCTCTGTGTTGGCATCGCGTACGACGATACCAGGCACCTCATGGGCGATGATGAT
ZmMRP 3 mRNA   (681) GGTGGTCTCCTTCGCGCTCTGCGTTGTCATTGCGTACGACGACTCCAGGCGCCTGATAGGCCAGGGCGCG
Consensus     (701) GGTGGTCTCCTTCG GCTCTG GTTG CAT GCGTACGACGA CCAGGC CCT AT GGC A  G
                    771                                                                  840
OsMRP 13 mRNA  (731) GATGATGAGGTGGACTACGCTCACATGGTTGCCAACTTCGCGTCGGCGCCGGCCCTCGGGTTCCTCTGCT
ZmMRP 3 mRNA   (751) CGCGCTG---TGGATTACGCGCACATGGTTGCCAACTTCGCGTCCGTGCCGGCCCTGGGCTTCCTGTGCT
Consensus     (771)     G TG   TGGA TACGC CACATGGTTGCCAACTTCGCGTC  G GCCGGCCC  GG TTCCT TGCT
                    841                                                                  910
OsMRP 13 mRNA  (801) TGGTTGGTGTCATGGGTTCCACCGGTGTTGAATTGGAGTTCACCGACGACGACAGCAGTGTTCATGAACC
ZmMRP 3 mRNA   (818) TGGTTGGTGTCATGGGTTCCACCGGTTTGGAATTGGAGTTTACGGAGGATGGCAACGGCCTGCATGAGCC
Consensus     (841) TGGTTGGTGTCATGGGTTCCACCGGT T GAATTGGAGTT AC GA GA G CA C G T CATGA CC
                    911                                                                  980
OsMRP 13 mRNA  (871) GCTCTTGCTCGGTGGGCAGCGGAGAGACGCCGACGAGGAGCCCGGGTGCTTGCGGGTGACGCCGTATGGC
ZmMRP 3 mRNA   (888) GCTGCTCGGCAGGCAGCGCAGAGAGGCAGAGGAGGAGCTCGGCTGTCTGAGGGTCACTCCCTACGCT
Consensus     (911) GCT   TGCTCGG   GGCAGCG  AGAGA GC GA GAGGAGC CGG TG  TG GGGT AC CC TA G
                    981                                                                 1050
OsMRP 13 mRNA  (941) GATGCTGGGATTGTTAGCCTTGCAACATTATCATGGCTTAGTCCGCTGCTGTCAGTTGGTGCGCAGCGAC
ZmMRP 3 mRNA   (958) GATGCTGGGATCCTCAGCCTTGCAACATTGTCATGGCTTAGTCCGTTGCTCTCTGTTGGTGCGCAGCGGC
Consensus     (981) GATGCTGGGAT   T AGCCTTGCAACATT TCATGGCTTAGTCCG TGCT TC GTTGGTGCGCAGCG C
                    1051                                                                1120
OsMRP 13 mRNA (1011) CACTTGAGCTGGCTGACATACCCTTGATGGCACACAAAGACCGTGCCAAATCCTGCTACAAGGCGATGAG
ZmMRP 3 mRNA  (1028) CACTTGAGTTGGCTGACATACCCTTGCTGGCGCACAAGGACCGTGCAAAGTCATGCTATAAGGCGATGAG
Consensus    (1051) CACTTGAG TGGCTGACATACCCTTG TGGC CACAA GACCGTGC AA TC TGCTA AAGGCGATGAG
                    1121                                                                1190
OsMRP 13 mRNA (1081) CAGTCACTATGAACGCCAGCGGATGGAGCGCCCCGGCAGCGAACCATCACTGGCATGGGCAATATTGAAG
ZmMRP 3 mRNA  (1098) CGCTCACTACGAGCGCCAGCGGCTAGAATACCCTGGCAGGGAGCCATCACTCACATGGGCAATACTCAAG
Consensus    (1121) C TCACTA GA CGCCAGCGG T GA   CCC GGCAG GA CCATCACT CATGGGCAATA T AAG
```

FIG. 4A

```
                        1191                                                        1260
OsMRP 13 mRNA  (1151)  TCGTTCTGGCGTGAGGCAGCGATCAATGGTGCTTTCGCAGCGGTGAACACAATTGTCTCCTATGTTGGCC
ZmMRP 3 mRNA   (1168)  TCATTCTGGCGAGAGGCCGCGGTCAATGGCACATTTGCTGCTGTCAACACGATTGTGTCGTATGTTGGAC
    Consensus  (1191)  TC TTCTGGCG GAGGC GCG TCAATGG  C TT GC GC GT AACAC ATTGT TC TATGTTGG C
                        1261                                                        1330
OsMRP 13 mRNA  (1221)  CATACCTGATCAGCTACTTTGTGGACTACCTCAGTGGCAAAATTGAATTCCCCCATGAAGGTTACATCCT
ZmMRP 3 mRNA   (1238)  CTTACTTGATCAGCTATTTTGTGGACTACCTCAGTGGCAACATTGCTTTCCCCCATGAAGGTTACATCCT
    Consensus  (1261)  C TAC TGATCAGCTA TTTGTGGACTACCTCAGTGGCAA ATTG  TTCCCCCATGAAGGTTACATCCT
                        1331                                                        1400
OsMRP 13 mRNA  (1291)  TGCCTCTGTATTTTTTGTAGCAAAGTTACTTGAGACGCTCACTGCTCGGCAGTGGTACTTGGGCGTGGAT
ZmMRP 3 mRNA   (1308)  TGCCTCTATATTTTTTGTAGCAAAACTGCTTGAGACACTCACTGCCCGACAGTGGTACTTGGGTGTGGAC
    Consensus  (1331)  TGCCTCT TATTTTTTGTAGCAAA  T CTTGAGAC CTCACTGC CG CAGTGGTACTTGGG GTGGA
                        1401                                                        1470
OsMRP 13 mRNA  (1361)  GTCATGGGGATCCATGTCAAGTCTGGGCTGACGGCCATGGTGTACAGGAAGGGCCTTAGGCTGTCGAATT
ZmMRP 3 mRNA   (1378)  ATCATGGGGATCCATGTCAAGTCTGGCCTCACTGCCATGGTGTATAGGAAGGGTCTCCGACTGTCAAACG
    Consensus  (1401)   TCATGGGGATCCATGTCAAGTCTGG CT AC GCCATGGTGTA AGGAAGGG CT  G CTGTC AA
                        1471                                                        1540
OsMRP 13 mRNA  (1431)  CCTCGCGGCAGAGCCACACCAGTGGTGAGATTGTGAATTACATGGCGGTTGATGTACAGCGTGTGGGGGA
ZmMRP 3 mRNA   (1448)  CCTCACGGCAGAGCCACACGAGTGGTGAGATTGTGAATTACATGGCCGTCGATGTGCAGCGTGTGGGGGA
    Consensus  (1471)  CCTC CGGCAGAGCCACAC AGTGGTGAGATTGTGAATTACATGGC GT GATGT CAGCGTGTGGGGGA
                        1541                                                        1610
OsMRP 13 mRNA  (1501)  CTATGCATGGTACTTTCATGACATCTGGATGCTTCCACTGCAGATCATCCTCGCCCTCGCCATCCTGTAC
ZmMRP 3 mRNA   (1518)  CTATGCATGGTATTTCCATGACATCTGGATGCTTCCCCTGCAGATCATTCTTGCTCTCGCCATCCTGTAC
    Consensus  (1541)  CTATGCATGGTA TT CATGACATCTGGATGCTTCC CTGCAGATCAT CT GC CTCGCCATCCTGTAC
                        1611                                                        1680
OsMRP 13 mRNA  (1571)  AAGAATGTTGGAATCGCCATGGTTTCAACATTGGTAGCTACTGTATTATCAATTGCTGCCTCAGTTCCTG
ZmMRP 3 mRNA   (1588)  AAGAACGTCGGGATCGCCATGGTTTCAACATTGGTAGCAACTGTGCTATCGATCGCAGCCTCTGTTCCTG
    Consensus  (1611)  AAGAA GT GG ATCGCCATGGTTTCAACATTGGTAGC ACTGT  TATC AT GC GCCTC GTTCCTG
                        1681                                                        1750
OsMRP 13 mRNA  (1641)  TGGCGAAGCTGCAGGAGCACTACCAAGATAAGCTTATGGCCTCAAAGGATGAGCGCATGCGCAAGACATC
ZmMRP 3 mRNA   (1658)  TGGCAAAGCTGCAGGAGCACTACCAAGATAAGTTAATGGCATCAAAAGATGAGCGCATGCGCAAGACTTC
    Consensus  (1681)  TGGC AAGCTGCAGGAGCACTACCAAGATAAG T ATGGC TCAAA GATGAGCGCATGCGCAAGAC TC
                        1751                                                        1820
OsMRP 13 mRNA  (1711)  AGAGTGCCTGAAGAATATGAGGATTTTGAAGCTCCAAGCGTGGGAGGATCGATACAGGCTGAAGTTGGAA
ZmMRP 3 mRNA   (1728)  AGAGTGCCTTGAAAAATATGAGGATTTTGAAGCTTCAGGCATGGGAGGATCGGTACCGGCTGCAGTTGGAA
    Consensus  (1751)  AGAGTGC TGAA AATATGAGGATTTTGAAGCT CA GC TGGGAGGATCG TAC GGCTG AGTTGGAA
                        1821                                                        1890
OsMRP 13 mRNA  (1781)  GAGATGAGAAATGTGGAATGCAAGTGGCTTCGGTGGGCTCTGTATTCACAGGCCGCAGTTACATTTGTTT
ZmMRP 3 mRNA   (1798)  GAGATGAGGAACGTGGAATGCAGATGGCTTCGGTGGGCTCTGTACTCACAGGCTGCAGTTACATTTGTTT
    Consensus  (1821)  GAGATGAG AA GTGGAATGCA  TGGCTTCGGTGGGCTCTGTA TCACAGG GCAGTTACATTTGTTT
                        1891                                                        1960
OsMRP 13 mRNA  (1851)  TCTGGAGTTCACCAATCTTTGTCGCCGTGATAACATTTGGGACTTGTATATTGCTTGGTGGCGAACTCAC
ZmMRP 3 mRNA   (1868)  TCTGGAGCTCGCCAATCTTTGTCGCAGTCATAACTTTTGGGACTTGCATATTACTCGGTGGCCAGCTCAC
    Consensus  (1891)  TCTGGAG TC CCAATCTTTGTCGC GT ATAAC TTTGGGACTTG ATATT CT GGTGGC A CTCAC
                        1961                                                        2030
OsMRP 13 mRNA  (1921)  TGCTGGAGGTGTTCTTTCTGCTTTAGCAACATTTAGGATCCTTCAAGAACCACTTAGGAATTTCCCAGAT
ZmMRP 3 mRNA   (1938)  TGCAGGAGGGGTTCTATCCGCTTTAGCAACGTTTCGGATCCTCCAAGAGCCTCTGAGGAACTTCCCGGAT
    Consensus  (1961)  TGC GGAGG GTTCT TC GCTTTAGCAAC TTT GGATCCT CAAGA CC CT AGGAA TTCCC GAT
                        2031                                                        2100
OsMRP 13 mRNA  (1991)  CTTATCTCTATGATTGCTCAGACGAGGGTATCTTTGGACCGGTTGTCTCACTTTCTTCAACAAGAAGAAT
ZmMRP 3 mRNA   (2008)  CTCATCTCTATGATGGCACAGACAAGGGTGTCTTTGGACCGTTTGTCTCATTTTCTGCAGCAAGAAGAAC
    Consensus  (2031)  CT ATCTCTATGAT GC CAGAC AGGGT TCTTTGGACCG TTGTCTCA TTTCT CA CAAGAAGAA
                        2101                                                        2170
OsMRP 13 mRNA  (2061)  TGCCAGATGATGCAACTATAACGGTTCCACATGGTAGTACAGATAAGGCAATCAATATAAATGATGCTAC
ZmMRP 3 mRNA   (2078)  TGCCAGATGACGCAACTATAAATGTTCCACAAAGTAGTACAGATAAGGCAGTCGATATTAAGGATGGCGC
    Consensus  (2101)  TGCCAGATGA GCAACTATAA  GTTCCACA  GTAGTACAGATAAGGCA TC ATAT AA GATG    C
                        2171                                                        2240
OsMRP 13 mRNA  (2131)  ATTCTCTTGGAACCCATCTTCTCCAACCCCTACACTTTCTGGCATCAACCTTAGTGTGGTGAGGGGTATG
ZmMRP 3 mRNA   (2148)  ATTCTCTTGGAACCCATACACTCTGACCCCTACACTTTCTGATATACACCTTAGTGTAGTGAGAGGCATG
    Consensus  (2171)  ATTCTCTTGGAACCCAT   CTC  ACCCCTACACTTTCTG  AT ACCTTAGTGT GTGAG GG ATG
                        2241                                                        2310
OsMRP 13 mRNA  (2201)  CGAGTAGCAGTGTGTGGTGTCATTGGTTCTGGCAAATCAAGCTTGTTGTCTTCTATACTCGGCGAGATAC
ZmMRP 3 mRNA   (2218)  AGAGTAGCAGTCTGTGGTGTCATTGGTTCTGGTAAATCAAGTCTACTATCGTCTATACTCGGGGAGATAC
    Consensus  (2241)   GAGTAGCAGT TGTGGTGTCATTGGTTCTGG AAATCAAG  T  TC TCTATACTCGG GAGATAC
                        2311                                                        2380
OsMRP 13 mRNA  (2271)  CCAAATTGTGTGGTCAAGTGAGGATCAGTGGATCAGCAGCATATGTCCCTCAGACTGCCTGGATACAGTC
ZmMRP 3 mRNA   (2288)  CCAAATTATGTGGCCATGTCAGGATAAGTGGCACAGCAGCGTATGTTCCTCAGACTGCATGGATACAGTC
    Consensus  (2311)  CCAAATT TGTGG CA GT AGGAT AGTGG CAGCAGC TATGT CCTCAGACTGC TGGATACAGTC
```

FIG. 4B

```
              2381                                                          2450
OsMRP 13 mRNA  (2341) CGGAAACATTGAGGAGAACATTCTTTTTGGCAGTCCAATGGACAAACAGCGTTACAAGAGAGTTATTGAG
ZmMRP 3 mRNA   (2358) TGGAAATATTGAGGAGAATATTCTGTTTGGCAGTCAAATGGATAGACAACGTTACAAGAGAGTCATTGCA
    Consensus  (2381)  GGAAA ATTGAGGAGAA ATTCT TTTGGCAGTC AATGGA A ACA CGTTACAAGAGAGT ATTG
              2451                                                          2520
OsMRP 13 mRNA  (2411) GCTTGCTCCCTGAAGAAAGATCTTCAGTTGCTCCAATATGGAGATCAGACCATCATCGGTGATAGGGGCA
ZmMRP 3 mRNA   (2428) GCTTGCTGTCTTAAGAAAGATCTTGAGCTGCTCCAGTACGGAGATCAGACTGTTATTGGTGATAGAGGCA
    Consensus  (2451) GCTTGCT  CT AAGAAAGATCTT AG TGCTCCA TA GGAGATCAGAC  T AT GGTGATAG GGCA
              2521                                                          2590
OsMRP 13 mRNA  (2481) TTAATTTGAGTGGGGGTCAGAAACAAAGAGTACAGCTTGCAAGAGCACTATACCAAGATGCTGATATTTA
ZmMRP 3 mRNA   (2498) TTAATTTGAGTGGAGGTCAGAAACAAAGAGTTCAGCTTGCTAGAGCACTCTACCAAGATGCTGATATTTA
    Consensus  (2521) TTAATTTGAGTGG GGTCAGAAACAAAGAGT CAGCTTGC AGAGCACT TACCAAGATGCTGATATTTA
              2591                                                          2660
OsMRP 13 mRNA  (2551) TTTGCTCGATGATCCCTTCAGTGCGGTTGATGCTCATACTGGGAGTGAATTATTTAGGGAATATATATTG
ZmMRP 3 mRNA   (2568) TTTGCTTGATGATCCCTTCAGTGCTGTTGATGCTCATACTGGGAGCGAACTGTTTAAGGAGTATATATTG
    Consensus  (2591) TTTGCT GATGATCCCTTCAGTGC GTTGATGCTCATACTGGGAG GAA T TTTA GGA TATATATTG
              2661                                                          2730
OsMRP 13 mRNA  (2621) ACTGCACTAGCAAGCAAGACCGTAATTTATGTAACCCATCAAATTGAGTTTCTACCAGCTGCTGACTTGA
ZmMRP 3 mRNA   (2638) ACTGCACTAGCAACCAAAACAGTAATCTATGTAACACATCAAGTTGAATTTCTACCAGCTGCTGATCTGA
    Consensus  (2661) ACTGCACTAGCAA CAA AC GTAAT TATGTAAC CATCAA TTGA TTTCTACCAGCTGCTGA  TGA
              2731                                                          2800
OsMRP 13 mRNA  (2691) TACTGGTTCTTAAGGATGGTCATATCACCCAAGCTGGAAAATATGATGATCTTCTCCAAGCTGGCACTGA
ZmMRP 3 mRNA   (2708) TATTGGTTCTTAAGGATGGCCATATCACACAAGCTGGAAAGTATGATGATCTTCTGCAAGCTGGAACTGA
    Consensus  (2731) TA TGGTTCTTAAGGATGG CATATCAC CAAGCTGGAAA TATGATGATCTTCT CAAGCTGG ACTGA
              2801                                                          2870
OsMRP 13 mRNA  (2761) TTTCAATGCTTTGGTTTGTGCTCATAAGGAAGCTATTGAGACCATGGAATTTTCCGAAGATTCCGATGAG
ZmMRP 3 mRNA   (2778) TTTCAATGCTCTGGTTTCTGCTCATAAGGAAGCTATTGAAACCATGGATATATTTGAAGATTCCGATAGT
    Consensus  (2801) TTTCAATGCT TGGTTT TGCTCATAAGGAAGCTATTGA ACCATGGA  T T GAAGATTCCGAT
              2871                                                          2940
OsMRP 13 mRNA  (2831) GATACTGTCTCTTCTGTTCCTATCAAAAGACTGACGCCAAGTGTTAGCAATATAGATAATCTGAAAAACA
ZmMRP 3 mRNA   (2848) GATACAGTTTCTTCTATTCCCAACAAAAGATTGACACCAAGTATCAGCAATATTGATAACCTGAAAAATA
    Consensus  (2871) GATAC GT TCTTCT TTCC A CAAAAGA TGAC CCAAGT T AGCAATAT GATAA CTGAAAAA A
              2941                                                          3010
OsMRP 13 mRNA  (2901) AGGTGTCCAATAATGAAAAACCATCTAGTACGCGTGGAATAAAAGAAAAGAAGAAGAAGCCTGAAGAGCG
ZmMRP 3 mRNA   (2918) AGATGTGTGAAAATGGACAACCATCTAATACACGGGGAATTAAGGAAAAAAAGAAGAA---AGAAGAGCG
    Consensus  (2941) AG TGT   A AATG A AACCATCTA TAC CG GGAAT AA GAAAA AAGAAGAA    GAAGAGCG
              3011                                                          3080
OsMRP 13 mRNA  (2971) TAAGAAGAAGCGGTCTGTTCAAGAGGAGGAGAGGGAGCGAGGAAGGGTTAGCTTACAGGTTTACTTGTCA
ZmMRP 3 mRNA   (2985) TAAGAAGAAGCGTACTGTTCAAGAGGAGGAAAGGGAACGTGGAAAAGTGAGCTCCAAAGTTTATTTGTCA
    Consensus  (3011) TAAGAAGAAGCG  CTGTTCAAGAGGAGGA AGGGA CG GGAA  GT AGCT  A GTTTA TTGTCA
              3081                                                          3150
OsMRP 13 mRNA  (3041) TACATGGGAGAAGCATACAAAGGTACACTGATACCCCTCATTATCCTGGCCCAAACCATGTTTCAAGTAC
ZmMRP 3 mRNA   (3055) TACATGGGGGAAGCTTACAAAGGTACACTGATACCACTAATTATCTTGGCTCAAACCATGTTCCAAGTTC
    Consensus  (3081) TACATGGG GAAGC TACAAAGGTACACTGATACC CT ATTATC TGGC CAAACCATGTT CAAGT C
              3151                                                          3220
OsMRP 13 mRNA  (3111) TTCAGATTGCGAGTAACTGGTGGATGGCATGGGCAAACCCACAAACAGAAGGAGATGCACCTAAGACAGA
ZmMRP 3 mRNA   (3125) TTCAGATTGCGAGCAACTGGTGGATGGCATGGGCAAACCCACAAACAGAAGGAGATGCTCCCAAGACAGA
    Consensus  (3151) TTCAGATTGCGAG AACTGGTGGATGGCATGGGCAAACCCACAAACAGAAGGAGATGC CC AAGACAGA
              3221                                                          3290
OsMRP 13 mRNA  (3181) CAGTGTGGTTCTCTTGGTTGTTTATATGTCCCTTGCCTTTGGGAGTTCATTGTTTGTGTTTGTGAGAAGT
ZmMRP 3 mRNA   (3195) TAGTGTGGTCCTTCTGGTTGTTTATATGTCCCTTGCCTTTGGAAGTTCACTATTTGTGTTCATGAGAAGC
    Consensus  (3221)  AGTGTGGT CT  TGGTTGTTTATATGTCCCTTGCCTTTGG AGTTCA T TTTGTGTT  TGAGAAG
              3291                                                          3360
OsMRP 13 mRNA  (3251) CTTCTTGTGGCTACATTTGGTTTAGCAACTGCACAGAAGCTGTTTGTAAAGATGCTAAGGTGTGTTTTTC
ZmMRP 3 mRNA   (3265) CTTCTTGTGGCTACGTTTGGTTTAGCAGCTGCCCAGAAGCTTTTTATAAAAATGCTTAGGTGTGTCTTTC
    Consensus  (3291) CTTCTTGTGGCTAC TTTGGTTTAGCA CTGC CAGAAGCT TTT TAAA ATGCT AGGTGTGT TTTC
              3361                                                          3430
OsMRP 13 mRNA  (3321) GAGCGCCAATGTCATTCTTTGATACTACACCATCTGGTCGAATTTTGAACCGAGTTTCTGTAGATCAAAG
ZmMRP 3 mRNA   (3335) GAGCTCCAATGTCATTCTTTGACACCACACCATCTGGTCGGATTTTGAACAGAGTTTCTGTAGATCAAAG
    Consensus  (3361) GAGC CCAATGTCATTCTTTGA AC ACACCATCTGGTCG ATTTTGAAC GAGTTTCTGTAGATCAAAG
              3431                                                          3500
OsMRP 13 mRNA  (3391) TGTCGTGGACCTTGATATAGCATTCAGACTTGGTGGATTTGCATCAACAACAATTCAACTACTTGGAATT
ZmMRP 3 mRNA   (3405) TGTTGTGGACCTTGATATAGCGTTCAGACTTGGTGGATTTGCATCAACGACAATTCAACTCCTTGGAATT
    Consensus  (3431) TGT GTGGACCTTGATATAGC TTCAGACTTGGTGGATTTGCATCAAC ACAATTCAACT CTTGGAATT
              3501                                                          3570
OsMRP 13 mRNA  (3461) GTTGCTGTCATGAGCAAAGTCACATGGCAAGTTTTGATTCTTATAGTTCCTATGGCTGTTGCATGCATGT
ZmMRP 3 mRNA   (3475) GTTGCTGTCATGAGCAAAGTCACATGGCAAGTTCTGATTCTTATAGTCCCCATGGCTGTTGCATGCATGT
    Consensus  (3501) GTTGCTGTCATGAGCAAAGTCACATGGCAAGTT TGATTCTTATAGT CC ATGGCTGTTGCATGCATGT
```

FIG. 4C

```
                         3571                                                           3640
OsMRP 13 mRNA    (3531)  GGATGCAGAGATATTATATTGCTTCATCAAGGGAATTGACTAGGATCTTAAGCGTACAGAAGTCGCCGGT
ZmMRP  3 mRNA    (3545)  GGATGCAGAGGTATTATATTGCTTCATCAAGGGAACTAACTAGGATTTTGAGTGTTCAGAAGTCTCCAGT
    Consensus    (3571)  GGATGCAGAG TATTATATTGCTTCATCAAGGGAA T ACTAGGAT TT AG GT CAGAAGTC CC GT
                         3641                                                           3710
OsMRP 13 mRNA    (3601)  GATCCATTTGTTTAGTGAGTCAATTGCTGGTGCTGCTACAATCAGAGGTTTTGGTCAAGAGAAACGATTC
ZmMRP  3 mRNA    (3615)  GATCCATTTGTTTAGTGAATCAATTGCTGGTGCTGCTACAATAAGGGGTTTTGGTCAAGAGAAGCGGTTT
    Consensus    (3641)  GATCCATTTGTTTAGTGA TCAATTGCTGGTGCTGCTACAAT AG GGTTTTGGTCAAGAGAA CG TT
                         3711                                                           3780
OsMRP 13 mRNA    (3671)  ATGAAAAGAAATCTTTACCTTCTTGACTGTTTTGCTCGGCCTCTATTTTCCAGCCTGGCAGCTATTGAAT
ZmMRP  3 mRNA    (3685)  ATGAAAAGGAATCTTTATCTTCTTGACTGTTTTGCTCGCCCTTTATTTTCCAGCCTGCTGCTATTGAAT
    Consensus    (3711)  ATGAAAAG AATCTTTA CTTCTTGACTGTTTTGCTCG CCT TATTTTCCAGCCT GC GCTATTGAAT
                         3781                                                           3850
OsMRP 13 mRNA    (3741)  GGCTGTGCCTGCGAATGGAATTGCTCTCGACCTTTGTCTTCGCTTTTTGCATGGCGATACTAGTGAGCTT
ZmMRP  3 mRNA    (3755)  GGCTCTGCCTGCGAATGGAATTGCTTTCGACTTTCGTCTTTGCTTTTTGCATGGCAATACTTGTGAGCTT
    Consensus    (3781)  GGCT TGCCTGCGAATGGAATTGCT TCGAC TT GTCTT GCTTTTTGCATGGC ATACT GTGAGCTT
                         3851                                                           3920
OsMRP 13 mRNA    (3811)  CCCTCCTGGCACAATTGAACCAAGTATGGCTGGGCTTGCTGTCACTTATGGACTTAATTTAAATGCTCGC
ZmMRP  3 mRNA    (3825)  TCCTCCTGGCACAATCGAACCAAGTATGGCTGGCCTCGCTGTAACATATGGACTTAATTTAAATGCTCGC
    Consensus    (3851)   CCTCCTGGCACAAT GAACCAAGTATGGCTGG CT GCTGT AC TATGGACTTAATTTAAATGCTCGC
                         3921                                                           3990
OsMRP 13 mRNA    (3881)  ATGTCAAGGTGGATACTGAGCTTCTGTAAATTAGAGAATAGAATCATCTCTGTTGAACGCATTTATCAGT
ZmMRP  3 mRNA    (3895)  ATGTCAAGATGGATATTGAGCTTCTGTAAATTAGAGAACAGGATAATCTCTGTTGAGCGCATTTATCAAT
    Consensus    (3921)  ATGTCAAG TGGATA TGAGCTTCTGTAAATTAGAGAA AG AT ATCTCTGTTGA CGCATTTATCA T
                         3991                                                           4060
OsMRP 13 mRNA    (3951)  ATTGCAAGCTTCCCAGTGAAGCACCACTCATCATTGAGAATAGCCGTCCCTCATCCTCGTGGCCTGAGAA
ZmMRP  3 mRNA    (3965)  ATTGCAGGCTTCCTAGTGAAGCACCATTGATTATTGAGAACTGCCGTCCACCATCATCATGGCCTCAGAA
    Consensus    (3991)  ATTGCA GCTTCC AGTGAAGCACCA T AT ATTGAGAA GCCGTCC  CATC TC TGGCCT AGAA
                         4061                                                           4130
OsMRP 13 mRNA    (4021)  TGGAAACATTGAGCTGGTCGATCTCAAGGTACGGTACAAAGATGACCTGCCCTTAGTTCTACATGGAATC
ZmMRP  3 mRNA    (4035)  TGGAAACATTGAACTGATTGATCTCAAGGTCCGCTACAAGGACGATCTACCATTAGTTCTTCATGGTGTA
    Consensus    (4061)  TGGAAACATTGA CTG T GATCTCAAGGT CG TACAA GA GA CT CC TTAGTTCT CATGG  T
                         4131                                                           4200
OsMRP 13 mRNA    (4091)  AGTTGTATATTTCCCGGTGGAAAAAAGATTGGGATTGTGGGGCGAACTGGAAGTGGTAAATCTACTCTTA
ZmMRP  3 mRNA    (4105)  AGTTGTATGTTTCCTGGCGGGAAAAAGATTGGGATTGTAGGGCGTACTGGAAGCGGTAAATCTACTCTTA
    Consensus    (4131)  AGTTGTAT TTTCC GG GG AAAAAGATTGGGATTGT GGGCG ACTGGAAG GGTAAATCTACTCTTA
                         4201                                                           4270
OsMRP 13 mRNA    (4161)  TTCAGGCCCTTTTCCGCTTAATTGAACCTACAGGAGGGAAAGTTATCATCGATGACGTCGATATTTCTAG
ZmMRP  3 mRNA    (4175)  TTCAGGCCCTTTTCCGCCTAATTGAGCCCACTGGAGGGAAGATTATAATTGACAACATTGACATCTCTGC
    Consensus    (4201)  TTCAGGCCCTTTTCCGC TAATTGA CC AC GGAGGGAA  TTAT AT GA  AC T GA AT TCT
                         4271                                                           4340
OsMRP 13 mRNA    (4231)  AATTGGCCTGCATGATCTGCGGTCACGGTTGAGCATCATTCCCCAGGACCCTACGTTGTTGAGGGTACT
ZmMRP  3 mRNA    (4245)  AATTGGCCTTCATGATCTGCGGTCACGGTTGAGCATCATTCCCCAAGACCCTACATTGTTGAGGGTACT
    Consensus    (4271)  AATTGGCCT CATGATCTGCGGTCACGGTTGAGCATCATTCCCCA GACCCTAC TTGTTGAGGGTACT
                         4341                                                           4410
OsMRP 13 mRNA    (4301)  ATCAGAATGAATCTTGATCCTCTTGAAGAATGTACTGATCAGGAAATTTGGGAGGCACTAGAAAAGTGTC
ZmMRP  3 mRNA    (4315)  ATCAGAATGAACCTTGATCCTCTTGAGGAGTGCACTGATCAAGAAATTTGGGAGGCACTAGAAAAGTGTC
    Consensus    (4341)  ATCAGAATGAA CTTGATCCTCTTGA GA TG ACTGATCA GAAATTTGGGAGGCACTAGAAAAGTGTC
                         4411                                                           4480
OsMRP 13 mRNA    (4371)  AGCTCGGAGAGGTCATTCGGTCCAAGGATGAAAAGCTGGACAGTCCAGTACTGGAGAATGGAGATAACTG
ZmMRP  3 mRNA    (4385)  AGCTAGGAGAGGTCATTCGTTCCAAGGAAGAGAAACTTGACAGTCCAGTGCTAGAAAACGGGGATAACTG
    Consensus    (4411)  AGCT GGAGAGGTCATTCG TCCAAGGA GA AA CT GACAGTCCAGT CT GA AA GG GATAACTG
                         4481                                                           4550
OsMRP 13 mRNA    (4441)  GAGTGTGGGACAACGCCAGCTTATTGCATTGGGTAGGGCCCTGCTGAAACAGGCAAAAATTTTGGTGCTT
ZmMRP  3 mRNA    (4455)  GAGCGTGGGACAGCGCCAACTTATTGCACTGGGTAGGGCGCTGCTCAAGCAGGCAAAAATTTTGGTACTC
    Consensus    (4481)  GAG GTGGGACA CGCCA CTTATTGCA TGGGTAGGGC CTGCT AA CAGGCAAAAATTTTGGT CT
                         4551                                                           4620
OsMRP 13 mRNA    (4511)  GACGAGGCAACAGCATCAGTTGACACAGCTACGGACAATCTTATTCAAAAGATTATTCGCAGTGAATTCA
ZmMRP  3 mRNA    (4525)  GATGAGGCGACAGCATCTGTCGACACAGCAACAGACAATCTTATCCAAAAGATCATCCGCAGTGAATTCA
    Consensus    (4551)  GA GAGGC ACAGCATC GT GACACAGC AC GACAATCTTAT CAAAAGAT AT CGCAGTGAATTCA
                         4621                                                           4690
OsMRP 13 mRNA    (4581)  AGGATTGCACGGTCTGCACCATTGCACACCGTATCCCGACGGTTATTGATAGTGACCTAGTCCTGGTGCT
ZmMRP  3 mRNA    (4595)  AGGACTGCACAGTCTGTACCATTGCTCACCGTATTCCCACCGTTATTGACAGTGACCTTGTTCTGGTCCT
    Consensus    (4621)  AGGA TGCAC GTCTG ACCATTGC CACCGTAT CC AC GTTATTGA AGTGACCT GT CTGGT CT
                         4691                                                           4760
OsMRP 13 mRNA    (4651)  TAGTGATGGTAAAATTGCAGAGTTTGACACACCCCAGAGGCTCTTGGAGGACAAGTCCTCCATGTTCATG
ZmMRP  3 mRNA    (4665)  TAGTGATGGTAAAATCGCAGAGTTCGACACGCCCCAGAGGCTTTTAGAGGACAAGTCATCTATGTTCATA
    Consensus    (4691)  TAGTGATGGTAAAAT GCAGAGTT GACAC CCCCAGAGGCT TT GAGGACAAGTC TC ATGTTCAT
```

FIG. 4D

```
                    4761                                                          4830
OsMRP 13 mRNA  (4721) CAGCTAGTATCTGAATACTCAACTCGGTCAAGCTGTATATAGAGAGGCTTAGCTTAAAATCCCCCACACC
ZmMRP 3 mRNA   (4735) CAGCTAGTATCGGAATACTCCACTCGGTCGAGCTGTATATAGAGAGGCTTAGCTTAAAACCCCGCCCCAA
    Consensus  (4761) CAGCTAGTATC GAATACTC ACTCGGTC AGCTGTATATAGAGAGGCTTAGCTTAAAA CCC C C
                    4831                                                          4900
OsMRP 13 mRNA  (4791) AAGTAGGAACAGGGA--GGTAGG---ATAGCCAC-ATCTGCCAGTGGACTCACGCCATAGAAGTACC---
ZmMRP 3 mRNA   (4805) ACCTGGCAACAGAGGCTGGGAGGCAAATAGCCCGTATCTGCCA-TG--CTTGCGCCATAGAGGTCCCTGC
    Consensus  (4831) A  T G AACAG G   GG AGG    ATAGCC  ATCTGCCA TG  CT  CGCCATAGA GT CC
                    4901                                                          4970
OsMRP 13 mRNA  (4852) -AACATCATAGGGCAAGACACAAGCCGAGGTGTATATGAGCGGAAACAAAAT-----GTTCCCTGACGTG
ZmMRP 3 mRNA   (4872) GAACACCGGAGGGCGGCGTAGAAGACGAGGTGTACATGAGTGGGAGGAACACTGGGCGTTCCCTGACCTG
    Consensus  (4901)  AACA C  AGGGC    A AAG C GAGGTGTA ATGAG GG A  AA A     GTTCCCTGAC TG
                    4971                                                          5040
OsMRP 13 mRNA  (4916) AATAAACCATGGAATCGATGAGGGAACGCAGCGGGCA-------GCACCACGGGAGGAGTTGGTGAGA--
ZmMRP 3 mRNA   (4942) AATA--CCGTGGAATCGGCGAGGGAGCGCGGTTGGTATTGGTAGGCACCAGGGGAGGAGTTGGTGACACT
    Consensus  (4971) AATA  CC TGGAATCG GAGGGA CGC G  GG A       GCACCA GGGAGGAGTTGGTGA A
                    5041                                                          5110
OsMRP 13 mRNA  (4977) ------TTACCCGAAGCTCTGATGCTTC----TGAATGTATAA--ACAATGCGGTACTACTTCTCCCTT-
ZmMRP 3 mRNA   (5010) AGTACATTACCCGAAGC--TGATGCTTCAGTATGTATGTATAACAACAATGCA-TACTGCTTCTCCCTTT
    Consensus  (5041)       TTACCCGAAGC  TGATGCTTC    TG ATGTATAA  ACAATGC  TACT CTTCTCCCTT
                    5111                                                          5180
OsMRP 13 mRNA  (5034) GCATAGTGGAAAAAGGGAAGGCAATGT-TCATGGGTAATAAAGGGGTAACAAGTTTCATTTTGGCACCAG
ZmMRP 3 mRNA   (5077) GCAGAGTGGAGAAC--CAAGGGAATAACTCGTGCGTAATAAGAGGAGAAAGATTTGTTTTTTGGC-----
    Consensus  (5111) GCA AGTGGA AA    AAGG AAT   TC TG GTAATAA GG  A A  T  TT   TTTTGGC
                    5181               5201
OsMRP 13 mRNA  (5103) ATTGGAGTGCTTTGGTCTACT
ZmMRP 3 mRNA   (5140) ---------------------
    Consensus  (5181)
```

FIG. 4E

```
                          1                                                           60
ZmMRP3        (1)   --MPPSFPSLPLPEAVAATAHAALLALAALLLLLRAARALASRCASCLKAPRRRGGPAVV
OsMRP13       (1)   ---MPHFPNLPLPEAAAAAHAALLALALLLLLLRSARALASRCASCLKTAPRR------
AtMRP5        (1)   MDFIEISLIFREHLPLLELCSVIINLLLFLVFLFAVSARQILVCVRRGRDRLSKDDTVSA
Consensus     (1)      IP FP LPLPEALAA AHAALLALA LLLLLRAARALASRCASCLK    RR
                          61                                                          120
ZmMRP3       (59)   VGDGAGGALAAATAGAWHRAVLASCAYALLSQVAVLSYEVAVAGSRVS-ARALLLPAVQA
OsMRP13      (52)   AAAVDGGLAAASSVGAWYRAALACCGYALLAQVAALSYEVAVAGSHVA-VEALLLPAVQA
AtMRP5       (61)   SNLSLEREVNHVSVGFGFNLSLLCCLYVLGVQVLVLVYDGVKVRREVSDWFVLCFPASQS
Consensus    (61)   AA   GG LAAASVGAWHRAALACCAYALLAQVAVLSYEVAVAGS VS   ALLLPAVQA
                          121                                                         180
ZmMRP3      (118)   VSWAALLALALQARAVGWARFPALVRLWWVVSFALCVVIAYDDSRRLIGQGARA-VDYAH
OsMRP13     (111)   LAWAALLALAMQARAVGWGRFPVLVRVWWVVSFVLCVGIAYDDTRHLMGDDDDDEVDYAH
AtMRP5      (121)   LAWFVLSFLVLHLKYKSSEKLPFLVRIWWFLAFSICLCTMYVDGRRLAIEGWSRCS--SH
Consensus   (121)   LAWAALLALALQARAVGWARFP LVRIWWVVSFALCV IAYDDSRRLIGDG        AH
                          181                                                         240
ZmMRP3      (177)   MVANFASVPALGFLCLVGVMGSTGLELEFTEDGNGLHEPLLLGRQRREAEEELGCLRVTP
OsMRP13     (171)   MVANFASAPALGFLCLVGVMGSTGVELEFTDDDSSVHEPLLLGGQRRDADEEPGCLRVTP
AtMRP5      (179)   VVANLAVTPALGFLCFLAWRGVSGIQVTRSSSD--LQEPLLV------EEEAACLKVTP
Consensus   (181)   MVANFAS PALGFLCLVGVMGSTGIELEFTDD   LHEPLLLG QRRDAEEE GCLRVTP
                          241                                                         300
ZmMRP3      (237)   YADAGILSLATLSWLSPLLSVGAQRPLELADIPLLAHKDRAKSCYKAMSAHYERQRLEYP
OsMRP13     (231)   YGDAGIVSLATLSWLSPLLSVGAQRPLELADIPLMAHKDRAKSCYKAMSSHYERQRMERP
AtMRP5      (230)   YSTAGLVSLITLSWLDPLLSAGSKRPLELKDIPLLAPRDRAKSSYKVLKSNWKRCKSENP
Consensus   (241)   YADAGIVSLATLSWLSPLLSVGAQRPLELADIPLLAHKDRAKSCYKAMSSHYERQRLE P
                          301                                                         360
ZmMRP3      (297)   GREPSLTWAILKSFWREAAVNGTFAAVNTIVSYVGPYLISYFVDYLSGNIAFPHEGYILA
OsMRP13     (291)   GSEPSLAWAILKSFWREAAINGAFAAVNTIVSYVGPYLISYFVDYLSGKIEFPHEGYILA
AtMRP5      (290)   SKPPSLARAIMKSFWKEAACNAVFAGLNTLVSYVGPYLISYFVDYLGGKEIFPHEGYVLA
Consensus   (301)   GKEPSLAWAILKSFWREAAING FAAVNTIVSYVGPYLISYFVDYLSGKI FPHEGYILA
                          361                                                         420
ZmMRP3      (357)   SIFFVAKLLETLTARQWYLGVDIMGIHVKSGLTAMVYRKGLRLSNASRQSHTSGEIVNYM
OsMRP13     (351)   SVFFVAKLLETLTARQWYLGVDVMGIHVKSGLTAMVYRKGLRLSNSSRQSHTSGEIVNYM
AtMRP5      (350)   GIFFTSKLIETVTTRQWYMGVDILGMHVRSALTAMVYRKGLKLSSIAKQNHTSGEIVNYM
Consensus   (361)   SIFFVAKLLETLTARQWYLGVDIMGIHVKSGLTAMVYRKGLRLSNASRQSHTSGEIVNYM
                          421                                                         480
ZmMRP3      (417)   AVDVQRVGDYAWYFHDIWMLPLQIILALAILYKNVGIAMVSTLVATVLSIAASVPVAKLQ
OsMRP13     (411)   AVDVQRVGDYAWYFHDIWMLPLQIILALAILYKNVGIAMVSTLVATVLSIAASVPVAKLQ
AtMRP5      (410)   AVDVQRIGDYSWYLHDIWMLPMQIVLALAILYKSVGIAAVATLVATIISILVTIPLAKVQ
Consensus   (421)   AVDVQRVGDYAWYFHDIWMLPLQIILALAILYKNVGIAMVSTLVATVLSIAASVPVAKLQ
                          481                                                         540
ZmMRP3      (477)   EHYQDKLMASKDERMRKTSECLKNMRILKLQAWEDRYRLQLEEMRNVECRWLRWALYSQA
OsMRP13     (471)   EHYQDKLMASKDERMRKTSECLKNMRILKLQAWEDRYRLKLEEMRNVECKWLRWALYSQA
AtMRP5      (470)   EDYQDKLMTAKDERMRKTSECLRNMRVLKLQAWEDRYRVRLEEMREEYGWLRKALYSQA
Consensus   (481)   EHYQDKLMASKDERMRKTSECLKNMRILKLQAWEDRYRLKLEEMRNVECKWLRWALYSQA
                          541                                                         600
ZmMRP3      (537)   AVTFVFWSSPIFVAVITFGTCILLGGQLTAGGVLSALATFRILQEPLRNFPDLISMMAQT
OsMRP13     (531)   AVTFVFWSSPIFVAVITFGTCILLGGELTAGGVLSALATFRILQEPLRNFPDLISMIAQT
AtMRP5      (530)   FVTFIFWSSPIFVAAVTFATSIFLGTQLTAGGVLSALATFRILQEPLRNFPDLVSMMAQT
Consensus   (541)   AVTFVFWSSPIFVAVITFGTCILLGGQLTAGGVLSALATFRILQEPLRNFPDLISMMAQT
                          601                                                         660
ZmMRP3      (597)   RVSLDRLSHFLQQEELPDDATINVPQSSTDKAVDIKDGAFSWNPYTLTPTLSDIHLSVVR
OsMRP13     (591)   RVSLDRLSHFLQQEELPDDATITVPHGSTDKAININDATFSWNPSSPTPTLSGINLSVVR
AtMRP5      (590)   KVSLDRISGFLQEEELQEDATVVIPRGLSNIAIEIKDGVFCWDPFSSRPTLSGIQMKVEK
Consensus   (601)   RVSLDRLSHFLQQEELPDDATI VP GSTDKAIDIKDG FSWNPFS TPTLSGINLSVVR
```

FIG. 5A

```
                    661                                                          720
ZmMRP3    (657) GMRVAVCGVIGSGKSSLLSSILGEIPKLCGHVRISGTAAYVPQTAWIQSGNIEENILFGS
OsMRP13   (651) GMRVAVCGVIGSGKSSLLSSILGEIPKLCGQVRISGSAAYVPQTAWIQSGNIEENILFGS
AtMRP5    (650) GMRVAVCGTVGSGKSSFISCILGEIPKISGEVRICGTTGYVSQSAWIQSGNIEENILFGS
Consensus (661) GMRVAVCGVIGSGKSSLLSSILGEIPKLCG VRISGTAAYVPQTAWIQSGNIEENILFGS
                    721                                                          780
ZmMRP3    (717) QMDRQRYKRVIAACCLKKDLELLQYGDQTVIGDRGINLSGGQKQRVQLARALYQDADIYL
OsMRP13   (711) PMDKQRYKRVIEACSLKKDLQLLQYGDQTIIGDRGINLSGGQKQRVQLARALYQDADIYL
AtMRP5    (710) PMEKTKYKNVIQACSLKKDIELFSHGDQTIIGERGINLSGGQKQRVQLARALYQDADIYL
Consensus (721) PMDKQRYKRVI ACSLKKDLELLQYGDQTIIGDRGINLSGGQKQRVQLARALYQDADIYL
                    781                                                          840
ZmMRP3    (777) LDDPFSAVDAHTGSELFKEYILTALATKTVIYVTHQVEFLPAADLILVLKDGHITQAGKY
OsMRP13   (771) LDDPFSAVDAHTGSELFREYILTALASKTVIYVTHQIEFLPAADLILVLKDGHITQAGKY
AtMRP5    (770) LDDPFSALDAHTGSDLFRDYILSALAEKTVVFVTHQVEFLPAADLILVLKEGRIIQSGKY
Consensus (781) LDDPFSAVDAHTGSELFREYILTALASKTVIYVTHQVEFLPAADLILVLKDGHITQAGKY
                    841                                                          900
ZmMRP3    (837) DDLLQAGTDFNALVSAHKEAIETMDIFEDSDSDTVS-----SIP--NKRLTPSISNIDNL
OsMRP13   (831) DDLLQAGTDFNALVCAHKEAIETMEFSEDSDEDTVS-----SVP--IKRLTPSVSNIDNL
AtMRP5    (830) DDLLQAGTDFKALVSAHHEAIEAMDIPSPSSEDSDENPIRDSLVLHNPKSDVFENDIETL
Consensus (841) DDLLQAGTDFNALVSAHKEAIETMDI EDSDEDTVS     SI   NKRLTPSISNIDNL
                    901                                                          960
ZmMRP3    (890) KNKMCENGQPSNTRGIKEKKKKEER-KKKRTVQEEERERGKVSSKVYLSYMGEAYKGTLI
OsMRP13   (884) KNKVSNNEKPSSTRGIKEKKKKPEERKKKRSVQEEERERGRVSLQVYLSYMGEAYKGTLI
AtMRP5    (890) AKEVQEGGSASDLKAIKEKKKKAKRSRKKQLVQEEERVKGKVSMKVYLSYMGAAYKGALI
Consensus (901) KNKV ENG PS TRGIKEKKKK ER KKKRSVQEEERERGKVSLKVYLSYMGEAYKGTLI
                    961                                                         1020
ZmMRP3    (949) PLIILAQTMFQVLQIASNWWMAWANPQTEGDAPKTDSVVLLVVYMSLAFGSSLFVFMRSL
OsMRP13   (944) PLIILAQTMFQVLQIASNWWMAWANPQTEGDAPKTDSVVLLVVYMSLAFGSSLFVFVRSL
AtMRP5    (950) PLIILAQAAFQFLQIASNWWMAWANPQTEGDESKVDPTLLLIVYTALAFGSSVFIFVRAA
Consensus (961) PLIILAQTMFQVLQIASNWWMAWANPQTEGDAPKTDSVVLLVVYMSLAFGSSLFVFVRSL
                   1021                                                         1080
ZmMRP3   (1009) LVATFGLAAAQKLFIKMLRCVFRAPMSFFDTTPSGRILNRVSVDQSVVDLDIAFRLGGFA
OsMRP13  (1004) LVATFGLATAQKLFVKMLRCVFRAPMSFFDTTPSGRILNRVSVDQSVVDLDIAFRLGGFA
AtMRP5   (1010) LVATFGLAAAQKLFLNMLRSVFRAPMSFFDSTPAGRILNRVSIDQSVVDLDIPFRLGGFA
Consensus(1021) LVATFGLAAAQKLFIKMLRCVFRAPMSFFDTTPSGRILNRVSVDQSVVDLDIAFRLGGFA
                   1081                                                         1140
ZmMRP3   (1069) STTIQLLGIVAVMSKVTWQVLILIVPMAVACMWMQRYYIASSRELTRILSVQKSPVIHLF
OsMRP13  (1064) STTIQLLGIVAVMSKVTWQVLILIVPMAVACMWMQRYYIASSRELTRILSVQKSPVIHLF
AtMRP5   (1070) STTIQLCGIVAVMTNVTWQVFLLVVPVAVACFWMQKYYMASSRELVRIVSIQKSPIIHLF
Consensus(1081) STTIQLLGIVAVMSKVTWQVLILIVPMAVACMWMQRYYIASSRELTRILSVQKSPVIHLF
                   1141                                                         1200
ZmMRP3   (1129) SESIAGAATIRGFGQEKRFMKRNLYLLDCFARPLFSSLAAIEWLCLRMELLSTFVFAFCM
OsMRP13  (1124) SESIAGAATIRGFGQEKRFMKRNLYLLDCFARPLFSSLAAIEWLCLRMELLSTFVFAFCM
AtMRP5   (1130) GESIAGAATIRGFGQEKRFIKRNLYLLDCFVRPFFCSIAAIEWLCLRMELLSTLVFAFCM
Consensus(1141) SESIAGAATIRGFGQEKRFMKRNLYLLDCFARPLFSSLAAIEWLCLRMELLSTFVFAFCM
                   1201                                                         1260
ZmMRP3   (1189) AILVSFPPGTIEPSMAGLAVTYGLNLNARMSRWILSFCKLENRIISVERIYQYCRLPSEA
OsMRP13  (1184) AILVSFPPGTIEPSMAGLAVTYGLNLNARMSRWILSFCKLENRIISVERIYQYCKLPSEA
AtMRP5   (1190) VLLVSFPHGTIDPSMAGLAVTYGLNLNGRLSRWILSFCKLENKIISIERIYQYSQIVGEA
Consensus(1201) AILVSFPPGTIEPSMAGLAVTYGLNLNARMSRWILSFCKLENRIISVERIYQYCKLPSEA
                   1261                                                         1320
ZmMRP3   (1249) PLIIENCRPPSSWPQNGNIELIDLKVRYKDDLPLVHGVSCMFPGGKKIGIVGRTGSGKS
OsMRP13  (1244) PLIIENSRPSSSWPENGNIELVDLKVRYKDDLPLVHGISCIFPGGKKIGIVGRTGSGKS
AtMRP5   (1250) PAIIEDFRPPSSWPATGTIELVDVKVRYAENLPTVLHGVSCVFPGGKKIGIVGRTGSGKS
Consensus(1261) PLIIEN RPPSSWP NGNIELVDLKVRYKDDLPLVHGVSCIFPGGKKIGIVGRTGSGKS
```

FIG. 5B

```
                    1321                                                        1380
ZmMRP3    (1309)  TLIQALFRLIEPTGGKIIIDNIDISAIGLHDLRSRLSIIPQDPTLFEGTIRMNLDPLEEC
OsMRP13   (1304)  TLIQALFRLIEPTGGKVIIDDVDISRIGLHDLRSRLSIIPQDPTLFEGTIRMNLDPLEEC
AtMRP5    (1310)  TLIQALFRLIEPTAGKITIDNIDISQIGLHDLRSRLGIIPQDPTLFEGTIRANLDPLEEH
Consensus (1321)  TLIQALFRLIEPTGGKIIIDNIDIS IGLHDLRSRLSIIPQDPTLFEGTIRMNLDPLEEC
                    1381                                                        1440
ZmMRP3    (1369)  TDQEIWEALEKCQLGEVIRSKEEKLDSPVLENGDNWSVGQRQLIALGRALLKQAKILVLD
OsMRP13   (1364)  TDQEIWEALEKCQLGEVIRSKDEKLDSPVLENGDNWSVGQRQLIALGRALLKQAKILVLD
AtMRP5    (1370)  SDDKIWEALDKSQLGDVVRGKDLKLDSPVLENGDNWSVGQRQLVSLGRALLKQAKILVLD
Consensus (1381)  TDQEIWEALEKCQLGEVIRSKDEKLDSPVLENGDNWSVGQRQLIALGRALLKQAKILVLD
                    1441                                                        1500
ZmMRP3    (1429)  EATASVDTATDNLIQKIIRSEFKDCTVCTIAHRIPTVIDSDLVLVLSDGKIAEFDTPQRL
OsMRP13   (1424)  EATASVDTATDNLIQKIIRSEFKDCTVCTIAHRIPTVIDSDLVLVLSDGKIAEFDTPQRL
AtMRP5    (1430)  EATASVDTATDNLIQKIIRTEFEDCTVCTIAHRIPTVIDSDLVLVLSDGRVAEFDTPARL
Consensus (1441)  EATASVDTATDNLIQKIIRSEFKDCTVCTIAHRIPTVIDSDLVLVLSDGKIAEFDTPQRL
                    1501             1525
ZmMRP3    (1489)  LEDKSSMFIQLVSEYSTRSSCI---
OsMRP13   (1484)  LEDKSSMFMQLVSEYSTRSSCI---
AtMRP5    (1490)  LEDKSSMFLKLVTEYSSRSTGIPEL
Consensus (1501)  LEDKSSMFIQLVSEYSTRSSCI
```

FIG. 5C

Sample Construct 1
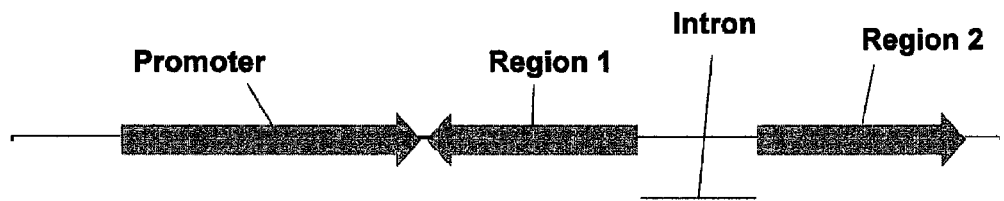
Sample Construct 2
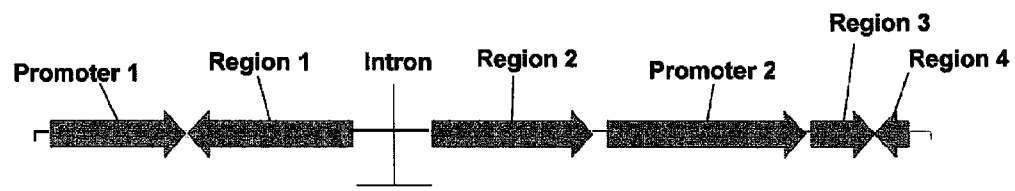
Sample Construct 3
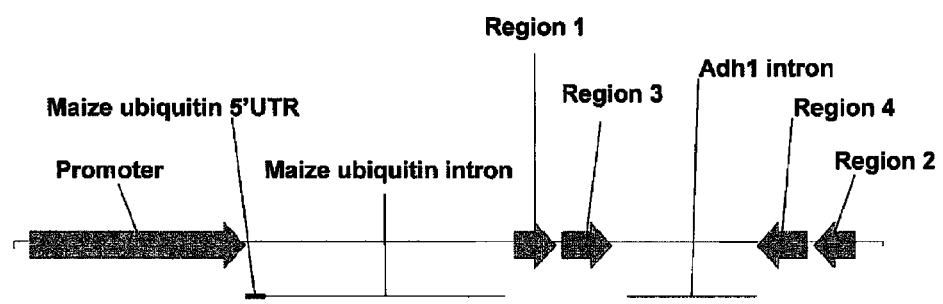
FIG. 6

SEQUENCE LISTING

```
<160> NUMBER OF SEQ ID NOS: 79

<210> SEQ ID NO 1
<211> LENGTH: 11347
<212> TYPE: DNA
<213> ORGANISM: Zea mays
<220> FEATURE:
<221> NAME/KEY: promoter
<222> LOCATION: (1)...(2495)
<220> FEATURE:
<221> NAME/KEY: exon
<222> LOCATION: (3135)...(5195)
<220> FEATURE:
<221> NAME/KEY: exon
<222> LOCATION: (5276)...(5596)
<220> FEATURE:
<221> NAME/KEY: exon
<222> LOCATION: (5674)...(5760)
<220> FEATURE:
<221> NAME/KEY: exon
<222> LOCATION: (6018)...(6692)
<220> FEATURE:
<221> NAME/KEY: exon
<222> LOCATION: (6767)...(6931)
<220> FEATURE:
<221> NAME/KEY: exon
<222> LOCATION: (7380)...(7674)
<220> FEATURE:
<221> NAME/KEY: exon
<222> LOCATION: (7818)...(8032)
<220> FEATURE:
<221> NAME/KEY: exon
<222> LOCATION: (8238)...(8543)
<220> FEATURE:
<221> NAME/KEY: exon
<222> LOCATION: (8622)...(8685)
<220> FEATURE:
<221> NAME/KEY: exon
<222> LOCATION: (8788)...(9027)
<220> FEATURE:
<221> NAME/KEY: exon
<222> LOCATION: (9233)...(9698)
<220> FEATURE:
<221> NAME/KEY: 3'UTR
<222> LOCATION: (9302)...(9699)
<220> FEATURE:
<221> NAME/KEY: terminator
<222> LOCATION: (9699)...(11347)

<400> SEQUENCE: 1
ggtaaataac cgcggttatt tacccgttgg gtacggatat ggtgaagttt catatccgcg      60
ggtacgggta tggatactat atggtatcca cgggtaataa tttcgcgggt atggatatct     120
gctatccata tccgttaccc ggtggacata tgtcatgtgg acccaaacat ctaatggacg     180
catcccaggt cccagcggcc agcatccttg ggcttgttca ctgcttcacg gatggagtct     240
ggatcagcgc ctcaacactt cagcagcaag gccgcattgc cacaaggcca gcagacagca     300
gtccaagcgg cccaagactg ctcacggacg gagtcttaga gtctcggtca gtctctctct     360
cactctctct tatctcccag ttttaaccct agccgccaag gccaagctcc ctcccaaatc     420
ccaatctgct cgtctgcggt gcagggctgc aggcatccac ctccaccagg cgctggccca     480
```

```
gttttcgcca tccaccaggc gtccttagaa tatggtgcag ggctaccgag cagcgagcaa    540
caagctgccg agcacagggc gccgaccgtc gagcagcgag caccgaggac cgccgagtag    600
tcgagcaccg agcagctagc accgagcagc cgagcagcaa gcagagggct gcgaccaccg    660
agcagccgag ccgcctcgtc ttctctcgtc ttctctagta aattaaacag cttggatga    720
attagttttt tgatttagag ttttggagag attatttgta cggatttgaa aagattactt    780
gtatggaacg ttgaaattat tgtttggtgc taaaaatat tattggaatg ttgttggaat     840
gttaatttgt gataaatttc tgctagaatg atgctgtaat tttagtgggc gggcgggtaa    900
tggatatccg ttggataacg gatacccgac gggtatgggt acggatatag atccgtaccc    960
acgagcgtaa atgggtatgg gtatggattg ggttttacct cgtgggtatg gatacgcgaa   1020
acatatatcc gccttctacc cgcccgattg ccatccctac tcgcctcgcc tccccgtgga   1080
cgggcgggcc gggcgtgctc ggcactgacc ggtgccccac cgcgatatac catagggggc   1140
cacgcgagat tcccgccccc catcccatct ggtgccgccg ccgcgctgcc gctgcgtgcg   1200
gcctccccac ctgggcagcc tacgcccgca gccggcgcgc atgcatgtgc cacgtcgcgg   1260
cagacctacc accacgccgc tcgatctggc gactggcggt gcggtggtcc gctgctgctg   1320
cacggcgttt tccgcgtttg tttgcttgtt ccgttgtgtt gtccgcatcg cgcctctctc   1380
tctctctcgc cctcgctcgc cgggacggag acggcgaggc cggggcggca tctttctgct   1440
ggctttccgg catctcgtca gaccagaggg gaaaaaggc gcctttccgg ccgtaacact    1500
aaccccctgt ctttttttta tcacccgtgt gccatctgtt tctaggatgg taggacgtga   1560
tcgatccaac gtttcgcaag taccaccacc accaccgtga ctgttcggcc ccagacggac   1620
gcaacgccaa ccgtgcctgc gtcggctcaa caatcattgc cacgcgtacc cggtatcccg   1680
gccaggcggt tccagtcagt ccgcggacgc caagaagaat ttttaggtgc acggagtcca   1740
ggttctttgt tcatgacagt actcaaagcg aaaacgcaga agcattgtct cgactgaaca   1800
gcgggttcag ttcagttttct gaggctgtct gaactggatt acagcacagc gccagcgcgc   1860
gcccgcgtac acacagacga cacatctgtg acactgtcgt gttccctcct gcgtacgaag   1920
cgatcgcttt tccccccact cgctgcacgt tatccctgtc gcctcctcct cagaacgcct   1980
cccttttatt agtagtacaa agaaagatgt ccataaaaat aaagcctttt gtaataaatg   2040
gtaaataaag gcggatattc tgcgacctcc gcaaatacgc gcacaacaat cttgtgctcc   2100
gctcgatata agcctcaatc tcataagata atgtgtgtat gttttcagaa acaaaatcaa   2160
cgttttaaaa ttttgaccaa cagttcagaa aaaacatat tttttagtg tatgtatgtt     2220
gtatacctga atttatacta aaaatacttt aacgtaatac ttgatttgtt tttattgatg   2280
ttctatttca cagtaaatac tttatcaaaa gaatatacgc ctcgtgtttt atggaacgga   2340
gggagtattt gttttcatgt atagacaata aaaacatatt aatcctgtat aataaaaatt   2400
taatgcggca tgcacgtcat ggtagtagcc ggaaggcaaa gccggctacg aactctcctc   2460
ctctataaaa accatcaatc gccgttccat ctgtttgcaa gccgaccgaa accaggcagt   2520
ggtgtggagt ggacacaaca caacaggaga ggaggaaaag ggaaaacgga aattcactgc   2580
tactactccg tctccgtact agcacgccca taacctctct ctctctcctg cctctcaccg   2640
catcgtcttc ctctccccc accacacccc ccacccgccg atccatcccc caaaagccga   2700
agccgaaacc gaaacctccc tccgcacgcc acctgctacc acacacacac ccgcgccgcc   2760
gccccacgg ccggccgcgc ggaggtgact cgagaaggac gcaggaacca aggagagagt   2820
ttggtgaggg gatcagagac gtaacccgcc cggacccggg ctgcattagc cggaatccca   2880
```

```
tcccaggcga gcctctctct cccctcctcg aaccaggcgc aggcgagcgt ctctgcccgc    2940
ccgcctgctg ctaccgccaa aacgcctcct ttgttgccat ccgccgatgc cgtaatccgc    3000
cgcccaaagc tcttcctttt tccctctctc tcgcccgcgg ccgcactccc tgccccagtg    3060
cctgccgtgg cgagcccaac cccaatgcct tttaaacccc tccccgctcc ctcactgatc    3120
cccaccgcct cccaatgccg ccctccttcc cctccctccc gctcccggag gccgttgccg    3180
ccaccgccca cgccgcgctg ctcgcgctcg ccgcactcct gctcctcctc cgcgccgcgc    3240
gcgcgctcgc ctcccgctgc gcgtcatgcc tcaaggcgcc gcgccgccgc gggggcccg    3300
ccgtcgtcgt gggcgacggc gccggcggcg cctcgcggc ggcgactgcc ggcgcctggc    3360
acagggccgt gctggcgtcc tgcgcctacg ccctgctctc gcaggtcgcc gtgctgagct    3420
acgaggtggc cgtcgccggc tcgcgcgtct cggcgcgggc gctgctgctg ccggccgtgc    3480
aggcggtgtc ctgggccgcg ctgctggcgc tcgcgcttca ggcccgcgcc gtcggctggg    3540
ccaggttccc tgcgctggtg cggctctggt ggtggtctc cttcgcgctc tgcgttgtca    3600
ttgcgtacga cgactccagg cgcctgatag gccagggcgc gcgcgctgtg gattacgcgc    3660
acatggttgc caacttcgcg tccgtgccgg ccctgggctt cctgtgcttg gttggtgtca    3720
tgggttccac cggtttggaa ttggagttta cggaggatgg caacggcctg catgagccgc    3780
tgctgctcgg caggcagcgc agagaggcag aggaggagct cggctgtctg agggtcactc    3840
cctacgctga tgctgggatc ctcagccttg caacattgtc atggcttagt ccgttgctct    3900
ctgttggtgc gcagcggcca cttgagttgg ctgacatacc cttgctggcg cacaaggacc    3960
gtgcaaagtc atgctataag gcgatgagcg ctcactacga gcgccagcgg ctagaatacc    4020
ctggcaggga gccatcactc acatgggcaa tactcaagtc attctggcga gaggccgcgg    4080
tcaatggcac atttgctgct gtcaacacga ttgtgtcgta tgttggacct tacttgatca    4140
gctattttgt ggactacctc agtggcaaca ttgctttccc ccatgaaggt tacatccttg    4200
cctctatatt ttttgtagca aaactgcttg agacactcac tgcccgacag tggtacttgg    4260
gtgtggacat catggggatc catgtcaagt ctggcctcac tgccatggtg tataggaagg    4320
gtctccgact gtcaaacgcc tcacggcaga gccacacgag tggtgagatt gtgaattaca    4380
tggccgtcga tgtgcagcgt gtgggggact atgcatggta tttccatgac atctggatgc    4440
ttcccctgca gatcattctt gctctcgcca tcctgtacaa gaacgtcggg atcgccatgg    4500
tttcaacatt ggtagcaact gtgctatcga tcgcagcctc tgttcctgtg caaagctgc    4560
aggagcacta ccaagataag ttaatggcat caaaagatga gcgcatgcgc aagacttcag    4620
agtgcttgaa aaatatgagg attttgaagc ttcaggcatg ggaggatcgg taccggctgc    4680
agttggaaga gatgaggaac gtggaatgca gatggcttcg gtgggctctg tactcacagg    4740
ctgcagttac atttgttttc tggagctcgc caatctttgt cgcagtcata acttttggga    4800
cttgcatatt actcggtggc cagctcactg caggagggg tctatccgct ttagcaacgt    4860
ttcggatcct ccaagagcct ctgaggaact tcccggatct catctctatg atggcacaga    4920
caagggtgtc tttggaccgt ttgtctcatt ttctgcagca agaagaactg ccagatgacg    4980
caactataaa tgttccacaa agtagtacag ataaggcagt cgatattaag gatggcgcat    5040
tctcttggaa cccatacact ctgaccccta cactttctga tatacacctt agtgtagtga    5100
gaggcatgag agtagcagtc gtggtgtca ttggttctgg taaatcaagt ctactatcgt    5160
ctatactcgg ggagatacc aaattatgtg gccatgtaag tataaatgca aaaaaaatc    5220
gacattgatt ttgcttgttc tgttacattg acctttctcc tgcctcatat tccaggtcag    5280
```

-continued

```
gataagtggc acagcagcgt atgttcctca gactgcatgg atacagtctg gaaatattga    5340
ggagaatatt ctgtttggca gtcaaatgga tagacaacgt tacaagagag tcattgcagc    5400
ttgctgtctt aagaaagatc ttgagctgct ccagtacgga gatcagactg ttattggtga    5460
tagaggcatt aatttgagtg gaggtcagaa acaaagagtt cagcttgcta gagcactcta    5520
ccaagatgct gatatttatt tgcttgatga tcccttcagt gctgttgatg ctcatactgg    5580
gagcgaactg tttaaggttg gtacagctgt ttgcctatta tatttgtttc taagctgttt    5640
ctgttccata acacatctgc ttctgtgtta caggagtata tattgactgc actagcaacc    5700
aaaacagtaa tctatgtaac acatcaagtt gaatttctac cagctgctga tctgatattg    5760
gtaagcggta gacatatttt cgtattgata tgtatgctat tatgagtaat tcttatgggc    5820
atgcttttct gattttcatc atcatatcga gttgttctct gtaatatcct attggttcat    5880
cttttccttt tggaagctaa ccatgcatgt aacctctaaa tgagagctag ttaccttcag    5940
gattgttttc atgggactat aagtgtgact agtgggcctg tattaatctc tctttgatgg    6000
ttctgtcgca tttacaggtt cttaaggatg gccatatcac acaagctgga agtatgatg    6060
atcttctgca agctggaact gatttcaatg ctctggtttc tgctcataag gaagctattg    6120
aaaccatgga tatatttgaa gattccgata gtgatacagt ttcttctatt cccaacaaaa    6180
gattgacacc aagtatcagc aatattgata acctgaaaaa taagatgtgt gaaaatggac    6240
aaccatctaa tacacgggga attaaggaaa aaagaagaa agaagagcgt aagaagaagc    6300
gtactgttca agaggaggaa agggaacgtg gaaagtgag ctccaaagtt tatttgtcat    6360
acatggggga agcttacaaa ggtacactga taccactaat tatcttggct caaaccatgt    6420
tccaagttct tcagattgcg agcaactggt ggatggcatg ggcaaaccca caaacagaag    6480
gagatgctcc caagacagat agtgtggtcc ttctggttgt ttatatgtcc cttgcctttg    6540
gaagttcact atttgtgttc atgagaagcc ttcttgtggc tacgtttggt ttagcagctg    6600
cccagaagct ttttataaaa atgcttaggt gtgtctttcg agctccaatg tcattctttg    6660
acaccacacc atctggtcgg attttgaaca gagtaagtat tgctcttgcc tatgctaata    6720
taagtttgta atatgtgctt tcctcctatt cattctttta tatcaggttt ctgtagatca    6780
aagtgttgtg gaccttgata tagcgttcag acttggtgga tttgcatcaa cgacaattca    6840
actccttgga attgttgctg tcatgagcaa agtcacatgg caagttctga ttcttatagt    6900
ccccatggct gttgcatgca tgtggatgca ggtaaatgtt gtgatcacca acattacat    6960
ttcaatctat atttgaggtt taatatcaca agctgttttt tcccttaaca tttagcaaat    7020
tggtatatga cagtctagat ttatttgaga acaccttttg caagatgggc catataacta    7080
gagtttactt tcagctaatg atccttattc cttaaagaat gtttattagt cactcggcat    7140
aggcacatca tgtattgcac tctatgttta gtaattagta tgtcattggt tcactgttga    7200
tgtcttagaa attgctatgc ttgcagatgt ttattaattg agatacttct agctcaattc    7260
tcttaatttt ttatattaaa ccattgtagt cataaggaat tacctgttta aaaggatatg    7320
ttttctggta aatcagagtg gcatttttac taaagctcca attactgtca cctttgcaga    7380
ggtattatat tgcttcatca agggaactaa ctaggatttt gagtgttcag aagtctccag    7440
tgatccattt gtttagtgaa tcaattgctg gtgctgctac aataagggt tttggtcaag    7500
agaagcggtt tatgaaaagg aatctttatc ttcttgactg ttttgctcgc cctttatttt    7560
ccagccttgc tgctattgaa tggctctgcc tgcgaatgga attgctttcg actttcgtct    7620
ttgcttttg catggcaata cttgtgagct ttcctcctgg cacaatcgaa ccaagtatgt    7680
```

```
ttatgttcca catgctgctc cagttctcta ctatgtttgg tcgctttctc caatgcctta    7740
ttctgtgcag tagaaaacct gcatcttctt gtctgttaaa atttattcag catctaaatg    7800
gattttcaaa ttgataggta tggctggcct cgctgtaaca tatggactta atttaaatgc    7860
tcgcatgtca agatggatat tgagcttctg taaattagag aacaggataa tctctgttga    7920
gcgcatttat caatattgca ggcttcctag tgaagcacca ttgattattg agaactgccg    7980
tccaccatca tcatggcctc agaatggaaa cattgaactg attgatctca aggtatgctt    8040
tatcattggg gggcagttaa ggatacgatt tcattagca ttgctataga gctgattgtc     8100
atttccagca tgcaaatatt atattctaac ataatctatt tacatttttc tctttactat    8160
gtataattac catacatatc taatttatga tctatttagt tttggcttct gagtttgctt    8220
tttcatgatt atgaaaggtc cgctacaagg acgatctacc attagttctt catggtgtaa    8280
gttgtatgtt tcctggcggg aaaaagattg ggattgtagg gcgtactgga agcggtaaat    8340
ctactcttat tcaggccctt ttccgcctaa ttgagcccac tggagggaag attataattg    8400
acaacattga catctctgca attggccttc atgatctgcg gtcacggttg agcatcattc    8460
cccaagaccc tacattgttt gagggtacta tcagaatgaa ccttgatcct cttgaggagt    8520
gcactgatca agaaatttgg gaggtacatc ctggtcactt tgacgctata ctcatgttga    8580
gtctgtgtga ttcttatctt aaggaacaca atctgttgca ggcactagaa aagtgtcagc    8640
taggagaggt cattcgttcc aaggaagaga aacttgacag tccaggttag cctgacattt    8700
tgctgccaag cctcctttga agagtgggaa tgtggtttct taatgcgtaa acttattgct    8760
cctggacctt ttttttttgct tttgcagtgc tagaaaacgg ggataactgg agcgtgggac   8820
agcgccaact tattgcactg ggtagggcgc tgctcaagca ggcaaaaatt ttggtactcg    8880
atgaggcgac agcatctgtc gacacagcaa cagacaatct tatccaaaag atcatccgca    8940
gtgaattcaa ggactgcaca gtctgtacca ttgctcaccg tattcccacc gttattgaca    9000
gtgaccttgt tctggtcctt agtgatggta tgagttcttt gactaaacta accacgcctc    9060 cttacctgt tcatagttag atttcctgag ctctggtcct tttccaactc gtgcatccga     9120
ttcttggata aacatttaga aagtagaaac cgtagcaaac tgacagtttt tcttctgcac    9180
agaatttgga aacaagcctt cgctgaactt ttctcatcgt cttgatttcc aggtaaaatc    9240
gcagagttcg acacgcccca gaggctttta gaggacaagt catctatgtt catacagcta    9300
gtatcggaat actccactcg gtcgagctgt atatagagag gcttagctta aaaccccgcc    9360
ccaaacctgg caacagaggc tgggaggcaa atagcccgta tctgccatgc ttgcgccata    9420
gaggtccctg cgaacaccgg agggcggcgt agaagacgag gtgtacatga gtgggaggaa    9480
cactgggcgt tccctgacct gaataccgtg gaatcggcga gggagcgcgg ttggtattgg    9540
taggcaccag gggaggagtt ggtgacacta gtacattacc cgaagctgat gcttcagtat    9600
gtatgtataa caacaatgca tactgcttct ccctttgcag agtggagaac caagggaata    9660
actcgtgcgt aataagagga gaaagatttg ttttttggca tcagactggt gtgtgtgcgc    9720
ttttgtttgc tgtgtccatt agaccattac tgtatttctc tgccaaattt tactgtagcc    9780
ggtgccagtt tctgcttcag aaattcagca tctcaaatcg ccaggtgaaa aaggttcagc    9840
aaccagcagt ttgctcgatg gccgaggcta gtaactcatc ctgtgctgaa tacagagtat    9900
caccacgtca ggttcactgc cctgacctga aaacaatact ccctgtggag atgacggctg    9960
gattacgcag atactgtagt gtaaaataag agatttacat tgtagattat acttttttaca 10020 gattaaagct ttaaatagga gatgaataga ctgtgtagtg taaaataaga tatttacatt  10080
```

```
gtagattata ctgtttacag attaaagcta tgaatagatt gctgttttta gagagagaga    10140
ggctgtaggg taaaccctac atcataattt ttgtttagtg gaaaaaggta acaagatcaa    10200
tagaaacaag agagagggag ggagggggggg ggggggggggg gtgttatctt ttttctaaaa   10260
aaaccaggct ctggaggaaa aagggtttag ttctcctaag ttaaatttta tctgtgcccc    10320
acacctccaa tatttccaaa tttatttaga atattaaata gatttatttt gatttaaaaa    10380
aattgttttg gcttttactt agattttaac aagtttaaaa acaacgcgcc ctctctagtg    10440
taaaatttat tttttggcgc gcacgattaa aatggagcaa attacccccta tttattttat   10500 atagccctct ttttttatct ctgtaaaata tatgagcttt attttttatag tgttaaatat    10560 acaattttgt ataaggaaga agcctaaatt taattattta attattgaac ttcaaactca    10620
ggtatctttg gtatcgaacc agggcagac ctacgtgtat atgagtgggg gatcaggccc     10680
cactcatttc tttgttgtaa gtagtagaac ctagattttc accatgaggg tccctgctaa    10740
gcataactta gatgctcctg ctctgatatt ttggtacttg ttttttggaag tgtgccctca   10800 ttttgtatt tgttctggga ccacctctgt atcgaactac taaaattaga catacttggt     10860
tcatcgagaa gccttcgatt gtactttctc catttttttat ttgacgtagt tgtccccccc   10920
tcccaaaaaa aaaactctaa tcgcttatct tattaaaaat ttgtgtgttc tttaaaagct    10980
actccatcct aaagtatagt tttgtccatc ctaaagtata gtttgaagtt caatggttaa    11040
atctaaactt cttccattat agaacatgtg tttatttata tgtttaacac tatacttaac    11100
aatatgaaaa tagagctctt tacttgtaa cagaatagat aaaaaataag ctatgaaatg     11160
ataagggaca atttggataa tttgcttgag aggtgagaaa taaaagaatg gaaaatatag    11220
atagagtgct attttctgaa tttatttgat gaaactactg ttgttcttat aattgcttga    11280
aaacgagtgc ttttttttaa cacagtctca taccagtgtt gtttcgtgga ttcgaaggaa    11340
ggctttg                                                              11347
```

<210> SEQ ID NO 2
<211> LENGTH: 5139
<212> TYPE: DNA
<213> ORGANISM: Zea mays
<220> FEATURE:
<221> NAME/KEY: CDS
<222> LOCATION: (244)...(4776)

<400> SEQUENCE: 2

```
cctctctctc ccctcctcga accaggcgca ggcgagcgtc tctgcccgcc cgcctgctgc     60
taccgccaaa acgcctcctt tgttgccatc cgccgatgcc gtaatccgcc gcccaaagct    120 cttcctttt ccctctctct cgcccgcggc cgcactccct gccccagtgc ctgccgtggc    180
gagcccaacc ccaatgccct ttaaacccct ccccgctccc tcactgatcc ccaccgcctc    240 cca atg ccg ccc tcc ttc ccc tcc ctc ccg ctc ccg gag gcc gtt gcc      288
    Met Pro Pro Ser Phe Pro Ser Leu Pro Leu Pro Glu Ala Val Ala
    1               5                   10                  15 gcc acc gcc cac gcc gcg ctg ctc gcg ctc gcc gca ctc ctg ctc ctc      336
Ala Thr Ala His Ala Ala Leu Leu Ala Leu Ala Ala Leu Leu Leu Leu
                20                  25                  30 ctc cgc gcc gcg cgc gcg ctc gcc tcc cgc tgc gcg tca tgc ctc aag      384
Leu Arg Ala Ala Arg Ala Leu Ala Ser Arg Cys Ala Ser Cys Leu Lys
            35                  40                  45 gcg ccg cgc cgc cgc ggg ggc ccc gcc gtc gtc gtg ggc gac ggc gcc      432
Ala Pro Arg Arg Arg Gly Gly Pro Ala Val Val Val Gly Asp Gly Ala
        50                  55                  60
```

-continued

| | | |
|---|---|---|
| ggc ggc gcc ctc gcg gcg gcg act gcc ggc gcc tgg cac agg gcc gtg<br>Gly Gly Ala Leu Ala Ala Ala Thr Ala Gly Ala Trp His Arg Ala Val<br>    65                        70                      75 | | 480 |
| ctg gcg tcc tgc gcc tac gcc ctg ctc tcg cag gtc gcc gtg ctg agc<br>Leu Ala Ser Cys Ala Tyr Ala Leu Leu Ser Gln Val Ala Val Leu Ser<br>80                        85                        90                        95 | | 528 |
| tac gag gtg gcc gtc gcc ggc tcg cgc gtc tcg gcg cgg gcg ctg ctg<br>Tyr Glu Val Ala Val Ala Gly Ser Arg Val Ser Ala Arg Ala Leu Leu<br>                        100                      105                      110 | | 576 |
| ctg ccg gcc gtg cag gcg gtg tcc tgg gcc gcg ctg gcg ctc gcg<br>Leu Pro Ala Val Gln Ala Val Ser Trp Ala Ala Leu Ala Leu Ala<br>                115                      120                      125 | | 624 |
| ctt cag gcc cgc gcc gtc ggc tgg gcc agg ttc cct gcg ctg gtg cgg<br>Leu Gln Ala Arg Ala Val Gly Trp Ala Arg Phe Pro Ala Leu Val Arg<br>        130                      135                      140 | | 672 |
| ctc tgg tgg gtg gtc tcc ttc gcg ctc tgc gtt gtc att gcg tac gac<br>Leu Trp Trp Val Val Ser Phe Ala Leu Cys Val Val Ile Ala Tyr Asp<br>    145                      150                      155 | | 720 |
| gac tcc agg cgc ctg ata ggc cag ggc gcg cgc gct gtg gat tac gcg<br>Asp Ser Arg Arg Leu Ile Gly Gln Gly Ala Arg Ala Val Asp Tyr Ala<br>160                        165                      170                      175 | | 768 |
| cac atg gtt gcc aac ttc gcg tcc gtg ccg gcc ctg ggc ttc ctg tgc<br>His Met Val Ala Asn Phe Ala Ser Val Pro Ala Leu Gly Phe Leu Cys<br>                    180                      185                      190 | | 816 |
| ttg gtt ggt gtc atg ggt tcc acc ggt ttg gaa ttg gag ttt acg gag<br>Leu Val Gly Val Met Gly Ser Thr Gly Leu Glu Leu Glu Phe Thr Glu<br>              195                      200                      205 | | 864 |
| gat ggc aac ggc ctg cat gag ccg ctg ctc ggc agg cag cgc aga<br>Asp Gly Asn Gly Leu His Glu Pro Leu Leu Leu Gly Arg Gln Arg Arg<br>210                        215                      220 | | 912 |
| gag gca gag gag gag ctc ggc tgt ctg agg gtc act ccc tac gct gat<br>Glu Ala Glu Glu Glu Leu Gly Cys Leu Arg Val Thr Pro Tyr Ala Asp<br>    225                      230                      235 | | 960 |
| gct ggg atc ctc agc ctt gca aca ttg tca tgg ctt agt ccg ttg ctc<br>Ala Gly Ile Leu Ser Leu Ala Thr Leu Ser Trp Leu Ser Pro Leu Leu<br>240                        245                      250                      255 | | 1008 |
| tct gtt ggt gcg cag cgg cca ctt gag ttg gct gac ata ccc ttg ctg<br>Ser Val Gly Ala Gln Arg Pro Leu Glu Leu Ala Asp Ile Pro Leu Leu<br>                    260                      265                      270 | | 1056 |
| gcg cac aag gac cgt gca aag tca tgc tat aag gcg atg agc gct cac<br>Ala His Lys Asp Arg Ala Lys Ser Cys Tyr Lys Ala Met Ser Ala His<br>        275                      280                      285 | | 1104 |
| tac gag cgc cag cgg cta gaa tac cct ggc agg gag cca tca ctc aca<br>Tyr Glu Arg Gln Arg Leu Glu Tyr Pro Gly Arg Glu Pro Ser Leu Thr<br>                290                      295                      300 | | 1152 |
| tgg gca ata ctc aag tca ttc tgg cga gag gcc gcg gtc aat ggc aca<br>Trp Ala Ile Leu Lys Ser Phe Trp Arg Glu Ala Ala Val Asn Gly Thr<br>305                        310                      315 | | 1200 |
| ttt gct gct gtc aac acg att gtg tcg tat gtt gga cct tac ttg atc<br>Phe Ala Ala Val Asn Thr Ile Val Ser Tyr Val Gly Pro Tyr Leu Ile<br>320                        325                      330                      335 | | 1248 |
| agc tat ttt gtg gac tac ctc agt ggc aac att gct ttc ccc cat gaa<br>Ser Tyr Phe Val Asp Tyr Leu Ser Gly Asn Ile Ala Phe Pro His Glu<br>                    340                      345                      350 | | 1296 |
| ggt tac atc ctt gcc tct ata ttt ttt gta gca aaa ctg ctt gag aca<br>Gly Tyr Ile Leu Ala Ser Ile Phe Phe Val Ala Lys Leu Leu Glu Thr<br>                  355                      360                      365 | | 1344 |
| ctc act gcc cga cag tgg tac ttg ggt gtg gac atc atg ggg atc cat<br>Leu Thr Ala Arg Gln Trp Tyr Leu Gly Val Asp Ile Met Gly Ile His<br>              370                      375                      380 | | 1392 |

```
gtc aag tct ggc ctc act gcc atg gtg tat agg aag ggt ctc cga ctg    1440
Val Lys Ser Gly Leu Thr Ala Met Val Tyr Arg Lys Gly Leu Arg Leu
385             390                 395 tca aac gcc tca cgg cag agc cac acg agt ggt gag att gtg aat tac    1488
Ser Asn Ala Ser Arg Gln Ser His Thr Ser Gly Glu Ile Val Asn Tyr
400             405                 410                 415 atg gcc gtc gat gtg cag cgt gtg ggg gac tat gca tgg tat ttc cat    1536
Met Ala Val Asp Val Gln Arg Val Gly Asp Tyr Ala Trp Tyr Phe His
                420                 425                 430 gac atc tgg atg ctt ccc ctg cag atc att ctt gct ctc gcc atc ctg    1584
Asp Ile Trp Met Leu Pro Leu Gln Ile Ile Leu Ala Leu Ala Ile Leu
            435                 440                 445 tac aag aac gtc ggg atc gcc atg gtt tca aca ttg gta gca act gtg    1632
Tyr Lys Asn Val Gly Ile Ala Met Val Ser Thr Leu Val Ala Thr Val
        450                 455                 460 cta tcg atc gca gcc tct gtt cct gtg gca aag ctg cag gag cac tac    1680
Leu Ser Ile Ala Ala Ser Val Pro Val Ala Lys Leu Gln Glu His Tyr
465                 470                 475 caa gat aag tta atg gca tca aaa gat gag cgc atg cgc aag act tca    1728
Gln Asp Lys Leu Met Ala Ser Lys Asp Glu Arg Met Arg Lys Thr Ser
480                 485                 490                 495 gag tgc ttg aaa aat atg agg att ttg aag ctt cag gca tgg gag gat    1776
Glu Cys Leu Lys Asn Met Arg Ile Leu Lys Leu Gln Ala Trp Glu Asp
                500                 505                 510 cgg tac cgg ctg cag ttg gaa gag atg agg aac gtg gaa tgc aga tgg    1824
Arg Tyr Arg Leu Gln Leu Glu Glu Met Arg Asn Val Glu Cys Arg Trp
            515                 520                 525 ctt cgg tgg gct ctg tac tca cag gct gca gtt aca ttt gtt ttc tgg    1872
Leu Arg Trp Ala Leu Tyr Ser Gln Ala Ala Val Thr Phe Val Phe Trp
        530                 535                 540 agc tcg cca atc ttt gtc gca gtc ata act ttt ggg act tgc ata tta    1920
Ser Ser Pro Ile Phe Val Ala Val Ile Thr Phe Gly Thr Cys Ile Leu
545                 550                 555 ctc ggt ggc cag ctc act gca gga ggg gtt cta tcc gct tta gca acg    1968
Leu Gly Gly Gln Leu Thr Ala Gly Gly Val Leu Ser Ala Leu Ala Thr
560                 565                 570                 575 ttt cgg atc ctc caa gag cct ctg agg aac ttc ccg gat ctc atc tct    2016
Phe Arg Ile Leu Gln Glu Pro Leu Arg Asn Phe Pro Asp Leu Ile Ser
                580                 585                 590 atg atg gca cag aca agg gtg tct ttg gac cgt ttg tct cat ttt ctg    2064
Met Met Ala Gln Thr Arg Val Ser Leu Asp Arg Leu Ser His Phe Leu
            595                 600                 605 cag caa gaa gaa ctg cca gat gac gca act ata aat gtt cca caa agt    2112
Gln Gln Glu Glu Leu Pro Asp Asp Ala Thr Ile Asn Val Pro Gln Ser
        610                 615                 620 agt aca gat aag gca gtc gat att aag gat ggc gca ttc tct tgg aac    2160
Ser Thr Asp Lys Ala Val Asp Ile Lys Asp Gly Ala Phe Ser Trp Asn
625                 630                 635 cca tac act ctg acc cct aca ctt tct gat ata cac ctt agt gta gtg    2208
Pro Tyr Thr Leu Thr Pro Thr Leu Ser Asp Ile His Leu Ser Val Val
640                 645                 650                 655 aga ggc atg aga gta gca gtc tgt ggt gtc att ggt tct ggt aaa tca    2256
Arg Gly Met Arg Val Ala Val Cys Gly Val Ile Gly Ser Gly Lys Ser
                660                 665                 670 agt cta cta tcg tct ata ctc ggg gag ata ccc aaa tta tgt ggc cat    2304
Ser Leu Leu Ser Ser Ile Leu Gly Glu Ile Pro Lys Leu Cys Gly His
            675                 680                 685 gtc agg ata agt ggc aca gca gcg tat gtt cct cag act gca tgg ata    2352
Val Arg Ile Ser Gly Thr Ala Ala Tyr Val Pro Gln Thr Ala Trp Ile
        690                 695                 700
```

| | | | | | | | | | | | | | | | |
|---|---|---|---|---|---|---|---|---|---|---|---|---|---|---|---|
| cag | tct | gga | aat | att | gag | gag | aat | att | ctg | ttt | ggc | agt | caa | atg | gat | 2400 |
| Gln | Ser | Gly | Asn | Ile | Glu | Glu | Asn | Ile | Leu | Phe | Gly | Ser | Gln | Met | Asp | |
| 705 | | | | 710 | | | | | 715 | | | | | | |
| aga | caa | cgt | tac | aag | aga | gtc | att | gca | gct | tgc | tgt | ctt | aag | aaa | gat | 2448 |
| Arg | Gln | Arg | Tyr | Lys | Arg | Val | Ile | Ala | Ala | Cys | Cys | Leu | Lys | Lys | Asp | |
| 720 | | | | | 725 | | | | | 730 | | | | | 735 | |
| ctt | gag | ctg | ctc | cag | tac | gga | gat | cag | act | gtt | att | ggt | gat | aga | ggc | 2496 |
| Leu | Glu | Leu | Leu | Gln | Tyr | Gly | Asp | Gln | Thr | Val | Ile | Gly | Asp | Arg | Gly | |
| | | | 740 | | | | | 745 | | | | | 750 | | | |
| att | aat | ttg | agt | gga | ggt | cag | aaa | caa | aga | gtt | cag | ctt | gct | aga | gca | 2544 |
| Ile | Asn | Leu | Ser | Gly | Gly | Gln | Lys | Gln | Arg | Val | Gln | Leu | Ala | Arg | Ala | |
| | | | 755 | | | | | 760 | | | | | 765 | | | |
| ctc | tac | caa | gat | gct | gat | att | tat | ttg | ctt | gat | gat | ccc | ttc | agt | gct | 2592 |
| Leu | Tyr | Gln | Asp | Ala | Asp | Ile | Tyr | Leu | Leu | Asp | Asp | Pro | Phe | Ser | Ala | |
| | | 770 | | | | | 775 | | | | | 780 | | | | |
| gtt | gat | gct | cat | act | ggg | agc | gaa | ctg | ttt | aag | gag | tat | ata | ttg | act | 2640 |
| Val | Asp | Ala | His | Thr | Gly | Ser | Glu | Leu | Phe | Lys | Glu | Tyr | Ile | Leu | Thr | |
| 785 | | | | | 790 | | | | | 795 | | | | | | |
| gca | cta | gca | acc | aaa | aca | gta | atc | tat | gta | aca | cat | caa | gtt | gaa | ttt | 2688 |
| Ala | Leu | Ala | Thr | Lys | Thr | Val | Ile | Tyr | Val | Thr | His | Gln | Val | Glu | Phe | |
| 800 | | | | | 805 | | | | | 810 | | | | | 815 | |
| cta | cca | gct | gct | gat | ctg | ata | ttg | gtt | ctt | aag | gat | ggc | cat | atc | aca | 2736 |
| Leu | Pro | Ala | Ala | Asp | Leu | Ile | Leu | Val | Leu | Lys | Asp | Gly | His | Ile | Thr | |
| | | | 820 | | | | | 825 | | | | | 830 | | | |
| caa | gct | gga | aag | tat | gat | gat | ctt | ctg | caa | gct | gga | act | gat | ttc | aat | 2784 |
| Gln | Ala | Gly | Lys | Tyr | Asp | Asp | Leu | Leu | Gln | Ala | Gly | Thr | Asp | Phe | Asn | |
| | | | 835 | | | | | 840 | | | | | 845 | | | |
| gct | ctg | gtt | tct | gct | cat | aag | gaa | gct | att | gaa | acc | atg | gat | ata | ttt | 2832 |
| Ala | Leu | Val | Ser | Ala | His | Lys | Glu | Ala | Ile | Glu | Thr | Met | Asp | Ile | Phe | |
| | | 850 | | | | | 855 | | | | | 860 | | | | |
| gaa | gat | tcc | gat | agt | gat | aca | gtt | tct | tct | att | ccc | aac | aaa | aga | ttg | 2880 |
| Glu | Asp | Ser | Asp | Ser | Asp | Thr | Val | Ser | Ser | Ile | Pro | Asn | Lys | Arg | Leu | |
| 865 | | | | | 870 | | | | | 875 | | | | | | |
| aca | cca | agt | atc | agc | aat | att | gat | aac | ctg | aaa | aat | aag | atg | tgt | gaa | 2928 |
| Thr | Pro | Ser | Ile | Ser | Asn | Ile | Asp | Asn | Leu | Lys | Asn | Lys | Met | Cys | Glu | |
| 880 | | | | | 885 | | | | | 890 | | | | | 895 | |
| aat | gga | caa | cca | tct | aat | aca | cgg | gga | att | aag | gaa | aaa | aag | aag | aaa | 2976 |
| Asn | Gly | Gln | Pro | Ser | Asn | Thr | Arg | Gly | Ile | Lys | Glu | Lys | Lys | Lys | Lys | |
| | | | | 900 | | | | | 905 | | | | | 910 | | |
| gaa | gag | cgt | aag | aag | aag | cgt | act | gtt | caa | gag | gag | gaa | agg | gaa | cgt | 3024 |
| Glu | Glu | Arg | Lys | Lys | Lys | Arg | Thr | Val | Gln | Glu | Glu | Glu | Arg | Glu | Arg | |
| | | | 915 | | | | | 920 | | | | | 925 | | | |
| gga | aaa | gtg | agc | tcc | aaa | gtt | tat | ttg | tca | tac | atg | ggg | gaa | gct | tac | 3072 |
| Gly | Lys | Val | Ser | Ser | Lys | Val | Tyr | Leu | Ser | Tyr | Met | Gly | Glu | Ala | Tyr | |
| | | | 930 | | | | | 935 | | | | | 940 | | | |
| aaa | ggt | aca | ctg | ata | cca | cta | att | atc | ttg | gct | caa | acc | atg | ttc | caa | 3120 |
| Lys | Gly | Thr | Leu | Ile | Pro | Leu | Ile | Ile | Leu | Ala | Gln | Thr | Met | Phe | Gln | |
| | 945 | | | | | 950 | | | | | 955 | | | | | |
| gtt | ctt | cag | att | gcg | agc | aac | tgg | tgg | atg | gca | tgg | gca | aac | cca | caa | 3168 |
| Val | Leu | Gln | Ile | Ala | Ser | Asn | Trp | Trp | Met | Ala | Trp | Ala | Asn | Pro | Gln | |
| 960 | | | | | 965 | | | | | 970 | | | | | 975 | |
| aca | gaa | gga | gat | gct | ccc | aag | aca | gat | agt | gtg | gtc | ctt | ctg | gtt | gtt | 3216 |
| Thr | Glu | Gly | Asp | Ala | Pro | Lys | Thr | Asp | Ser | Val | Val | Leu | Leu | Val | Val | |
| | | | | 980 | | | | | 985 | | | | | 990 | | |
| tat | atg | tcc | ctt | gcc | ttt | gga | agt | tca | cta | ttt | gtg | ttc | atg | aga | agc | 3264 |
| Tyr | Met | Ser | Leu | Ala | Phe | Gly | Ser | Ser | Leu | Phe | Val | Phe | Met | Arg | Ser | |
| | | | 995 | | | | | 1000 | | | | | 1005 | | | |
| ctt | ctt | gtg | gct | acg | ttt | ggt | tta | gca | gct | gcc | cag | aag | ctt | ttt | ata | 3312 |
| Leu | Leu | Val | Ala | Thr | Phe | Gly | Leu | Ala | Ala | Ala | Gln | Lys | Leu | Phe | Ile | |
| | | 1010 | | | | | 1015 | | | | | 1020 | | | | |

| | | |
|---|---|---|
| aaa atg ctt agg tgt gtc ttt cga gct cca atg tca ttc ttt gac acc<br>Lys Met Leu Arg Cys Val Phe Arg Ala Pro Met Ser Phe Phe Asp Thr<br>　　1025　　　　　　　　1030　　　　　　　　1035 | | 3360 |
| aca cca tct ggt cgg att ttg aac aga gtt tct gta gat caa agt gtt<br>Thr Pro Ser Gly Arg Ile Leu Asn Arg Val Ser Val Asp Gln Ser Val<br>1040　　　　　　　　1045　　　　　　　　1050　　　　　　　　1055 | | 3408 |
| gtg gac ctt gat ata gcg ttc aga ctt ggt gga ttt gca tca acg aca<br>Val Asp Leu Asp Ile Ala Phe Arg Leu Gly Gly Phe Ala Ser Thr Thr<br>　　　　　　　　1060　　　　　　　　1065　　　　　　　　1070 | | 3456 |
| att caa ctc ctt gga att gtt gct gtc atg agc aaa gtc aca tgg caa<br>Ile Gln Leu Leu Gly Ile Val Ala Val Met Ser Lys Val Thr Trp Gln<br>　　1075　　　　　　　　1080　　　　　　　　1085 | | 3504 |
| gtt ctg att ctt ata gtc ccc atg gct gtt gca tgc atg tgg atg cag<br>Val Leu Ile Leu Ile Val Pro Met Ala Val Ala Cys Met Trp Met Gln<br>　　　　1090　　　　　　　　1095　　　　　　　　1100 | | 3552 |
| agg tat tat att gct tca tca agg gaa cta act agg att ttg agt gtt<br>Arg Tyr Tyr Ile Ala Ser Ser Arg Glu Leu Thr Arg Ile Leu Ser Val<br>　　1105　　　　　　　　1110　　　　　　　　1115 | | 3600 |
| cag aag tct cca gtg atc cat ttg ttt agt gaa tca att gct ggt gct<br>Gln Lys Ser Pro Val Ile His Leu Phe Ser Glu Ser Ile Ala Gly Ala<br>1120　　　　　　　　1125　　　　　　　　1130　　　　　　　　1135 | | 3648 |
| gct aca ata agg ggt ttt ggt caa gag aag cgg ttt atg aaa agg aat<br>Ala Thr Ile Arg Gly Phe Gly Gln Glu Lys Arg Phe Met Lys Arg Asn<br>　　　　　　　　1140　　　　　　　　1145　　　　　　　　1150 | | 3696 |
| ctt tat ctt ctt gac tgt ttt gct cgc cct tta ttt tcc agc ctt gct<br>Leu Tyr Leu Leu Asp Cys Phe Ala Arg Pro Leu Phe Ser Ser Leu Ala<br>　　1155　　　　　　　　1160　　　　　　　　1165 | | 3744 |
| gct att gaa tgg ctc tgc ctg cga atg gaa ttg ctt tcg act ttc gtc<br>Ala Ile Glu Trp Leu Cys Leu Arg Met Glu Leu Leu Ser Thr Phe Val<br>　　　　1170　　　　　　　　1175　　　　　　　　1180 | | 3792 |
| ttt gct ttt tgc atg gca ata ctt gtg agc ttt cct cct ggc aca atc<br>Phe Ala Phe Cys Met Ala Ile Leu Val Ser Phe Pro Pro Gly Thr Ile<br>　　1185　　　　　　　　1190　　　　　　　　1195 | | 3840 |
| gaa cca agt atg gct ggc ctc gct gta aca tat gga ctt aat tta aat<br>Glu Pro Ser Met Ala Gly Leu Ala Val Thr Tyr Gly Leu Asn Leu Asn<br>1200　　　　　　　　1205　　　　　　　　1210　　　　　　　　1215 | | 3888 |
| gct cgc atg tca aga tgg ata ttg agc ttc tgt aaa tta gag aac agg<br>Ala Arg Met Ser Arg Trp Ile Leu Ser Phe Cys Lys Leu Glu Asn Arg<br>　　　　　　　　1220　　　　　　　　1225　　　　　　　　1230 | | 3936 |
| ata atc tct gtt gag cgc att tat caa tat tgc agg ctt cct agt gaa<br>Ile Ile Ser Val Glu Arg Ile Tyr Gln Tyr Cys Arg Leu Pro Ser Glu<br>　　1235　　　　　　　　1240　　　　　　　　1245 | | 3984 |
| gca cca ttg att att gag aac tgc cgt cca cca tca tca tgg cct cag<br>Ala Pro Leu Ile Ile Glu Asn Cys Arg Pro Pro Ser Ser Trp Pro Gln<br>　　　　1250　　　　　　　　1255　　　　　　　　1260 | | 4032 |
| aat gga aac att gaa ctg att gat ctc aag gtc cgc tac aag gac gat<br>Asn Gly Asn Ile Glu Leu Ile Asp Leu Lys Val Arg Tyr Lys Asp Asp<br>　　1265　　　　　　　　1270　　　　　　　　1275 | | 4080 |
| cta cca tta gtt ctt cat ggt gta agt tgt atg ttt cct ggc ggg aaa<br>Leu Pro Leu Val Leu His Gly Val Ser Cys Met Phe Pro Gly Gly Lys<br>1280　　　　　　　　1285　　　　　　　　1290　　　　　　　　1295 | | 4128 |
| aag att ggg att gta ggg cgt act gga agc ggt aaa tct act ctt att<br>Lys Ile Gly Ile Val Gly Arg Thr Gly Ser Gly Lys Ser Thr Leu Ile<br>　　　　　　　　1300　　　　　　　　1305　　　　　　　　1310 | | 4176 |
| cag gcc ctt ttc cgc cta att gag ccc act gga ggg aag att ata att<br>Gln Ala Leu Phe Arg Leu Ile Glu Pro Thr Gly Gly Lys Ile Ile Ile<br>　　1315　　　　　　　　1320　　　　　　　　1325 | | 4224 |
| gac aac att gac atc tct gca att ggc ctt cat gat ctg cgg tca cgg<br>Asp Asn Ile Asp Ile Ser Ala Ile Gly Leu His Asp Leu Arg Ser Arg<br>　　　　1330　　　　　　　　1335　　　　　　　　1340 | | 4272 |

```
ttg agc atc att ccc caa gac cct aca ttg ttt gag ggt act atc aga    4320
Leu Ser Ile Ile Pro Gln Asp Pro Thr Leu Phe Glu Gly Thr Ile Arg
    1345                1350                1355 atg aac ctt gat cct ctt gag gag tgc act gat caa gaa att tgg gag    4368
Met Asn Leu Asp Pro Leu Glu Glu Cys Thr Asp Gln Glu Ile Trp Glu
1360                1365                1370                1375 gca cta gaa aag tgt cag cta gga gag gtc att cgt tcc aag gaa gag    4416
Ala Leu Glu Lys Cys Gln Leu Gly Glu Val Ile Arg Ser Lys Glu Glu
                1380                1385                1390 aaa ctt gac agt cca gtg cta gaa aac ggg gat aac tgg agc gtg gga    4464
Lys Leu Asp Ser Pro Val Leu Glu Asn Gly Asp Asn Trp Ser Val Gly
        1395                1400                1405 cag cgc caa ctt att gca ctg ggt agg gcg ctg ctc aag cag gca aaa    4512
Gln Arg Gln Leu Ile Ala Leu Gly Arg Ala Leu Leu Lys Gln Ala Lys
    1410                1415                1420 att ttg gta ctc gat gag gcg aca gca tct gtc gac aca gca aca gac    4560
Ile Leu Val Leu Asp Glu Ala Thr Ala Ser Val Asp Thr Ala Thr Asp
1425                1430                1435 aat ctt atc caa aag atc atc cgc agt gaa ttc aag gac tgc aca gtc    4608
Asn Leu Ile Gln Lys Ile Ile Arg Ser Glu Phe Lys Asp Cys Thr Val
1440                1445                1450                1455 tgt acc att gct cac cgt att ccc acc gtt att gac agt gac ctt gtt    4656
Cys Thr Ile Ala His Arg Ile Pro Thr Val Ile Asp Ser Asp Leu Val
                1460                1465                1470 ctg gtc ctt agt gat ggt aaa atc gca gag ttc gac acg ccc cag agg    4704
Leu Val Leu Ser Asp Gly Lys Ile Ala Glu Phe Asp Thr Pro Gln Arg
        1475                1480                1485 ctt tta gag gac aag tca tct atg ttc ata cag cta gta tcg gaa tac    4752
Leu Leu Glu Asp Lys Ser Ser Met Phe Ile Gln Leu Val Ser Glu Tyr
    1490                1495                1500 tcc act cgg tcg agc tgt ata tag agaggcttag cttaaaaccc cgccccaaac   4806
Ser Thr Arg Ser Ser Cys Ile *
1505                1510 ctggcaacag aggctgggag gcaaatagcc cgtatctgcc atgcttgcgc catagaggtc   4866
cctgcgaaca ccggaggggcg gcgtagaaga cgaggtgtac atgagtggga ggaacactgg   4926
gcgttccctg acctgaatac cgtggaatcg gcgagggagc gcggttggta ttggtaggca   4986
ccaggggagg agttggtgac actagtacat tacccgaagc tgatgcttca gtatgtatgt   5046
ataacaacaa tgcatactgc ttctcccttt gcagagtgga gaaccaaggg aataactcgt   5106
gcgtaataag aggagaaaga tttgtttttt ggc                                5139

<210> SEQ ID NO 3
<211> LENGTH: 1510
<212> TYPE: PRT
<213> ORGANISM: Zea mays

<400> SEQUENCE: 3

Met Pro Pro Ser Phe Pro Ser Leu Pro Leu Pro Glu Ala Val Ala Ala
1               5                   10                  15

Thr Ala His Ala Ala Leu Leu Ala Leu Ala Ala Leu Leu Leu Leu Leu
            20                  25                  30

Arg Ala Ala Arg Ala Leu Ala Ser Arg Cys Ala Ser Cys Leu Lys Ala
        35                  40                  45

Pro Arg Arg Gly Gly Pro Ala Val Val Val Gly Asp Gly Ala Gly
    50                  55                  60

Gly Ala Leu Ala Ala Ala Thr Ala Gly Ala Trp His Arg Ala Val Leu
65                  70                  75                  80
```

```
Ala Ser Cys Ala Tyr Ala Leu Leu Ser Gln Val Ala Val Leu Ser Tyr
                85                  90                  95

Glu Val Ala Val Ala Gly Ser Arg Val Ser Ala Arg Ala Leu Leu Leu
            100                 105                 110

Pro Ala Val Gln Ala Val Ser Trp Ala Ala Leu Leu Ala Leu Ala Leu
            115                 120                 125

Gln Ala Arg Ala Val Gly Trp Ala Arg Phe Pro Ala Leu Val Arg Leu
            130                 135                 140

Trp Trp Val Val Ser Phe Ala Leu Cys Val Val Ile Ala Tyr Asp Asp
145                 150                 155                 160

Ser Arg Arg Leu Ile Gly Gln Gly Ala Arg Ala Val Asp Tyr Ala His
                165                 170                 175

Met Val Ala Asn Phe Ala Ser Val Pro Ala Leu Gly Phe Leu Cys Leu
            180                 185                 190

Val Gly Val Met Gly Ser Thr Gly Leu Glu Leu Glu Phe Thr Glu Asp
            195                 200                 205

Gly Asn Gly Leu His Glu Pro Leu Leu Leu Gly Arg Gln Arg Arg Glu
    210                 215                 220

Ala Glu Glu Glu Leu Gly Cys Leu Arg Val Thr Pro Tyr Ala Asp Ala
225                 230                 235                 240

Gly Ile Leu Ser Leu Ala Thr Leu Ser Trp Leu Ser Pro Leu Leu Ser
                245                 250                 255

Val Gly Ala Gln Arg Pro Leu Glu Leu Ala Asp Ile Pro Leu Leu Ala
            260                 265                 270

His Lys Asp Arg Ala Lys Ser Cys Tyr Lys Ala Met Ser Ala His Tyr
            275                 280                 285

Glu Arg Gln Arg Leu Glu Tyr Pro Gly Arg Glu Pro Ser Leu Thr Trp
            290                 295                 300

Ala Ile Leu Lys Ser Phe Trp Arg Glu Ala Ala Val Asn Gly Thr Phe
305                 310                 315                 320

Ala Ala Val Asn Thr Ile Val Ser Tyr Val Gly Pro Tyr Leu Ile Ser
                325                 330                 335

Tyr Phe Val Asp Tyr Leu Ser Gly Asn Ile Ala Phe Pro His Glu Gly
            340                 345                 350

Tyr Ile Leu Ala Ser Ile Phe Phe Val Ala Lys Leu Leu Glu Thr Leu
            355                 360                 365

Thr Ala Arg Gln Trp Tyr Leu Gly Val Asp Ile Met Gly Ile His Val
            370                 375                 380

Lys Ser Gly Leu Thr Ala Met Val Tyr Arg Lys Gly Leu Arg Leu Ser
385                 390                 395                 400

Asn Ala Ser Arg Gln Ser His Thr Ser Gly Glu Ile Val Asn Tyr Met
                405                 410                 415

Ala Val Asp Val Gln Arg Val Gly Asp Tyr Ala Trp Tyr Phe His Asp
            420                 425                 430

Ile Trp Met Leu Pro Leu Gln Ile Ile Leu Ala Leu Ala Ile Leu Tyr
            435                 440                 445

Lys Asn Val Gly Ile Ala Met Val Ser Thr Leu Val Ala Thr Val Leu
            450                 455                 460

Ser Ile Ala Ala Ser Val Pro Val Ala Lys Leu Gln Glu His Tyr Gln
465                 470                 475                 480

Asp Lys Leu Met Ala Ser Lys Asp Glu Arg Met Arg Lys Thr Ser Glu
                485                 490                 495

Cys Leu Lys Asn Met Arg Ile Leu Lys Leu Gln Ala Trp Glu Asp Arg
            500                 505                 510
```

Tyr Arg Leu Gln Leu Glu Glu Met Arg Asn Val Glu Cys Arg Trp Leu
            515                 520                 525

Arg Trp Ala Leu Tyr Ser Gln Ala Ala Val Thr Phe Val Phe Trp Ser
        530                 535                 540

Ser Pro Ile Phe Val Ala Val Ile Thr Phe Gly Thr Cys Ile Leu Leu
545                 550                 555                 560

Gly Gly Gln Leu Thr Ala Gly Gly Val Leu Ser Ala Leu Ala Thr Phe
                565                 570                 575

Arg Ile Leu Gln Glu Pro Leu Arg Asn Phe Pro Asp Leu Ile Ser Met
            580                 585                 590

Met Ala Gln Thr Arg Val Ser Leu Asp Arg Leu Ser His Phe Leu Gln
        595                 600                 605

Gln Glu Glu Leu Pro Asp Asp Ala Thr Ile Asn Val Pro Gln Ser Ser
            610                 615                 620

Thr Asp Lys Ala Val Asp Ile Lys Asp Gly Ala Phe Ser Trp Asn Pro
625                 630                 635                 640

Tyr Thr Leu Thr Pro Thr Leu Ser Asp Ile His Leu Ser Val Val Arg
                645                 650                 655

Gly Met Arg Val Ala Val Cys Gly Val Ile Gly Ser Gly Lys Ser Ser
            660                 665                 670

Leu Leu Ser Ser Ile Leu Gly Glu Ile Pro Lys Leu Cys Gly His Val
        675                 680                 685

Arg Ile Ser Gly Thr Ala Ala Tyr Val Pro Gln Thr Ala Trp Ile Gln
        690                 695                 700

Ser Gly Asn Ile Glu Glu Asn Ile Leu Phe Gly Ser Gln Met Asp Arg
705                 710                 715                 720

Gln Arg Tyr Lys Arg Val Ile Ala Ala Cys Cys Leu Lys Lys Asp Leu
                725                 730                 735

Glu Leu Leu Gln Tyr Gly Asp Gln Thr Val Ile Gly Asp Arg Gly Ile
            740                 745                 750

Asn Leu Ser Gly Gly Gln Lys Gln Arg Val Gln Leu Ala Arg Ala Leu
        755                 760                 765

Tyr Gln Asp Ala Asp Ile Tyr Leu Leu Asp Asp Pro Phe Ser Ala Val
770                 775                 780

Asp Ala His Thr Gly Ser Glu Leu Phe Lys Glu Tyr Ile Leu Thr Ala
785                 790                 795                 800

Leu Ala Thr Lys Thr Val Ile Tyr Val Thr His Gln Val Glu Phe Leu
                805                 810                 815

Pro Ala Ala Asp Leu Ile Leu Val Leu Lys Asp Gly His Ile Thr Gln
            820                 825                 830

Ala Gly Lys Tyr Asp Asp Leu Leu Gln Ala Gly Thr Asp Phe Asn Ala
        835                 840                 845

Leu Val Ser Ala His Lys Glu Ala Ile Glu Thr Met Asp Ile Phe Glu
850                 855                 860

Asp Ser Asp Ser Asp Thr Val Ser Ser Ile Pro Asn Lys Arg Leu Thr
865                 870                 875                 880

Pro Ser Ile Ser Asn Ile Asp Asn Leu Lys Asn Lys Met Cys Glu Asn
                885                 890                 895

Gly Gln Pro Ser Asn Thr Arg Gly Ile Lys Glu Lys Lys Lys Lys Glu
            900                 905                 910

Glu Arg Lys Lys Lys Arg Thr Val Gln Glu Glu Arg Glu Arg Gly
        915                 920                 925

Lys Val Ser Ser Lys Val Tyr Leu Ser Tyr Met Gly Glu Ala Tyr Lys

```
                    930             935             940
Gly Thr Leu Ile Pro Leu Ile Leu Ala Gln Thr Met Phe Gln Val
945             950             955             960
Leu Gln Ile Ala Ser Asn Trp Trp Met Ala Trp Ala Asn Pro Gln Thr
            965             970             975
Glu Gly Asp Ala Pro Lys Thr Asp Ser Val Val Leu Val Val Tyr
            980             985             990
Met Ser Leu Ala Phe Gly Ser Ser Leu Phe Val Phe Met Arg Ser Leu
            995             1000            1005
Leu Val Ala Thr Phe Gly Leu Ala Ala Ala Gln Lys Leu Phe Ile Lys
            1010            1015            1020
Met Leu Arg Cys Val Phe Arg Ala Pro Met Ser Phe Phe Asp Thr Thr
1025            1030            1035            1040
Pro Ser Gly Arg Ile Leu Asn Arg Val Ser Val Asp Gln Ser Val Val
            1045            1050            1055
Asp Leu Asp Ile Ala Phe Arg Leu Gly Gly Phe Ala Ser Thr Thr Ile
            1060            1065            1070
Gln Leu Leu Gly Ile Val Ala Val Met Ser Lys Val Thr Trp Gln Val
            1075            1080            1085
Leu Ile Leu Ile Val Pro Met Ala Val Ala Cys Met Trp Met Gln Arg
            1090            1095            1100
Tyr Tyr Ile Ala Ser Ser Arg Glu Leu Thr Arg Ile Leu Ser Val Gln
1105            1110            1115            1120
Lys Ser Pro Val Ile His Leu Phe Ser Glu Ser Ile Ala Gly Ala Ala
            1125            1130            1135
Thr Ile Arg Gly Phe Gly Gln Glu Lys Arg Phe Met Lys Arg Asn Leu
            1140            1145            1150
Tyr Leu Leu Asp Cys Phe Ala Arg Pro Leu Phe Ser Ser Leu Ala Ala
            1155            1160            1165
Ile Glu Trp Leu Cys Leu Arg Met Glu Leu Leu Ser Thr Phe Val Phe
            1170            1175            1180
Ala Phe Cys Met Ala Ile Leu Val Ser Phe Pro Pro Gly Thr Ile Glu
1185            1190            1195            1200
Pro Ser Met Ala Gly Leu Ala Val Thr Tyr Gly Leu Asn Leu Asn Ala
            1205            1210            1215
Arg Met Ser Arg Trp Ile Leu Ser Phe Cys Lys Leu Glu Asn Arg Ile
            1220            1225            1230
Ile Ser Val Glu Arg Ile Tyr Gln Tyr Cys Arg Leu Pro Ser Glu Ala
            1235            1240            1245
Pro Leu Ile Ile Glu Asn Cys Arg Pro Pro Ser Ser Trp Pro Gln Asn
            1250            1255            1260
Gly Asn Ile Glu Leu Ile Asp Leu Lys Val Arg Tyr Lys Asp Asp Leu
1265            1270            1275            1280
Pro Leu Val Leu His Gly Val Ser Cys Met Phe Pro Gly Gly Lys Lys
            1285            1290            1295
Ile Gly Ile Val Gly Arg Thr Gly Ser Gly Lys Ser Thr Leu Ile Gln
            1300            1305            1310
Ala Leu Phe Arg Leu Ile Glu Pro Thr Gly Gly Lys Ile Ile Ile Asp
            1315            1320            1325
Asn Ile Asp Ile Ser Ala Ile Gly Leu His Asp Leu Arg Ser Arg Leu
            1330            1335            1340
Ser Ile Ile Pro Gln Asp Pro Thr Leu Phe Glu Gly Thr Ile Arg Met
1345            1350            1355            1360
```

-continued

```
Asn Leu Asp Pro Leu Glu Glu Cys Thr Asp Gln Glu Ile Trp Glu Ala
            1365                1370                1375

Leu Glu Lys Cys Gln Leu Gly Glu Val Ile Arg Ser Lys Glu Glu Lys
        1380                1385                1390

Leu Asp Ser Pro Val Leu Glu Asn Gly Asp Asn Trp Ser Val Gly Gln
        1395                1400                1405

Arg Gln Leu Ile Ala Leu Gly Arg Ala Leu Leu Lys Gln Ala Lys Ile
        1410                1415                1420

Leu Val Leu Asp Glu Ala Thr Ala Ser Val Asp Thr Ala Thr Asp Asn
1425                1430                1435                1440

Leu Ile Gln Lys Ile Ile Arg Ser Glu Phe Lys Asp Cys Thr Val Cys
            1445                1450                1455

Thr Ile Ala His Arg Ile Pro Thr Val Ile Asp Ser Asp Leu Val Leu
            1460                1465                1470

Val Leu Ser Asp Gly Lys Ile Ala Glu Phe Asp Thr Pro Gln Arg Leu
        1475                1480                1485

Leu Glu Asp Lys Ser Ser Met Phe Ile Gln Leu Val Ser Glu Tyr Ser
        1490                1495                1500

Thr Arg Ser Ser Cys Ile
1505                1510

<210> SEQ ID NO 4
<211> LENGTH: 5139
<212> TYPE: DNA
<213> ORGANISM: Zea mays
<220> FEATURE:
<221> NAME/KEY: CDS
<222> LOCATION: (244)...(4776)

<400> SEQUENCE: 4
cctctctctc ccctcctcga accaggcgca ggcgagcgtc tctgcccgcc cgcctgctgc       60
taccgccaaa acgcctcctt tgttgccatc cgccgatgcc gtaatccgcc gcccaaagct     120
cttccttttt ccctctctct cgcccgcggc cgcactccct gccccagtgc ctgccgtggc     180
gagcccaacc ccaatgcctt ttaaacccct ccccgctccc tcactgatcc ccaccgcctc     240 cca atg ccg ctc tcc ttc ccc tcc ctc ccg ctc ccg gag gcc gtt gcc       288
    Met Pro Leu Ser Phe Pro Ser Leu Pro Leu Pro Glu Ala Val Ala
      1               5                  10                  15 gcc gcc gcc cac gcc gcg ctg ctc gcg ctc gcc gca ctc ctg ctc ctc       336
Ala Ala Ala His Ala Ala Leu Leu Ala Leu Ala Ala Leu Leu Leu Leu
                 20                  25                  30 ctc cgc gcc gcg cgc gcg ctc gcc tcc cgc tgc gcg tca tgc ctc aag       384
Leu Arg Ala Ala Arg Ala Leu Ala Ser Arg Cys Ala Ser Cys Leu Lys
             35                  40                  45 gcg ccg cgc cgc cgc ggg ggc ccc gcc gtc gtc gtg ggc gcc ggc gcc       432
Ala Pro Arg Arg Arg Gly Gly Pro Ala Val Val Val Gly Ala Gly Ala
         50                  55                  60 ggc ggc gcc ctc gcg gcg gcg act gcc ggc gcc tgg cac agg gcc gtg       480
Gly Gly Ala Leu Ala Ala Ala Thr Ala Gly Ala Trp His Arg Ala Val
 65                  70                  75 ctg gcg tcc tgc gcc tac gcc ctg ctc tcg cag gtc gcc gtg ctg agc       528
Leu Ala Ser Cys Ala Tyr Ala Leu Leu Ser Gln Val Ala Val Leu Ser
 80                  85                  90                  95 tac gag gtg gcc gtc gcc ggc tcg cgc gtc tcg gcg cgg gcg ctg ctg       576
Tyr Glu Val Ala Val Ala Gly Ser Arg Val Ser Ala Arg Ala Leu Leu
                100                 105                 110 ctg ccg gcc gtg cag gcg gtg tcc tgg gcc gcg ctg ctg gcg ctc gcg       624
Leu Pro Ala Val Gln Ala Val Ser Trp Ala Ala Leu Leu Ala Leu Ala
            115                 120                 125
```

```
ctt cag gcc cgc gcc gtc ggc tgg gcc agg ttc cct gcg ctg gtg cgg      672
Leu Gln Ala Arg Ala Val Gly Trp Ala Arg Phe Pro Ala Leu Val Arg
        130                 135                 140 ctc tgg tgg gtg gtc tcc ttc gcg ctc tgc gtt gtc att gcg tac gac      720
Leu Trp Trp Val Val Ser Phe Ala Leu Cys Val Val Ile Ala Tyr Asp
145                 150                 155 gac tcc agg cgc ctg ata ggc cag ggc gcg cgc gct gtg gat tac gcg      768
Asp Ser Arg Arg Leu Ile Gly Gln Gly Ala Arg Ala Val Asp Tyr Ala
160                 165                 170                 175 cac atg gtt gcc aac ttc gcg tcc gtg ccg gcc ctg ggc ttc ctg tgc      816
His Met Val Ala Asn Phe Ala Ser Val Pro Ala Leu Gly Phe Leu Cys
                180                 185                 190 ttg gtt ggt gtc atg ggt tcc acc ggt ttg gaa ttg gag ttt acg gag      864
Leu Val Gly Val Met Gly Ser Thr Gly Leu Glu Leu Glu Phe Thr Glu
                    195                 200                 205 gat ggc aac ggc ctg cat gag ccg ctg ctc ggc agg cag cgc aga          912
Asp Gly Asn Gly Leu His Glu Pro Leu Leu Leu Gly Arg Gln Arg Arg
        210                 215                 220 gag gca gag gag gag ctc ggc tgt ctg agg gtc act ccc tac gct gat      960
Glu Ala Glu Glu Glu Leu Gly Cys Leu Arg Val Thr Pro Tyr Ala Asp
225                 230                 235 gct ggg atc ctc agc ctt gca aca ttg tca tgg ctt agt ccg ttg ctc     1008
Ala Gly Ile Leu Ser Leu Ala Thr Leu Ser Trp Leu Ser Pro Leu Leu
240                 245                 250                 255 tct gtt ggt gcg cag cgg cca ctt gag ttg gct gac ata ccc ttg ctg     1056
Ser Val Gly Ala Gln Arg Pro Leu Glu Leu Ala Asp Ile Pro Leu Leu
                260                 265                 270 gcg cac aag gac cgt gca aag tca tgc tat aag gcg atg agc gct cac     1104
Ala His Lys Asp Arg Ala Lys Ser Cys Tyr Lys Ala Met Ser Ala His
                    275                 280                 285 tac gag cgc cag cgg cta gaa tac cct ggc agg gag cca tca ctc aca     1152
Tyr Glu Arg Gln Arg Leu Glu Tyr Pro Gly Arg Glu Pro Ser Leu Thr
        290                 295                 300 tgg gca ata ctc aag tca ttc tgg cga gag gcc gcg gtc aat ggc aca     1200
Trp Ala Ile Leu Lys Ser Phe Trp Arg Glu Ala Ala Val Asn Gly Thr
305                 310                 315 ttt gct gct gtc aac acg att gtg tcg tat gtt gga cct tac ttg atc     1248
Phe Ala Ala Val Asn Thr Ile Val Ser Tyr Val Gly Pro Tyr Leu Ile
320                 325                 330                 335 agc tat ttt gtg gac tac ctc agt ggc aac att gct ttc ccc cat gaa     1296
Ser Tyr Phe Val Asp Tyr Leu Ser Gly Asn Ile Ala Phe Pro His Glu
                340                 345                 350 ggt tac atc ctt gcc tct ata ttt ttt gta gca aaa ctg ctt gag aca     1344
Gly Tyr Ile Leu Ala Ser Ile Phe Phe Val Ala Lys Leu Leu Glu Thr
                    355                 360                 365 ctc act gcc cga cag tgg tac ttg ggt gtg gac atc atg ggg atc cat     1392
Leu Thr Ala Arg Gln Trp Tyr Leu Gly Val Asp Ile Met Gly Ile His
        370                 375                 380 gtc aag tct ggc ctc act gcc atg gtg tat agg aag ggt ctc cga ctg     1440
Val Lys Ser Gly Leu Thr Ala Met Val Tyr Arg Lys Gly Leu Arg Leu
385                 390                 395 tca aac gcc tca cgg cag agc cac acg agt ggt gag att gtg aat tac     1488
Ser Asn Ala Ser Arg Gln Ser His Thr Ser Gly Glu Ile Val Asn Tyr
400                 405                 410                 415 atg gcc gtc gat gtg cag cgt gtg ggg gac tat gca tgg tat ttc cat     1536
Met Ala Val Asp Val Gln Arg Val Gly Asp Tyr Ala Trp Tyr Phe His
                420                 425                 430 gac atc tgg atg ctt ccc ctg cag atc att ctt gct ctc gcc atc ctg     1584
Asp Ile Trp Met Leu Pro Leu Gln Ile Ile Leu Ala Leu Ala Ile Leu
                    435                 440                 445
```

-continued

| | |
|---|---|
| tac aag aac gtc ggg atc gcc atg gtt tca aca ttg gta gca act gtg<br>Tyr Lys Asn Val Gly Ile Ala Met Val Ser Thr Leu Val Ala Thr Val<br>450             455             460 | 1632 |
| cta tcg atc gca gcc tct gtt cct gtg gca aag ctg cag gag cac tac<br>Leu Ser Ile Ala Ala Ser Val Pro Val Ala Lys Leu Gln Glu His Tyr<br>465             470             475 | 1680 |
| caa gat aag tta atg gca tca aaa gat gag cgc atg cgc aag act tca<br>Gln Asp Lys Leu Met Ala Ser Lys Asp Glu Arg Met Arg Lys Thr Ser<br>480             485             490             495 | 1728 |
| gag tgc ttg aaa aat atg agg att ttg aag ctt cag gca tgg gag gat<br>Glu Cys Leu Lys Asn Met Arg Ile Leu Lys Leu Gln Ala Trp Glu Asp<br>500             505             510 | 1776 |
| cgg tac cgg ctg cag ttg gaa gag atg agg aac gtg gaa tgc aga tgg<br>Arg Tyr Arg Leu Gln Leu Glu Glu Met Arg Asn Val Glu Cys Arg Trp<br>515             520             525 | 1824 |
| ctt cgg tgg gct ctg tac tca cag gct gca gtt aca ttt gtt ttc tgg<br>Leu Arg Trp Ala Leu Tyr Ser Gln Ala Ala Val Thr Phe Val Phe Trp<br>530             535             540 | 1872 |
| agc tcg cca atc ttt gtc gca gtc ata act ttt ggg act tgc ata tta<br>Ser Ser Pro Ile Phe Val Ala Val Ile Thr Phe Gly Thr Cys Ile Leu<br>545             550             555 | 1920 |
| ctc ggt ggc cag ctc act gca gga ggg gtt cta tcc gct tta gca acg<br>Leu Gly Gly Gln Leu Thr Ala Gly Gly Val Leu Ser Ala Leu Ala Thr<br>560             565             570             575 | 1968 |
| ttt cgg atc ctc caa gag cct ctg agg aac ttc ccg gat ctc atc tct<br>Phe Arg Ile Leu Gln Glu Pro Leu Arg Asn Phe Pro Asp Leu Ile Ser<br>580             585             590 | 2016 |
| atg atg gca cag aca agg gtg tct ttg gac cgt ttg tct cat ttt ctg<br>Met Met Ala Gln Thr Arg Val Ser Leu Asp Arg Leu Ser His Phe Leu<br>595             600             605 | 2064 |
| cag caa gaa gaa ctg cca gat gac gca act ata aat gtt cca caa agt<br>Gln Gln Glu Glu Leu Pro Asp Asp Ala Thr Ile Asn Val Pro Gln Ser<br>610             615             620 | 2112 |
| agt aca gat aag gca gtc gat att aag gat ggc gca ttc tct tgg aac<br>Ser Thr Asp Lys Ala Val Asp Ile Lys Asp Gly Ala Phe Ser Trp Asn<br>625             630             635 | 2160 |
| cca tac act ctg acc cct aca ctt tct gat ata cac ctt agt gta gtg<br>Pro Tyr Thr Leu Thr Pro Thr Leu Ser Asp Ile His Leu Ser Val Val<br>640             645             650             655 | 2208 |
| aga ggc atg aga gta gca gtc tgt ggt gtc att ggt tct ggt aaa tca<br>Arg Gly Met Arg Val Ala Val Cys Gly Val Ile Gly Ser Gly Lys Ser<br>660             665             670 | 2256 |
| agt cta cta tcg tct ata ctc ggg gag ata ccc aaa tta tgt ggc cat<br>Ser Leu Leu Ser Ser Ile Leu Gly Glu Ile Pro Lys Leu Cys Gly His<br>675             680             685 | 2304 |
| gtc agg ata agt ggc aca gca gcg tat gtt cct cag act gca tgg ata<br>Val Arg Ile Ser Gly Thr Ala Ala Tyr Val Pro Gln Thr Ala Trp Ile<br>690             695             700 | 2352 |
| cag tct gga aat att gag gag aat att ctg ttt ggc agt caa atg gat<br>Gln Ser Gly Asn Ile Glu Glu Asn Ile Leu Phe Gly Ser Gln Met Asp<br>705             710             715 | 2400 |
| aga caa cgt tac aag aga gtc att gca gct tgc tgt ctt aag aaa gat<br>Arg Gln Arg Tyr Lys Arg Val Ile Ala Ala Cys Cys Leu Lys Lys Asp<br>720             725             730             735 | 2448 |
| ctt gag ctg ctc cag tac gga gat cag act gtt att ggt gat aga ggc<br>Leu Glu Leu Leu Gln Tyr Gly Asp Gln Thr Val Ile Gly Asp Arg Gly<br>740             745             750 | 2496 |
| att aat ttg agt gga ggt cag aaa caa aga gtt cag ctt gct aga gca<br>Ile Asn Leu Ser Gly Gly Gln Lys Gln Arg Val Gln Leu Ala Arg Ala<br>755             760             765 | 2544 |

|  |  |
|---|---|
| ctc tac caa gat gct gat att tat ttg ctt gat gat ccc ttc agt gct<br>Leu Tyr Gln Asp Ala Asp Ile Tyr Leu Leu Asp Asp Pro Phe Ser Ala<br>770                      775                   780 | 2592 |
| gtt gat gct cat act ggg agc gaa ctg ttt aag gag tat ata ttg act<br>Val Asp Ala His Thr Gly Ser Glu Leu Phe Lys Glu Tyr Ile Leu Thr<br>785                    790                     795 | 2640 |
| gca cta gca acc aaa aca gta atc tat gta aca cat caa gtt gaa ttt<br>Ala Leu Ala Thr Lys Thr Val Ile Tyr Val Thr His Gln Val Glu Phe<br>800                   805                  810                815 | 2688 |
| cta cca gct gct gat ctg ata ttg gtt ctt aag gat ggc cat atc aca<br>Leu Pro Ala Ala Asp Leu Ile Leu Val Leu Lys Asp Gly His Ile Thr<br>                820                  825                830 | 2736 |
| caa gct gga aag tat gat gat ctt ctg caa gct gga act gat ttc aat<br>Gln Ala Gly Lys Tyr Asp Asp Leu Leu Gln Ala Gly Thr Asp Phe Asn<br>             835                  840               845 | 2784 |
| gct ctg gtt tct gct cat aag gaa gct att gaa acc atg gat ata ttt<br>Ala Leu Val Ser Ala His Lys Glu Ala Ile Glu Thr Met Asp Ile Phe<br>850                    855                  860 | 2832 |
| gaa gat tcc gat agt gat aca gtt tct tct att ccc aac aaa aga ttg<br>Glu Asp Ser Asp Ser Asp Thr Val Ser Ser Ile Pro Asn Lys Arg Leu<br>865                    870                  875 | 2880 |
| aca cca agt atc agc aat att gat aac ctg aaa aat aag atg tgt gaa<br>Thr Pro Ser Ile Ser Asn Ile Asp Asn Leu Lys Asn Lys Met Cys Glu<br>880                    885                  890                895 | 2928 |
| aat gga caa cca tct aat aca cgg gga att aag gaa aaa aag aag aaa<br>Asn Gly Gln Pro Ser Asn Thr Arg Gly Ile Lys Glu Lys Lys Lys Lys<br>             900                  905               910 | 2976 |
| gaa gag cgt aag aag aag cgt act gtt caa gag gag gaa agg gaa cgt<br>Glu Glu Arg Lys Lys Lys Arg Thr Val Gln Glu Glu Glu Arg Glu Arg<br>               915                  920               925 | 3024 |
| gga aaa gtg agc tcc aaa gtt tat ttg tca tac atg ggg gaa gct tac<br>Gly Lys Val Ser Ser Lys Val Tyr Leu Ser Tyr Met Gly Glu Ala Tyr<br>             930                  935               940 | 3072 |
| aaa ggt aca ctg ata cca cta att atc ttg gct caa acc atg ttc caa<br>Lys Gly Thr Leu Ile Pro Leu Ile Ile Leu Ala Gln Thr Met Phe Gln<br>945                    950                  955 | 3120 |
| gtt ctt cag att gcg agc aac tgg tgg atg gca tgg gca aac cca caa<br>Val Leu Gln Ile Ala Ser Asn Trp Trp Met Ala Trp Ala Asn Pro Gln<br>960                    965                  970                975 | 3168 |
| aca gaa gga gat gct ccc aag aca gat agt gtg gtc ctt ctg gtt gtt<br>Thr Glu Gly Asp Ala Pro Lys Thr Asp Ser Val Val Leu Leu Val Val<br>               980                  985               990 | 3216 |
| tat atg tcc ctt gcc ttt gga agt tca cta ttt gtg ttc atg aga agc<br>Tyr Met Ser Leu Ala Phe Gly Ser Ser Leu Phe Val Phe Met Arg Ser<br>             995                 1000               1005 | 3264 |
| ctt ctt gtg gct acg ttt ggt tta gca gct gcc cag aag ctt ttt ata<br>Leu Leu Val Ala Thr Phe Gly Leu Ala Ala Ala Gln Lys Leu Phe Ile<br>            1010                 1015               1020 | 3312 |
| aaa atg ctt agg tgt gtc ttt cga gct cca atg tca ttc ttt gac acc<br>Lys Met Leu Arg Cys Val Phe Arg Ala Pro Met Ser Phe Phe Asp Thr<br>1025                 1030                 1035 | 3360 |
| aca cca tct ggt cgg att ttg aac aga gtt tct gta gat caa agt gtt<br>Thr Pro Ser Gly Arg Ile Leu Asn Arg Val Ser Val Asp Gln Ser Val<br>1040                 1045                 1050               1055 | 3408 |
| gtg gac ctt gat ata gcg ttc aga ctt ggt gga ttt gca tca acg aca<br>Val Asp Leu Asp Ile Ala Phe Arg Leu Gly Gly Phe Ala Ser Thr Thr<br>            1060                 1065               1070 | 3456 |
| att caa ctc ctt gga att gtt gct gtc atg agc aaa gtc aca tgg caa<br>Ile Gln Leu Leu Gly Ile Val Ala Val Met Ser Lys Val Thr Trp Gln<br>1075                 1080                 1085 | 3504 |

```
gtt ctg att ctt ata gtc ccc atg gct gtt gca tgc atg tgg atg cag    3552
Val Leu Ile Leu Ile Val Pro Met Ala Val Ala Cys Met Trp Met Gln
        1090            1095            1100 agg tat tat att gct tca tca agg gaa cta act agg att ttg agt gtt    3600
Arg Tyr Tyr Ile Ala Ser Ser Arg Glu Leu Thr Arg Ile Leu Ser Val
    1105            1110            1115 cag aag tct cca gtg atc cat ttg ttt agt gaa tca att gct ggt gct    3648
Gln Lys Ser Pro Val Ile His Leu Phe Ser Glu Ser Ile Ala Gly Ala
1120            1125            1130            1135 gct aca ata agg ggt ttt ggt caa gag aag cgg ttt atg aaa agg aat    3696
Ala Thr Ile Arg Gly Phe Gly Gln Glu Lys Arg Phe Met Lys Arg Asn
            1140            1145            1150 ctt tat ctt ctt gac tgt ttt gct cgc cct tta ttt tcc agc ctt gct    3744
Leu Tyr Leu Leu Asp Cys Phe Ala Arg Pro Leu Phe Ser Ser Leu Ala
        1155            1160            1165 gct att gaa tgg ctc tgc ctg cga atg gaa ttg ctt tcg act ttc gtc    3792
Ala Ile Glu Trp Leu Cys Leu Arg Met Glu Leu Leu Ser Thr Phe Val
    1170            1175            1180 ttt gct ttt tgc atg gca ata ctt gtg agc ttt cct cct ggc aca atc    3840
Phe Ala Phe Cys Met Ala Ile Leu Val Ser Phe Pro Pro Gly Thr Ile
1185            1190            1195 gaa cca agt atg gct ggc ctc gct gta aca tat gga ctt aat tta aat    3888
Glu Pro Ser Met Ala Gly Leu Ala Val Thr Tyr Gly Leu Asn Leu Asn
1200            1205            1210            1215 gct cgc atg tca aga tgg ata ttg agc ttc tgt aaa tta gag aac agg    3936
Ala Arg Met Ser Arg Trp Ile Leu Ser Phe Cys Lys Leu Glu Asn Arg
        1220            1225            1230 ata atc tct gtt gag cgc att tat caa tat tgc agg ctt cct agt gaa    3984
Ile Ile Ser Val Glu Arg Ile Tyr Gln Tyr Cys Arg Leu Pro Ser Glu
    1235            1240            1245 gca cca ttg att att gag aac tgc cgt cca cca tca tca tgg cct cag    4032
Ala Pro Leu Ile Ile Glu Asn Cys Arg Pro Pro Ser Ser Trp Pro Gln
1250            1255            1260 aat gga aac att gaa ctg att gat ctc aag gtc cgc tac aag gac gat    4080
Asn Gly Asn Ile Glu Leu Ile Asp Leu Lys Val Arg Tyr Lys Asp Asp
        1265            1270            1275 cta cca tta gtt ctt cat ggt gta agt tgt atg ttt cct ggc ggg aaa    4128
Leu Pro Leu Val Leu His Gly Val Ser Cys Met Phe Pro Gly Gly Lys
1280            1285            1290            1295 aag att ggg att gta ggg cgt act gga agc ggt aaa tct act ctt att    4176
Lys Ile Gly Ile Val Gly Arg Thr Gly Ser Gly Lys Ser Thr Leu Ile
        1300            1305            1310 cag gcc ctt ttc cgc cta att gag ccc act gga ggg aag att ata att    4224
Gln Ala Leu Phe Arg Leu Ile Glu Pro Thr Gly Gly Lys Ile Ile Ile
    1315            1320            1325 gac aac att gac atc tct gca att ggc ctt cat gat ctg cgg tca cgg    4272
Asp Asn Ile Asp Ile Ser Ala Ile Gly Leu His Asp Leu Arg Ser Arg
1330            1335            1340 ttg agc atc att ccc caa gac cct aca ttg ttt gag ggt act atc aga    4320
Leu Ser Ile Ile Pro Gln Asp Pro Thr Leu Phe Glu Gly Thr Ile Arg
        1345            1350            1355 atg aac ctt gat cct ctt gag gag tgc act gat caa gaa att tgg gag    4368
Met Asn Leu Asp Pro Leu Glu Glu Cys Thr Asp Gln Glu Ile Trp Glu
1360            1365            1370            1375 gca cta gaa aag tgt cag cta gga gag gtc att cgt tcc aag gaa gag    4416
Ala Leu Glu Lys Cys Gln Leu Gly Glu Val Ile Arg Ser Lys Glu Glu
        1380            1385            1390 aaa ctt gac agt cca gtg cta gaa aac ggg gat aac tgg agc gtg gga    4464
Lys Leu Asp Ser Pro Val Leu Glu Asn Gly Asp Asn Trp Ser Val Gly
    1395            1400            1405
```

```
cag cgc caa ctt att gca ctg ggt agg gcg ctg ctc aag cag gca aaa    4512
Gln Arg Gln Leu Ile Ala Leu Gly Arg Ala Leu Leu Lys Gln Ala Lys
    1410                1415                1420 att ttg gta ctc gat gag gcg aca gca tct gtc gac aca gca aca gac    4560
Ile Leu Val Leu Asp Glu Ala Thr Ala Ser Val Asp Thr Ala Thr Asp
1425                1430                1435 aat ctt atc caa aag atc atc cgc agt gaa ttc aag gac tgc aca gtc    4608
Asn Leu Ile Gln Lys Ile Ile Arg Ser Glu Phe Lys Asp Cys Thr Val
1440                1445                1450                1455 tgt acc att gct cac cgt att ccc acc gtt att gac agt gac ctt gtt    4656
Cys Thr Ile Ala His Arg Ile Pro Thr Val Ile Asp Ser Asp Leu Val
                1460                1465                1470 ctg gtc ctt agt gat ggt aaa atc gca gag ttc gac acg ccc cag agg    4704
Leu Val Leu Ser Asp Gly Lys Ile Ala Glu Phe Asp Thr Pro Gln Arg
            1475                1480                1485 ctt tta gag gac aag tca tct atg ttc ata cag cta gta tcg gaa tac    4752
Leu Leu Glu Asp Lys Ser Ser Met Phe Ile Gln Leu Val Ser Glu Tyr
        1490                1495                1500 tcc act cgg tcg agc tgt ata tag agaggcttag cttaaaaccc cgccccaaac    4806
Ser Thr Arg Ser Ser Cys Ile  *
    1505                1510 ctggcaacag aggctgggag gcaaatagcc cgtatctgcc atgcttgcgc catagaggtc    4866
cctgcgaaca ccggagggcg gcgtagaaga cgaggtgtac atgagtggga ggaacactgg    4926
gcgttccctg acctgaatac cgtggaatcg gcgagggagc gcggttggta ttggtaggca    4986
ccaggggagg agttggtgac actagtacat tacccgaagc tgatgcttca gtatgtatgt    5046
ataacaacaa tgcatactgc ttctcccttt gcagagtgga gaaccaaggg aataactcgt    5106
gcgtaataag aggagaaaga tttgtttttt ggc                                 5139

<210> SEQ ID NO 5
<211> LENGTH: 1510
<212> TYPE: PRT
<213> ORGANISM: Zea mays

<400> SEQUENCE: 5

Met Pro Leu Ser Phe Pro Ser Leu Pro Leu Pro Glu Ala Val Ala Ala
1               5                   10                  15

Ala Ala His Ala Ala Leu Leu Ala Leu Ala Ala Leu Leu Leu Leu Leu
            20                  25                  30

Arg Ala Ala Arg Ala Leu Ala Ser Arg Cys Ala Ser Cys Leu Lys Ala
        35                  40                  45

Pro Arg Arg Gly Gly Pro Ala Val Val Gly Ala Gly Ala Gly
    50                  55                  60

Gly Ala Leu Ala Ala Ala Thr Ala Gly Ala Trp His Arg Ala Val Leu
65                  70                  75                  80

Ala Ser Cys Ala Tyr Ala Leu Leu Ser Gln Val Ala Val Leu Ser Tyr
                85                  90                  95

Glu Val Ala Val Ala Gly Ser Arg Val Ser Arg Ala Leu Leu Leu
            100                 105                 110

Pro Ala Val Gln Ala Val Ser Trp Ala Ala Leu Leu Ala Leu Ala Leu
        115                 120                 125

Gln Ala Arg Ala Val Gly Trp Ala Arg Phe Pro Ala Leu Val Arg Leu
    130                 135                 140

Trp Trp Val Val Ser Phe Ala Leu Cys Val Val Ile Ala Tyr Asp Asp
145                 150                 155                 160

Ser Arg Arg Leu Ile Gly Gln Gly Ala Arg Ala Val Asp Tyr Ala His
```

```
            165                 170                 175
Met Val Ala Asn Phe Ala Ser Val Pro Ala Leu Gly Phe Leu Cys Leu
            180                 185                 190

Val Gly Val Met Gly Ser Thr Gly Leu Glu Leu Glu Phe Thr Glu Asp
            195                 200                 205

Gly Asn Gly Leu His Glu Pro Leu Leu Leu Gly Arg Gln Arg Arg Glu
210                 215                 220

Ala Glu Glu Glu Leu Gly Cys Leu Arg Val Thr Pro Tyr Ala Asp Ala
225                 230                 235                 240

Gly Ile Leu Ser Leu Ala Thr Leu Ser Trp Leu Ser Pro Leu Leu Ser
            245                 250                 255

Val Gly Ala Gln Arg Pro Leu Glu Leu Ala Asp Ile Pro Leu Leu Ala
            260                 265                 270

His Lys Asp Arg Ala Lys Ser Cys Tyr Lys Ala Met Ser Ala His Tyr
            275                 280                 285

Glu Arg Gln Arg Leu Glu Tyr Pro Gly Arg Glu Pro Ser Leu Thr Trp
            290                 295                 300

Ala Ile Leu Lys Ser Phe Trp Arg Glu Ala Ala Val Asn Gly Thr Phe
305                 310                 315                 320

Ala Ala Val Asn Thr Ile Val Ser Tyr Val Gly Pro Tyr Leu Ile Ser
            325                 330                 335

Tyr Phe Val Asp Tyr Leu Ser Gly Asn Ile Ala Phe Pro His Glu Gly
            340                 345                 350

Tyr Ile Leu Ala Ser Ile Phe Phe Val Ala Lys Leu Leu Glu Thr Leu
            355                 360                 365

Thr Ala Arg Gln Trp Tyr Leu Gly Val Asp Ile Met Gly Ile His Val
            370                 375                 380

Lys Ser Gly Leu Thr Ala Met Val Tyr Arg Lys Gly Leu Arg Leu Ser
385                 390                 395                 400

Asn Ala Ser Arg Gln Ser His Thr Ser Gly Glu Ile Val Asn Tyr Met
            405                 410                 415

Ala Val Asp Val Gln Arg Val Gly Asp Tyr Ala Trp Tyr Phe His Asp
            420                 425                 430

Ile Trp Met Leu Pro Leu Gln Ile Ile Leu Ala Leu Ala Ile Leu Tyr
            435                 440                 445

Lys Asn Val Gly Ile Ala Met Val Ser Thr Leu Val Ala Thr Val Leu
            450                 455                 460

Ser Ile Ala Ala Ser Val Pro Val Ala Lys Leu Gln Glu His Tyr Gln
465                 470                 475                 480

Asp Lys Leu Met Ala Ser Lys Asp Glu Arg Met Arg Lys Thr Ser Glu
            485                 490                 495

Cys Leu Lys Asn Met Arg Ile Leu Lys Leu Gln Ala Trp Glu Asp Arg
            500                 505                 510

Tyr Arg Leu Gln Leu Glu Glu Met Arg Asn Val Glu Cys Arg Trp Leu
            515                 520                 525

Arg Trp Ala Leu Tyr Ser Gln Ala Ala Val Thr Phe Val Phe Trp Ser
530                 535                 540

Ser Pro Ile Phe Val Ala Val Ile Thr Phe Gly Thr Cys Ile Leu Leu
545                 550                 555                 560

Gly Gly Gln Leu Thr Ala Gly Gly Val Leu Ser Ala Leu Ala Thr Phe
            565                 570                 575

Arg Ile Leu Gln Glu Pro Leu Arg Asn Phe Pro Asp Leu Ile Ser Met
            580                 585                 590
```

-continued

Met Ala Gln Thr Arg Val Ser Leu Asp Arg Leu Ser His Phe Leu Gln
        595                 600                 605

Gln Glu Glu Leu Pro Asp Asp Ala Thr Ile Asn Val Pro Gln Ser Ser
    610                 615                 620

Thr Asp Lys Ala Val Asp Ile Lys Asp Gly Ala Phe Ser Trp Asn Pro
625                 630                 635                 640

Tyr Thr Leu Thr Pro Thr Leu Ser Asp Ile His Leu Ser Val Val Arg
                645                 650                 655

Gly Met Arg Val Ala Val Cys Gly Val Ile Gly Ser Gly Lys Ser Ser
            660                 665                 670

Leu Leu Ser Ser Ile Leu Gly Glu Ile Pro Lys Leu Cys Gly His Val
        675                 680                 685

Arg Ile Ser Gly Thr Ala Ala Tyr Val Pro Gln Thr Ala Trp Ile Gln
690                 695                 700

Ser Gly Asn Ile Glu Glu Asn Ile Leu Phe Gly Ser Gln Met Asp Arg
705                 710                 715                 720

Gln Arg Tyr Lys Arg Val Ile Ala Ala Cys Cys Leu Lys Lys Asp Leu
                725                 730                 735

Glu Leu Leu Gln Tyr Gly Asp Gln Thr Val Ile Gly Asp Arg Gly Ile
            740                 745                 750

Asn Leu Ser Gly Gly Gln Lys Gln Arg Val Gln Leu Ala Arg Ala Leu
        755                 760                 765

Tyr Gln Asp Ala Asp Ile Tyr Leu Leu Asp Asp Pro Phe Ser Ala Val
770                 775                 780

Asp Ala His Thr Gly Ser Glu Leu Phe Lys Glu Tyr Ile Leu Thr Ala
785                 790                 795                 800

Leu Ala Thr Lys Thr Val Ile Tyr Val Thr His Gln Val Glu Phe Leu
                805                 810                 815

Pro Ala Ala Asp Leu Ile Leu Val Leu Lys Asp Gly His Ile Thr Gln
            820                 825                 830

Ala Gly Lys Tyr Asp Asp Leu Leu Gln Ala Gly Thr Asp Phe Asn Ala
        835                 840                 845

Leu Val Ser Ala His Lys Glu Ala Ile Glu Thr Met Asp Ile Phe Glu
850                 855                 860

Asp Ser Asp Ser Asp Thr Val Ser Ser Ile Pro Asn Lys Arg Leu Thr
865                 870                 875                 880

Pro Ser Ile Ser Asn Ile Asp Asn Leu Lys Asn Lys Met Cys Glu Asn
                885                 890                 895

Gly Gln Pro Ser Asn Thr Arg Gly Ile Lys Glu Lys Lys Lys Lys Glu
            900                 905                 910

Glu Arg Lys Lys Lys Arg Thr Val Gln Glu Glu Glu Arg Glu Arg Gly
        915                 920                 925

Lys Val Ser Ser Lys Val Tyr Leu Ser Tyr Met Gly Glu Ala Tyr Lys
930                 935                 940

Gly Thr Leu Ile Pro Leu Ile Ile Leu Ala Gln Thr Met Phe Gln Val
945                 950                 955                 960

Leu Gln Ile Ala Ser Asn Trp Trp Met Ala Trp Ala Asn Pro Gln Thr
                965                 970                 975

Glu Gly Asp Ala Pro Lys Thr Asp Ser Val Val Leu Val Val Val Tyr
            980                 985                 990

Met Ser Leu Ala Phe Gly Ser Ser Leu Phe Val Phe Met Arg Ser Leu
        995                 1000                1005

Leu Val Ala Thr Phe Gly Leu Ala Ala Ala Gln Lys Leu Phe Ile Lys
        1010                1015                1020

```
Met Leu Arg Cys Val Phe Arg Ala Pro Met Ser Phe Asp Thr Thr
1025                1030                1035                1040

Pro Ser Gly Arg Ile Leu Asn Arg Val Ser Val Asp Gln Ser Val Val
            1045                1050                1055

Asp Leu Asp Ile Ala Phe Arg Leu Gly Gly Phe Ala Ser Thr Thr Ile
        1060                1065                1070

Gln Leu Leu Gly Ile Val Ala Val Met Ser Lys Val Thr Trp Gln Val
    1075                1080                1085

Leu Ile Leu Ile Val Pro Met Ala Val Ala Cys Met Trp Met Gln Arg
    1090                1095                1100

Tyr Tyr Ile Ala Ser Ser Arg Glu Leu Thr Arg Ile Leu Ser Val Gln
1105                1110                1115                1120

Lys Ser Pro Val Ile His Leu Phe Ser Glu Ser Ile Ala Gly Ala Ala
            1125                1130                1135

Thr Ile Arg Gly Phe Gly Gln Glu Lys Arg Phe Met Lys Arg Asn Leu
        1140                1145                1150

Tyr Leu Leu Asp Cys Phe Ala Arg Pro Leu Phe Ser Ser Leu Ala Ala
    1155                1160                1165

Ile Glu Trp Leu Cys Leu Arg Met Glu Leu Leu Ser Thr Phe Val Phe
    1170                1175                1180

Ala Phe Cys Met Ala Ile Leu Val Ser Phe Pro Pro Gly Thr Ile Glu
1185                1190                1195                1200

Pro Ser Met Ala Gly Leu Ala Val Thr Tyr Gly Leu Asn Leu Asn Ala
            1205                1210                1215

Arg Met Ser Arg Trp Ile Leu Ser Phe Cys Lys Leu Glu Asn Arg Ile
        1220                1225                1230

Ile Ser Val Glu Arg Ile Tyr Gln Tyr Cys Arg Leu Pro Ser Glu Ala
    1235                1240                1245

Pro Leu Ile Ile Glu Asn Cys Arg Pro Pro Ser Ser Trp Pro Gln Asn
    1250                1255                1260

Gly Asn Ile Glu Leu Ile Asp Leu Lys Val Arg Tyr Lys Asp Asp Leu
1265                1270                1275                1280

Pro Leu Val Leu His Gly Val Ser Cys Met Phe Pro Gly Gly Lys Lys
            1285                1290                1295

Ile Gly Ile Val Gly Arg Thr Gly Ser Gly Lys Ser Thr Leu Ile Gln
        1300                1305                1310

Ala Leu Phe Arg Leu Ile Glu Pro Thr Gly Gly Lys Ile Ile Ile Asp
    1315                1320                1325

Asn Ile Asp Ile Ser Ala Ile Gly Leu His Asp Leu Arg Ser Arg Leu
1330                1335                1340

Ser Ile Ile Pro Gln Asp Pro Thr Leu Phe Glu Gly Thr Ile Arg Met
1345                1350                1355                1360

Asn Leu Asp Pro Leu Glu Glu Cys Thr Asp Gln Glu Ile Trp Glu Ala
            1365                1370                1375

Leu Glu Lys Cys Gln Leu Gly Glu Val Ile Arg Ser Lys Glu Glu Lys
        1380                1385                1390

Leu Asp Ser Pro Val Leu Glu Asn Gly Asp Asn Trp Ser Val Gly Gln
    1395                1400                1405

Arg Gln Leu Ile Ala Leu Gly Arg Ala Leu Leu Lys Gln Ala Lys Ile
    1410                1415                1420

Leu Val Leu Asp Glu Ala Thr Ala Ser Val Asp Thr Ala Thr Asp Asn
1425                1430                1435                1440

Leu Ile Gln Lys Ile Ile Arg Ser Glu Phe Lys Asp Cys Thr Val Cys
```

```
                1445                1450                1455
Thr Ile Ala His Arg Ile Pro Thr Val Ile Asp Ser Asp Leu Val Leu
                1460                1465                1470

Val Leu Ser Asp Gly Lys Ile Ala Glu Phe Asp Thr Pro Gln Arg Leu
        1475                1480                1485

Leu Glu Asp Lys Ser Ser Met Phe Ile Gln Leu Val Ser Glu Tyr Ser
        1490                1495                1500

Thr Arg Ser Ser Cys Ile
1505                1510

<210> SEQ ID NO 6
<211> LENGTH: 5123
<212> TYPE: DNA
<213> ORGANISM: Oryza sativa
<220> FEATURE:
<221> NAME/KEY: CDS
<222> LOCATION: (245)...(4762)

<400> SEQUENCE: 6
actctttctc gctcgacgag gaggtgaggt gaggtgggag agctagcgaa caaaggcttg      60
gtttggtgcc atctggcggc tccgatggcg taacccgccg ccgccctcag agctcggcct     120
ttgcctgcct tgcctgcctt ctgccccgcc gccccctgcc ctctgccgtg cgtggcgag     180 gcccaatgcc ttttaaaccc cgcccgctg ccatcctgac gccccgatc cccaccgcct      240 ccca atg ccg cac ttc ccg aac ctc ccg ctc ccg gag gct gcc gcc gcc     289
     Met Pro His Phe Pro Asn Leu Pro Leu Pro Glu Ala Ala Ala Ala
       1               5                  10                  15 gcc gcg cac gcc gcg ctg ctc gcc ctc gcc ctg ctc ctg ctc ctc ctc     337
Ala Ala His Ala Ala Leu Leu Ala Leu Ala Leu Leu Leu Leu Leu Leu
                 20                  25                  30 cgc tcc gcg cgc gcc ctc gcc tcg cgc tgc gcg tca tgc ctc aag acc     385
Arg Ser Ala Arg Ala Leu Ala Ser Arg Cys Ala Ser Cys Leu Lys Thr
             35                  40                  45 gcc ccg cgc cga gcc gcg gcg gtc gac ggg ggg ctc gcc gcc gcg tcg     433
Ala Pro Arg Arg Ala Ala Ala Val Asp Gly Gly Leu Ala Ala Ala Ser
         50                  55                  60 tcc gtg ggc gcg tgg tac agg gcg gcg ctg gcg tgc tgc ggc tac gcc     481
Ser Val Gly Ala Trp Tyr Arg Ala Ala Leu Ala Cys Cys Gly Tyr Ala
 65                  70                  75 ctg ctg gcg cag gtc gcc gcc ctg agc tac gag gtc gcg gtg gcc ggt     529
Leu Leu Ala Gln Val Ala Ala Leu Ser Tyr Glu Val Ala Val Ala Gly
 80                  85                  90                  95 tct cat gtc gcc gtg gag gcc ctg ctg ccc gcg gtg cag gcg ctg         577
Ser His Val Ala Val Glu Ala Leu Leu Leu Pro Ala Val Gln Ala Leu
                100                 105                 110 gcg tgg gcg gcg ctc ctg gcg ctc gcg atg cag gcc cgg gcc gtc ggg     625
Ala Trp Ala Ala Leu Leu Ala Leu Ala Met Gln Ala Arg Ala Val Gly
             115                 120                 125 tgg ggc agg ttc ccc gta ctg gtg cgc gtc tgg gtg gtc tcc ttc         673
Trp Gly Arg Phe Pro Val Leu Val Arg Val Trp Trp Val Ser Phe
         130                 135                 140 gtg ctc tgt gtt ggc atc gcg tac gac gat acc agg cac ctc atg ggc     721
Val Leu Cys Val Gly Ile Ala Tyr Asp Asp Thr Arg His Leu Met Gly
145                 150                 155 gat gat gat gat gat gag gtg gac tac gct cac atg gtt gcc aac ttc     769
Asp Asp Asp Asp Asp Glu Val Asp Tyr Ala His Met Val Ala Asn Phe
160                 165                 170                 175 gcg tcg gcg ccg gcc ctc ggg ttc ctc tgc ttg gtt ggt gtc atg ggt     817
Ala Ser Ala Pro Ala Leu Gly Phe Leu Cys Leu Val Gly Val Met Gly
                 180                 185                 190
```

```
                                                       -continued tcc acc ggt gtt gaa ttg gag ttc acc gac gac gac agc agt gtt cat    865
Ser Thr Gly Val Glu Leu Glu Phe Thr Asp Asp Asp Ser Ser Val His
        195                 200                 205 gaa ccg ctc ttg ctc ggt ggg cag cgg aga gac gcc gac gag gag ccc    913
Glu Pro Leu Leu Leu Gly Gly Gln Arg Arg Asp Ala Asp Glu Glu Pro
210                 215                 220 ggg tgc ttg cgg gtg acg ccg tat ggc gat gct ggg att gtt agc ctt    961
Gly Cys Leu Arg Val Thr Pro Tyr Gly Asp Ala Gly Ile Val Ser Leu
    225                 230                 235 gca aca tta tca tgg ctt agt ccg ctg ctg tca gtt ggt gcg cag cga   1009
Ala Thr Leu Ser Trp Leu Ser Pro Leu Leu Ser Val Gly Ala Gln Arg
240                 245                 250                 255 cca ctt gag ctg gct gac ata ccc ttg atg gca cac aaa gac cgt gcc   1057
Pro Leu Glu Leu Ala Asp Ile Pro Leu Met Ala His Lys Asp Arg Ala
                260                 265                 270 aaa tcc tgc tac aag gcg atg agc agt cac tat gaa cgc cag cgg atg   1105
Lys Ser Cys Tyr Lys Ala Met Ser Ser His Tyr Glu Arg Gln Arg Met
            275                 280                 285 gag cgc ccc ggc agc gaa cca tca ctg gca tgg gca ata ttg aag tcg   1153
Glu Arg Pro Gly Ser Glu Pro Ser Leu Ala Trp Ala Ile Leu Lys Ser
        290                 295                 300 ttc tgg cgt gag gca gcg atc aat ggt gct ttc gca gcg gtg aac aca   1201
Phe Trp Arg Glu Ala Ala Ile Asn Gly Ala Phe Ala Ala Val Asn Thr
305                 310                 315 att gtc tcc tat gtt ggc cca tac ctg atc agc tac ttt gtg gac tac   1249
Ile Val Ser Tyr Val Gly Pro Tyr Leu Ile Ser Tyr Phe Val Asp Tyr
320                 325                 330                 335 ctc agt ggc aaa att gaa ttc ccc cat gaa ggt tac atc ctt gcc tct   1297
Leu Ser Gly Lys Ile Glu Phe Pro His Glu Gly Tyr Ile Leu Ala Ser
                340                 345                 350 gta ttt ttt gta gca aag tta ctt gag acg ctc act gct cgg cag tgg   1345
Val Phe Phe Val Ala Lys Leu Leu Glu Thr Leu Thr Ala Arg Gln Trp
            355                 360                 365 tac ttg ggc gtg gat gtc atg ggg atc cat gtc aag tct ggg ctg acg   1393
Tyr Leu Gly Val Asp Val Met Gly Ile His Val Lys Ser Gly Leu Thr
        370                 375                 380 gcc atg gtg tac agg aag ggc ctt agg ctg tcg aat tcc tcg cgg cag   1441
Ala Met Val Tyr Arg Lys Gly Leu Arg Leu Ser Asn Ser Ser Arg Gln
385                 390                 395 agc cac acc agt ggt gag att gtg aat tac atg gcg gtt gat gta cag   1489
Ser His Thr Ser Gly Glu Ile Val Asn Tyr Met Ala Val Asp Val Gln
400                 405                 410                 415 cgt gtg ggg gac tat gca tgg tac ttt cat gac atc tgg atg ctt cca   1537
Arg Val Gly Asp Tyr Ala Trp Tyr Phe His Asp Ile Trp Met Leu Pro
                420                 425                 430 ctg cag atc atc ctc gcc ctc gcc atc ctg tac aag aat gtt gga atc   1585
Leu Gln Ile Ile Leu Ala Leu Ala Ile Leu Tyr Lys Asn Val Gly Ile
            435                 440                 445 gcc atg gtt tca aca ttg gta gct act gta tta tca att gct gcc tca   1633
Ala Met Val Ser Thr Leu Val Ala Thr Val Leu Ser Ile Ala Ala Ser
        450                 455                 460 gtt cct gtg gcg aag ctg cag gag cac tac caa gat aag ctt atg gcc   1681
Val Pro Val Ala Lys Leu Gln Glu His Tyr Gln Asp Lys Leu Met Ala
465                 470                 475 tca aag gat gag cgc atg cgc aag aca tca gag tgc ctg aag aat atg   1729
Ser Lys Asp Glu Arg Met Arg Lys Thr Ser Glu Cys Leu Lys Asn Met
                480                 485                 490                 495 agg att ttg aag ctc caa gcg tgg gag gat cga tac agg ctg aag ttg   1777
Arg Ile Leu Lys Leu Gln Ala Trp Glu Asp Arg Tyr Arg Leu Lys Leu
            500                 505                 510
```

| | | |
|---|---|---|
| gaa gag atg aga aat gtg gaa tgc aag tgg ctt cgg tgg gct ctg tat<br>Glu Glu Met Arg Asn Val Glu Cys Lys Trp Leu Arg Trp Ala Leu Tyr<br>515                    520                    525 | 1825 |
| tca cag gcc gca gtt aca ttt gtt ttc tgg agt tca cca atc ttt gtc<br>Ser Gln Ala Ala Val Thr Phe Val Phe Trp Ser Ser Pro Ile Phe Val<br>    530                  535                    540 | 1873 |
| gcc gtg ata aca ttt ggg act tgt ata ttg ctt ggt ggc gaa ctc act<br>Ala Val Ile Thr Phe Gly Thr Cys Ile Leu Leu Gly Gly Glu Leu Thr<br>545                    550                    555 | 1921 |
| gct gga ggt gtt ctt tct gct tta gca aca ttt agg atc ctt caa gaa<br>Ala Gly Gly Val Leu Ser Ala Leu Ala Thr Phe Arg Ile Leu Gln Glu<br>560                    565                    570                    575 | 1969 |
| cca ctt agg aat ttc cca gat ctt atc tct atg att gct cag acg agg<br>Pro Leu Arg Asn Phe Pro Asp Leu Ile Ser Met Ile Ala Gln Thr Arg<br>                  580                    585                    590 | 2017 |
| gta tct ttg gac cgg ttg tct cac ttt ctt caa caa gaa gaa ttg cca<br>Val Ser Leu Asp Arg Leu Ser His Phe Leu Gln Gln Glu Glu Leu Pro<br>            595                  600                    605 | 2065 |
| gat gat gca act ata acg gtt cca cat ggt agt aca gat aag gca atc<br>Asp Asp Ala Thr Ile Thr Val Pro His Gly Ser Thr Asp Lys Ala Ile<br>610                    615                    620 | 2113 |
| aat ata aat gat gct aca ttc tct tgg aac cca tct tct cca acc cct<br>Asn Ile Asn Asp Ala Thr Phe Ser Trp Asn Pro Ser Ser Pro Thr Pro<br>625                    630                    635 | 2161 |
| aca ctt tct ggc atc aac ctt agt gtg gtg agg ggt atg cga gta gca<br>Thr Leu Ser Gly Ile Asn Leu Ser Val Val Arg Gly Met Arg Val Ala<br>640                    645                    650                    655 | 2209 |
| gtg tgt ggt gtc att ggt tct ggc aaa tca agc ttg ttg tct tct ata<br>Val Cys Gly Val Ile Gly Ser Gly Lys Ser Ser Leu Leu Ser Ser Ile<br>                  660                  665                    670 | 2257 |
| ctc ggc gag ata ccc aaa ttg tgt ggt caa gtg agg atc agt gga tca<br>Leu Gly Glu Ile Pro Lys Leu Cys Gly Gln Val Arg Ile Ser Gly Ser<br>675                    680                    685 | 2305 |
| gca gca tat gtc cct cag act gcc tgg ata cag tcc gga aac att gag<br>Ala Ala Tyr Val Pro Gln Thr Ala Trp Ile Gln Ser Gly Asn Ile Glu<br>            690                  695                    700 | 2353 |
| gag aac att ctt ttt ggc agt cca atg gac aaa cag cgt tac aag aga<br>Glu Asn Ile Leu Phe Gly Ser Pro Met Asp Lys Gln Arg Tyr Lys Arg<br>705                    710                    715 | 2401 |
| gtt att gag gct tgc tcc ctg aag aaa gat ctt cag ttg ctc caa tat<br>Val Ile Glu Ala Cys Ser Leu Lys Lys Asp Leu Gln Leu Leu Gln Tyr<br>720                    725                    730                    735 | 2449 |
| gga gat cag acc atc atc ggt gat agg ggc att aat ttg agt ggg ggt<br>Gly Asp Gln Thr Ile Ile Gly Asp Arg Gly Ile Asn Leu Ser Gly Gly<br>                  740                  745                    750 | 2497 |
| cag aaa caa aga gta cag ctt gca aga gca cta tac caa gat gct gat<br>Gln Lys Gln Arg Val Gln Leu Ala Arg Ala Leu Tyr Gln Asp Ala Asp<br>755                    760                    765 | 2545 |
| att tat ttg ctc gat gat ccc ttc agt gcg gtt gat gct cat act ggg<br>Ile Tyr Leu Leu Asp Asp Pro Phe Ser Ala Val Asp Ala His Thr Gly<br>            770                  775                    780 | 2593 |
| agt gaa tta ttt agg gaa tat ata ttg act gca cta gca agc aag acc<br>Ser Glu Leu Phe Arg Glu Tyr Ile Leu Thr Ala Leu Ala Ser Lys Thr<br>785                    790                    795 | 2641 |
| gta att tat gta acc cat caa att gag ttt cta cca gct gct gac ttg<br>Val Ile Tyr Val Thr His Gln Ile Glu Phe Leu Pro Ala Ala Asp Leu<br>800                    805                    810                    815 | 2689 |
| ata ctg gtt ctt aag gat ggt cat atc acc caa gct gga aaa tat gat<br>Ile Leu Val Leu Lys Asp Gly His Ile Thr Gln Ala Gly Lys Tyr Asp<br>            820                  825                    830 | 2737 |

```
gat ctt ctc caa gct ggc act gat ttc aat gct ttg gtt tgt gct cat    2785
Asp Leu Leu Gln Ala Gly Thr Asp Phe Asn Ala Leu Val Cys Ala His
            835                 840                 845 aag gaa gct att gag acc atg gaa ttt tcc gaa gat tcc gat gag gat    2833
Lys Glu Ala Ile Glu Thr Met Glu Phe Ser Glu Asp Ser Asp Glu Asp
        850                 855                 860 act gtc tct tct gtt cct atc aaa aga ctg acg cca agt gtt agc aat    2881
Thr Val Ser Ser Val Pro Ile Lys Arg Leu Thr Pro Ser Val Ser Asn
865                 870                 875 ata gat aat ctg aaa aac aag gtg tcc aat aat gaa aaa cca tct agt    2929
Ile Asp Asn Leu Lys Asn Lys Val Ser Asn Asn Glu Lys Pro Ser Ser
880                 885                 890                 895 acg cgt gga ata aaa gaa aag aag aag cct gaa gag cgt aag aag        2977
Thr Arg Gly Ile Lys Glu Lys Lys Lys Pro Glu Glu Arg Lys Lys
                900                 905                 910 aag cgg tct gtt caa gag gag gag agg gag cga gga agg gtt agc tta    3025
Lys Arg Ser Val Gln Glu Glu Glu Arg Glu Arg Gly Arg Val Ser Leu
            915                 920                 925 cag gtt tac ttg tca tac atg gga gaa gca tac aaa ggt aca ctg ata    3073
Gln Val Tyr Leu Ser Tyr Met Gly Glu Ala Tyr Lys Gly Thr Leu Ile
        930                 935                 940 ccc ctc att atc ctg gcc caa acc atg ttt caa gta ctt cag att gcg    3121
Pro Leu Ile Ile Leu Ala Gln Thr Met Phe Gln Val Leu Gln Ile Ala
945                 950                 955 agt aac tgg tgg atg gca tgg gca aac cca caa aca gaa gga gat gca    3169
Ser Asn Trp Trp Met Ala Trp Ala Asn Pro Gln Thr Glu Gly Asp Ala
960                 965                 970                 975 cct aag aca gac agt gtg gtt ctc ttg gtt gtt tat atg tcc ctt gcc    3217
Pro Lys Thr Asp Ser Val Val Leu Leu Val Val Tyr Met Ser Leu Ala
                980                 985                 990 ttt ggg agt tca ttg ttt gtg ttt gtg aga agt ctt ctt gtg gct aca    3265
Phe Gly Ser Ser Leu Phe Val Phe Val Arg Ser Leu Leu Val Ala Thr
            995                1000                1005 ttt ggt tta gca act gca cag aag ctg ttt gta aag atg cta agg tgt    3313
Phe Gly Leu Ala Thr Ala Gln Lys Leu Phe Val Lys Met Leu Arg Cys
        1010                1015                1020 gtt ttt cga gcg cca atg tca ttc ttt gat act aca cca tct ggt cga    3361
Val Phe Arg Ala Pro Met Ser Phe Phe Asp Thr Thr Pro Ser Gly Arg
    1025                1030                1035 att ttg aac cga gtt tct gta gat caa agt gtc gtg gac ctt gat ata    3409
Ile Leu Asn Arg Val Ser Val Asp Gln Ser Val Val Asp Leu Asp Ile
1040                1045                1050                1055 gca ttc aga ctt ggt gga ttt gca tca aca aca att caa cta ctt gga    3457
Ala Phe Arg Leu Gly Gly Phe Ala Ser Thr Thr Ile Gln Leu Leu Gly
                1060                1065                1070 att gtt gct gtc atg agc aaa gtc aca tgg caa gtt ttg att ctt ata    3505
Ile Val Ala Val Met Ser Lys Val Thr Trp Gln Val Leu Ile Leu Ile
            1075                1080                1085 gtt cct atg gct gtt gca tgc atg tgg atg cag aga tat tat att gct    3553
Val Pro Met Ala Val Ala Cys Met Trp Met Gln Arg Tyr Tyr Ile Ala
        1090                1095                1100 tca tca agg gaa ttg act agg atc tta agc gta cag aag tcg ccg gtg    3601
Ser Ser Arg Glu Leu Thr Arg Ile Leu Ser Val Gln Lys Ser Pro Val
    1105                1110                1115 atc cat ttg ttt agt gag tca att gct ggt gct gct aca atc aga ggt    3649
Ile His Leu Phe Ser Glu Ser Ile Ala Gly Ala Ala Thr Ile Arg Gly
1120                1125                1130                1135 ttt ggt caa gag aaa cga ttc atg aaa aga aat ctt tac ctt ctt gac    3697
Phe Gly Gln Glu Lys Arg Phe Met Lys Arg Asn Leu Tyr Leu Leu Asp
                1140                1145                1150
```

| | | |
|---|---|---|
| tgt ttt gct cgg cct cta ttt tcc agc ctg gca gct att gaa tgg ctg<br>Cys Phe Ala Arg Pro Leu Phe Ser Ser Leu Ala Ala Ile Glu Trp Leu<br>    1155                1160                1165 | 3745 | |
| tgc ctg cga atg gaa ttg ctc tcg acc ttt gtc ttc gct ttt tgc atg<br>Cys Leu Arg Met Glu Leu Leu Ser Thr Phe Val Phe Ala Phe Cys Met<br>1170                1175                1180 | 3793 | |
| gcg ata cta gtg agc ttc cct cct ggc aca att gaa cca agt atg gct<br>Ala Ile Leu Val Ser Phe Pro Pro Gly Thr Ile Glu Pro Ser Met Ala<br>    1185                1190                1195 | 3841 | |
| ggg ctt gct gtc act tat gga ctt aat tta aat gct cgc atg tca agg<br>Gly Leu Ala Val Thr Tyr Gly Leu Asn Leu Asn Ala Arg Met Ser Arg<br>1200                1205                1210                1215 | 3889 | |
| tgg ata ctg agc ttc tgt aaa tta gag aat aga atc atc tct gtt gaa<br>Trp Ile Leu Ser Phe Cys Lys Leu Glu Asn Arg Ile Ile Ser Val Glu<br>    1220                1225                1230 | 3937 | |
| cgc att tat cag tat tgc aag ctt ccc agt gaa gca cca ctc atc att<br>Arg Ile Tyr Gln Tyr Cys Lys Leu Pro Ser Glu Ala Pro Leu Ile Ile<br>    1235                1240                1245 | 3985 | |
| gag aat agc cgt ccc tca tcc tcg tgg cct gag aat gga aac att gag<br>Glu Asn Ser Arg Pro Ser Ser Ser Trp Pro Glu Asn Gly Asn Ile Glu<br>    1250                1255                1260 | 4033 | |
| ctg gtc gat ctc aag gta cgg tac aaa gat gac ctg ccc tta gtt cta<br>Leu Val Asp Leu Lys Val Arg Tyr Lys Asp Asp Leu Pro Leu Val Leu<br>    1265                1270                1275 | 4081 | |
| cat gga atc agt tgt ata ttt ccc ggt gga aaa aag att ggg att gtg<br>His Gly Ile Ser Cys Ile Phe Pro Gly Gly Lys Lys Ile Gly Ile Val<br>1280                1285                1290                1295 | 4129 | |
| ggg cga act gga agt ggt aaa tct act ctt att cag gcc ctt ttc cgc<br>Gly Arg Thr Gly Ser Gly Lys Ser Thr Leu Ile Gln Ala Leu Phe Arg<br>    1300                1305                1310 | 4177 | |
| tta att gaa cct aca gga ggg aaa gtt atc atc gat gac gtc gat att<br>Leu Ile Glu Pro Thr Gly Gly Lys Val Ile Ile Asp Asp Val Asp Ile<br>    1315                1320                1325 | 4225 | |
| tct aga att ggc ctg cat gat ctg cgg tca cgg ttg agc atc att ccc<br>Ser Arg Ile Gly Leu His Asp Leu Arg Ser Arg Leu Ser Ile Ile Pro<br>    1330                1335                1340 | 4273 | |
| cag gac cct acg ttg ttt gag ggt act atc aga atg aat ctt gat cct<br>Gln Asp Pro Thr Leu Phe Glu Gly Thr Ile Arg Met Asn Leu Asp Pro<br>1345                1350                1355 | 4321 | |
| ctt gaa gaa tgt act gat cag gaa att tgg gag gca cta gaa aag tgt<br>Leu Glu Glu Cys Thr Asp Gln Glu Ile Trp Glu Ala Leu Glu Lys Cys<br>1360                1365                1370                1375 | 4369 | |
| cag ctc gga gag gtc att cgg tcc aag gat gaa aag ctg gac agt cca<br>Gln Leu Gly Glu Val Ile Arg Ser Lys Asp Glu Lys Leu Asp Ser Pro<br>    1380                1385                1390 | 4417 | |
| gta ctg gag aat gga gat aac tgg agt gtg gga caa cgc cag ctt att<br>Val Leu Glu Asn Gly Asp Asn Trp Ser Val Gly Gln Arg Gln Leu Ile<br>    1395                1400                1405 | 4465 | |
| gca ttg ggt agg gcc ctg ctg aaa cag gca aaa att ttg gtg ctt gac<br>Ala Leu Gly Arg Ala Leu Leu Lys Gln Ala Lys Ile Leu Val Leu Asp<br>    1410                1415                1420 | 4513 | |
| gag gca aca gca tca gtt gac aca gct acg gac aat ctt att caa aag<br>Glu Ala Thr Ala Ser Val Asp Thr Ala Thr Asp Asn Leu Ile Gln Lys<br>    1425                1430                1435 | 4561 | |
| att att cgc agt gaa ttc aag gat tgc acg gtc tgc acc att gca cac<br>Ile Ile Arg Ser Glu Phe Lys Asp Cys Thr Val Cys Thr Ile Ala His<br>1440                1445                1450                1455 | 4609 | |
| cgt atc ccg acg gtt att gat agt gac cta gtc ctg gtg ctt agt gat<br>Arg Ile Pro Thr Val Ile Asp Ser Asp Leu Val Leu Val Leu Ser Asp<br>    1460                1465                1470 | 4657 | |

-continued

```
ggt aaa att gca gag ttt gac aca ccc cag agg ctc ttg gag gac aag      4705
Gly Lys Ile Ala Glu Phe Asp Thr Pro Gln Arg Leu Leu Glu Asp Lys
        1475                1480                1485 tcc tcc atg ttc atg cag cta gta tct gaa tac tca act cgg tca agc      4753
Ser Ser Met Phe Met Gln Leu Val Ser Glu Tyr Ser Thr Arg Ser Ser
    1490                1495                1500 tgt ata tag agaggcttag cttaaaatcc cccacaccaa gtaggaacag              4802
Cys Ile *
   1505 ggaggtagga tagccacatc tgccagtgga ctcacgccat agaagtacca acatcatagg    4862 gcaagacaca agccgaggtg tatatgagcg gaaacaaaat gttccctgac gtgaataaac    4922 catggaatcg atgagggaac gcagcgggca gcaccacggg aggagttggt gagattaccc    4982 gaagctctga tgcttctgaa tgtataaaca atgcggtact acttctccct tgcatagtgg    5042 aaaaagggaa ggcaatgttc atgggtaata aaggggtaac aagtttcatt ttggcaccag    5102 attggagtgc tttggtctac t                                              5123

<210> SEQ ID NO 7
<211> LENGTH: 1505
<212> TYPE: PRT
<213> ORGANISM: Oryza sativa

<400> SEQUENCE: 7

Met Pro His Phe Pro Asn Leu Pro Leu Pro Glu Ala Ala Ala Ala Ala
1               5                   10                  15

Ala His Ala Ala Leu Leu Ala Leu Ala Leu Leu Leu Leu Leu Leu Arg
            20                  25                  30

Ser Ala Arg Ala Leu Ala Ser Arg Cys Ala Ser Cys Leu Lys Thr Ala
        35                  40                  45

Pro Arg Arg Ala Ala Val Asp Gly Gly Leu Ala Ala Ala Ser Ser
    50                  55                  60

Val Gly Ala Trp Tyr Arg Ala Ala Leu Ala Cys Cys Gly Tyr Ala Leu
65                  70                  75                  80

Leu Ala Gln Val Ala Ala Leu Ser Tyr Glu Val Ala Val Ala Gly Ser
                85                  90                  95

His Val Ala Val Glu Ala Leu Leu Leu Pro Ala Val Gln Ala Leu Ala
            100                 105                 110

Trp Ala Ala Leu Leu Ala Leu Ala Met Gln Ala Arg Ala Val Gly Trp
        115                 120                 125

Gly Arg Phe Pro Val Leu Val Arg Val Trp Trp Val Ser Phe Val
    130                 135                 140

Leu Cys Val Gly Ile Ala Tyr Asp Asp Thr Arg His Leu Met Gly Asp
145                 150                 155                 160

Asp Asp Asp Asp Glu Val Asp Tyr Ala His Met Val Ala Asn Phe Ala
                165                 170                 175

Ser Ala Pro Ala Leu Gly Phe Leu Cys Leu Val Gly Val Met Gly Ser
            180                 185                 190

Thr Gly Val Glu Leu Glu Phe Thr Asp Asp Ser Ser Val His Glu
        195                 200                 205

Pro Leu Leu Leu Gly Gly Gln Arg Arg Asp Ala Asp Glu Glu Pro Gly
    210                 215                 220

Cys Leu Arg Val Thr Pro Tyr Gly Asp Ala Gly Ile Val Ser Leu Ala
225                 230                 235                 240

Thr Leu Ser Trp Leu Ser Pro Leu Leu Ser Val Gly Ala Gln Arg Pro
                245                 250                 255
```

```
Leu Glu Leu Ala Asp Ile Pro Leu Met Ala His Lys Asp Arg Ala Lys
            260                 265                 270

Ser Cys Tyr Lys Ala Met Ser Ser His Tyr Glu Arg Gln Arg Met Glu
        275                 280                 285

Arg Pro Gly Ser Glu Pro Ser Leu Ala Trp Ala Ile Leu Lys Ser Phe
    290                 295                 300

Trp Arg Glu Ala Ala Ile Asn Gly Ala Phe Ala Val Asn Thr Ile
305                 310                 315                 320

Val Ser Tyr Val Gly Pro Tyr Leu Ile Ser Tyr Phe Val Asp Tyr Leu
                325                 330                 335

Ser Gly Lys Ile Glu Phe Pro His Glu Gly Tyr Ile Leu Ala Ser Val
            340                 345                 350

Phe Phe Val Ala Lys Leu Leu Glu Thr Leu Thr Ala Arg Gln Trp Tyr
        355                 360                 365

Leu Gly Val Asp Val Met Gly Ile His Val Lys Ser Gly Leu Thr Ala
    370                 375                 380

Met Val Tyr Arg Lys Gly Leu Arg Leu Ser Asn Ser Ser Arg Gln Ser
385                 390                 395                 400

His Thr Ser Gly Glu Ile Val Asn Tyr Met Ala Val Asp Val Gln Arg
                405                 410                 415

Val Gly Asp Tyr Ala Trp Tyr Phe His Asp Ile Trp Met Leu Pro Leu
            420                 425                 430

Gln Ile Ile Leu Ala Leu Ala Ile Leu Tyr Lys Asn Val Gly Ile Ala
        435                 440                 445

Met Val Ser Thr Leu Val Ala Thr Val Leu Ser Ile Ala Ala Ser Val
    450                 455                 460

Pro Val Ala Lys Leu Gln Glu His Tyr Gln Asp Lys Leu Met Ala Ser
465                 470                 475                 480

Lys Asp Glu Arg Met Arg Lys Thr Ser Glu Cys Leu Lys Asn Met Arg
                485                 490                 495

Ile Leu Lys Leu Gln Ala Trp Glu Asp Arg Tyr Arg Leu Lys Leu Glu
            500                 505                 510

Glu Met Arg Asn Val Glu Cys Lys Trp Leu Arg Trp Ala Leu Tyr Ser
        515                 520                 525

Gln Ala Ala Val Thr Phe Val Phe Trp Ser Ser Pro Ile Phe Val Ala
    530                 535                 540

Val Ile Thr Phe Gly Thr Cys Ile Leu Leu Gly Gly Glu Leu Thr Ala
545                 550                 555                 560

Gly Gly Val Leu Ser Ala Leu Ala Thr Phe Arg Ile Leu Gln Glu Pro
                565                 570                 575

Leu Arg Asn Phe Pro Asp Leu Ile Ser Met Ile Ala Gln Thr Arg Val
            580                 585                 590

Ser Leu Asp Arg Leu Ser His Phe Leu Gln Gln Glu Glu Leu Pro Asp
        595                 600                 605

Asp Ala Thr Ile Thr Val Pro His Gly Ser Thr Asp Lys Ala Ile Asn
    610                 615                 620

Ile Asn Asp Ala Thr Phe Ser Trp Asn Pro Ser Ser Pro Thr Pro Thr
625                 630                 635                 640

Leu Ser Gly Ile Asn Leu Ser Val Val Arg Gly Met Arg Val Ala Val
                645                 650                 655

Cys Gly Val Ile Gly Ser Gly Lys Ser Ser Leu Leu Ser Ser Ile Leu
            660                 665                 670

Gly Glu Ile Pro Lys Leu Cys Gly Gln Val Arg Ile Ser Gly Ser Ala
```

```
                675                 680                 685
Ala Tyr Val Pro Gln Thr Ala Trp Ile Gln Ser Gly Asn Ile Glu Glu
690                 695                 700
Asn Ile Leu Phe Gly Ser Pro Met Asp Lys Gln Arg Tyr Lys Arg Val
705                 710                 715                 720
Ile Glu Ala Cys Ser Leu Lys Lys Asp Leu Gln Leu Gln Tyr Gly
                725                 730                 735
Asp Gln Thr Ile Ile Gly Asp Arg Gly Ile Asn Leu Ser Gly Gly Gln
            740                 745                 750
Lys Gln Arg Val Gln Leu Ala Arg Ala Leu Tyr Gln Asp Ala Asp Ile
        755                 760                 765
Tyr Leu Leu Asp Asp Pro Phe Ser Ala Val Asp Ala His Thr Gly Ser
    770                 775                 780
Glu Leu Phe Arg Glu Tyr Ile Leu Thr Ala Leu Ala Ser Lys Thr Val
785                 790                 795                 800
Ile Tyr Val Thr His Gln Ile Glu Phe Leu Pro Ala Ala Asp Leu Ile
                805                 810                 815
Leu Val Leu Lys Asp Gly His Ile Thr Gln Ala Gly Lys Tyr Asp Asp
            820                 825                 830
Leu Leu Gln Ala Gly Thr Asp Phe Asn Ala Leu Val Cys Ala His Lys
        835                 840                 845
Glu Ala Ile Glu Thr Met Glu Phe Ser Glu Asp Ser Asp Glu Asp Thr
    850                 855                 860
Val Ser Ser Val Pro Ile Lys Arg Leu Thr Pro Ser Val Ser Asn Ile
865                 870                 875                 880
Asp Asn Leu Lys Asn Lys Val Ser Asn Glu Lys Pro Ser Ser Thr
                885                 890                 895
Arg Gly Ile Lys Glu Lys Lys Lys Pro Glu Arg Lys Lys Lys
            900                 905                 910
Arg Ser Val Gln Glu Glu Arg Glu Arg Gly Arg Val Ser Leu Gln
        915                 920                 925
Val Tyr Leu Ser Tyr Met Gly Glu Ala Tyr Lys Gly Thr Leu Ile Pro
    930                 935                 940
Leu Ile Ile Leu Ala Gln Thr Met Phe Gln Val Leu Gln Ile Ala Ser
945                 950                 955                 960
Asn Trp Trp Met Ala Trp Ala Asn Pro Gln Thr Glu Gly Asp Ala Pro
                965                 970                 975
Lys Thr Asp Ser Val Val Leu Leu Val Val Tyr Met Ser Leu Ala Phe
            980                 985                 990
Gly Ser Ser Leu Phe Val Phe Val Arg Ser Leu Leu Val Ala Thr Phe
        995                 1000                1005
Gly Leu Ala Thr Ala Gln Lys Leu Phe Val Lys Met Leu Arg Cys Val
    1010                1015                1020
Phe Arg Ala Pro Met Ser Phe Phe Asp Thr Thr Pro Ser Gly Arg Ile
1025                1030                1035                1040
Leu Asn Arg Val Ser Val Asp Gln Ser Val Val Asp Leu Asp Ile Ala
                1045                1050                1055
Phe Arg Leu Gly Gly Phe Ala Ser Thr Thr Ile Gln Leu Leu Gly Ile
            1060                1065                1070
Val Ala Val Met Ser Lys Val Thr Trp Gln Val Leu Ile Leu Ile Val
        1075                1080                1085
Pro Met Ala Val Ala Cys Met Trp Met Gln Arg Tyr Tyr Ile Ala Ser
    1090                1095                1100
```

-continued

```
Ser Arg Glu Leu Thr Arg Ile Leu Ser Val Gln Lys Ser Pro Val Ile
1105                1110                1115                1120

His Leu Phe Ser Glu Ser Ile Ala Gly Ala Ala Thr Ile Arg Gly Phe
            1125                1130                1135

Gly Gln Glu Lys Arg Phe Met Lys Arg Asn Leu Tyr Leu Leu Asp Cys
        1140                1145                1150

Phe Ala Arg Pro Leu Phe Ser Ser Leu Ala Ala Ile Glu Trp Leu Cys
    1155                1160                1165

Leu Arg Met Glu Leu Leu Ser Thr Phe Val Phe Ala Phe Cys Met Ala
1170                1175                1180

Ile Leu Val Ser Phe Pro Pro Gly Thr Ile Glu Pro Ser Met Ala Gly
1185                1190                1195                1200

Leu Ala Val Thr Tyr Gly Leu Asn Leu Asn Ala Arg Met Ser Arg Trp
            1205                1210                1215

Ile Leu Ser Phe Cys Lys Leu Glu Asn Arg Ile Ile Ser Val Glu Arg
        1220                1225                1230

Ile Tyr Gln Tyr Cys Lys Leu Pro Ser Glu Ala Pro Leu Ile Ile Glu
    1235                1240                1245

Asn Ser Arg Pro Ser Ser Ser Trp Pro Glu Asn Gly Asn Ile Glu Leu
1250                1255                1260

Val Asp Leu Lys Val Arg Tyr Lys Asp Asp Leu Pro Leu Val Leu His
1265                1270                1275                1280

Gly Ile Ser Cys Ile Phe Pro Gly Gly Lys Lys Ile Gly Ile Val Gly
            1285                1290                1295

Arg Thr Gly Ser Gly Lys Ser Thr Leu Ile Gln Ala Leu Phe Arg Leu
        1300                1305                1310

Ile Glu Pro Thr Gly Gly Lys Val Ile Ile Asp Asp Val Asp Ile Ser
    1315                1320                1325

Arg Ile Gly Leu His Asp Leu Arg Ser Arg Leu Ser Ile Ile Pro Gln
1330                1335                1340

Asp Pro Thr Leu Phe Glu Gly Thr Ile Arg Met Asn Leu Asp Pro Leu
1345                1350                1355                1360

Glu Glu Cys Thr Asp Gln Glu Ile Trp Glu Ala Leu Glu Lys Cys Gln
            1365                1370                1375

Leu Gly Glu Val Ile Arg Ser Lys Asp Glu Lys Leu Asp Ser Pro Val
        1380                1385                1390

Leu Glu Asn Gly Asp Asn Trp Ser Val Gly Gln Arg Gln Leu Ile Ala
    1395                1400                1405

Leu Gly Arg Ala Leu Leu Lys Gln Ala Lys Ile Leu Val Leu Asp Glu
1410                1415                1420

Ala Thr Ala Ser Val Asp Thr Ala Thr Asp Asn Leu Ile Gln Lys Ile
1425                1430                1435                1440

Ile Arg Ser Glu Phe Lys Asp Cys Thr Val Cys Thr Ile Ala His Arg
            1445                1450                1455

Ile Pro Thr Val Ile Asp Ser Asp Leu Val Leu Val Leu Ser Asp Gly
        1460                1465                1470

Lys Ile Ala Glu Phe Asp Thr Pro Gln Arg Leu Leu Glu Asp Lys Ser
    1475                1480                1485

Ser Met Phe Met Gln Leu Val Ser Glu Tyr Ser Thr Arg Ser Ser Cys
1490                1495                1500

Ile
1505
```

<210> SEQ ID NO 8

-continued

```
<211> LENGTH: 4992
<212> TYPE: DNA
<213> ORGANISM: Arabidopsis thaliana
<220> FEATURE:
<221> NAME/KEY: CDS
<222> LOCATION: (207)...(4751)

<400> SEQUENCE: 8
ctcgattgct ctcaagaacc caagtgacgt ctggtttcag ctgatttgtt tcttctcatt        60
ctctatcttc ttctctggga aatatcgatt ttgatctatt aagagctgct acgagctttg       120
ggatgtggtg agatgcttgt tctatctcga acaatccgcc ggttgttgat tttaaacaaa       180
ctctctatca caaatctttc ccgatc atg gat ttt att gag atc tcg ttg atc       233
                              Met Asp Phe Ile Glu Ile Ser Leu Ile
                                1               5 ttt cga gag cat ttg cca cta ctg gaa cta tgt tcg gtc atc atc aac       281
Phe Arg Glu His Leu Pro Leu Leu Glu Leu Cys Ser Val Ile Ile Asn
 10              15                  20                  25 ctc cta ctc ttt ctt gtc ttt cta ttt gct gtc tcc gcg agg cag att       329
Leu Leu Leu Phe Leu Val Phe Leu Phe Ala Val Ser Ala Arg Gln Ile
                 30                  35                  40 ctc gtc tgc gtg aga aga ggc aga gat agg ctc tct aag gac gat acg       377
Leu Val Cys Val Arg Arg Gly Arg Asp Arg Leu Ser Lys Asp Asp Thr
             45                  50                  55 gtt tca gct tct aat ctt agc ttg gaa aga gag gtt aac cat gtt agt       425
Val Ser Ala Ser Asn Leu Ser Leu Glu Arg Glu Val Asn His Val Ser
         60                  65                  70 gtt ggg ttt ggg ttt aat ctg tct ttg ctc tgt tgc tta tat gtg tta       473
Val Gly Phe Gly Phe Asn Leu Ser Leu Leu Cys Cys Leu Tyr Val Leu
     75                  80                  85 ggc gtc caa gtt ttg gtg tta gta tat gat ggg gtt aag gtt aga aga       521
Gly Val Gln Val Leu Val Leu Val Tyr Asp Gly Val Lys Val Arg Arg
 90                  95                 100                 105 gaa gtc agt gac tgg ttt gtt ctt tgc ttt cca gct tct cag agt tta       569
Glu Val Ser Asp Trp Phe Val Leu Cys Phe Pro Ala Ser Gln Ser Leu
                110                 115                 120 gct tgg ttt gtc ctt agc ttc tta gtt ctt cat ttg aaa tac aag tct       617
Ala Trp Phe Val Leu Ser Phe Leu Val Leu His Leu Lys Tyr Lys Ser
            125                 130                 135 tca gag aag cta ccc ttc ttg gtg agg ata tgg tgg ttc ctg gcg ttt       665
Ser Glu Lys Leu Pro Phe Leu Val Arg Ile Trp Trp Phe Leu Ala Phe
        140                 145                 150 tcg att tgc ctc tgt act atg tat gtc gat gga aga agg cta gcc att       713
Ser Ile Cys Leu Cys Thr Met Tyr Val Asp Gly Arg Arg Leu Ala Ile
    155                 160                 165 gaa ggt tgg agc aga tgt tct tct cat gtt gtc gcc aat tta gct gtt       761
Glu Gly Trp Ser Arg Cys Ser Ser His Val Val Ala Asn Leu Ala Val
170                 175                 180                 185 aca cct gct ctt ggg ttt ctc tgc ttt ctg gcc tgg aga ggc gtt tct       809
Thr Pro Ala Leu Gly Phe Leu Cys Phe Leu Ala Trp Arg Gly Val Ser
                190                 195                 200 ggt att caa gtt acc aga agc tcc tct gat ctt caa gag cct ttg ctt       857
Gly Ile Gln Val Thr Arg Ser Ser Ser Asp Leu Gln Glu Pro Leu Leu
            205                 210                 215 gtt gaa gaa gag gca gct tgt ctt aaa gtt act cca tat agt act gct       905
Val Glu Glu Glu Ala Ala Cys Leu Lys Val Thr Pro Tyr Ser Thr Ala
        220                 225                 230 ggg cta gtt agc ctt att acg ctt tca tgg ttg gat cca ctt ctc tcg       953
Gly Leu Val Ser Leu Ile Thr Leu Ser Trp Leu Asp Pro Leu Leu Ser
    235                 240                 245 gct ggt tca aaa aga ccg ctt gag ctt aag gat ata ccg ctt ctt gca      1001
Ala Gly Ser Lys Arg Pro Leu Glu Leu Lys Asp Ile Pro Leu Leu Ala
```

```
              Ala Gly Ser Lys Arg Pro Leu Glu Leu Lys Asp Ile Pro Leu Leu Ala
              250                 255                 260                 265 cca aga gat aga gcc aaa tca agt tac aag gtc ttg aag tcg aat tgg           1049
Pro Arg Asp Arg Ala Lys Ser Ser Tyr Lys Val Leu Lys Ser Asn Trp
                    270                 275                 280 aag aga tgc aag tcc gag aat cct tca aag cct cct tct tta gct cgt           1097
Lys Arg Cys Lys Ser Glu Asn Pro Ser Lys Pro Pro Ser Leu Ala Arg
                285                 290                 295 gca att atg aaa tca ttt tgg aaa gaa gct gct tgc aat gcc gta ttt           1145
Ala Ile Met Lys Ser Phe Trp Lys Glu Ala Ala Cys Asn Ala Val Phe
            300                 305                 310 gct ggg ttg aat act ctt gtg tcc tat gtc ggt cct tac ttg atc agc           1193
Ala Gly Leu Asn Thr Leu Val Ser Tyr Val Gly Pro Tyr Leu Ile Ser
        315                 320                 325 tac ttt gtt gat tat ctt gga ggg aag gag att ttc cct cat gaa gga           1241
Tyr Phe Val Asp Tyr Leu Gly Gly Lys Glu Ile Phe Pro His Glu Gly
    330                 335                 340                 345 tac gta ctc gct ggg ata ttc ttt acg tcc aag ctt ata gag aca gtc           1289
Tyr Val Leu Ala Gly Ile Phe Phe Thr Ser Lys Leu Ile Glu Thr Val
                    350                 355                 360 acc acc cgc cag tgg tat atg ggt gtt gat atc cta ggg atg cat gtt           1337
Thr Thr Arg Gln Trp Tyr Met Gly Val Asp Ile Leu Gly Met His Val
                365                 370                 375 aga tca gct ctt aca gca atg gta tac cga aaa ggt ctc aaa ctt tca           1385
Arg Ser Ala Leu Thr Ala Met Val Tyr Arg Lys Gly Leu Lys Leu Ser
            380                 385                 390 agt ata gcc aag cag aac cac acg agc ggt gaa att gta aac tac atg           1433
Ser Ile Ala Lys Gln Asn His Thr Ser Gly Glu Ile Val Asn Tyr Met
        395                 400                 405 gca gtc gat gtc cag cgc ata gga gat tac tca tgg tat ctt cat gat           1481
Ala Val Asp Val Gln Arg Ile Gly Asp Tyr Ser Trp Tyr Leu His Asp
410                 415                 420                 425 att tgg atg ctt ccg atg caa ata gtt ctt gct ctt gca atc cta tat           1529
Ile Trp Met Leu Pro Met Gln Ile Val Leu Ala Leu Ala Ile Leu Tyr
                    430                 435                 440 aaa agc gtg ggc ata gct gct gta gct aca ttg gtt gct aca ata atc           1577
Lys Ser Val Gly Ile Ala Ala Val Ala Thr Leu Val Ala Thr Ile Ile
                445                 450                 455 tcg att ctt gtc acg att cca ctc gct aag gtc cag gaa gac tat caa           1625
Ser Ile Leu Val Thr Ile Pro Leu Ala Lys Val Gln Glu Asp Tyr Gln
            460                 465                 470 gat aag ttg atg act gcg aaa gat gaa aga atg agg aaa acc tca gag           1673
Asp Lys Leu Met Thr Ala Lys Asp Glu Arg Met Arg Lys Thr Ser Glu
        475                 480                 485 tgt ctt agg aac atg aga gtt ctg aaa ttg cag gca tgg gaa gat cgt           1721
Cys Leu Arg Asn Met Arg Val Leu Lys Leu Gln Ala Trp Glu Asp Arg
490                 495                 500                 505 tat aga gtg aga ttg gaa gaa atg agg gaa gag tat ggt tgg ctt           1769
Tyr Arg Val Arg Leu Glu Glu Met Arg Glu Glu Tyr Gly Trp Leu
                    510                 515                 520 cgc aaa gcc tta tat tct cag gct ttt gtt act ttt atc ttt tgg agt           1817
Arg Lys Ala Leu Tyr Ser Gln Ala Phe Val Thr Phe Ile Phe Trp Ser
                525                 530                 535 tcc ccc att ttt gtc gcc gca gtt aca ttc gct act tcg ata ttt cta           1865
Ser Pro Ile Phe Val Ala Ala Val Thr Phe Ala Thr Ser Ile Phe Leu
            540                 545                 550 ggc act caa ctt acc gct gga ggt gtt ctt tct gct ctg gcg aca ttc           1913
Gly Thr Gln Leu Thr Ala Gly Gly Val Leu Ser Ala Leu Ala Thr Phe
        555                 560                 565 aga att ctt cag gag cca ctt cgg aac ttt cct gat ctg gtt tca atg           1961
```

-continued

| | | |
|---|---|---|
| Arg Ile Leu Gln Glu Pro Leu Arg Asn Phe Pro Asp Leu Val Ser Met<br>570                       575                     580                      585 | | |
| atg gct cag aca aag gtt tct ctt gat agg att tct ggg ttc ttg cag<br>Met Ala Gln Thr Lys Val Ser Leu Asp Arg Ile Ser Gly Phe Leu Gln<br>                    590                     595                      600 | 2009 | |
| gag gaa gaa ctt caa gaa gat gca act gtt gtt att cca cgg gga ctt<br>Glu Glu Glu Leu Gln Glu Asp Ala Thr Val Val Ile Pro Arg Gly Leu<br>            605                     610                      615 | 2057 | |
| tcg aat ata gcc ata gag att aaa gat ggt gtg ttt tgt tgg gac cct<br>Ser Asn Ile Ala Ile Glu Ile Lys Asp Gly Val Phe Cys Trp Asp Pro<br>      620                     625                     630 | 2105 | |
| ttt tct tca agg ccg aca tta tct ggg att cag atg aaa gtg gag aag<br>Phe Ser Ser Arg Pro Thr Leu Ser Gly Ile Gln Met Lys Val Glu Lys<br>635                       640                     645 | 2153 | |
| ggt atg cgt gtg gct gtc tgt ggc aca gtt ggc tct gga aaa tca agt<br>Gly Met Arg Val Ala Val Cys Gly Thr Val Gly Ser Gly Lys Ser Ser<br>650                       655                     660                     665 | 2201 | |
| ttt atc tct tgc atc cta ggg gaa atc cca aaa atc tct ggc gaa gtt<br>Phe Ile Ser Cys Ile Leu Gly Glu Ile Pro Lys Ile Ser Gly Glu Val<br>                    670                     675                      680 | 2249 | |
| aga ata tgt ggt act act ggt tat gtg tct caa tcg gct tgg att cag<br>Arg Ile Cys Gly Thr Thr Gly Tyr Val Ser Gln Ser Ala Trp Ile Gln<br>            685                     690                     695 | 2297 | |
| tct ggt aac att gaa gaa aac att cta ttt ggc agt cca atg gag aaa<br>Ser Gly Asn Ile Glu Glu Asn Ile Leu Phe Gly Ser Pro Met Glu Lys<br>                    700                     705                     710 | 2345 | |
| aca aag tac aag aat gtg ata caa gca tgt tcc cta aag aaa gat ata<br>Thr Lys Tyr Lys Asn Val Ile Gln Ala Cys Ser Leu Lys Lys Asp Ile<br>715                       720                     725 | 2393 | |
| gag ctt ttc tca cat ggg gac caa act att atc ggg gag aga ggt ata<br>Glu Leu Phe Ser His Gly Asp Gln Thr Ile Ile Gly Glu Arg Gly Ile<br>730                       735                     740                     745 | 2441 | |
| aat ctc agc gga ggt cag aaa cag cgt gta caa ctt gca agg gca tta<br>Asn Leu Ser Gly Gly Gln Lys Gln Arg Val Gln Leu Ala Arg Ala Leu<br>                    750                     755                     760 | 2489 | |
| tat caa gat gct gac att tat tta cta gac gac cct ttt agt gct ctt<br>Tyr Gln Asp Ala Asp Ile Tyr Leu Leu Asp Asp Pro Phe Ser Ala Leu<br>            765                     770                     775 | 2537 | |
| gat gca cac act ggc tct gat ttg ttt agg gat tat att cta tct gca<br>Asp Ala His Thr Gly Ser Asp Leu Phe Arg Asp Tyr Ile Leu Ser Ala<br>                    780                     785                      790 | 2585 | |
| ttg gct gag aaa act gtg gtt ttt gta acg cat caa gtt gag ttt ctc<br>Leu Ala Glu Lys Thr Val Val Phe Val Thr His Gln Val Glu Phe Leu<br>795                       800                     805 | 2633 | |
| cct gca gct gat cta ata ttg gtt ctg aag gaa ggc agg att att caa<br>Pro Ala Ala Asp Leu Ile Leu Val Leu Lys Glu Gly Arg Ile Ile Gln<br>810                       815                     820                     825 | 2681 | |
| tcg ggt aaa tat gat gat ctg ctg caa gca ggt act gat ttt aag gcc<br>Ser Gly Lys Tyr Asp Asp Leu Leu Gln Ala Gly Thr Asp Phe Lys Ala<br>                    830                     835                     840 | 2729 | |
| tta gtg tct gcc cac cat gaa gca atc gag gca atg gac atc cca agt<br>Leu Val Ser Ala His His Glu Ala Ile Glu Ala Met Asp Ile Pro Ser<br>            845                     850                     855 | 2777 | |
| ccc tcc tca gaa gac tct gat gaa aat cct att cgc gat agt ttg gtc<br>Pro Ser Ser Glu Asp Ser Asp Glu Asn Pro Ile Arg Asp Ser Leu Val<br>                    860                     865                     870 | 2825 | |
| ttg cat aat cca aag tct gat gtt ttt gaa aat gac atc gag act ttg<br>Leu His Asn Pro Lys Ser Asp Val Phe Glu Asn Asp Ile Glu Thr Leu<br>875                       880                     885 | 2873 | |
| gca aag gaa gta caa gag gga gga tct gct tca gat cta aag gca atc | 2921 | |

-continued

| | | |
|---|---|---|
| Ala Lys Glu Val Gln Glu Gly Gly Ser Ala Ser Asp Leu Lys Ala Ile<br>890                     895                        900                     905 | |
| aaa gag aag aag aag aaa gct aag cgt tcc cgc aaa aag cag ctt gtt<br>Lys Glu Lys Lys Lys Lys Ala Lys Arg Ser Arg Lys Lys Gln Leu Val<br>910                         915                           920 | 2969 |
| caa gaa gag gaa cga gta aag gga aaa gtc agc atg aag gtg tac ttg<br>Gln Glu Glu Glu Arg Val Lys Gly Lys Val Ser Met Lys Val Tyr Leu<br>925                     930                        935 | 3017 |
| tca tac atg ggt gct gca tat aaa ggg gct ctg att cct ctt att ata<br>Ser Tyr Met Gly Ala Ala Tyr Lys Gly Ala Leu Ile Pro Leu Ile Ile<br>940                     945                        950 | 3065 |
| ctc gca caa gct gct ttc caa ttt ctt cag att gct agt aat tgg tgg<br>Leu Ala Gln Ala Ala Phe Gln Phe Leu Gln Ile Ala Ser Asn Trp Trp<br>955                     960                        965 | 3113 |
| atg gct tgg gca aat cct caa act gaa ggt gac gaa tct aaa gtg gat<br>Met Ala Trp Ala Asn Pro Gln Thr Glu Gly Asp Glu Ser Lys Val Asp<br>970                     975                      980                     985 | 3161 |
| cct act ctg ctt ctc atc gtt tat acg gct tta gct ttc ggg agc tct<br>Pro Thr Leu Leu Leu Ile Val Tyr Thr Ala Leu Ala Phe Gly Ser Ser<br>                   990                        995                     1000 | 3209 |
| gtg ttc ata ttt gtt cga gct gct ctg gtt gca act ttt ggt ctt gca<br>Val Phe Ile Phe Val Arg Ala Ala Leu Val Ala Thr Phe Gly Leu Ala<br>              1005                     1010                     1015 | 3257 |
| gct gca cag aaa ctg ttc tta aat atg ctc aga agt gtg ttc cga gcg<br>Ala Ala Gln Lys Leu Phe Leu Asn Met Leu Arg Ser Val Phe Arg Ala<br>              1020                     1025                     1030 | 3305 |
| cca atg tca ttc ttt gat tcc act cct gca gga aga att ttg aat cgg<br>Pro Met Ser Phe Phe Asp Ser Thr Pro Ala Gly Arg Ile Leu Asn Arg<br>1035                     1040                     1045 | 3353 |
| gtt tct att gat caa agt gtt gta gat ctt gac att cct ttt aga ctc<br>Val Ser Ile Asp Gln Ser Val Val Asp Leu Asp Ile Pro Phe Arg Leu<br>1050                     1055                     1060                     1065 | 3401 |
| ggt ggg ttt gct tca aca aca ata caa ctc tgt ggc att gtc gct gta<br>Gly Gly Phe Ala Ser Thr Thr Ile Gln Leu Cys Gly Ile Val Ala Val<br>              1070                     1075                     1080 | 3449 |
| atg acc aat gtt acc tgg caa gtt ttc ctt ctt gtt gtt ccg gta gct<br>Met Thr Asn Val Thr Trp Gln Val Phe Leu Leu Val Val Pro Val Ala<br>              1085                     1090                     1095 | 3497 |
| gtt gct tgc ttt tgg atg cag aaa tat tac atg gct tct tca aga gaa<br>Val Ala Cys Phe Trp Met Gln Lys Tyr Tyr Met Ala Ser Ser Arg Glu<br>1100                     1105                     1110 | 3545 |
| ttg gtt cgg ata gtt agt atc cag aag tct cca ata att cat ctt ttt<br>Leu Val Arg Ile Val Ser Ile Gln Lys Ser Pro Ile Ile His Leu Phe<br>1115                     1120                     1125 | 3593 |
| gga gaa tca att gct ggt gct gcc aca ata aga gga ttt ggc cag gaa<br>Gly Glu Ser Ile Ala Gly Ala Ala Thr Ile Arg Gly Phe Gly Gln Glu<br>1130                     1135                     1140                     1145 | 3641 |
| aaa aga ttt atc aaa agg aat ctt tat ctt cta gat tgt ttt gtt cga<br>Lys Arg Phe Ile Lys Arg Asn Leu Tyr Leu Leu Asp Cys Phe Val Arg<br>              1150                     1155                     1160 | 3689 |
| cct ttc ttc tgc agt atc gct gct atc gaa tgg ctt tgt tta cgc atg<br>Pro Phe Phe Cys Ser Ile Ala Ala Ile Glu Trp Leu Cys Leu Arg Met<br>              1165                     1170                     1175 | 3737 |
| gaa tta ctt tcc aca ctt gta ttt gct ttc tgt atg gtt tta ctc gtc<br>Glu Leu Leu Ser Thr Leu Val Phe Ala Phe Cys Met Val Leu Leu Val<br>              1180                     1185                     1190 | 3785 |
| agt ttt cca cat gga acc att gat cca agc atg gca ggt ctt gct gtg<br>Ser Phe Pro His Gly Thr Ile Asp Pro Ser Met Ala Gly Leu Ala Val<br>              1195                     1200                     1205 | 3833 |
| aca tat gga ctt aac ttg aat gga cgt cta tca cga tgg ata ctt agc | 3881 |

```
Thr Tyr Gly Leu Asn Leu Asn Gly Arg Leu Ser Arg Trp Ile Leu Ser
1210                1215                1220                1225 ttt tgt aag ctt gaa aac aaa ata atc tca atc gaa agg att tat cag       3929
Phe Cys Lys Leu Glu Asn Lys Ile Ile Ser Ile Glu Arg Ile Tyr Gln
        1230                1235                1240 tac agt cag att gta gga gag gcc cca gca att ata gaa gat ttc cgc       3977
Tyr Ser Gln Ile Val Gly Glu Ala Pro Ala Ile Ile Glu Asp Phe Arg
            1245                1250                1255 ccg cct tcc tcg tgg cct gca acg gga aca att gag cta gtt gat gtt       4025
Pro Pro Ser Ser Trp Pro Ala Thr Gly Thr Ile Glu Leu Val Asp Val
                1260                1265                1270 aag gtt cgt tat gct gag aat ctt cca aca gta ctc cat ggg gtg agc       4073
Lys Val Arg Tyr Ala Glu Asn Leu Pro Thr Val Leu His Gly Val Ser
    1275                1280                1285 tgt gtg ttt ccg ggt gga aaa aag att ggg att gtt ggg cga acg gga       4121
Cys Val Phe Pro Gly Gly Lys Lys Ile Gly Ile Val Gly Arg Thr Gly
1290                1295                1300                1305 agc gga aag tcg act ttg att caa gct ttg ttt cga ttg att gag cca       4169
Ser Gly Lys Ser Thr Leu Ile Gln Ala Leu Phe Arg Leu Ile Glu Pro
            1310                1315                1320 act gct gga aaa att act att gac aac att gac att tct caa att ggt       4217
Thr Ala Gly Lys Ile Thr Ile Asp Asn Ile Asp Ile Ser Gln Ile Gly
                1325                1330                1335 ctt cat gat ctt cgt agt cgc ctt ggg att ata cct caa gat cct aca       4265
Leu His Asp Leu Arg Ser Arg Leu Gly Ile Ile Pro Gln Asp Pro Thr
    1340                1345                1350 tta ttt gaa gga aca atc cga gca aat ctt gac cca ctt gaa gaa cat       4313
Leu Phe Glu Gly Thr Ile Arg Ala Asn Leu Asp Pro Leu Glu Glu His
1355                1360                1365 tca gat gat aaa atc tgg gag gcg ctt gat aaa tcc cag ctt gga gac       4361
Ser Asp Asp Lys Ile Trp Glu Ala Leu Asp Lys Ser Gln Leu Gly Asp
1370                1375                1380                1385 gtt gtt aga gga aaa gac cta aaa ctt gac tct cca gta ctg gaa aat       4409
Val Val Arg Gly Lys Asp Leu Lys Leu Asp Ser Pro Val Leu Glu Asn
            1390                1395                1400 gga gat aac tgg agt gta ggg cag aga cag ctt gtg tca ctt gga cga       4457
Gly Asp Asn Trp Ser Val Gly Gln Arg Gln Leu Val Ser Leu Gly Arg
                1405                1410                1415 gca tta ctg aaa caa gcc aaa ata ctt gtt ctt gat gaa gca aca gca       4505
Ala Leu Leu Lys Gln Ala Lys Ile Leu Val Leu Asp Glu Ala Thr Ala
    1420                1425                1430 tcg gtt gac aca gca aca gac aat ctg atc cag aag ata atc aga aca       4553
Ser Val Asp Thr Ala Thr Asp Asn Leu Ile Gln Lys Ile Ile Arg Thr
1435                1440                1445 gag ttt gaa gac tgc acg gtc tgc acc att gct cac cgg ata cca act       4601
Glu Phe Glu Asp Cys Thr Val Cys Thr Ile Ala His Arg Ile Pro Thr
1450                1455                1460                1465 gtt ata gac agt gac cta gtt ttg gtt ctc agc gac ggt aga gta gca       4649
Val Ile Asp Ser Asp Leu Val Leu Val Leu Ser Asp Gly Arg Val Ala
            1470                1475                1480 gag ttt gat act cct gca cgg cta tta gaa gac aaa tca tcg atg ttc       4697
Glu Phe Asp Thr Pro Ala Arg Leu Leu Glu Asp Lys Ser Ser Met Phe
                1485                1490                1495 ttg aaa ttg gta aca gaa tac tcc tca aga tct act gga atc cct gaa       4745
Leu Lys Leu Val Thr Glu Tyr Ser Ser Arg Ser Thr Gly Ile Pro Glu
    1500                1505                1510 tta tga tcctccatgt taaaaattca gtttaggggg tttctttttct caagaggata      4801
Leu  * taaaagaact gatatgtgac aaaagcttaa ggtctaaagt aagagagagt tttccacagg    4861
```

-continued

```
gtttaagaaa agaaaaagca tgaaaggatg ccaaaatctc cgcgcttaaa aaactttggg    4921
tttaaatctc ttctgtcgaa cattgggaga aacttttttt gtatggaaca gttagtttct    4981
ttggttttca t                                                         4992
```

<210> SEQ ID NO 9
<211> LENGTH: 1514
<212> TYPE: PRT
<213> ORGANISM: Arabidopsis thaliana

<400> SEQUENCE: 9

```
Met Asp Phe Ile Glu Ile Ser Leu Ile Phe Arg Glu His Leu Pro Leu
1               5                   10                  15

Leu Glu Leu Cys Ser Val Ile Ile Asn Leu Leu Phe Leu Val Phe
            20                  25                  30

Leu Phe Ala Val Ser Ala Arg Gln Ile Leu Val Cys Val Arg Arg Gly
        35                  40                  45

Arg Asp Arg Leu Ser Lys Asp Asp Thr Val Ser Ala Ser Asn Leu Ser
    50                  55                  60

Leu Glu Arg Glu Val Asn His Val Ser Val Gly Phe Gly Phe Asn Leu
65                  70                  75                  80

Ser Leu Leu Cys Cys Leu Tyr Val Leu Gly Val Gln Val Leu Val Leu
                85                  90                  95

Val Tyr Asp Gly Val Lys Val Arg Arg Glu Val Ser Asp Trp Phe Val
            100                 105                 110

Leu Cys Phe Pro Ala Ser Gln Ser Leu Ala Trp Phe Val Leu Ser Phe
        115                 120                 125

Leu Val Leu His Leu Lys Tyr Lys Ser Ser Glu Lys Leu Pro Phe Leu
    130                 135                 140

Val Arg Ile Trp Trp Phe Leu Ala Phe Ser Ile Cys Leu Cys Thr Met
145                 150                 155                 160

Tyr Val Asp Gly Arg Arg Leu Ala Ile Glu Gly Trp Ser Arg Cys Ser
                165                 170                 175

Ser His Val Val Ala Asn Leu Ala Val Thr Pro Ala Leu Gly Phe Leu
            180                 185                 190

Cys Phe Leu Ala Trp Arg Gly Val Ser Gly Ile Gln Val Thr Arg Ser
        195                 200                 205

Ser Ser Asp Leu Gln Glu Pro Leu Leu Val Glu Glu Ala Ala Cys
    210                 215                 220

Leu Lys Val Thr Pro Tyr Ser Thr Ala Gly Leu Val Ser Leu Ile Thr
225                 230                 235                 240

Leu Ser Trp Leu Asp Pro Leu Leu Ser Ala Gly Ser Lys Arg Pro Leu
                245                 250                 255

Glu Leu Lys Asp Ile Pro Leu Leu Ala Pro Arg Asp Arg Ala Lys Ser
            260                 265                 270

Ser Tyr Lys Val Leu Lys Ser Asn Trp Lys Arg Cys Lys Ser Glu Asn
        275                 280                 285

Pro Ser Lys Pro Pro Ser Leu Ala Arg Ala Ile Met Lys Ser Phe Trp
    290                 295                 300

Lys Glu Ala Ala Cys Asn Ala Val Phe Ala Gly Leu Asn Thr Leu Val
305                 310                 315                 320

Ser Tyr Val Gly Pro Tyr Leu Ile Ser Tyr Phe Val Asp Tyr Leu Gly
                325                 330                 335

Gly Lys Glu Ile Phe Pro His Gly Tyr Val Leu Ala Gly Ile Phe
            340                 345                 350
```

```
Phe Thr Ser Lys Leu Ile Glu Thr Val Thr Arg Gln Trp Tyr Met
            355                 360                 365

Gly Val Asp Ile Leu Gly Met His Val Arg Ser Ala Leu Thr Ala Met
    370                 375                 380

Val Tyr Arg Lys Gly Leu Lys Leu Ser Ser Ile Ala Lys Gln Asn His
385                 390                 395                 400

Thr Ser Gly Glu Ile Val Asn Tyr Met Ala Val Asp Val Gln Arg Ile
                405                 410                 415

Gly Asp Tyr Ser Trp Tyr Leu His Asp Ile Trp Met Leu Pro Met Gln
            420                 425                 430

Ile Val Leu Ala Leu Ala Ile Leu Tyr Lys Ser Val Gly Ile Ala Ala
            435                 440                 445

Val Ala Thr Leu Val Ala Thr Ile Ile Ser Ile Leu Val Thr Ile Pro
450                 455                 460

Leu Ala Lys Val Gln Glu Asp Tyr Gln Asp Lys Leu Met Thr Ala Lys
465                 470                 475                 480

Asp Glu Arg Met Arg Lys Thr Ser Glu Cys Leu Arg Asn Met Arg Val
                485                 490                 495

Leu Lys Leu Gln Ala Trp Glu Asp Arg Tyr Arg Val Arg Leu Glu Glu
            500                 505                 510

Met Arg Glu Glu Glu Tyr Gly Trp Leu Arg Lys Ala Leu Tyr Ser Gln
            515                 520                 525

Ala Phe Val Thr Phe Ile Phe Trp Ser Ser Pro Ile Phe Val Ala Ala
530                 535                 540

Val Thr Phe Ala Thr Ser Ile Phe Leu Gly Thr Gln Leu Thr Ala Gly
545                 550                 555                 560

Gly Val Leu Ser Ala Leu Ala Thr Phe Arg Ile Leu Gln Glu Pro Leu
                565                 570                 575

Arg Asn Phe Pro Asp Leu Val Ser Met Met Ala Gln Thr Lys Val Ser
            580                 585                 590

Leu Asp Arg Ile Ser Gly Phe Leu Gln Glu Glu Leu Gln Glu Asp
            595                 600                 605

Ala Thr Val Val Ile Pro Arg Gly Leu Ser Asn Ile Ala Ile Glu Ile
610                 615                 620

Lys Asp Gly Val Phe Cys Trp Asp Pro Phe Ser Ser Arg Pro Thr Leu
625                 630                 635                 640

Ser Gly Ile Gln Met Lys Val Glu Lys Gly Met Arg Val Ala Val Cys
                645                 650                 655

Gly Thr Val Gly Ser Gly Lys Ser Ser Phe Ile Ser Cys Ile Leu Gly
            660                 665                 670

Glu Ile Pro Lys Ile Ser Gly Glu Val Arg Ile Cys Gly Thr Thr Gly
            675                 680                 685

Tyr Val Ser Gln Ser Ala Trp Ile Gln Ser Gly Asn Ile Glu Glu Asn
690                 695                 700

Ile Leu Phe Gly Ser Pro Met Glu Lys Thr Lys Tyr Lys Asn Val Ile
705                 710                 715                 720

Gln Ala Cys Ser Leu Lys Lys Asp Ile Glu Leu Phe Ser His Gly Asp
                725                 730                 735

Gln Thr Ile Ile Gly Glu Arg Gly Ile Asn Leu Ser Gly Gly Gln Lys
            740                 745                 750

Gln Arg Val Gln Leu Ala Arg Ala Leu Tyr Gln Asp Ala Asp Ile Tyr
            755                 760                 765

Leu Leu Asp Asp Pro Phe Ser Ala Leu Asp Ala His Thr Gly Ser Asp
770                 775                 780
```

```
Leu Phe Arg Asp Tyr Ile Leu Ser Ala Leu Ala Glu Lys Thr Val Val
785                 790                 795                 800

Phe Val Thr His Gln Val Glu Phe Leu Pro Ala Ala Asp Leu Ile Leu
                805                 810                 815

Val Leu Lys Glu Gly Arg Ile Ile Gln Ser Gly Lys Tyr Asp Asp Leu
            820                 825                 830

Leu Gln Ala Gly Thr Asp Phe Lys Ala Leu Val Ser Ala His His Glu
        835                 840                 845

Ala Ile Glu Ala Met Asp Ile Pro Ser Pro Ser Ser Glu Asp Ser Asp
850                 855                 860

Glu Asn Pro Ile Arg Asp Ser Leu Val Leu His Asn Pro Lys Ser Asp
865                 870                 875                 880

Val Phe Glu Asn Asp Ile Glu Thr Leu Ala Lys Glu Val Gln Glu Gly
                885                 890                 895

Gly Ser Ala Ser Asp Leu Lys Ala Ile Lys Glu Lys Lys Lys Lys Ala
            900                 905                 910

Lys Arg Ser Arg Lys Lys Gln Leu Val Gln Glu Glu Arg Val Lys
        915                 920                 925

Gly Lys Val Ser Met Lys Val Tyr Leu Ser Tyr Met Gly Ala Ala Tyr
    930                 935                 940

Lys Gly Ala Leu Ile Pro Leu Ile Ile Leu Ala Gln Ala Ala Phe Gln
945                 950                 955                 960

Phe Leu Gln Ile Ala Ser Asn Trp Trp Met Ala Trp Ala Asn Pro Gln
                965                 970                 975

Thr Glu Gly Asp Glu Ser Lys Val Asp Pro Thr Leu Leu Ile Val
            980                 985                 990

Tyr Thr Ala Leu Ala Phe Gly Ser Ser Val Phe Ile Phe Val Arg Ala
        995                 1000                1005

Ala Leu Val Ala Thr Phe Gly Leu Ala Ala Gln Lys Leu Phe Leu
    1010                1015                1020

Asn Met Leu Arg Ser Val Phe Arg Ala Pro Met Ser Phe Phe Asp Ser
1025                1030                1035                1040

Thr Pro Ala Gly Arg Ile Leu Asn Arg Val Ser Ile Asp Gln Ser Val
                1045                1050                1055

Val Asp Leu Asp Ile Pro Phe Arg Leu Gly Gly Phe Ala Ser Thr Thr
            1060                1065                1070

Ile Gln Leu Cys Gly Ile Val Ala Val Met Thr Asn Val Thr Trp Gln
        1075                1080                1085

Val Phe Leu Leu Val Val Pro Val Ala Val Ala Cys Phe Trp Met Gln
    1090                1095                1100

Lys Tyr Tyr Met Ala Ser Ser Arg Glu Leu Val Arg Ile Val Ser Ile
1105                1110                1115                1120

Gln Lys Ser Pro Ile Ile His Leu Phe Gly Glu Ser Ile Ala Gly Ala
                1125                1130                1135

Ala Thr Ile Arg Gly Phe Gly Gln Glu Lys Arg Phe Ile Lys Arg Asn
            1140                1145                1150

Leu Tyr Leu Leu Asp Cys Phe Val Arg Pro Phe Phe Cys Ser Ile Ala
        1155                1160                1165

Ala Ile Glu Trp Leu Cys Leu Arg Met Glu Leu Leu Ser Thr Leu Val
    1170                1175                1180

Phe Ala Phe Cys Met Val Leu Leu Val Ser Phe Pro His Gly Thr Ile
1185                1190                1195                1200

Asp Pro Ser Met Ala Gly Leu Ala Val Thr Tyr Gly Leu Asn Leu Asn
```

```
                    1205                1210                1215
Gly Arg Leu Ser Arg Trp Ile Leu Ser Phe Cys Lys Leu Glu Asn Lys
                1220                1225                1230

Ile Ile Ser Ile Glu Arg Ile Tyr Gln Tyr Ser Gln Ile Val Gly Glu
            1235                1240                1245

Ala Pro Ala Ile Ile Glu Asp Phe Arg Pro Pro Ser Ser Trp Pro Ala
        1250                1255                1260

Thr Gly Thr Ile Glu Leu Val Asp Val Lys Val Arg Tyr Ala Glu Asn
1265                1270                1275                1280

Leu Pro Thr Val Leu His Gly Val Ser Cys Val Phe Pro Gly Gly Lys
                1285                1290                1295

Lys Ile Gly Ile Val Gly Arg Thr Gly Ser Gly Lys Ser Thr Leu Ile
            1300                1305                1310

Gln Ala Leu Phe Arg Leu Ile Glu Pro Thr Ala Gly Lys Ile Thr Ile
        1315                1320                1325

Asp Asn Ile Asp Ile Ser Gln Ile Gly Leu His Asp Leu Arg Ser Arg
    1330                1335                1340

Leu Gly Ile Ile Pro Gln Asp Pro Thr Leu Phe Glu Gly Thr Ile Arg
1345                1350                1355                1360

Ala Asn Leu Asp Pro Leu Glu Glu His Ser Asp Asp Lys Ile Trp Glu
                1365                1370                1375

Ala Leu Asp Lys Ser Gln Leu Gly Asp Val Val Arg Gly Lys Asp Leu
            1380                1385                1390

Lys Leu Asp Ser Pro Val Leu Glu Asn Gly Asp Asn Trp Ser Val Gly
        1395                1400                1405

Gln Arg Gln Leu Val Ser Leu Gly Arg Ala Leu Leu Lys Gln Ala Lys
    1410                1415                1420

Ile Leu Val Leu Asp Glu Ala Thr Ala Ser Val Asp Thr Ala Thr Asp
1425                1430                1435                1440

Asn Leu Ile Gln Lys Ile Ile Arg Thr Glu Phe Glu Asp Cys Thr Val
                1445                1450                1455

Cys Thr Ile Ala His Arg Ile Pro Thr Val Ile Asp Ser Asp Leu Val
            1460                1465                1470

Leu Val Leu Ser Asp Gly Arg Val Ala Glu Phe Asp Thr Pro Ala Arg
        1475                1480                1485

Leu Leu Glu Asp Lys Ser Ser Met Phe Leu Lys Leu Val Thr Glu Tyr
    1490                1495                1500

Ser Ser Arg Ser Thr Gly Ile Pro Glu Leu
1505                1510

<210> SEQ ID NO 10
<211> LENGTH: 1350
<212> TYPE: DNA
<213> ORGANISM: Glycine max
<220> FEATURE:
<221> NAME/KEY: CDS
<222> LOCATION: (3)...(1350)

<400> SEQUENCE: 10 gc acg agt gga ctt gct gtg aca tat ggc ctg aat tta aat gca cgt       47
   Thr Ser Gly Leu Ala Val Thr Tyr Gly Leu Asn Leu Asn Ala Arg
   1               5                  10                  15 cta tca cgg tgg ata ctc agc ttt tgc aaa ctt gaa aat aaa att ata      95
Leu Ser Arg Trp Ile Leu Ser Phe Cys Lys Leu Glu Asn Lys Ile Ile
           20                  25                  30 tct att gag aga att tat cag tac agc caa att cct agt gaa gca ccc     143
Ser Ile Glu Arg Ile Tyr Gln Tyr Ser Gln Ile Pro Ser Glu Ala Pro
```

```
              35                  40                  45
aca gtt att gaa gat tat cgc cct cca tcc tca tgg cct gaa aat ggg     191
Thr Val Ile Glu Asp Tyr Arg Pro Pro Ser Ser Trp Pro Glu Asn Gly
         50                  55                  60 aca att gaa ata att gat ttg aag att cgt tac aag gag aat ctt cct     239
Thr Ile Glu Ile Ile Asp Leu Lys Ile Arg Tyr Lys Glu Asn Leu Pro
 65                  70                  75 ttg gtg ctt tat gga gta aca tgc aca ttt cct ggt gga aag aag att     287
Leu Val Leu Tyr Gly Val Thr Cys Thr Phe Pro Gly Gly Lys Lys Ile
 80                  85                  90                  95 gga ata gta gga cgt act ggc agt gga aaa tct act tta att cag gcg     335
Gly Ile Val Gly Arg Thr Gly Ser Gly Lys Ser Thr Leu Ile Gln Ala
                100                 105                 110 tta ttt cga ttg att gaa cca aca agt ggg agt atc ctt ata gac aac     383
Leu Phe Arg Leu Ile Glu Pro Thr Ser Gly Ser Ile Leu Ile Asp Asn
            115                 120                 125 att aat att tca gag att ggc ctt cat gac ctt cga agc cat ctc agt     431
Ile Asn Ile Ser Glu Ile Gly Leu His Asp Leu Arg Ser His Leu Ser
        130                 135                 140 atc ata cca caa gat cca acc tta ttt gaa ggt acc att cga ggc aat     479
Ile Ile Pro Gln Asp Pro Thr Leu Phe Glu Gly Thr Ile Arg Gly Asn
    145                 150                 155 ctt gat cct ctg gat gag cac tca gat aaa gag att tgg gag gca ctt     527
Leu Asp Pro Leu Asp Glu His Ser Asp Lys Glu Ile Trp Glu Ala Leu
160                 165                 170                 175 gat aag tct cag ctt gga gag gtt atc cgt gag aaa gga caa cag ctt     575
Asp Lys Ser Gln Leu Gly Glu Val Ile Arg Glu Lys Gly Gln Gln Leu
                180                 185                 190 gat acg cca gtt cta gaa aat gga gat aat tgg agt gta gga cag cga     623
Asp Thr Pro Val Leu Glu Asn Gly Asp Asn Trp Ser Val Gly Gln Arg
            195                 200                 205 caa ctt gtt gct ctg ggc cga gct ctg ctg cag cag tca aga ata ctt     671
Gln Leu Val Ala Leu Gly Arg Ala Leu Leu Gln Gln Ser Arg Ile Leu
        210                 215                 220 gta cta gat gaa gca aca gca tca gtt gat acc gcc aca gat aat ctt     719
Val Leu Asp Glu Ala Thr Ala Ser Val Asp Thr Ala Thr Asp Asn Leu
    225                 230                 235 ata cag aag att atc cga agt gag ttc aaa gaa tgc act gtt tgc acc     767
Ile Gln Lys Ile Ile Arg Ser Glu Phe Lys Glu Cys Thr Val Cys Thr
240                 245                 250                 255 att gca cat cga ata cct act gtc att gac agt gat cta gtt ctt gtg     815
Ile Ala His Arg Ile Pro Thr Val Ile Asp Ser Asp Leu Val Leu Val
                260                 265                 270 ctc agt gat ggt cga gtt gca gag ttc aac act cct tca aga cta tta     863
Leu Ser Asp Gly Arg Val Ala Glu Phe Asn Thr Pro Ser Arg Leu Leu
            275                 280                 285 gag gat aag tca tcc atg ttt ctg aag ctg gtg act gag tac tca tca     911
Glu Asp Lys Ser Ser Met Phe Leu Lys Leu Val Thr Glu Tyr Ser Ser
        290                 295                 300 cgt tca agt ggc ata cca gac ttt tag aac aaa tgg aag gtg tga atg     959
Arg Ser Ser Gly Ile Pro Asp Phe  *  Asn Lys Trp Lys Val  *  Met
    305                 310                 315 ctt tca tag tgt ggt ggc tgg agc tta aga tag ttc aaa agt tga atc    1007
Leu Ser  *  Cys Gly Gly Trp Ser Leu Arg  *  Phe Lys Ser  *  Ile
                320                 325                 330 agg aag tga tgc cac cct tgc atg tca ctg ctg cat tcg ggg cat gca    1055
Arg Lys  *  Cys His Pro Cys Met Ser Leu Leu His Ser Gly His Ala
            335                 340                 345 tag aga cac gag atg gaa aca aac aaa ata aaa ggg aga ggt ttg tgc    1103
 *  Arg His Glu Met Glu Thr Asn Lys Ile Lys Gly Arg Gly Leu Cys
```

```
                         350                   355                  360
ctc ctc atg aat caa gca tcc tac tgg ggg aaa ttt gtt tga tta ttc        1151
Leu Leu Met Asn Gln Ala Ser Tyr Trp Gly Lys Phe Val  *  Leu Phe
                         365                   370                  375 ccc tta aag ttg aga aat tca tgc aag gtt agc atg ctt tgt aac aca        1199
Pro Leu Lys Leu Arg Asn Ser Cys Lys Val Ser Met Leu Cys Asn Thr
                         380                   385                  390 aaa taa gat gat ctg tga tta cag gaa agt aac gaa ata gtt tgt aga        1247
Lys  *  Asp Asp Leu  *  Leu Gln Glu Ser Asn Glu Ile Val Cys Arg
                         395                   400                  405 atg agg cac tag gat ttt gct tgg tta gaa aaa gtg tag agt tta aac        1295
Met Arg His  *  Asp Phe Ala Trp Leu Glu Lys Val  *  Ser Leu Asn
                         410                   415 tag ttt tgt gta ttc cac aat ttt ctt gta gtg aaa gtt tag aat taa        1343
 *  Phe Cys Val Phe His Asn Phe Leu Val Val Lys Val  *  Asn  *
                         420                   425                  430 gcc aaa a                                                              1350
Ala Lys <210> SEQ ID NO 11
<211> LENGTH: 434
<212> TYPE: PRT
<213> ORGANISM: Glycine max

<400> SEQUENCE: 11

Thr Ser Gly Leu Ala Val Thr Tyr Gly Leu Asn Leu Asn Ala Arg Leu
1               5                   10                  15

Ser Arg Trp Ile Leu Ser Phe Cys Lys Leu Glu Asn Lys Ile Ile Ser
            20                  25                  30

Ile Glu Arg Ile Tyr Gln Tyr Ser Gln Ile Pro Ser Glu Ala Pro Thr
        35                  40                  45

Val Ile Glu Asp Tyr Arg Pro Pro Ser Ser Trp Pro Glu Asn Gly Thr
    50                  55                  60

Ile Glu Ile Ile Asp Leu Lys Ile Arg Tyr Lys Glu Asn Leu Pro Leu
65                  70                  75                  80

Val Leu Tyr Gly Val Thr Cys Thr Phe Pro Gly Gly Lys Lys Ile Gly
                85                  90                  95

Ile Val Gly Arg Thr Gly Ser Gly Lys Ser Thr Leu Ile Gln Ala Leu
            100                 105                 110

Phe Arg Leu Ile Glu Pro Thr Ser Gly Ser Ile Leu Ile Asp Asn Ile
        115                 120                 125

Asn Ile Ser Glu Ile Gly Leu His Asp Leu Arg Ser His Leu Ser Ile
130                 135                 140

Ile Pro Gln Asp Pro Thr Leu Phe Glu Gly Thr Ile Arg Gly Asn Leu
145                 150                 155                 160

Asp Pro Leu Asp Glu His Ser Asp Lys Glu Ile Trp Glu Ala Leu Asp
                165                 170                 175

Lys Ser Gln Leu Gly Glu Val Ile Arg Glu Lys Gly Gln Gln Leu Asp
            180                 185                 190

Thr Pro Val Leu Glu Asn Gly Asp Asn Trp Ser Val Gly Gln Arg Gln
        195                 200                 205

Leu Val Ala Leu Gly Arg Ala Leu Leu Gln Gln Ser Arg Ile Leu Val
    210                 215                 220

Leu Asp Glu Ala Thr Ala Ser Val Asp Thr Ala Thr Asp Asn Leu Ile
225                 230                 235                 240

Gln Lys Ile Ile Arg Ser Glu Phe Lys Glu Cys Thr Val Cys Thr Ile
                245                 250                 255
```

```
Ala His Arg Ile Pro Thr Val Ile Asp Ser Asp Leu Val Leu Val Leu
            260                 265                 270

Ser Asp Gly Arg Val Ala Glu Phe Asn Thr Pro Ser Arg Leu Leu Glu
        275                 280                 285

Asp Lys Ser Ser Met Phe Leu Lys Leu Val Thr Glu Tyr Ser Ser Arg
    290                 295                 300

Ser Ser Gly Ile Pro Asp Phe Asn Lys Trp Lys Val Met Leu Ser Cys
305                 310                 315                 320

Gly Gly Trp Ser Leu Arg Phe Lys Ser Ile Arg Lys Cys His Pro Cys
                325                 330                 335

Met Ser Leu Leu His Ser Gly His Ala Arg His Glu Met Glu Thr Asn
            340                 345                 350

Lys Ile Lys Gly Arg Gly Leu Cys Leu Leu Met Asn Gln Ala Ser Tyr
        355                 360                 365

Trp Gly Lys Phe Val Leu Phe Pro Leu Lys Leu Arg Asn Ser Cys Lys
    370                 375                 380

Val Ser Met Leu Cys Asn Thr Lys Asp Asp Leu Leu Gln Glu Ser Asn
385                 390                 395                 400

Glu Ile Val Cys Arg Met Arg His Asp Phe Ala Trp Leu Glu Lys Val
                405                 410                 415

Ser Leu Asn Phe Cys Val Phe His Asn Phe Leu Val Val Lys Val Asn
            420                 425                 430

Ala Lys

<210> SEQ ID NO 12
<211> LENGTH: 465
<212> TYPE: DNA
<213> ORGANISM: Glycine max
<220> FEATURE:
<221> NAME/KEY: CDS
<222> LOCATION: (1)...(465)
<220> FEATURE:
<221> NAME/KEY: misc_feature
<222> LOCATION: (0)...(0)
<223> OTHER INFORMATION: "n" can be any nucleotide

<400> SEQUENCE: 12 ngn aat tgc ttn cnt ngg tgc ana cgt ttg gtt gct nnc aac caa tnc      48
Xaa Asn Cys Xaa Xaa Cys Xaa Arg Leu Val Ala Xaa Asn Gln Xaa
1               5                   10                  15 ccc att ngt tgc can ntg tnc ctt gtg gcc tag ggt cca nga aga ttt      96
Pro Ile Xaa Cys Xaa Xaa Xaa Leu Val Ala  *  Gly Pro Xaa Arg Phe
            20                  25                  30 ttc agg aca aat tgn tgc cca cct aag gan tga aag gnt gag aaa gcc     144
Phe Arg Thr Asn Xaa Cys Pro Pro Lys Xaa  *  Lys Xaa Glu Lys Ala
        35                  40                  45 act cag agt gtc tta gga ntn tga gga ttc tca agc tnc aag ctt ggg     192
Thr Gln Ser Val Leu Gly Xaa  *  Gly Phe Ser Ser Xaa Lys Leu Gly
    50                  55                  60 agg atc gat atc gat tga agt tgg agg aaa tgc gtg gag tng agt tca     240
Arg Ile Asp Ile Asp  *  Ser Trp Arg Lys Cys Val Glu Xaa Ser Ser
65                  70                  75 agt ggc ata agg aaa nca ctc tat tct cag gct tgc ata act ttc atg     288
Ser Gly Ile Arg Lys Xaa Leu Tyr Ser Gln Ala Cys Ile Thr Phe Met
                80                  85                  90 ttc tgg agc tcc cct ata ttt gtt tca gct gtt act ttt gct act tcc     336
Phe Trp Ser Ser Pro Ile Phe Val Ser Ala Val Thr Phe Ala Thr Ser
            95                  100                 105 ata ttg ttg ggg ggt cag ttg aca gca ggt ggt gtt ctc tct gct cta     384
```

```
Ile Leu Leu Gly Gly Gln Leu Thr Ala Gly Gly Val Leu Ser Ala Leu
            110                 115                 120 gct act ttc agg att cgc caa gan cct ntg agg aat ttt cct gac ttg    432
Ala Thr Phe Arg Ile Arg Gln Xaa Pro Xaa Arg Asn Phe Pro Asp Leu
125                 130                 135                 140 gta tca acc atg gct cag aca aaa gtt tct ctt                        465
Val Ser Thr Met Ala Gln Thr Lys Val Ser Leu
                145                 150

<210> SEQ ID NO 13
<211> LENGTH: 151
<212> TYPE: PRT
<213> ORGANISM: Glycine max
<220> FEATURE:
<221> NAME/KEY: VARIANT
<222> LOCATION: (0)...(0)
<223> OTHER INFORMATION: "Xaa" can be any amino acid

<400> SEQUENCE: 13

Xaa Asn Cys Xaa Xaa Cys Xaa Arg Leu Val Ala Xaa Asn Gln Xaa
1               5                   10                  15

Pro Ile Xaa Cys Xaa Xaa Xaa Leu Val Ala Gly Pro Xaa Arg Phe Phe
                20                  25                  30

Arg Thr Asn Xaa Cys Pro Pro Lys Xaa Lys Xaa Glu Lys Ala Thr Gln
                35                  40                  45

Ser Val Leu Gly Xaa Gly Phe Ser Ser Xaa Lys Leu Gly Arg Ile Asp
            50                  55                  60

Ile Asp Ser Trp Arg Lys Cys Val Glu Xaa Ser Ser Gly Ile Arg
65                  70                  75                  80

Lys Xaa Leu Tyr Ser Gln Ala Cys Ile Thr Phe Met Phe Trp Ser Ser
                85                  90                  95

Pro Ile Phe Val Ser Ala Val Thr Phe Ala Thr Ser Ile Leu Leu Gly
                100                 105                 110

Gly Gln Leu Thr Ala Gly Gly Val Leu Ser Ala Leu Ala Thr Phe Arg
            115                 120                 125

Ile Arg Gln Xaa Pro Xaa Arg Asn Phe Pro Asp Leu Val Ser Thr Met
130                 135                 140

Ala Gln Thr Lys Val Ser Leu
145                 150

<210> SEQ ID NO 14
<211> LENGTH: 4050
<212> TYPE: DNA
<213> ORGANISM: Artificial Sequence
<220> FEATURE:
<223> OTHER INFORMATION: Consensus sequence

<400> SEQUENCE: 14
tggaytacgc kcacatggtt gccaacttcg cgtcsgygcc ggccctsggs ttcctstgct     60
tggttggtgt catgggttcc accggtktkg aattggagtt yacsgasgay grcarcrgys   120
tkcatgarcc gctsytgctc ggyrggcagc gsagagasgc mgasgaggag cycggstgyy   180
tgmgggtsac kccstaygsy gatgctggga tystyagcct tgcaacattr tcatggctta   240
gtccgytgct stcwgttggt gcgcagcgrc cacttgagyt ggctgacata cccttgmtgg   300
crcacaarga ccgtgcmaar tcmtgctaya aggcgatgag crstcactay garcgccagc   360
ggmtrgaryr cccyggcags garccatcac tsrcatgggc aataytsaag tcrttctggc   420
gwgaggcmgc grtcaatggy rcwttygcwg ckgtsaacac rattgtstcs tatgttggmc   480
cwtacytgat cagctayttt gtggactacc tcagtggcaa mattgmwttc ccccatgaag   540
```

```
gttacatcct tgcctctrta tttttttgtag caaarytrct tgagacrctc actgcycgrc      600
agtggtactt gggygtggay rtcatgggga tccatgtcaa gtctggscts ackgccatgg      660
tgtayaggaa gggyctymgr ctgtcraayk cctcrcggca gagccacacs agtggtgaga      720
ttgtgaatta catggcsgty gatgtrcagc gtgtggggga ctatgcatgg tayttycatg      780
acatctggat gcttccmctg cagatcatyc tygcyctcgc catcctgtac aagaaygtyg      840
gratcgccat ggtttcaaca ttggtagcwa ctgtrytatc ratygcwgcc tcwgttcctg      900
tggcraagct gcaggagcac taccaagata agytwatggc mtcaaargat gagcgcatgc      960
gcaagacwtc agagtgcytg aaraatatga ggattttgaa gctycargcr tgggaggatc     1020
grtacmggct gmagttggaa gagatgagra aygtggaatg carrtggctt cggtgggctc     1080
tgtaytcaca ggcygcagtt acatttgttt tctggagytc rccaatcttt gtcgcmgtsa     1140
taacwtttgg gacttgyata ttrctyggtg gcsarctcac tgcwggaggk gttctwtcyg     1200
ctttagcaac rtttmggatc ctycaagarc cwctkaggaa yttcccrgat ctyatctcta     1260
tgatkgcwca gacragggtr tctttggacc gkttgtctca ytttctkcar caagaagaay     1320
tgccagatga ygcaactata amkgttccac awrgtagtac agataaggca rtcratatwa     1380
akgatgsyrc attctcttgg aacccatmyw ctcyraccc  tacactttct gryatmmacc     1440
ttagtgtrgt gagrggyatg mgagtagcag tstgtggtgt cattggttct ggyaaatcaa     1500
gyytrytrtc ktctatactc ggsgagatac ccaaattrtg tggycawgts aggatmagtg     1560
gmwcagcagc rtatgtycct cagactgcmt ggatacagtc yggaaayatt gaggagaaya     1620
ttctktttgg cagtcmaatg gayaracarc gttacaagag agtyattgmr gcttgctsyc     1680
tkaagaaaga tcttsagytg ctccartayg gagatcagac yrtyatyggt gatagrggca     1740
ttaatttgag tggrggtcag aaacaaagag twcagcttgc wagagcactm taccaagatg     1800
ctgatattta tttgctygat gatcccttca gtgckgttga tgctcatact gggagygaay     1860
trtttargga rtatatattg actgcactag caascaaarac mgtaatytat gtaacmcatc     1920
aarttgartt tctaccagct gctgayytga taytggttct taaggatggy catatcacmc     1980
aagctggaaa rtatgatgat cttctscaag ctggmactga tttcaatgct ytggtttstg     2040
ctcataagga agctattgar accatggaww twtyygaaga ttccgatrrk gatacwgtyt     2100
cttctrttcc yawcaaaaga ytgacrccaa gtrtyagcaa tatwgataay ctgaaaaaya     2160
agrtgtsyra waatgramaa ccatctarta crcgkggaat waargaaaar aagaagaagc     2220
cwgaagagcg taagaagaag cgkwctgttc aagaggagga ragggarcgw ggaarrgtka     2280
gctymmargt ttayttgtca tacatgggrg aagcwtacaa aggtacactg ataccmctma     2340
ttatcytggc ycaaaccatg ttycaagtwc ttcagattgc gagyaactgg tggatggcat     2400
gggcaaaccc acaaacagaa ggagatgcwc cyaagacaga yagtgtggty ctyytggttg     2460
tttatatgtc ccttgccttt ggragttcay trtttgtgtt yrtgagaagy cttcttgtgg     2520
ctacrtttgg tttagcarct gcmcagaagc tktttrtaaa ratgctwagg tgtgtytttc     2580
gagckccaat gtcattcttt gayacyacac catctggtcg rattttgaac mgagtttctg     2640
tagatcaaag tgtygtggac cttgatatag crttcagact tggtggattt gcatcaacra     2700
caattcaact mcttggaatt gttgctgtca tgagcaaagt cacatggcaa gttytgattc     2760
ttatagtycc yatggctgtt gcatgcatgt ggatgcagag rtattatatt gcttcatcaa     2820
gggaaytrac taggatyttr agygtwcaga agtckccrgt gatccatttg tttagtgart     2880
caattgctgg tgctgctaca atmagrggtt ttggtcaaga gaarcgrtty atgaaaagra     2940
```

```
atctttayct tcttgactgt tttgctcgsc ctytattttc cagcctkgcw gctattgaat    3000
ggctstgcct gcgaatggaa ttgctytcga cyttygtctt ygcttttgc atggcratac     3060 twgtgagctt ycctcctggc acaatygaac caagtatggc tggsctygct gtmacwtatg    3120
gacttaattt aaatgctcgc atgtcaagrt ggatavtgag cttctgtaaa ttagagaaya    3180
gratmatctc tgttgarcgc atttatcart attgcargct tccyagtgaa gcaccaytsa    3240
tyattgagaa ywgccgtccm ycatcmtcrt ggcctsagaa tggaaacatt garctgrtyg    3300
atctcaaggt mcgstacaar gaygayctrc cmttagttct wcatggwrtm agttgtatrt    3360
ttccyggygg raaaaagatt gggattgtrg ggcgwactgg aagyggtaaa tctactctta    3420
ttcaggccct tttccgcyta attgarccya cwggagggaa rrttatmaty gaymacrtyg    3480
ayatytctrs aattggccts catgatctgc ggtcacggtt gagcatcatt ccccargacc    3540
ctacrttgtt tgagggtact atcagaatga aycttgatcc tcttgargar tgyactgatc    3600
argaaatttg ggaggcacta gaaaagtgtc agctmggaga ggtcattcgk tccaaggawg    3660
araarctkga cagtccagtr ctrgaraayg grgataactg gagygtggga carcgccarc    3720
ttattgcayt ggggtagggcs ctgctsaarc aggcaaaaat tttggtrcty gaygaggcra    3780
cagcatcwgt ygacacagcw acrgacaatc ttatycaaaa gatyatycgc agtgaattca    3840
aggaytgcac rgtctgyacc attgcwcacc gtatyccsac sgttattgay agtgacctwg    3900
tyctggtsct tagtgatggt aaaatygcag agttygacac rccccagagg ctyttrgagg    3960
acaagtcmtc yatgttcatr cagctagtat ckgaatactc mactcggtcr agctgtatat    4020
agagaggctt agcttaaaay cccscmcmmm                                     4050
```

<210> SEQ ID NO 15  
<211> LENGTH: 1522  
<212> TYPE: PRT  
<213> ORGANISM: Artificial Sequence  
<220> FEATURE:  
<223> OTHER INFORMATION: Consensus sequence  
<220> FEATURE:  
<221> NAME/KEY: VARIANT  
<222> LOCATION: (0)...(0)  
<223> OTHER INFORMATION: Xaa can be any amino acid

<400> SEQUENCE: 15

```
Xaa Xaa Xaa Ile Pro Xaa Phe Pro Xaa Leu Pro Leu Pro Glu Ala Leu
1               5                   10                  15

Ala Ala Xaa Ala His Ala Ala Leu Leu Ala Leu Ala Xaa Leu Leu Leu
            20                  25                  30

Leu Leu Arg Ala Ala Arg Ala Leu Ala Ser Arg Cys Ala Ser Cys Leu
        35                  40                  45

Lys Xaa Xaa Xaa Arg Arg Xaa Xaa Xaa Xaa Xaa Ala Ala Xaa Xaa
        50                  55                  60

Xaa Gly Gly Xaa Leu Ala Ala Ala Ser Val Gly Ala Trp His Arg Ala
65                  70                  75                  80

Ala Leu Ala Cys Cys Ala Tyr Ala Leu Leu Ala Gln Val Ala Val Leu
                85                  90                  95

Ser Tyr Glu Val Ala Val Ala Gly Ser Xaa Val Ser Xaa Xaa Xaa Ala
            100                 105                 110

Leu Leu Leu Pro Ala Val Gln Ala Leu Ala Trp Ala Ala Leu Leu Ala
        115                 120                 125

Leu Ala Leu Gln Ala Arg Ala Val Gly Trp Ala Arg Phe Pro Xaa Leu
    130                 135                 140
```

```
Val Arg Ile Trp Trp Val Val Ser Phe Ala Leu Cys Val Xaa Ile Ala
145                 150                 155                 160

Tyr Asp Asp Ser Arg Arg Leu Ile Gly Asp Gly Xaa Xaa Xaa Xaa
            165                 170                 175

Xaa Xaa Ala His Met Val Ala Asn Phe Ala Ser Xaa Pro Ala Leu Gly
        180                 185                 190

Phe Leu Cys Leu Val Gly Val Met Gly Ser Thr Gly Ile Glu Leu Glu
            195                 200                 205

Phe Thr Asp Asp Xaa Xaa Leu His Glu Pro Leu Leu Leu Gly Xaa
            210                 215                 220

Gln Arg Arg Asp Ala Glu Glu Xaa Gly Cys Leu Arg Val Thr Pro
225                 230                 235                 240

Tyr Ala Asp Ala Gly Ile Val Ser Leu Ala Thr Leu Ser Trp Leu Ser
                245                 250                 255

Pro Leu Leu Ser Val Gly Ala Gln Arg Pro Leu Glu Leu Ala Asp Ile
            260                 265                 270

Pro Leu Leu Ala His Lys Asp Arg Ala Lys Ser Cys Tyr Lys Ala Met
            275                 280                 285

Ser Ser His Tyr Glu Arg Gln Arg Leu Glu Xaa Pro Gly Lys Glu Pro
290                 295                 300

Ser Leu Ala Trp Ala Ile Leu Lys Ser Phe Trp Arg Glu Ala Ala Ile
305                 310                 315                 320

Asn Gly Xaa Phe Ala Ala Val Asn Thr Ile Val Ser Tyr Val Gly Pro
            325                 330                 335

Tyr Leu Ile Ser Tyr Phe Val Asp Tyr Leu Ser Gly Lys Ile Xaa Phe
            340                 345                 350

Pro His Glu Gly Tyr Ile Leu Ala Ser Ile Phe Phe Val Ala Lys Leu
            355                 360                 365

Leu Glu Thr Leu Thr Ala Arg Gln Trp Tyr Leu Gly Val Asp Ile Met
            370                 375                 380

Gly Ile His Val Lys Ser Gly Leu Thr Ala Met Val Tyr Arg Lys Gly
385                 390                 395                 400

Leu Arg Leu Ser Asn Ala Ser Arg Gln Ser His Thr Ser Gly Glu Ile
                405                 410                 415

Val Asn Tyr Met Ala Val Asp Val Gln Arg Val Gly Asp Tyr Ala Trp
            420                 425                 430

Tyr Phe His Asp Ile Trp Met Leu Pro Leu Gln Ile Ile Leu Ala Leu
            435                 440                 445

Ala Ile Leu Tyr Lys Asn Val Gly Ile Ala Met Val Ser Thr Leu Val
            450                 455                 460

Ala Thr Val Leu Ser Ile Ala Ala Ser Val Pro Val Ala Lys Leu Gln
465                 470                 475                 480

Glu His Tyr Gln Asp Lys Leu Met Ala Ser Lys Asp Glu Arg Met Arg
            485                 490                 495

Lys Thr Ser Glu Cys Leu Lys Asn Met Arg Ile Leu Lys Leu Gln Ala
            500                 505                 510

Trp Glu Asp Arg Tyr Arg Leu Lys Leu Glu Glu Met Arg Asn Val Glu
            515                 520                 525

Cys Lys Trp Leu Arg Trp Ala Leu Tyr Ser Gln Ala Ala Val Thr Phe
530                 535                 540

Val Phe Trp Ser Ser Pro Ile Phe Val Ala Val Ile Thr Phe Gly Thr
545                 550                 555                 560

Cys Ile Leu Leu Gly Gly Gln Leu Thr Ala Gly Gly Val Leu Ser Ala
                565                 570                 575
```

```
Leu Ala Thr Phe Arg Ile Leu Gln Glu Pro Leu Arg Asn Phe Pro Asp
            580                 585                 590

Leu Ile Ser Met Met Ala Gln Thr Arg Val Ser Leu Asp Arg Leu Ser
        595                 600                 605

His Phe Leu Gln Gln Glu Glu Leu Pro Asp Asp Ala Thr Ile Xaa Val
    610                 615                 620

Pro Xaa Gly Ser Thr Asp Lys Ala Ile Asp Ile Lys Asp Gly Xaa Phe
625                 630                 635                 640

Ser Trp Asn Pro Phe Ser Xaa Thr Pro Thr Leu Ser Gly Ile Asn Leu
                645                 650                 655

Ser Val Val Arg Gly Met Arg Val Ala Val Cys Gly Val Ile Gly Ser
            660                 665                 670

Gly Lys Ser Ser Leu Leu Ser Ser Ile Leu Gly Glu Ile Pro Lys Leu
        675                 680                 685

Cys Gly Xaa Val Arg Ile Ser Gly Thr Ala Ala Tyr Val Pro Gln Thr
    690                 695                 700

Ala Trp Ile Gln Ser Gly Asn Ile Glu Glu Asn Ile Leu Phe Gly Ser
705                 710                 715                 720

Pro Met Asp Lys Gln Arg Tyr Lys Arg Val Ile Xaa Ala Cys Ser Leu
                725                 730                 735

Lys Lys Asp Leu Glu Leu Leu Gln Tyr Gly Asp Gln Thr Ile Ile Gly
            740                 745                 750

Asp Arg Gly Ile Asn Leu Ser Gly Gly Gln Lys Gln Arg Val Gln Leu
        755                 760                 765

Ala Arg Ala Leu Tyr Gln Asp Ala Asp Ile Tyr Leu Leu Asp Asp Pro
    770                 775                 780

Phe Ser Ala Val Asp Ala His Thr Gly Ser Leu Phe Arg Glu Tyr
785                 790                 795                 800

Ile Leu Thr Ala Leu Ala Ser Lys Thr Val Ile Tyr Val Thr His Gln
                805                 810                 815

Val Glu Phe Leu Pro Ala Ala Asp Leu Ile Leu Val Leu Lys Asp Gly
            820                 825                 830

His Ile Thr Gln Ala Gly Lys Tyr Asp Asp Leu Leu Gln Ala Gly Thr
        835                 840                 845

Asp Phe Asn Ala Leu Val Ser Ala His Lys Glu Ala Ile Glu Thr Met
    850                 855                 860

Asp Ile Xaa Glu Asp Ser Asp Glu Asp Thr Val Ser Xaa Xaa Xaa Xaa
865                 870                 875                 880

Xaa Ser Ile Xaa Xaa Xaa Asn Lys Arg Leu Thr Pro Ser Ile Ser Asn
                885                 890                 895

Ile Asp Asn Leu Lys Asn Lys Val Xaa Glu Asn Gly Xaa Pro Ser Xaa
            900                 905                 910

Thr Arg Gly Ile Lys Glu Lys Lys Lys Xaa Glu Arg Xaa Lys Lys
        915                 920                 925

Lys Arg Ser Val Gln Glu Glu Glu Arg Glu Arg Gly Lys Val Ser Leu
    930                 935                 940

Lys Val Tyr Leu Ser Tyr Met Gly Glu Ala Tyr Lys Gly Thr Leu Ile
945                 950                 955                 960

Pro Leu Ile Ile Leu Ala Gln Thr Met Phe Gln Val Leu Gln Ile Ala
                965                 970                 975

Ser Asn Trp Trp Met Ala Trp Ala Asn Pro Gln Thr Glu Gly Asp Ala
            980                 985                 990

Pro Lys Thr Asp Ser Val Val Leu Leu Val Val Tyr Met Ser Leu Ala
```

```
                995            1000           1005
Phe Gly Ser Ser Leu Phe Val Phe Val Arg Ser Leu Leu Val Ala Thr
    1010           1015           1020

Phe Gly Leu Ala Ala Ala Gln Lys Leu Phe Ile Lys Met Leu Arg Cys
1025           1030           1035           1040

Val Phe Arg Ala Pro Met Ser Phe Phe Asp Thr Thr Pro Ser Gly Arg
            1045           1050           1055

Ile Leu Asn Arg Val Ser Val Asp Gln Ser Val Val Asp Leu Asp Ile
        1060           1065           1070

Ala Phe Arg Leu Gly Gly Phe Ala Ser Thr Thr Ile Gln Leu Leu Gly
    1075           1080           1085

Ile Val Ala Val Met Ser Lys Val Thr Trp Gln Val Leu Ile Leu Ile
1090           1095           1100

Val Pro Met Ala Val Ala Cys Met Trp Met Gln Arg Tyr Tyr Ile Ala
1105           1110           1115           1120

Ser Ser Arg Glu Leu Thr Arg Ile Leu Ser Val Gln Lys Ser Pro Val
            1125           1130           1135

Ile His Leu Phe Ser Glu Ser Ile Ala Gly Ala Ala Thr Ile Arg Gly
        1140           1145           1150

Phe Gly Gln Glu Lys Arg Phe Met Lys Arg Asn Leu Tyr Leu Leu Asp
    1155           1160           1165

Cys Phe Ala Arg Pro Leu Phe Ser Ser Leu Ala Ala Ile Glu Trp Leu
    1170           1175           1180

Cys Leu Arg Met Glu Leu Leu Ser Thr Phe Val Phe Ala Phe Cys Met
1185           1190           1195           1200

Ala Ile Leu Val Ser Phe Pro Pro Gly Thr Ile Glu Pro Ser Met Ala
            1205           1210           1215

Gly Leu Ala Val Thr Tyr Gly Leu Asn Leu Asn Ala Arg Met Ser Arg
        1220           1225           1230

Trp Ile Leu Ser Phe Cys Lys Leu Glu Asn Arg Ile Ile Ser Val Glu
    1235           1240           1245

Arg Ile Tyr Gln Tyr Cys Lys Leu Pro Ser Glu Ala Pro Leu Ile Ile
    1250           1255           1260

Glu Asn Xaa Arg Pro Pro Ser Ser Trp Pro Xaa Asn Gly Asn Ile Glu
1265           1270           1275           1280

Leu Val Asp Leu Lys Val Arg Tyr Lys Asp Asp Leu Pro Leu Val Leu
            1285           1290           1295

His Gly Val Ser Cys Ile Phe Pro Gly Gly Lys Lys Ile Gly Ile Val
        1300           1305           1310

Gly Arg Thr Gly Ser Gly Lys Ser Thr Leu Ile Gln Ala Leu Phe Arg
    1315           1320           1325

Leu Ile Glu Pro Thr Gly Gly Lys Ile Ile Ile Asp Asn Ile Asp Ile
    1330           1335           1340

Ser Xaa Ile Gly Leu His Asp Leu Arg Ser Arg Leu Ser Ile Ile Pro
1345           1350           1355           1360

Gln Asp Pro Thr Leu Phe Glu Gly Thr Ile Arg Met Asn Leu Asp Pro
            1365           1370           1375

Leu Glu Glu Cys Thr Asp Gln Glu Ile Trp Glu Ala Leu Glu Lys Cys
        1380           1385           1390

Gln Leu Gly Glu Val Ile Arg Ser Lys Asp Glu Lys Leu Asp Ser Pro
    1395           1400           1405

Val Leu Glu Asn Gly Asp Asn Trp Ser Val Gly Gln Arg Gln Leu Ile
    1410           1415           1420
```

```
Ala Leu Gly Arg Ala Leu Leu Lys Gln Ala Lys Ile Leu Val Leu Asp
1425                1430                1435                1440

Glu Ala Thr Ala Ser Val Asp Thr Ala Thr Asp Asn Leu Ile Gln Lys
            1445                1450                1455

Ile Ile Arg Ser Glu Phe Lys Asp Cys Thr Val Cys Thr Ile Ala His
        1460                1465                1470

Arg Ile Pro Thr Val Ile Asp Ser Asp Leu Val Leu Val Leu Ser Asp
    1475                1480                1485

Gly Lys Ile Ala Glu Phe Asp Thr Pro Gln Arg Leu Leu Glu Asp Lys
1490                1495                1500

Ser Ser Met Phe Ile Gln Leu Val Ser Glu Tyr Ser Thr Arg Ser Ser
1505                1510                1515                1520

Cys Ile

<210> SEQ ID NO 16
<211> LENGTH: 213
<212> TYPE: PRT
<213> ORGANISM: Zea mays

<400> SEQUENCE: 16

Ile Lys Asp Gly Ala Phe Ser Trp Asn Pro Tyr Thr Leu Thr Pro Thr
1               5                   10                  15

Leu Ser Asp Ile His Leu Ser Val Val Arg Gly Met Arg Val Ala Val
            20                  25                  30

Cys Gly Val Ile Gly Ser Gly Lys Ser Ser Leu Leu Ser Ser Ile Leu
        35                  40                  45

Gly Glu Ile Pro Lys Leu Cys Gly His Val Arg Ile Ser Gly Thr Ala
    50                  55                  60

Ala Tyr Val Pro Gln Thr Ala Trp Ile Gln Ser Gly Asn Ile Glu Glu
65                  70                  75                  80

Asn Ile Leu Phe Gly Ser Gln Met Asp Arg Gln Arg Tyr Lys Arg Val
                85                  90                  95

Ile Ala Ala Cys Cys Leu Lys Lys Asp Leu Glu Leu Leu Gln Tyr Gly
            100                 105                 110

Asp Gln Thr Val Ile Gly Asp Arg Gly Ile Asn Leu Ser Gly Gly Gln
        115                 120                 125

Lys Gln Arg Val Gln Leu Ala Arg Ala Leu Tyr Gln Asp Ala Asp Ile
    130                 135                 140

Tyr Leu Leu Asp Asp Pro Phe Ser Ala Val Asp Ala His Thr Gly Ser
145                 150                 155                 160

Glu Leu Phe Lys Glu Tyr Ile Leu Thr Ala Leu Ala Thr Lys Thr Val
                165                 170                 175

Ile Tyr Val Thr His Gln Val Glu Phe Leu Pro Ala Ala Asp Leu Ile
            180                 185                 190

Leu Val Leu Lys Asp Gly His Ile Thr Gln Ala Gly Lys Tyr Asp Asp
        195                 200                 205

Leu Leu Gln Ala Gly
    210

<210> SEQ ID NO 17
<211> LENGTH: 184
<212> TYPE: PRT
<213> ORGANISM: Zea mays

<400> SEQUENCE: 17

Ile Glu Leu Ile Asp Leu Lys Val Arg Tyr Lys Asp Asp Leu Pro Leu
1               5                   10                  15
```

Val Leu His Gly Val Ser Cys Met Phe Pro Gly Gly Lys Lys Ile Gly
            20                  25                  30

Ile Val Gly Arg Thr Gly Ser Gly Lys Ser Thr Leu Ile Gln Ala Leu
            35                  40                  45

Phe Arg Leu Ile Glu Pro Thr Gly Gly Lys Ile Ile Ile Asp Asn Ile
50                  55                  60

Asp Ile Ser Ala Ile Gly Leu His Asp Leu Arg Ser Arg Leu Ser Ile
65                  70                  75                  80

Ile Pro Gln Asp Pro Thr Leu Phe Glu Gly Thr Ile Arg Met Asn Leu
                85                  90                  95

Asp Pro Leu Glu Glu Cys Thr Asp Gln Glu Ile Trp Glu Ala Leu Glu
            100                 105                 110

Lys Cys Gln Leu Gly Glu Val Ile Arg Ser Lys Glu Glu Lys Leu Asp
            115                 120                 125

Ser Pro Val Leu Glu Asn Gly Asp Asn Trp Ser Val Gly Gln Arg Gln
130                 135                 140

Leu Ile Ala Leu Gly Arg Ala Leu Leu Lys Gln Ala Lys Ile Leu Val
145                 150                 155                 160

Leu Asp Glu Ala Thr Ala Ser Val Asp Thr Ala Thr Asp Asn Leu Ile
                165                 170                 175

Gln Lys Ile Ile Arg Ser Glu Phe
            180

<210> SEQ ID NO 18
<211> LENGTH: 9
<212> TYPE: PRT
<213> ORGANISM: Zea mays

<400> SEQUENCE: 18

Gly Val Ile Gly Ser Gly Lys Ser Ser
1               5

<210> SEQ ID NO 19
<211> LENGTH: 9
<212> TYPE: PRT
<213> ORGANISM: Zea mays

<400> SEQUENCE: 19

Gly Arg Thr Gly Ser Gly Lys Ser Thr
1               5

<210> SEQ ID NO 20
<211> LENGTH: 12
<212> TYPE: PRT
<213> ORGANISM: Zea mays

<400> SEQUENCE: 20

Leu Ser Gly Gly Gln Lys Gln Arg Val Gln Leu Ala
1               5                   10

<210> SEQ ID NO 21
<211> LENGTH: 12
<212> TYPE: PRT
<213> ORGANISM: Zea mays

<400> SEQUENCE: 21

Trp Ser Val Gly Gln Arg Gln Leu Ile Ala Leu Gly
1               5                   10

<210> SEQ ID NO 22

```
<211> LENGTH: 6
<212> TYPE: PRT
<213> ORGANISM: Zea mays

<400> SEQUENCE: 22

Ile Tyr Leu Leu Asp Asp
1               5

<210> SEQ ID NO 23
<211> LENGTH: 5
<212> TYPE: PRT
<213> ORGANISM: Zea mays

<400> SEQUENCE: 23

Ile Leu Val Leu Asp
1               5

<210> SEQ ID NO 24
<211> LENGTH: 5
<212> TYPE: PRT
<213> ORGANISM: Zea mays

<400> SEQUENCE: 24

Ile Ala His Arg Ile
1               5

<210> SEQ ID NO 25
<211> LENGTH: 1931
<212> TYPE: DNA
<213> ORGANISM: Zea mays

<400> SEQUENCE: 25
ggcacgagca gcagcctcct tcctcctctc actctcgctc gcgctgcgct cgctacctcg      60
cttcgcattc cattcgaaaa gaggggagga aaggcaagat gttcatcgag agcttccgcg     120
tcgagagccc ccacgtgcgg tacgcccga tggagatcga gtcggagtac cggtacgaca     180
cgacggagct ggtacacgag ggcaaggacg gcgcctcacg ctgggtcgtc cgccccaagt     240
ccgtcaagta caacttccgg accagaaccg ccgtccccaa gctcggggtg atgcttgtgg     300
ggtggggagg caacaacggg tccacgctga cggctggggt cattgccaac agggagggga     360
tctcatgggc gaccaaggac aaggtgcagc aagccaacta ctacggctcc ctcacccacg     420
cctccaccat cagagtcggc agctacaacg gggaggagat ctatgcgccg ttcaagagcc     480
tccttcccat agtgaaccca gacgacattg tgttcggagg ctgggacatt agcaacatga     540
acctggccga ctccatgacc agggccaagg tgctggatat tgacctgcag aagcagctca     600
ggccctacat ggagtccatg gtgccacttc ccggtatcta tgatccggac ttcatcgcgg     660
ctaaccaggg ctctcgcgcc aacagtgtca tcaagggcac caagaaagaa caggtggagc     720
agatcatcaa ggatatcagg gagtttaagg agaagaacaa agtggacaag atagttgtgt     780
tgtggactgc aaacactgaa aggtatagca atgtgtgcgc tggtctcaac gacacgatgg     840
agaatctact ggcatctgtg acaagaacg aagcggaggt atcaccatca acactatatg     900
ccattgcctg tgtcatggaa ggggtgccgt tcatcaatgg gagcccccag aacacctttg     960
tgcctgggct gattgatctt gctataaaaa caaactgctt gattggtggt gacgacttca    1020
agagtggaca gaccaagatg aaatctgtct tggtcgattt ccttgttggt gctggaataa    1080
agcccacctc aatcgtgagc tacaaccact tgggaaacaa cgatggcatg aacctgtctg    1140 ccctcaaac attcaggtcc aaggagatct ccaagagcaa cgtggtggat gacatggtct    1200
cgagcaatgc catcctctat gagcccggcg agcatcccga tcatgtcgtt gtcatcaagt    1260
```

```
atgtgccgta cgtgggagac agcaagaggg ctatggacga gtacacctca gagatcttca    1320
tgggcggcaa gaacaccatc gtgctgcaca acacctgtga ggactcgctc ctcgccgcac    1380
ctatcatcct tgatctggtg ctcttggctg agctcagcac caggatccag ctgaaagctg    1440
agggagagga caaattccac tccttccacc cggtggccac catcttgagt tacttcacca    1500
aggcacccct ggttcccccct ggcacaccgg tggtgaacgc tctggccaag cagagggcga    1560
tgctggagaa catcatgagg gcctgcgttg ggctggcccc agagaacaac atgatcttgg    1620
agtacaagtg agccaagtgg cgtgccctgc agcgcgaggt tagctgctgg aagggaacta    1680
gaaaggcgag attagctgtg ggattgtgtt gggcttgtcg tgttttcttt tgcgttcttt    1740
cctagtcatt gctgttgcgc ttttgtattt gtcggacccg taactaccag ggctctgcta    1800
ttagcggcac ggagcctgta attgtattgt atgataatgt gatcgagggt gctacttccc    1860
ctcggcattc ctagtgttgg ttaaaagtcg ttcgacagca acttatcgac ccaaaaaaaa    1920 aaaaaaaaa a                                                         1931
```

<210> SEQ ID NO 26
<211> LENGTH: 21
<212> TYPE: DNA
<213> ORGANISM: Artificial Sequence
<220> FEATURE:
<223> OTHER INFORMATION: Adaptor/primer

<400> SEQUENCE: 26

```
tactcaggac tcatcgaccg t                                             21
```

<210> SEQ ID NO 27
<211> LENGTH: 23
<212> TYPE: DNA
<213> ORGANISM: Artificial Sequence
<220> FEATURE:
<223> OTHER INFORMATION: Adaptor/primer

<400> SEQUENCE: 27

```
gtgaacggtc gatgagtcct gag                                           23
```

<210> SEQ ID NO 28
<211> LENGTH: 18
<212> TYPE: DNA
<213> ORGANISM: Artificial Sequence
<220> FEATURE:
<223> OTHER INFORMATION: Adaptor/primer

<400> SEQUENCE: 28

```
gtgaacggtc gatgagtc                                                 18
```

<210> SEQ ID NO 29
<211> LENGTH: 18
<212> TYPE: DNA
<213> ORGANISM: Artificial Sequence
<220> FEATURE:
<223> OTHER INFORMATION: Adaptor/primer

<400> SEQUENCE: 29

```
gtcgatgagt cctgagta                                                 18
```

<210> SEQ ID NO 30
<211> LENGTH: 18
<212> TYPE: DNA
<213> ORGANISM: Artificial Sequence
<220> FEATURE:
<223> OTHER INFORMATION: Primer

```
<400> SEQUENCE: 30
gatgagtcct gagtagaa                                                 18

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gatgagtcct gagtagac                                                 18

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
gatgagtcct gagtagag                                                 18

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
gatgagtcct gagtagat                                                 18

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
gatgagtcct gagtagca                                                 18

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
gatgagtcct gagtagcc                                                 18

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
gatgagtcct gagtagcg                                                 18

<210> SEQ ID NO 37
<211> LENGTH: 18
```

```
<212> TYPE: DNA
<213> ORGANISM: Artificial Sequence
<220> FEATURE:
<223> OTHER INFORMATION: Primer

<400> SEQUENCE: 37
gatgagtcct gagtagct                                                 18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
gatgagtcct gagtagga                                                 18

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
gatgagtcct gagtaggc                                                 18

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gatgagtcct gagtaggg                                                 18

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
gatgagtcct gagtaggt                                                 18

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
gatgagtcct gagtagta                                                 18

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
gatgagtcct gagtagtc                                                 18
```

```
<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
gatgagtcct gagtagtg                                                18

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45
gatgagtcct gagtagtt                                                18

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
cgatgagtcc tgagtaaaa                                               19

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
cgatgagtcc tgagtaaac                                               19

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
cgatgagtcc tgagtaaag                                               19

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
cgatgagtcc tgagtaaat                                               19

<210> SEQ ID NO 50
<211> LENGTH: 19
<212> TYPE: DNA
<213> ORGANISM: Artificial Sequence
<220> FEATURE:
<223> OTHER INFORMATION: Primer
```

```
<400> SEQUENCE: 50
cgatgagtcc tgagtaaca                                           19

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
gatgagtcct gagtaacc                                            18

<210> SEQ ID NO 52
<211> LENGTH: 18
<212> TYPE: DNA
<213> ORGANISM: Artificial Sequence
<220> FEATURE:
<223> OTHER INFORMATION: Primer

<400> SEQUENCE: 52
gatgagtcct gagtaacg                                            18

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53
gatgagtcct gagtaact                                            18

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
cgatgagtcc tgagtaaga                                           19

<210> SEQ ID NO 55
<211> LENGTH: 18
<212> TYPE: DNA
<213> ORGANISM: Artificial Sequence
<220> FEATURE:
<223> OTHER INFORMATION: Primer

<400> SEQUENCE: 55
gatgagtcct gagtaagc                                            18

<210> SEQ ID NO 56
<211> LENGTH: 18
<212> TYPE: DNA
<213> ORGANISM: Artificial Sequence
<220> FEATURE:
<223> OTHER INFORMATION: Primer

<400> SEQUENCE: 56
gatgagtcct gagtaagg                                            18

<210> SEQ ID NO 57
<211> LENGTH: 19
```

-continued

<212> TYPE: DNA
<213> ORGANISM: Artificial Sequence
<220> FEATURE:
<223> OTHER INFORMATION: Primer

<400> SEQUENCE: 57
cgatgagtcc tgagtaagt                                                19

<210> SEQ ID NO 58
<211> LENGTH: 19
<212> TYPE: DNA
<213> ORGANISM: Artificial Sequence
<220> FEATURE:
<223> OTHER INFORMATION: primer

<400> SEQUENCE: 58
cgatgagtcc tgagtaata                                                19

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59
gatgagtcct gagtaatc                                                 18

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
gatgagtcct gagtaatg                                                 18

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
cgatgagtcc tgagtaatt                                                19

<210> SEQ ID NO 62
<211> LENGTH: 199
<212> TYPE: PRT
<213> ORGANISM: Artificial Sequence
<220> FEATURE:
<223> OTHER INFORMATION: Pfam consensus sequence

<400> SEQUENCE: 62

Gly Glu Val Leu Ala Leu Val Gly Pro Asn Gly Ala Gly Lys Ser Thr
1               5                   10                  15

Leu Leu Lys Leu Ile Ser Gly Leu Leu Pro Pro Thr Glu Gly Thr Ile
            20                  25                  30

Leu Leu Asp Gly Ala Arg Asp Leu Ser Asp Leu Ser Lys Leu Lys Glu
        35                  40                  45

Arg Leu Glu Leu Leu Arg Lys Asn Ile Gly Val Val Phe Gln Asp Pro
    50                  55                  60

Thr Leu Phe Pro Asn Pro Glu Leu Thr Val Arg Glu Asn Ile Ala Phe

```
                65                  70                  75                  80
Gly Leu Arg Leu Ser Leu Gly Leu Ser Lys Asp Glu Gln Asp Arg
                        85                  90                  95
Leu Lys Lys Ala Gly Ala Glu Glu Leu Leu Glu Arg Leu Gly Leu Gly
                        100                 105                 110
Tyr Asp Asp Leu Leu Asp Arg Arg Pro Gly Thr Leu Ser Gly Gly Gln
                        115                 120                 125
Lys Gln Arg Val Ala Ile Ala Arg Ala Leu Leu Thr Lys Pro Lys Leu
                        130                 135                 140
Leu Leu Leu Asp Glu Pro Thr Ala Gly Leu Asp Pro Ala Ser Arg Ala
145                     150                 155                 160
Gln Leu Leu Glu Leu Leu Arg Glu Leu Arg Gln Gln Gly Gly Thr Val
                        165                 170                 175
Leu Leu Val Thr His Asp Leu Asp Leu Leu Asp Arg Leu Ala Asp Arg
                        180                 185                 190
Ile Leu Val Leu Glu Asp Gly
                        195

<210> SEQ ID NO 63
<211> LENGTH: 286
<212> TYPE: PRT
<213> ORGANISM: Artificial Sequence
<220> FEATURE:
<223> OTHER INFORMATION: Pfam consensus sequence

<400> SEQUENCE: 63

Leu Leu Ile Ala Ile Leu Leu Leu Ile Leu Ala Gly Ala Thr Ala Leu
1               5                   10                  15
Val Thr Phe Pro Leu Leu Gly Arg Leu Leu Asp Ser Gly Phe Pro
                20                  25                  30
Leu Ser Asp Gly Asn Asp Asp His Glu Ala Arg Ser Ser Leu Ile Ser
                35                  40                  45
Leu Ala Ile Leu Ser Leu Leu Ala Val Phe Val Leu Ile Gly Leu Leu
            50                  55                  60
Leu Gln Gly Ser Phe Tyr Leu Leu Ala Gly Glu Arg Leu Gly Gln Arg
65                  70                  75                  80
Leu Arg Lys Arg Leu Phe Arg Ala Leu Leu Arg Gln Ile Leu Gly Leu
                        85                  90                  95
Phe Asp Ser Phe Phe Asp Thr Asn Ser Val Gly Glu Leu Thr Ser Arg
                        100                 105                 110
Leu Thr Asn Asp Val Glu Lys Ile Arg Asp Gly Leu Gly Glu Lys Leu
                        115                 120                 125
Gly Leu Leu Phe Gln Ser Leu Ala Thr Val Val Gly Gly Leu Ile Val
                        130                 135                 140
Met Phe Tyr Tyr Ser Trp Lys Leu Thr Leu Ile Leu Leu Ala Ile Leu
145                     150                 155                 160
Pro Leu Leu Ile Leu Leu Ser Ala Val Leu Ala Lys Lys Leu Arg Lys
                        165                 170                 175
Leu Ser Arg Lys Glu Gln Lys Ala Tyr Ala Lys Ala Gly Ser Val Ala
                        180                 185                 190
Glu Glu Ser Leu Ser Gly Ile Arg Thr Val Lys Ala Phe Gly Arg Glu
                        195                 200                 205
Glu Tyr Glu Leu Glu Arg Phe Asp Lys Ala Leu Glu Asp Ala Glu Lys
                        210                 215                 220
Ala Gly Ile Lys Lys Ala Ile Ile Ala Gly Leu Leu Phe Gly Ile Thr
225                     230                 235                 240
```

```
Gln Leu Ile Ser Tyr Leu Ser Tyr Ala Leu Ala Leu Trp Phe Gly Gly
                245                 250                 255

Tyr Leu Val Ala Ser Val Ile Ser Gly Gly Leu Ser Val Gly Thr Leu
            260                 265                 270

Phe Ala Phe Leu Ser Leu Gly Asn Gln Leu Ile Gly Pro Leu
            275                 280                 285

<210> SEQ ID NO 64
<211> LENGTH: 1170
<212> TYPE: DNA
<213> ORGANISM: Zea mays

<400> SEQUENCE: 64
gaaaatctct ttctccgctg cgctgcaaac ccaccgcttc caccatcgcc actcgtcacc      60
ccttgctccc atagtcccca tacc atg ccc gac ctc cac ccg ccg gag cac       111 caa gtc gcc ggt cac cgc gcc tcc gcc agc aag ctg ggc ccg ctc atc      159 gac ggc tcc ggc ctc ttc tac aag ccg ctc cag gcc ggc gac cgt ggg      207 gag cac gag gtc gcc ttc tat gag gcg ttc tcc gcc cac gcc gcc gtc      255 ccg gcc cgc atc cga gac acc ttc ttc ccc cgg ttc cac ggc acg cga      303 ctc ctc ccc acc gag gcg cag ccc ggg gag ccg cat ccg cac ctc gtc      351 ctc gac gac ctc ctc gcg ggg ttt gag gcg ccc tgc gtc gca gac atc      399 aag atc ggc gcc atc acg tgg cca ccg agt tcg ccg gag ccc tac atc      447 gcc aag tac ctc gcc aag gac cgc ggg acc acg agc gtt ctg ctc gga      495 ttc cgc gtc ttg cgt ccg agt cgt cgg ccc cga ggg cgc cgt gtg gcg      543 gac gga gcg ccc gga ggt gaa ggc tat gga cac cgt cgg cgt ccg ccg      591 cgt gct ccg gcg cta cgt gtc atc cgc ttg ccg acg agg gga tgg act      639 gcg cgc tcg cgg cgg cgg tgt acg gag gaa aag gtg gag tct tgt cac      687 agc tgc gcg agc tca agg cat ggt tgg agg agc aga ctc tgt tcc act      735 tct act cgg cgt cga ttc ttc tgg gct atg atg ctg ctg cag tcg cag      783 cag gcg gag gtg ggg gtg ggg taa cagtgaagct ggtggacttt gcccatgtgc      837
ccgagggtga tggggtgatt gaccacaact tcctgggcga gctctgctag ctgatcaagt      897
tcgtttctga cattgttcca gagactcctt agacgcagcc tttgggtcct tcttaagaga      957
ggatcctgac atttttgatt tgataacaaa ggaagcactt tcagctgcaa aaaagaaag    1017 cagcagtgag gatgaagatg acagtagtga ggaaagttcg gatgatgagc aacaaaagt    1077 tgaagaaaag aaggctccaa aagtatcaga aacattgga tctgaggatg aatcttctga    1137
agacgagagt gataaagaca gtgaagagcc tca                                1170

<210> SEQ ID NO 65
<211> LENGTH: 1388
<212> TYPE: DNA
<213> ORGANISM: Zea mays

<400> SEQUENCE: 65
ccacgcgtcc gcaaatttca atctccatcg atcgattcct cccgaacccg acccgatggc       60
ctccgacgcc gccgccgagc cctcctccgg cgtcacccac ccccgcgct acgtcatcgg      120 ttacgcgctc gcgccgaaga agcagcaaag cttcatccag ccgtcgctgg tggcccaggc      180
ggcgtcgcgg ggcatggacc tcgtcccccgt ggatgcgtcg cagcccctgg cagagcaagg      240
```

```
gcccttccac ctcctcatcc acaagctcta cggagacgac tggcgcgccc agctcgtggc    300
cttcgccgcg cgccacccgg ccgtcccat cgtcgacccg ccccacgcca tcgaccgcct     360
ccacaaccgc atctccatgc tccaggtcgt ctccgagctc gaccacgccg ccgaccagga    420
cagcactttc ggtatcccca gccaggtcgt cgtctacgac gctgccgcgc tcgccgactt    480
cggactcctt gccgcgctcc gcttcccgct catcgccaag cccctcgtcg ccgacggcac    540
cgccaagtcc cacaagatgt cgctcgtcta ccaccgcgag ggcctcggca agctccgccc    600
gccgcttgtg ctccaggagt cgtcaaccca tggcggcgtc atcttcaagg tctacgtcgt    660
cggcggccac gtcacttgcg tcaagcgccg tagcctgccc gacgtgtccc ccgaggatga    720
cgcatcggcc cagggatccg tctccttctc ccaggtctcc aacctcccca ctgagcgcac    780
ggcggaggag tactacggcg aaaagagtct cgaggacgcc gtcgtgccgc ccgccgcatt    840
catcaaccag atcgcgggcg gcctccgccg cgcgctgggc ctgcaactct tcaacttcga    900
catgatccgc gacgtccgcg ccggcgaccg ctatctcgtc attgacatca actacttccc    960
gggctacgcc aagatgccag gatacgagac tgtcctcacg gatttcttct gggagatggt   1020
ccataaggac ggcgtgggca accaacagga ggagaaaggg gccaaccatg ttgtcgtgaa   1080
ataagatgat gattgatggc actggatatc tggcgaatgc tgctgattct ggatgcagaa   1140
ttcgatgagg ggatttagtt ggttgtagta tctggcgaat gctgctggtt ctggatgcag   1200
aatttgatga ggggatttag ttggatttca acccatagca tgccgaggac ctcctagctc   1260
tttccaaacc agttgtttag gtatcttttc tgggtaagtc agcttcatct agtttagtct   1320
gtctgaacaa aagagtggga catgacccaa acggaattct aatgaaaaac gagctctcta   1380
tctgcaaa                                                             1388

<210> SEQ ID NO 66
<211> LENGTH: 1313
<212> TYPE: DNA
<213> ORGANISM: Zea mays

<400> SEQUENCE: 66
ctactactca aatccatcct tattgagctt agtgtttgat ccatggactc ggaaggagta     60
gcagcaaagg tggcagatga gactactaaa ccggcaagcc aagaagacgg cgagagcaag    120
gccgggatga ctgatctgct gatgctgacc gacaagtcgc agctgcaggc gctagcgatg    180
ctgctgcgga caacgagga gctcatgatg agccaagcga tcaagtcgga cggagcgc      240
gttgagtacc tcaagacggt gagcgactgc tacacgcgcga caatgaagct ccttgacgac    300
tccatggcgg ccaggatcac gtacgagcgt cgggcggaa cgaggagcct cgtcgcccgg    360
gacatggacg actacgtcgt ctacggcctc aacgcgtgct gcagaacgt ccgcaactgc     420
tgcgtgcgtc tggacgccat cgacaagctg cgggcgcact acgacgccct cgccgacgcc    480
gtcgccgaac cggccgccaa cgtcgagggc ctcgccgcgg aggcgtccga gtacaaggcc    540
gccatgtggc agtactgcta caaccagcgg agcgcctccg cgcgggcgca ctcccgcgcc    600
tactcccagg cgctcaagct ggagggcatc gacttcgccg agcttgtgcg gaggcaccag    660
ctccggctcg ggtacggcag caagggcgag gagttcgagg acctggacga caccccagaag   720
ctggaggtgt acaacagcat catcgtcgag tcggggcggg cggggctacc ggtgcggatg    780
ttctcgtcgg gccgctctgc cggtggccct aagattgcag ccacgacgtg ggcgcaggcg    840
gtgagcgtct tcatcatggc ggcgggcaac ctggcgtggg acgtgttcac cacgagcac    900
gaggtggagg ccatcctcaa gggcagcctc aacctcctgg cggggctagg ggcttcgcc    960
```

-continued

```
gtggaggccg tcgtcggcgc ggctgtcacc aaggcggtcg caaacgtcgg cgccggcgtc      1020
tttgcttgct ctctcgcggg cttcgtcgtg ggcgccatag ccgggctgat cttcatcggc      1080
gtcagcggcc tcctcattaa cctcatcatc ggctcccta ggaaggtgcc tgacatgagc       1140
aagctcatgt tccacaccgc cgtcatgccc gatggaatgg cccttgcgta tgcggtatct      1200
cattaattac ttattatcat cgcagtgact accgatgcaa ctgcttcaga tcctactgtt      1260
ggaacgcgtg tggaaataat aaaggaataa taataattat tattgtaata aaa             1313
```

<210> SEQ ID NO 67
<211> LENGTH: 1932
<212> TYPE: DNA
<213> ORGANISM: Zea mays

<400> SEQUENCE: 67

```
gtcgacccac gcgtccgagc accagcatct cttcaggtct ccaccaagcg cagacaccgc       60
agcagcggca gcggcacgat ctggtgaccc ccccgccgcg tcaagcctgc tcctccggtg      120
atcgccggac tggcggggta ggaaccagcg gagcgcagcc cgcctccttc cgctgtgtct      180
gacagcagca gatcctcgat ggagatggat ggggttctgc aagccgcgga tgccaaggat      240
tgggtttaca aggggggaagg cgccgcgaat cttatcctca gctacaccgg ctcgtcgccc      300
tccatgcttg gcaaggtact gcggctcaag aagattctaa aaacaagtc gcagcgggca       360 ccaagttgta ttgtattctc aagtcatgag caactcctgt ggggccatat cccagaactg      420
gttgagtcgg tcaaacaaga ttgcttggct caagcctatg cagtgcatgt tatgagccaa      480
cacctgggtg ccaatcatgt cgatggtggg gtccgtgtac gtgtttctag gattttctg       540 gagcttgtcg aaaagaatgt tcttagcagc cgtcctgctg ggagagtaaa tgcaagttca      600
attgataaca ctgctgatgc cgctcttctg atagcagacc actctttatt ttctggcaat      660
cctaagggta gcagctgcat agctgtagag ataaaggcca aatgtgggtt tctgccatca      720
tcagaatata tatcagaaga taatactatc aagaaacaag taacgagata taagatgcat      780
cagcacctca aattttatca gggtgagata tcgaagacta gtgagtacaa tcctcttgat      840 ctatttctg ggtcaaaaga gagaatatgc atggccatca agtccctttt ctcaactcct       900
cagaacaact taaggatttt tgtcaatgga tctttagctt ttggtggcat gggaggtggt      960
gcagatagtg ttcatcctgc tgacactctt aagtgtcttg aagatctcag caagattagt      1020
ggcctaaaac tccctgactt cactgagctc ctgtcagaga caattttttag gtctgaggta      1080 ttaggcaacc tgttggccac tcaaaagttg gatgatcatg acattgaagg ggtaattcat      1140
ctgtactaca acataaattc tcagccttgt ttagtctgca aaacctaac tgatgtagag       1200 ctattgcgga gtacacttt cttgcattct cttccgttgg acaaaagcct gaagatcgtt       1260
agggacttcc tcatttctgc taccgcaaag gactgtagcc tgatgatcag ctttcggcca      1320
agagagaatg gtagtacaga ttctgagtat gattcagtgt tcttgaatc agtgaagcga       1380 acctatgagt acaaggcata tttccttgat ctggatgtga aacctctgga taagatggag      1440
cattatttta aactggatca gaggatagtc aatttctaca caagaaatgg gggaggtctt      1500
gccatctcca aagggcagta ataccaaaga cacttcgagg atttatacat ctggagaagg      1560
gtgcatcagg gagtgttggt tgttgttcct gctgcttggt gctgctgttg taacttcatg      1620
agtacagtcc caaggttggg aggctcgacc cttaacgcct ggaaagggca cagggagctg      1680
tgttgtccgt cagtcgctgt tgtaactcaa actagtgcat acaccgtggc ttgtcacggt      1740
aatttccgaa gatgtccaac gttagttgag acaaccgaac tgcttaccgt ggcaatcact      1800
```

```
cattgtaaca tcaagttgaa aatgagggct gaagtttccc tcacaggcta ccatatgtca   1860
gatatgtcct ttgtaccact aataagtgcc cctggggtca tgtatgaatg tatctcaatt   1920
tgctattgca aa                                                       1932

<210> SEQ ID NO 68
<211> LENGTH: 1879
<212> TYPE: DNA
<213> ORGANISM: Zea mays

<400> SEQUENCE: 68
caaacgtacg tcgccgcagc agctcagacg tgcgccgcta ccacgtgtcc tgccgcacgc     60
cccgcgtcag cggcatctgt aaagccgctt gtcgccgccc cgacgcccac cccgccccgc    120
gcttttattc cccacttcac cgcatctccc cctcgtctac gatgccgttg cgcacctctt    180
ctctctcgcc gccccgagac ccccacgctt ccctctccgc cccgaactg tggcgcctcc     240 ccccgccgcc gcagcgatgc cactcgcggc agagcccgac gacgctcatg aggaaaggga    300
gaatcagcag ctgctaatta cgacgaaggg agggcccggg cttgagggac tggtggtggg    360
gagctactgc cacgatgtgc taatccgggg cgggcgcata tgggggaga ctctcggcgg    420 ggctgcggcc ttcgtgtcca acgtgctcga cgccgcttcg ccccaggacg cggcgctcaa    480
cgagacatcc ccctttgtcg ttgtggccaa ggtgggccac gacttcatct acgcccgcgc    540
gccggcgtcc gcgcggcatc cgcctctgct ctgctcgtcc caaccacct ccttccacgc     600 ccagttctcg gagaccgccg cctcggcgca cgcccccgac cgggagctcc ggcgcgtgcg    660
cgcctgcgac ccgatctacc ccgccgacct cccgaccgc cgcttcgcct atggcctcgc     720
tgtcggcgtc gcggggagg tgctaccgga gacgctcgag cagatgatca ggctctgccg     780
cacggtgctc gtggacgcgc aggcgctgat ccgggcgttc gacggtgacg cgccgtcgg    840 tcacgtggcg cttgacgata ccccgtacgc gcggcttctg ccccgagtgg cgttcgttaa    900
ggcgtcgtcg gaggaagcgc atacgttgg ggtggaaacg acgaggcggc agtgctgtgt     960
gatcgtcacg gaggggaggg acgggtgccg gctgtactgg gacggtgggg aggcgcacgt   1020
tgcgccgttc cccgccgtcc aggtggaccc tactggcgcc ggagatagct ttctcgcggg    1080
ctttgcagcc ggattgctgt gggggttgtc ggccacggac gccgcgctgc tggggaactt   1140
ctttggcgcc gctgctgtat cgcaggtcgg cgtgcccacc ttccatccca agatgttgca   1200
ggcagttaaa gaaatacttg aagagaagac aaggaaacga tctagtccat gtatgaacgg   1260
cgctagtttt accttggaga agtcaaatat gcacaacgag ttacacgcag ctctccaaga   1320
agctgcggtg ctgatgtctg aacagcagca ggctgatccg gcgaacgca gtggcggtga   1380 tatttgctcg gcataggtac ctcacagtga agctgaagca gtcagacgcc aaactgaaat   1440
ttgtggcaaa ataaccagc actgcagtcc tgaactcctg atctcacatt gagatctgta    1500
aacacggtgc caacaagtgg aggaagtttg tacatacgct ctctccggcc tttacactac   1560
tattctgctg gcaaggccgt cagggatcgt ttctaccttg ctatcgctga cgaggaaatg   1620
aagacaactg aacagttgag ctgtggcgct tgcacgcacc atgttttctc cgctgaacaa   1680
gtgcgcattt ttgagctttc gggcattcgt gctgttaact ttttaccatt ctatatgtcg   1740
acttctacca aaaggtctag cgttttaccc tgactgaaca cagggaaatt tgtgtgactg   1800
aactgagaag ggccaacaca caagttagga tgtgtttggt tggatgtaca cggagggatg   1860
aaatggggcg gccataaaa                                                1879
```

<210> SEQ ID NO 69
<211> LENGTH: 41
<212> TYPE: DNA
<213> ORGANISM: Artificial Sequence
<220> FEATURE:
<223> OTHER INFORMATION: primer

<400> SEQUENCE: 69
atcgtcgacg cggccgctga gagaatttat cagtacagga t                41

<210> SEQ ID NO 70
<211> LENGTH: 46
<212> TYPE: DNA
<213> ORGANISM: Artificial Sequence
<220> FEATURE:
<223> OTHER INFORMATION: primer

<400> SEQUENCE: 70
atggcggccg cctaggcgta cgttactgca gcagagctcg gcccag            46

<210> SEQ ID NO 71
<211> LENGTH: 556
<212> TYPE: DNA
<213> ORGANISM: Glycine max

<400> SEQUENCE: 71
tgagagaatt tatcagtaca gccaaattcc tagtgaagca cccacagtta ttgaagatta    60
tcgccctcca tcctcatggc ctgaaaatgg acaattgaa ataattgatt tgaagattcg    120
ttacaaggag aatcttcctt tggtgcttta tggagtaaca tgcacatttc ctggtggaaa   180
gaagattgga atagtaggac gtactggcag tggaaaatct actttaattc aggcgttatt   240
tcgattgatt gaaccaacaa gtgggagtat cctatatagac aacattaata tttcagagat   300
tggccttcat gaccttcgaa gccatctcag tatcatacca caagatccaa ccttatttga   360
aggtaccatt cgaggcaatc ttgatcctct ggatgagcac tcagataaag agatttggga   420
ggcacttgat aagtctcagc ttggagaggt tatccgtgag aaaggacaac agcttgatac   480
gccagttcta gaaaatggag ataattggag tgtaggacag cgacaacttg ttgctctggg   540
ccgagctctg ctgcag                                                  556

<210> SEQ ID NO 72
<211> LENGTH: 890
<212> TYPE: DNA
<213> ORGANISM: Artificial Sequence
<220> FEATURE:
<223> OTHER INFORMATION: recombinant DNA fragment

<400> SEQUENCE: 72
cggtcctctc tctttccgtg gcatggcaat ctattgggct gtccagggtt gcatccttac    60
tggtgtttgg gtcattgccc atgagtgtgg tcaccatgca ttcagtgact accagctgct   120
tgatgatatt gttggcctta tcctccactc cgctctccta gtcccgtact tttcatggaa   180
atacagccat cgccgtcacc actccaacac tggttctctt gagcgggatg aagtatttgt   240
gccaaagcag aagtcctgta tcaagtggta ctctaaatac cttaacaatc ctccaggcag   300
agtcctcact cttgctgtca ccctcacact tggttggccc ttgtacttgg ctttaaatgt   360
ttctggaagg ccttatgata gatttgcttg ccactatgac ccatatggtc ccatttactc   420
tgatcgtgaa cgacttcaaa tatatatc agatgcagga gtacttgcag gacttactct   480
ctctaccgtg ttgcaaccct gaaagggttg gtttggctgc tatgtgttta tggggtgcct   540
ttgctcattg tgaacggttt tcttgtgact atcacatatt tgcagcacac acactttgcc   600

-continued

| | |
|---|---|
| ttgcctcatt acgattcatc agaatgggac tggctgaagg gagctttggc aactatggac | 660 |
| agagattatg ggattctgaa caaggtgttt catcacataa ctgatactca tgtggctcac | 720 |
| catctcttct ctacaatgcc acattaccat gcaatggagg caaccaatgc aatcaagcca | 780 |
| atattgggtg agtactacca atttgatgac acaccatttt acaaggcact gtggagagaa | 840 |
| gcgagagagt gcctctatgt ggagccagat gaaggaacat ccgagaaggg | 890 |

<210> SEQ ID NO 73
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 73
gcggccgccg gtcctctctc tttccgtg                                28

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
tagagagagt aagtcctgca agtactcctg                              30

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
caggagtact tgcaggactt actctctcta                              30

<210> SEQ ID NO 76
<211> LENGTH: 29
<212> TYPE: DNA
<213> ORGANISM: Artificial Sequence
<220> FEATURE:
<223> OTHER INFORMATION: primer

<400> SEQUENCE: 76
gcggccggcc ccttctcgga tgttccttc                               29

<210> SEQ ID NO 77
<211> LENGTH: 39
<212> TYPE: DNA
<213> ORGANISM: Artificial Sequence
<220> FEATURE:
<223> OTHER INFORMATION: primer

<400> SEQUENCE: 77
gcggccgcgt acgtgacggt cctctctctt tccgtggca                    39

<210> SEQ ID NO 78
<211> LENGTH: 37
<212> TYPE: DNA
<213> ORGANISM: Artificial Sequence
<220> FEATURE:
<223> OTHER INFORMATION: primer -continued

```
<400> SEQUENCE: 78
gcggccgcct aggtcacttc tcggatgttc cttcatc                                37

<210> SEQ ID NO 79
<211> LENGTH: 921
<212> TYPE: DNA
<213> ORGANISM: Artificial Sequence
<220> FEATURE:
<223> OTHER INFORMATION: spacer sequence

<400> SEQUENCE: 79
gcggccgcgt acgtgacggt cctctctctt tccgtggcat ggccaatcta ttgggctgtc       60
cagggttgca tccttactgg tgtttgggtc attgcccatg agtgtggtca ccatgcattc      120
agtgactacc agctgcttga tgatattgtt ggccttatcc tccactccgc tctcctagtc      180 ccgtacttt  catggaaata cagccatcgc cgtcaccact ccaacacagg ttctcttgag      240
cgagatgaag tatttgtgcc aaagcagaag tccagtatca tgtggtactc taaatacctt      300
aacaatccac caggcagagt cctcactctt gccgtcaccc tcacgcttgg ttggcccttg      360
tacttggctt ttaatgtttc tggaaggcct tatgatagat ttgcttgcca ctatgaccct      420
tatggtccca tttactctga ccgagaacga cttcaaatat atatatcaga tgcaggagta      480
cttgcaggac ttactctctc taccgtgttg caaccctgaa agggttggtt tggctgctat      540
gtgtttatgg ggtgcctttg ctcattgtga acggttttct tgtgactatc acatatttgc      600
agcacacaca ctttgccttg cctcattacg attcatcaga atgggactgg ctgaagggag      660
ctttggcaac tatggacaga gattatggga ttctgaacaa ggtgtttcat cacataactg      720
atactcatgt ggctcaccat ctcttctcta caatgccaca ttaccatgca atggaggcaa      780
ccaatgcaat caagccaata ttgggtgagt actaccaatt tgatgacaca ccattttaca      840
aggcactgtg gagagaagcg agagagtgcc tctatgtgga gccagatgaa ggaacatccg      900
agaagtgacc taggcggccg c                                                921
```

MAIZE MULTIDRUG RESISTANCE-ASSOCIATED PROTEIN POLYNUCLEOTIDES AND METHODS OF USE

CROSS-REFERENCE TO RELATED APPLICATIONS

This application is a continuation of U.S. application Ser. No. 11/133,075, filed May 19, 2005, which claims the benefit of U.S. Provisional Application No. 60/572,704, filed May 20, 2004, the contents of which are hereby incorporated by reference in their entirety.

INCORPORATION OF SEQUENCE LISTING

The application contains a sequence listing, a paper copy of which is filed concurrently herewith via EFS Web. The CRF copy of the sequence listing filed on May 19, 2005 has been transferred from the parent application (U.S. application Ser. No. 11/133,075). The content of the attached paper copy of the listing and the CRF copy transferred from U.S. application Ser. No. 11/133,075 are the same. The sequence listing is hereby incorporated in its entirety into the instant specification.

FIELD OF THE INVENTION

The present invention relates to the field of animal nutrition. Specifically, the present invention relates to the identification and use of genes encoding enzymes involved in the metabolism of phytate in plants and the use of these genes and mutants thereof to reduce the levels of phytate, and/or increase the levels of non-phytate phosphorus in food or feed.

BACKGROUND OF THE INVENTION

The role of phosphorous in animal nutrition is well recognized. Phosphorus is a critical component of the skeleton, nucleic acids, cell membranes and some vitamins. Though phosphorous is essential for the health of animals, not all phosphorous in feed is bioavailable.

Phytates are the major form of phosphorous in seeds. For example, phytate represents about 60-80% of total phosphorous in corn and soybean. When seed-based diets are fed to non-ruminants, the consumed phytic acid forms salts with several important mineral nutrients, such as potassium, calcium, and iron, and also binds proteins in the intestinal tract. These phytate complexes cannot be metabolized by monogastric animals and are excreted, effectively acting as anti-nutritional factors by reducing the bioavailability of dietary phosphorous and minerals. Phytate-bound phosphorous in animal excreta also has a negative environmental impact, contributing to surface and ground water pollution.

There have been two major approaches to reducing the negative nutritional and environmental impacts of phytate in seed. The first involves post-harvest interventions, which increase the cost and processing time of feed. Post-harvest processing technologies remove phytic acid by fermentation or by the addition of compounds, such as phytases.

The second is a genetic approach. One genetic approach involves developing crop germplasm with heritable reductions in seed phytic acid. While some variability for phytic acid was observed, there was no change in non-phytate phosphorous. Further, only 2% of the observed variation in phytic acid was heritable, whereas 98% of the variation was attributed to environmental factors. Another genetic approach involves selecting low phytate lines from a mutagenized population to produce germplasm. Most mutant lines exhibit a loss of function and are presumably blocked in the phytic acid biosynthetic pathway; therefore, low phytic acid accumulation will likely be a recessive trait. In certain cases, this approach has revealed that homozygosity for substantially reduced phytate can be lethal. Another genetic approach is transgenic technology, which has been used to increase phytase levels in plants. These transgenic plant tissues or seed have been used as dietary supplements.

The biosynthetic route leading to phytate is complex and not completely understood, and it has been proposed that the production of phytic acid occurs by one of two possible pathways. One possible pathway involves the sequential phosphorylation of Ins(3)P or myo-inositol, leading to the production of phytic acid. Another possible pathway involves hydrolysis of phosphatidylinositol 4,5-bisphosphate by phospholipase C, followed by the phosphorylation of $Ins(1,4,5)P_3$ by inositol phosphate kinases. In developing plant seeds, accumulating evidence favors the sequential phosphorylation pathway. Such evidence includes studies of the Lpa2 gene, a gene encoding a maize inositol phosphate kinase which has multiple kinase activities. The Lpa2 gene has been cloned, and the lpa2 mutation has been shown to impair phytic acid synthesis. Mutant lpa2 seeds accumulate myo-inositol and inositol phosphate intermediates.

The maize low phytic acid 1 mutant (lpa1) was isolated from an EMS-mutagenized population in the early 1990s by USDA scientists. However, the original lpa1-1 allele was previously known to have a phenotype of up to 15% loss of seed dry weight, which could translate into a yield drag if the lpa1-1 mutant was used in product development. Since the discovery of lpa1, the gene responsible for the lpa1 mutation has been sought for two reasons: 1) the mutant has a phenotype of low phytic acid and high available phosphorus in grain which makes it useful in animal feeding and phosphorus waste management; and 2) the lpa1 mutant does not accumulate myo-inositol phosphate intermediates, indicating that mutation in this locus impairs a critical step in the phytic acid biosynthesis pathway which was previously uncharacterized.

Based on the foregoing, there exists the need to improve the nutritional content of plants, particularly corn and soybean, by increasing non-phytate phosphorous and reducing seed phytate. Accordingly, it is desirable to isolate and characterize the Lpa1 gene in order to place the expression of this gene under tight control so as to produce plants which have reduced seed phytate and increased non-phytate phosphorus.

SUMMARY OF THE INVENTION

Compositions and methods are provided for modulating the level of phytate in plants. More specifically, the invention relates to methods of modulating the level of phytate utilizing Lpa1 (ZmMRP3) nucleic acids to produce transformed plants that exhibit decreased expression of at least one multidrug resistance-associated protein (MRP). The compositions and methods of the invention find use in agriculture for improving the nutritional quality of food and feed by reducing the levels of phytate and/or increasing the levels of non-phytate phosphorus in food and feed. Thus, the invention finds use in producing food and feed products as well as in reducing the environmental impact of animal waste. Also provided are compositions and methods for producing MRP proteins.

BRIEF DESCRIPTION OF THE DRAWINGS

FIGS. 1A and 1B: Alignment of ZmMRP3 (SEQ ID NO: 3) with Pfam consensus sequences for ABC transporter ("ABC- _tran"; SEQ ID NO: 62) and ABC transporter transmembrane ("ABC_membrane"; SEQ ID NO: 63) region.

FIGS. 4A, 4B, 4C, 4D, 4E: cDNA sequence alignment of the maize Lpa1 gene (SEQ ID NO: 2) and its rice homolog OsMRP13 (SEQ ID NO: 6).

FIGS. 5A, 5B, 5C: Protein Sequence alignment of maize Lpa1 (ZmMRP3; SEQ ID NO: 3) with rice and *Arabidopsis* homologs OsMRP13 (SEQ ID NO: 7) and AtMRP5 (SEQ ID NO: 9). Matches to the consensus are indicated by bold type; conservative changes are indicated by underlined text.

FIG. 6: Diagram of sample constructs. These sample constructs illustrate various configurations that can be used in expression cassettes for use in inhibition of expression, for example, for use in hairpin RNA interference. Sample construct 1 shows a single promoter and fully or partially complementary sequences of "region 1" and "region 2." Sample construct 2 illustrates a configuration of two sets of fully or partially complementary sequences. In this sample construct, "region 1" is fully or partially complementary to "region 2" and "region 3" is fully or partially complementary to "region 4." Sample construct 3 illustrates yet another configuration of two sets of fully or partially complementary sequences; here, too, "region 1" is fully or partially complementary to "region 2" and "region 3" is fully or partially complementary to "region 4."

DETAILED DESCRIPTION OF THE INVENTION

Figure 2:
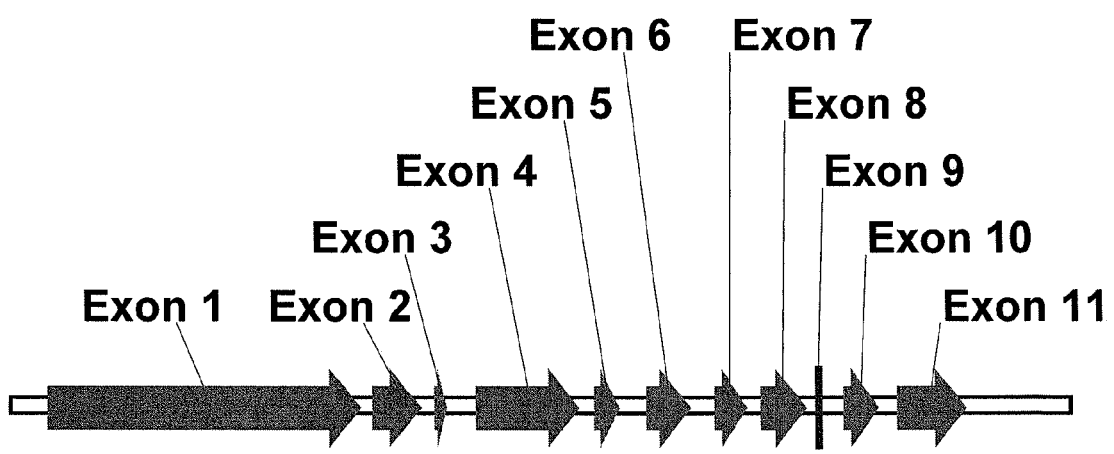
FIG. 2: Diagram of ZmMRP3 and rice OsMRP13 gene structure.
Figure 3:
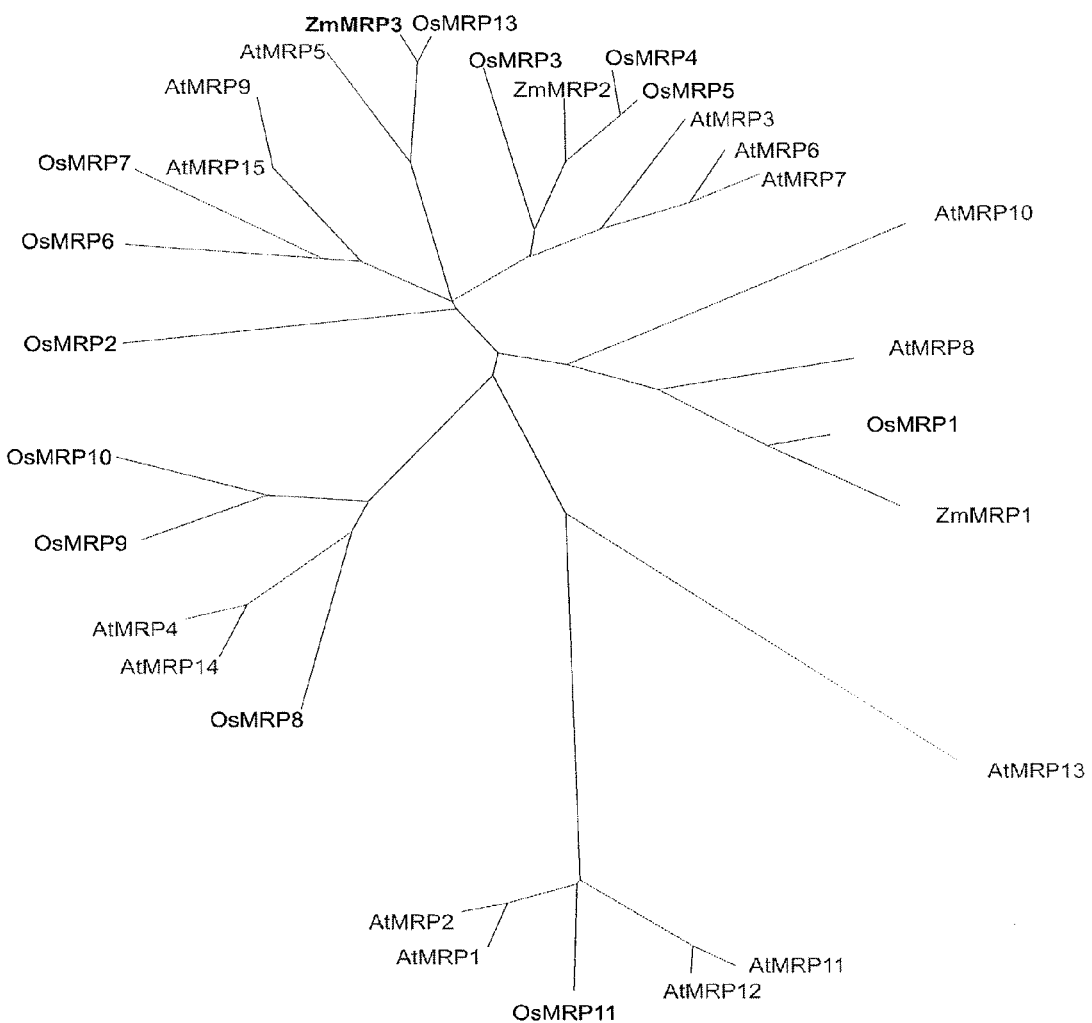
FIG. 3: Phylogenetic comparison of maize, rice and *Arabidopsis* MRP genes, showing that maize ZmMRP3, rice OsMRP13 and *Arabidopsis* AtMRP5 are closely related.

The invention is drawn to compositions and methods for modulating the level of phytate in plants. Compositions of the invention comprise multidrug resistance-associated proteins ("MRPs") of the invention (i.e., proteins that have multidrug resistance-associated protein activity ("MRP activity")), polynucleotides that encode them, and associated noncoding regions as well as fragments and variants of the exemplary disclosed sequences. For example, the disclosed Lpa1 polypeptides having amino acid sequences set forth in SEQ ID NOs: 3, 5, 7, 9, 11, 13, and 15 are MRPs and therefore have multidrug resistance-associated protein ("MRP") activity. In particular, the present invention provides for isolated polynucleotides comprising nucleotide sequences set forth in SEQ ID NOs: 1, 2, 4, 6, 8, 10, 12, and 14, or encoding the amino acid sequences shown in SEQ ID NOs: 3, 5, 7, 9, 11, 13, and 15, and fragments and variants thereof. In addition, the invention provides polynucleotides comprising the complements of these nucleotide sequences. Also provided are polypeptides comprising the amino acid sequences shown in SEQ ID NOs: 3, 5, 7, 9, 11, 13, and 15, polypeptides comprising the conserved domains set forth in SEQ ID NOs: 16, 17, 18, 19, 20, 21, 22, 23, and 24, fragments and variants thereof, and nucleotide sequences encoding these polypeptides. Compositions of the invention also include polynucleotides comprising at least a portion of the promoter sequence set forth in nucleotides 1 to 3134 of SEQ ID NO: 1 as well as polynucleotides comprising other noncoding regions Thus, the compositions of the invention comprise isolated nucleic acids that encode MRP proteins (e.g., Lpa1), fragments and variants thereof, cassettes comprising polynucleotides of the invention, and isolated MRP proteins. The compositions also include nucleic acids comprising nucleotide sequences which are the complement, or antisense, of these MRP nucleotide sequences. The invention further provides plants and microorganisms transformed with these novel nucleic acids as well as methods involving the use of such nucleic acids, proteins, and transformed plants in producing food (including food products) and feed with reduced phytate and/or increased non-phytate phosphorus levels. In some embodiments, the transformed plants of the invention and food and feed produced therefrom have improved nutritional quality due to increased availability (bioavailability) of nutrients including, for example, zinc and iron.

In some embodiments, MRP activity is reduced or eliminated by transforming a maize plant cell with an expression cassette that expresses a polynucleotide that inhibits the expression of an MRP enzyme such as, for example, an Lpa1 polypeptide. The polynucleotide may inhibit the expression of one or more MRPs directly, by preventing translation of the MRP messenger RNA, or indirectly, by encoding a polypeptide that inhibits the transcription or translation of a maize gene encoding an MRP. Methods for inhibiting or eliminating the expression of a gene in a plant are well known in the art, and any such method may be used in the present invention to inhibit the expression of one or more maize MRPs. Because MRP activity is difficult to measure directly, a decrease in MRP activity can be measured by a decreased level of phytate in a plant or plant part. See, e.g., the working examples in the Experimental section.

In accordance with the present invention, the expression of an MRP protein is inhibited if the transcript or protein level of the MRP is statistically lower than the transcript or protein level of the same MRP in a plant that has not been genetically modified or mutagenized to inhibit the expression of that MRP. In particular embodiments of the invention, the transcript or protein level of the MRP in a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of the protein level of the same MRP in a plant that is not a mutant or that has not been genetically modified to inhibit the expression of that MRP. The expression level of the MRP may be measured directly, for example, by assaying for the level of MRP expressed in the cell or plant, or indirectly, for example, by measuring the amount of phytate in the cell or plant. The activity of an MRP protein is "eliminated" according to the invention when it is not detectable by at least one assay method.

In other embodiments of the invention, the activity of one or more MRPs is reduced or eliminated by transforming a plant cell with an expression cassette comprising a polynucleotide encoding a polypeptide that inhibits the activity of one or more MRPs. The activity of an MRP is inhibited according to the present invention if the activity of that MRP in the transformed plant or cell is statistically lower than the activity of that MRP in a plant that has not been genetically modified to inhibit the activity of at least one MRP. In particular embodiments of the invention, an MRP activity of a modified plant according to the invention is less than 95%, less than 90%, less than 85%, less than 80%, less than 75%, less than 70%, less than 60%, less than 50%, less than 40%, less than 30%, less than 20%, less than 10%, or less than 5% of that MRP activity in an appropriate control plant that has not been genetically modified to inhibit the expression of that MRP. Changes in MRP activity may be inferred, for example, by alterations in phytate content of a transformed plant or plant cell.

In other embodiments, the activity of an MRP may be reduced or eliminated by disrupting the gene encoding the MRP. The invention encompasses mutagenized plants that carry at least one mutation in an MRP gene, wherein the at least one mutation reduces expression of an MRP gene or inhibits the activity of an MRP.

Thus, many methods may be used to reduce or eliminate the activity of an MRP. More than one method may be used to reduce the activity of a single plant MRP. In addition, combinations of methods may be employed to reduce or eliminate the activity of two or more different MRPs. Non-limiting examples of methods of reducing or eliminating the expression of a plant MRP are given below.

In some embodiments of the present invention, a plant cell is transformed with an expression cassette that is capable of producing a polynucleotide that inhibits the expression of an MRP. The term "expression" as used herein refers to the biosynthesis of a gene product, including the transcription and/or translation of said gene product. For example, for the purposes of the present invention, an expression cassette capable of expressing a polynucleotide that inhibits the expression of at least one maize MRP is an expression cassette capable of producing an RNA molecule that inhibits the transcription and/or translation of at least one maize MRP.

"Expression" generally refers to the transcription and/or translation of a coding region of a DNA molecule, messenger RNA, or other nucleic acid molecule to produce the encoded protein or polypeptide. In other contexts, "expression" refers to the transcription of RNA from an expression cassette, such as, for example, the transcription of a hairpin construct from an expression cassette for use in hpRNA interference.

"Coding region" refers to the portion of a messenger RNA (or the corresponding portion of another nucleic acid molecule such as a DNA molecule) which encodes a protein or polypeptide. "Noncoding region" refers to all portions of a messenger RNA or other nucleic acid molecule that are not a coding region, including, for example, the promoter region, 5' untranslated region ("UTR"), and/or 3' UTR.

Some examples of polynucleotides and methods that inhibit the expression of an MRP are given below. While specific examples are given below, a variety of methods are known in the art by which it is possible to inhibit expression. While the invention is not bound by any particular theory of operation or mechanism of action, the invention provides the exemplary nucleotide and protein sequences disclosed herein and thereby provides a variety of methods by which expression can be inhibited. For example, fragments of noncoding region can be used to make constructs that inhibit expression of an MRP; such fragments can include portions of the promoter region or portions of the 3' noncoding region (i.e., the 3' UTR).

In some embodiments of the invention, inhibition of the expression of an MRP may be obtained by sense suppression or cosuppression. For cosuppression, an expression cassette is designed to express an RNA molecule corresponding to all or part of a messenger RNA encoding an MRP in the "sense" orientation. Overexpression of the RNA molecule can result in reduced expression of the native gene. Accordingly, multiple plant lines transformed with the cosuppression expression cassette are screened to identify those that show suitable inhibition of MRP expression.

The polynucleotide used for cosuppression or other methods to inhibit expression may correspond to all or part of the sequence encoding the MRP, all or part of the 5' and/or 3' untranslated region of an MRP transcript, or all or part of both the coding region and the untranslated regions of a transcript encoding MRP. A polynucleotide used for cosuppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides are used to disrupt the expression of the target gene, generally, sequences of at least 15, 20, 30, 35, 40, 45, 50, 60, 70, 80, 90, 100, 200, 300, 400, 450, 500, 550, 600, 650, 700, 750, 800, or 900 nucleotides or 1 kb or greater may be used. In some embodiments where the polynucleotide comprises all or part of the coding region for the MRP, the expression cassette is designed to eliminate the start codon of the polynucleotide so that no protein product will be transcribed. In this manner, an expression cassette may cause permanent modification of the coding and/or noncoding region of an endogenous gene.

Thus, in some embodiments, for example, the polynucleotide used for cosuppression or another method to inhibit expression will comprise a sequence selected from a particular region of the coding and/or noncoding region. That is, the polynucleotide will comprise a sequence or the complement of a sequence selected from the region between nucleotides 1 and 5139 of the sequence set forth in SEQ ID NO: 2, or selected from the region with a first endpoint at nucleotide 1, 150, 250, 400, 550, 700, 850, 1000, 1150, 1300, 1450, 1600, 1750, 1900, 2050, 2200, 2350, 2500, 2650, 2800, 2950, 3100, 3250, 3400, 3550, 3700, 3850, 4000, 4150, 4300, 4450, 4600, 4750, 4900, 5050, or 5139 and a second endpoint at nucleotide 244, 400, 550, 700, 850, 1000, 1150, 1300, 1450, 1600, 1750, 1900, 2050, 2200, 2350, 2500, 2650, 2800, 2950, 3100, 3250, 3400, 3550, 3700, 3850, 4000, 4150, 4300, 4450, 4600, 4750, 4900, 5050, or 5139. As discussed elsewhere herein, fragments and/or variants of the exemplary disclosed sequences may also be used.

In some embodiments, for example, the polynucleotide will comprise a sequence or the complement of a sequence selected from the region between nucleotides 1 and 3134 of the sequence set forth in SEQ ID NO:1, or selected from the region with a first endpoint at nucleotide 1, 150, 400, 550, 700, 850, 1000, 1150, 1300, 1450, 1600, 1750, 1900, 2050, 2200, 2350, 2500, 2650, 2800, 2950, or 3134, and a second endpoint at nucleotide 1, 150, 400, 550, 700, 850, 1000, 1150, 1300, 1450, 1600, 1750, 1900, 2050, 2200, 2350, 2500, 2650, 2800, 2950, or 3134. Where a noncoding region is used for cosuppression or other method to inhibit expression, it may be advantageous to use a noncoding region that comprises CpG islands (see, e.g., Tariq et al. (2004) *Trends Genet*. 20: 244-251). As discussed elsewhere herein, variants and/or fragments of the exemplary disclosed sequences may also be used.

In some embodiments, for example, the polynucleotide will comprise a sequence or the complement of a sequence selected from the region between nucleotides 1 and 5123 of the sequence set forth in SEQ ID NO:6, or selected from the region with a first endpoint at nucleotide 1, 150, 300, 450, 550, 700, 850, 1000, 1150, 1300, 1450, 1600, 1750, 1900, 2050, 2200, 2350, 2500, 2650, 2800, 2950, 3100, 3250, 3400, 3550, 3700, 3850, 4000, 4150, 4300, 4450, 4600, 4750, 4900, or 5123, and a second endpoint at nucleotide 1, 150, 300, 450, 550, 700, 850, 1000, 1150, 1300, 1450, 1600, 1750, 1900, 2050, 2200, 2350, 2500, 2650, 2800, 2950, 3100, 3250, 3400, 3550, 3700, 3850, 4000, 4150, 4300, 4450, 4600, 4750, 4900, or 5123. As discussed elsewhere herein, variants and/or fragments of the exemplary disclosed sequences may also be used.

In some embodiments, for example, the polynucleotide will comprise a sequence or the complement of a sequence selected from the region between nucleotides 1 and 1350 of the sequence set forth in SEQ ID NO:10, or selected from the region with a first endpoint at nucleotide 1, 150, 300, 450, 550, 700, 850, 1000, 1150, 1300, or 1350, and a second endpoint at nucleotide 1, 150, 300, 450, 550, 700, 850, 1000, 1150, 1300, or 1350. As discussed elsewhere herein, variants and/or fragments of the exemplary disclosed sequences may also be used.

In some embodiments, for example, the polynucleotide will comprise a sequence or the complement of a sequence selected from the region between nucleotides 1 and 465 of the sequence set forth in SEQ ID NO:12, or selected from the region with a first endpoint at nucleotide 1, 150, 300, 450, or 465, and a second endpoint at nucleotide 1, 150, 300, 450, or 465. As discussed elsewhere herein, variants and/or fragments of the exemplary disclosed sequences may also be used.

In some embodiments, for example, the polynucleotide will comprise a sequence or the complement of a sequence selected from the region between nucleotides 1 and 556 of the sequence set forth in SEQ ID NO:71, or selected from the region with a first endpoint at nucleotide 1, 150, 300, 450, or 556, and a second endpoint at nucleotide 1, 150, 300, 450, or 556. As discussed elsewhere herein, variants and/or fragments of the exemplary disclosed sequences may also be used.

Cosuppression may be used to inhibit the expression of plant genes to produce plants having undetectable protein levels for the proteins encoded by these genes. See, for example, Broin et al. (2002) *Plant Cell* 14: 1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91: 3490-3496; Jorgensen et al. (1996) *Plant Mol. Biol.* 31: 957-973; Johansen and Carrington (2001) *Plant Physiol.* 126: 930-938; Broin et al. (2002) *Plant Cell* 14: 1417-1432; Stoutjesdijk et al (2002) *Plant Physiol.* 129: 1723-1731; Yu et al. (2003) *Phytochemistry* 63: 753-763; and U.S. Pat. Nos. 5,034,323; 5,283,184; and 5,942,657; each of which is herein incorporated by reference. The efficiency of cosuppression may be increased by including a poly-dT region in the expression cassette at a position 3' to the sense sequence and 5' of the polyadenylation signal. See, e.g., U.S. Patent Publication No. 20020048814, herein incorporated by reference. Typically, such a nucleotide sequence has substantial sequence identity to the sequence of the transcript of the endogenous gene, for example, greater than about 65%, 80%, 85%, 90%, 95%, or more sequence identity. See, U.S. Pat. Nos. 5,283,184 and 5,034,323, herein incorporated by reference.

In some embodiments of the invention, inhibition of the expression of the MRP may be obtained by antisense suppression. For antisense suppression, the expression cassette is designed to express an RNA molecule complementary to all or part of a messenger RNA comprising a region encoding the MRP. Overexpression of the antisense RNA molecule can result in reduced expression of the native gene. Accordingly, multiple plant lines transformed with the antisense suppression expression cassette are screened to identify those that show the greatest inhibition of MRP expression.

The polynucleotide for use in antisense suppression may correspond to all or part of the complement of the sequence encoding the MRP, all or part of the complement of the 5' and/or 3' untranslated region of the MRP transcript, or all or part of the complement of both the coding sequence and the untranslated regions of a transcript encoding the MRP. In addition, the antisense polynucleotide may be fully complementary (i.e., 100% identical to the complement of the target sequence) or partially complementary (i.e., less than 100% identical to the complement of the target sequence) to the target sequence. That is, an antisense polynucleotide may share 99%, 98%, 97%, 96%, 95%, 94%, 93%, 92%, 91%, 90%, 89%, 88%, 87%, 85%, 80%, or less sequence identity with the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 30, 40, 50, 60, 70, 80, 90, 100, 200, 300, 400, 450, 500, or 550 nucleotides or greater may be used.

Methods for using antisense suppression to inhibit the expression of endogenous genes in plants are described, for example, in Liu et at (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

In some embodiments of the invention, inhibition of the expression of an MRP may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of MRP expression. Methods for using dsRNA interference to inhibit the expression of endogenous plant genes are described in Waterhouse et al. (1998) *Proc. Natl. Acad. Sci. USA* 95: 13959-13964, Liu et al. (2002) *Plant Physiol.* 129: 1732-1743, and WO 99/49029, WO 99/53050, WO 99/61631, and WO 00/49035; each of which is herein incorporated by reference.

In some embodiments of the invention, inhibition of the expression of one or more MRPs may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4: 29-38 and the references cited therein. These methods can make use of either coding region sequences or promoter or regulatory region sequences.

For hpRNA interference, the expression cassette is designed to express an RNA molecule that hybridizes with itself to form a hairpin structure that comprises a single-stranded loop or "spacer" region and a base-paired stem. In some embodiments, the base-paired stem region comprises a sense sequence corresponding to all or part of the endogenous messenger RNA encoding the gene whose expression is to be inhibited, and an antisense sequence that is fully or partially complementary to the sense sequence. The antisense sequence may be located "upstream" of the sense sequence (i.e., the antisense sequence may be closer to the promoter driving expression of the hairpin RNA than the sense sequence). In some embodiments, the base-paired stem region comprises a first portion of a noncoding region such as a promoter and a second portion of the noncoding region that is in inverted orientation relative to the first portion and that is fully or partially complementary to the first portion. In some embodiments, the base-paired stem region comprises a first portion and a second portion which are fully or partially complementary to each other but which comprise both coding and noncoding regions.

In some embodiments, the expression cassette comprises more than one base-paired "stem" region; that is, the expression cassette comprises sequences from different coding and/or noncoding regions which have the potential to form more than one base-paired "stem" region, for example, as diagrammed in FIG. 6 (construct 2 and construct 3). Where more than one base-paired "stem" region is present in an expression cassette, the "stem" regions may flank one another as diagrammed in FIG. 6 (construct 3) or may be in some other configuration (for example, as diagrammed in FIG. 6 (construct 2)). That is, for example, an expression cassette may comprise more than one combination of promoter and complementary sequences as shown in FIG. 6 (construct 1), and each such combination may be driven by a separate promoter. One of skill will be able to create and test a variety of configurations to determine the optimal construct for use in this or any other method for inhibition of expression.

Thus, the base-paired stem region of the molecule generally determines the specificity of the RNA interference. The sense sequence and the antisense sequence (or first and second portion of the noncoding region) are generally of similar lengths but may differ in length. Thus, these sequences may be portions or fragments of at least 10, 19, 20, 30, 50, 70, 90, 100, 120, 140, 160, 180, 200, 220, 240, 260, 280, 300, 320, 340, 360, 380, 400, 500, 600, 700, 800, 900 nucleotides in length, or at least 1, 2, 3, 4, 5, 6, 7, 8, 9, or 10 kb in length. The loop region of the expression cassette may vary in length. Thus, the loop region may be at least 100, 200, 300, 400, 500, 600, 700, 800, 900 nucleotides in length, or at least 1, 2, 3, 4, 5, 6, 7, 8, 9, or 10 kb in length. In some embodiments, the loop region comprises an intron such as, for example, the Adh1 intron.

hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97: 4985-4990; Stoutjesdijk et al. (2002) *Plant Physiol.* 129: 1723-1731; and Waterhouse and Helliwell (2003) *Nat. Rev. Genet.* 4: 29-38. Methods for using hpRNA interference to inhibit or silence the expression of genes are described, for example, in Chuang and Meyerowitz (2000) *Proc. Natl. Acad. Sci. USA* 97: 4985-4990; Stoutjesdijk et al. (2002) *Plant Physiol.* 129: 1723-1731; Waterhouse and Helliwell (2003) *Nat. Rev. Genet.* 4: 29-38; Pandolfini et al. *BMC Biotechnology* 3: 7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30: 135-140, herein incorporated by reference.

For ihpRNA, the interfering molecules have the same general structure as for hpRNA (including the same sizes of sense sequences and antisense sequences), but the RNA molecule additionally comprises an intron in the loop or "spacer" region that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320 (which demonstrated 100% suppression of endogenous gene expression using ihpRNA-mediated interference). Methods for using ihpRNA interference to inhibit the expression of endogenous plant genes are described, for example, in Smith et al. (2000) *Nature* 407: 319-320; Wesley et al. (2001) *Plant J.* 27: 581-590; Wang and Waterhouse (2001) *Curr. Opin. Plant Biol.* 5: 146-150; Waterhouse and Helliwell (2003) *Nat. Rev. Genet.* 4: 29-38; Helliwell and Waterhouse (2003) *Methods* 30: 289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, in this embodiment, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *Proc. Nat'l. Acad. Sci. USA* 99 (Suppl. 4): 16499-16506; Mette et al. (2000) *EMBO J.* 19(19): 5194-5201). As the invention is not bound by a particular mechanism or mode of operation, a decrease in expression may also be achieved by other mechanisms.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for MRP). Methods of using amplicons to inhibit the expression of endogenous plant genes are described, for example, in Angell and Baulcombe (1997) *EMBO J.* 16: 3675-3684, Angell and Baulcombe (1999) *Plant J.* 20: 357-362, and U.S. Pat. No. 6,646,805, each of which is herein incorporated by reference.

In some embodiments, the polynucleotide expressed by the expression cassette of the invention is catalytic RNA or has ribozyme activity specific for the messenger RNA of MRP. Thus, the polynucleotide causes the degradation of the endogenous messenger RNA, resulting in reduced expression of the MRP. This method is described, for example, in U.S. Pat. No. 4,987,071, herein incorporated by reference.

In some embodiments of the invention, inhibition of the expression of one or more MRPs may be obtained by RNA interference by expression of a gene encoding a micro RNA (miRNA). miRNAs are regulatory agents consisting of about 22 ribonucleotides. miRNAs are highly efficient at inhibiting the expression of endogenous genes. See, for example Javier et al. (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of MRP expression, the 22-nucleotide sequence is selected from an MRP transcript sequence and contains 22 nucleotides of said MRP sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

In one embodiment, the polynucleotide encodes a zinc finger protein that binds to a gene encoding an MRP resulting in reduced expression of the gene. In particular embodiments, the zinc finger protein binds to a regulatory region of an MRP gene. In other embodiments, the zinc finger protein binds to a messenger RNA encoding an MRP and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

In some embodiments of the invention, the polynucleotide encodes an antibody that binds to at least one maize MRP and reduces the phytate level of the plant. In another embodiment, the binding of the antibody results in increased turnover of the antibody-MRP complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21: 35-36, incorporated herein by reference. In other embodiments of the invention, the polynucleotide encodes a polypeptide that specifically inhibits the MRP activity of a maize MRP, i.e., an MRP inhibitor.

In some embodiments of the present invention, the activity of an MRP is reduced or eliminated by disrupting the gene encoding the MRP. The gene encoding the MRP may be disrupted by any method known in the art. For example, in one embodiment, the gene is disrupted by transposon tagging. In another embodiment, the gene is disrupted by mutagenizing maize plants using random or targeted mutagenesis, and selecting for plants that have reduced MRP activity.

In one embodiment of the invention, transposon tagging is used to reduce or eliminate the activity of one or more MRPs. Transposon tagging comprises inserting a transposon within an endogenous MRP gene to reduce or eliminate expression of the MRP. "MRP gene" is intended to mean the gene that encodes an MRP protein according to the invention.

In this embodiment, the expression of one or more MRPs is reduced or eliminated by inserting a transposon within a regulatory region or coding region of the gene encoding the MRP. A transposon that is within an exon, intron, 5' or 3' untranslated sequence, a promoter, or any other regulatory sequence of an MRP gene may be used to reduce or eliminate the expression and/or activity of the encoded MRP.

Methods for the transposon tagging of specific genes in plants are well known in the art. See, for example, Maes et al. (1999) *Trends Plant Sci.* 4: 90-96; Dharmapuri and Sonti (1999) *FEMS Microbiol. Lett.* 179: 53-59; Meissner et al. (2000) *Plant J.* 22: 265-274; Phogat et al. (2000) *J. Biosci.* 25: 57-63; Walbot (2000) *Curr. Opin. Plant Biol.* 2: 103-107; Gai et al. (2000) *Nucleic Acids Res.* 28: 94-96; Fitzmaurice et al. (1999) *Genetics* 153: 1919-1928. In addition, the TUSC process for selecting Mu insertions in selected genes has been described in Bensen et al. (1995) *Plant Cell* 7: 75-84; Mena et al. (1996) *Science* 274: 1537-1540; and U.S. Pat. No. 5,962,764; each of which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 243: 472-481; Okubara et al. (1994) *Genetics* 137: 867-874; and Quesada et al. (2000) *Genetics* 154: 421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al. (2000) *Nat. Biotechnol.* 18: 455-457, herein incorporated by reference.

Mutations that impact gene expression or that interfere with the function of the encoded protein are well known in the art. Insertional mutations in gene exons usually result in null-mutants. Mutations in conserved residues are particularly effective in inhibiting the MRP activity of the encoded protein. Conserved residues of plant MRPs suitable for mutagenesis with the goal to eliminate MRP activity are described herein, for example in the conserved domains set forth in SEQ ID NOs: 15, 16, 17, 18, 19, 20, 21, 22, 23, and 24. Such mutants can be isolated according to well-known procedures, and mutations in different MRP loci can be stacked by genetic crossing. See, for example, Gruis et al. (2002) *Plant Cell* 14: 2863-2882.

In another embodiment of this invention, dominant mutants can be used to trigger RNA silencing due to gene inversion and recombination of a duplicated gene locus. See, for example, Kusaba et al. (2003) *Plant Cell* 15: 1455-1467.

The invention encompasses additional methods for reducing or eliminating the activity of one or more MRPs. Examples of other methods for altering or mutating a genomic nucleotide sequence in a plant are known in the art and include, but are not limited to, the use of chimeric vectors, chimeric mutational vectors, chimeric repair vectors, mixed-duplex oligonucleotides, self-complementary oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham et al. (1999) *Proc. Natl. Acad. Sci. USA* 96: 8774-8778; each of which is herein incorporated by reference. Other methods of suppressing expression of a gene involve promoter-based silencing. See, for example, Mette et al. (2000) *EMBO J.* 19: 5194-5201; Sijen et al. (2001) *Curr. Biol.* 11: 436-440; Jones et al. (2001) *Curr. Biol.* 11: 747-757.

Where polynucleotides are used to decrease or inhibit MRP activity, it is recognized that modifications of the exemplary sequences disclosed herein may be made as long as the sequences act to decrease or inhibit expression of the corresponding mRNA. Thus, for example, polynucleotides having at least 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein may be used. Furthermore, portions or fragments of the exemplary sequences or portions or fragments of polynucleotides sharing a particular percent sequence identity to the exemplary sequences may be used to disrupt the expression of the target gene. Generally, fragments or sequences of at least 10, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more contiguous nucleotides, or greater may be used. It is recognized that in particular embodiments, the complementary sequence of such sequences may be used. For example, hairpin constructs comprise both a sense sequence fragment and a complementary, or antisense, sequence fragment corresponding to the gene of interest. Antisense constructs may share less than 100% sequence identity with the gene of interest, and may comprise portions or fragments of the gene of interest, so long as the object of the embodiment is achieved, i.e., so long as expression of the gene of interest is decreased.

Accordingly, the methods of the invention include methods for modulating the levels of endogenous transcription and/or gene expression by transforming plants with antisense or sense constructs to produce plants with reduced levels of phytate. In some embodiments, such modifications will alter the amino acid sequence of the proteins encoded by the genomic sequence as to reduce or eliminate the activity of a particular endogenous gene, such as MRP, in a plant or part thereof, for example, in a seed.

Furthermore, it is recognized that the methods of the invention may employ a nucleotide construct that is capable of directing, in a transformed plant, the expression of at least one protein, or the transcription of at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or transcription of an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

By "modulating" or "modulate" as used herein is intended that the level or amount of a product is increased or decreased in accordance with the goal of the particular embodiment. For example, if a particular embodiment were useful for producing purified MRP enzyme, it would be desirable to increase the amount of MRP protein produced. As another example, if a particular embodiment were useful for decreasing the amount of phytate in a transgenic plant, it would be desirable to decrease the amount of MRP protein expressed by the plant.

The article "a" and "an" are used herein to refer to one or more than one (i.e., to at least one) of the grammatical object of the article. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps.

Fragments and/or variants of the disclosed polynucleotides and proteins encoded thereby are also encompassed by the present invention. By "fragment" is intended a portion of the polynucleotide or a portion of the nucleotide sequence and hence protein encoded thereby, if any. Fragments of a nucleotide sequence may encode protein fragments that retain the biological activity of the native protein and hence have MRP activity. Alternatively, fragments of a nucleotide sequence that are useful as hybridization probes or in sense or antisense suppression generally do not encode fragment proteins retaining biological activity. Thus, fragments of a nucleotide sequence may range in length from at least about 20 nucleotides, about 50 nucleotides, about 100 nucleotides, and up to the full-length nucleotide sequence encoding the proteins of the invention.

A fragment of an MRP nucleotide sequence that encodes a biologically active portion of an MRP protein of the invention will encode at least 15, 25, 30, 50, 100, 150, 200, 250, 300, 350, 400, 450, 500, 550, 600, 650, 700, 750, 800, 850, 900, 950, 1000, 1100, 1200, 1300, 1400, or 1500 contiguous amino acids, or up to the total number of amino acids present in a full-length MRP protein of the invention (for example, 1510 amino acids for SEQ ID NO: 3). Fragments of an MRP nucleotide sequence that are useful in non-coding embodiments, for example, as PCR primers or for sense or antisense suppression, generally need not encode a biologically active portion of an MRP protein. A fragment of an MRP polypeptide of the invention will contain at least 15, 25, 30, 50, 100, 150, 200, 250, 300, 350, 400, 450, 500, 550, 600, 650, 700, 750, 800, 850, 900, 950, 1000, 1100, 1200, 1300, 1400, or 1500 contiguous amino acids, or up to the total number of amino acids present in a full-length MRP protein of the invention (for example, 1510 amino acids for SEQ ID NO: 3).

Thus, a fragment of an MRP nucleotide sequence may encode a biologically active portion of an MRP protein, or it may be a fragment that can be used, for example, as a hybridization probe or in sense or antisense suppression using methods disclosed herein and known in the art. A biologically active portion of an MRP protein can be prepared by isolating a portion of one of the MRP polynucleotides of the invention, expressing the encoded portion of the MRP protein (e.g., by recombinant expression in vitro), and assessing the activity of the encoded portion of the MRP protein. Nucleic acid molecules that are fragments or portions of an MRP polynucleotide comprise at least 15, 16, 17, 18, 19, 20, 21, 22, 23, 24, 25, 26, 27, 28, 29, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2,000, 3,000, 4,000, or 5,000 contiguous nucleotides, or up to the number of nucleotides present in a full-length MRP polynucleotide disclosed herein (for example, 5139 nucleotides for SEQ ID NO: 2).

"Variants" is intended to mean substantially similar sequences. For polynucleotides, a variant comprises a deletion and/or addition at one or more nucleotides at one or more internal sites within the native polynucleotide and/or a substitution of one or more nucleotides at one or more sites in the native polynucleotide. As used herein, a "native" polypeptide or polynucleotide comprises a naturally occurring amino acid sequence or nucleotide sequence. For polynucleotides, conservative variants include those sequences that, because of the degeneracy of the genetic code, encode the amino acid sequence of one of the MRP polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically-derived polynucleotides, such as those generated, for example, by using site-directed mutagenesis but which still encode an MRP protein of the invention. Generally, variants of a particular polynucleotide of the invention will have at least about 40%, 45%, 50%, 55%, 60%, 65%, 70%, 75%, 80%, 85%, 87%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 3 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 87%, 90%, 91%, 92%, 93%, 94%, 95%, 96%, 97%, 98%, 99% or more sequence identity. Sequences of the invention may be variants or fragments of an exemplary polynucleotide sequence, or they may be both a variant and a fragment of an exemplary sequence.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, MRP activity as described herein. Such variants may result from, for example, genetic polymorphism or from human manipulation. Biologically active variants of a native MRP protein of the invention will have at least about 40%, 45%, 50%, 55%, 60%, 65%, 70%, 75%, 80%, 85%, 87%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue. Sequences of the invention may be variants or fragments of an exemplary protein sequence, or they may be both a variant and a fragment of an exemplary sequence.

The proteins of the invention may be altered in various ways including amino acid substitutions, deletions, truncations, and insertions. Methods for such manipulations are generally known in the art. For example, amino acid sequence variants and fragments of the MRP proteins can be prepared by the creation of mutations in the DNA. Methods for mutagenesis and nucleotide sequence alterations are well known in the art. See, for example, Kunkel (1985) *Proc. Natl. Acad. Sci. USA* 82: 488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Nat'l. Biomed. Res. Found., Washington, D.C.), herein incorporated by reference. Conservative substitutions, such as exchanging one amino acid with another having similar properties, may be made.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired MRP activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the methods used in Example 1 and references cited therein as well as by other assays known in the art.

Variant polynucleotides and proteins also encompass sequences and proteins derived from a mutagenic and recombinogenic procedure such as DNA shuffling. With such a procedure, one or more different MRP coding sequences can be manipulated to create a new MRP possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the MRP gene of the invention and other known MRP genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91: 10747-10751; Stemmer (1994) *Nature* 370: 389-391; Crameri et al. (1997) *Nature Biotech.* 15: 436-438; Moore et al. (1997) *J. Mol. Biol.* 272: 336-347; Zhang et al. (1997) *Proc. Natl. Acad. Sci. USA* 94: 4504-4509; Crameri et al. (1998) *Nature* 391: 288-291; and U.S. Pat. Nos. 5,605,793 and 5,837,458.

The present invention further provides a method for modulating (i.e., increasing or decreasing) the concentration or composition of the polypeptides of the claimed invention in a plant or part thereof. Modulation can be effected by increasing or decreasing the concentration and/or the composition (i.e., the ratio of the polypeptides of the claimed invention) in a plant.

In some embodiments, the method comprises transforming a plant cell with a cassette comprising a polynucleotide of the invention to obtain a transformed plant cell, growing the transformed plant cell under conditions allowing expression of the polynucleotide in the plant cell in an amount sufficient to modulate concentration and/or composition of the corresponding protein in the plant cell. In some embodiments, the method comprises utilizing the polynucleotides of the invention to create a deletion or inactivation of the native gene. Thus, a deletion may constitute a functional deletion, i.e., the creation of a "null" mutant, or it may constitute removal of part or all of the coding region of the native gene. Methods for creating null mutants are well-known in the art and include, for example, chimeraplasty as discussed elsewhere herein.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. One method of down-regulation of the protein involves using PEST sequences that provide a target for degradation of the protein.

In addition to sense and antisense suppression, catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al. (1988) *Nature* 334: 585-591.

A variety of cross-linking agents, alkylating agents and radical-generating species as pendant groups on polynucleotides of the present invention can be used to bind, label, detect, and/or cleave nucleic acids. For example, Vlassov et al. (1986) *Nucl. Acids Res.* 14: 4065-4076 describes covalent bonding of a single-stranded DNA fragment with alkylating derivatives of nucleotides complementary to target sequences. Similar work is reported in Knorre et al. (1985) *Biochimie* 67: 785-789. Others have also showed sequence-specific cleavage of single-stranded DNA mediated by incorporation of a modified nucleotide which was capable of activating cleavage (Iverson and Dervan (1987) *J. Am. Chem. Soc.* 109: 1241-1243). Meyer et al. ((1989) *J. Am. Chem. Soc.* 111: 8517-8519) demonstrated covalent crosslinking to a target nucleotide using an alkylating agent complementary to the single-stranded target nucleotide sequence. Lee et al. ((1988) *Biochemistry* 27: 3197-3203) disclosed a photoactivated crosslinking to single-stranded oligonucleotides mediated by psoralen. Home et al. ((1990) *J. Am. Chem. Soc.* 112: 2435-2437) used crosslinking with triple-helix-forming probes. Webb and Matteucci ((1986) *J. Am. Chem. Soc.* 108: 2764-2765) and Feteritz et al. ((1991) *J. Am. Chem. Soc.* 113: 4000) used N4, N4-ethanocytosine as an alkylating agent to crosslink to single-stranded oligonucleotides. In addition, various compounds to bind, detect, label, and/or cleave nucleic acids are known in the art. See, for example, U.S. Pat. Nos. 5,543,507; 5,672,593; 5,484,908; 5,256,648; and 5,681,941. Such embodiments are collectively referred to herein as "chemical destruction."

In some embodiments, an isolated nucleic acid (e.g., a vector) comprising a promoter sequence is transfected into a plant cell. Subsequently, a plant cell comprising the promoter operably linked to a nucleic acid or polynucleotide comprising a nucleotide sequence of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant-forming conditions for a time sufficient to modulate the concentration and/or composition of polypeptides of the present invention in the plant. Plant-forming conditions are well known in the art.

In general, when an endogenous polypeptide is modulated using the methods of the invention, the content of the polypeptide in a plant or part or cell thereof is increased or decreased by at least 5%, 10%, 20%, 30%, 40%, 50%, 60%, 70%, 80%, 90%, or more relative to a native control plant, plant part, or cell lacking the aforementioned cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation.

A transformed plant or transformed plant cell of the invention is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire MRP sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated sequences that encode an MRP protein or have Lpa1 promoter activity and which hybridize under stringent conditions to the Lpa1 sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other nucleic acids comprising corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the MRP sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire MRP sequences disclosed herein, or one or more portions thereof, may be used as probes capable of specifically hybridizing to corresponding MRP sequences and messenger RNAs. To achieve specific hybridization under a variety of conditions, such probes include sequences that are unique among MRP sequences and are at least about 10, 12, 15, 16, 17, 18, 19, 20, 21, 22, 23, 24, 25, 30, 35, 40, 50, 60, 70, 80, 90, or more nucleotides in length. Such probes may be used to amplify corresponding MRP sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.)).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4, 8, or 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, "% form" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/ or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$, of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). The duration of the wash time will be at least a length of time sufficient to reach equilibrium, for example, 4 hours, 8 hours, or 12 hours.

The following terms are used to describe the sequence relationships between two or more nucleic acids or polynucleotides: (a) "reference sequence", (b) "comparison window", (c) "sequence identity", and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4: 11-17; the local alignment algorithm of Smith et al. (1981) *Adv. Appl. Math.* 2: 482; the global alignment algorithm of Needleman and Wunsch (1970) *J. Mol. Biol.* 48: 443-453; the search-for-local-alignment-method of Pearson and Lipman (1988) *Proc. Natl. Acad. Sci.* 85: 2444-2448; the algorithm of Karlin and Altschul (1990) *Proc. Natl. Acad. Sci. USA* 87: 2264, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The MRP polynucleotide of the invention can be provided in expression cassettes for expression in the plant of interest. The cassette will include any necessary 5' and 3' regulatory sequences operably linked to an MRP polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, "operably linked" is intended to mean that the coding regions are in the same reading frame. The cassette may additionally contain at least one additional gene to be cotransformed into the organism. Alternatively, the additional gene (s) can be provided on multiple expression cassettes. Such an expression cassette is provided with a plurality of restriction sites and/or recombination sites for insertion of the MRP polynucleotide to be under the transcriptional regulation of the regulatory regions. The expression cassette may additionally contain selectable marker genes. If protein expression is desired, the cassette may be referred to as a protein expression cassette and will include in the 5'-3' direction of transcription: a transcriptional and translational initiation region (i.e., a promoter), an MRP nucleotide sequence of the invention, and a transcriptional and translational termination region (i.e., termination region) functional in plants.

The regulatory regions (i.e., promoters, transcriptional regulatory regions, and translational termination regions) and/or the MRP polynucleotide of the invention may be native/analogous to the host cell or to each other. Alternatively, the regulatory regions and/or the MRP polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from that from which the polynucleotide was derived, or, if from the same/analogous species, one or both are substantially modified from their original form, or the promoter is not the native promoter for the operably linked polynucleotide.

While it may be optimal to express the sequences using heterologous promoters, the native promoter sequences (e.g., the promoter sequence set forth in SEQ ID NO: 1) may be used. Such constructs can change expression levels of MRP in the plant or plant cell. Thus, the phenotype of the plant or plant cell can be altered. The promoter sequence set forth in SEQ ID NO:1 contains a putative TATA box from nucleotides 2464 to 2470; the 5' UTR may contain an intron.

In an expression cassette, the termination region may be native with the transcriptional initiation region, may be native with the operably linked nucleotide sequence of interest, may be native with the plant host, or may be derived from another source (i.e., foreign or heterologous to the promoter, the nucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262: 141-144; Proudfoot (1991) *Cell* 64: 671-674; Sanfacon et al. (1991) *Genes Dev.* 5: 141-149; Mogen et al. (1990) *Plant Cell* 2:

1261-1272; Munroe et al. (1990) *Gene* 91: 151-158; Ballas et al. (1989) *Nucleic Acids Res.* 17: 7891-7903; and Joshi et al. (1987) *Nucleic Acid Res.* 15: 9627-9639.

Where appropriate, the polynucleotides may be optimized for increased expression in the transformed plant. That is, the genes can be synthesized using plant-preferred codons for improved expression. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17: 477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell, and the sequence may be modified to avoid predicted hairpin secondary mRNA structures.

The expression cassettes may additionally contain 5' leader sequences in the cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus) (*Virology* 154: 9-20), and human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85: 610-9 and Fetter et al. (2004) *Plant Cell* 16: 215-28), cyan florescent protein (CYP) (Bolte et al. (2004) *J. Cell Science* 117: 943-54 and Kato et al. (2002) *Plant Physiol* 129: 913-42), and yellow florescent protein (PhiYFP™ from Evrogen; see Bolte et al. (2004) *J. Cell Science* 117: 943-54).

See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Aci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); Gill et al. (1988) *Nature* 334: 721-724. Such disclosures are herein incorporated by reference.

The above list of selectable marker genes is not meant to be limiting. Any suitable selectable marker gene can be used in the present invention, and one of skill in the art will be able to determine which selectable marker gene is suitable for a particular application.

In preparing the cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3: 2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the transcription and/or expression of a particular nucleotide sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88: 10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227: 229-237, and U.S. Pat. Nos. 5,814,618 and 5,789,156), herein incorporated by reference.

Tissue-preferred promoters can be utilized to target enhanced MRP transcription and/or expression within a particular plant tissue. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen. Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol. Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505. Such promoters can be modified, if necessary, for weak expression.

Leaf-preferred promoters are known in the art. See, for example, Yamamoto et al. (1997) *Plant J.* 12(2): 255-265; Kwon et al. (1994) *Plant Physiol.* 105: 357-67; Yamamoto et al. (1994) *Plant Cell Physiol.* 35(5): 773-778; Gotor et al. (1993) *Plant J.* 3: 509-18; Orozco et al. (1993) *Plant Mol. Biol.* 23(6): 1129-1138; and Matsuoka et al. (1993) *Proc. Natl. Acad. Sci. USA* 90(20): 9586-9590.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3): 433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase); oleosin; and celA (cellulose synthase) (see WO 00/11177 and U.S. Pat. No. 6,225,529, herein incorporated by reference). Gamma-zein is a preferred endosperm-specific promoter. Globulin (Glb-1) is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level transcription or expression is desired, weak promoters will be used. Generally, by "weak promoter" is intended a promoter that drives transcription and/or expression of a coding sequence at a low level. By low level is intended at levels of about 1/1000 transcripts to about 1/100, 000 transcripts to about 1/500,000 transcripts. Alternatively, it is recognized that weak promoters also encompasses promoters that are expressed in only a few cells and not in others to give a total low level of transcription and/or expression. Where a promoter is expressed at unacceptably high levels, portions of the promoter sequence can be deleted or modified to decrease transcription and/or expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

In one embodiment, the polynucleotides of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5): 3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11): 6081-6087); plastocyanin (Lawrence et al. (1997) *J. Biol. Chem.* 272(33): 20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263: 14996-14999). See also Von Heijne et al. (1991) *Plant Mol. Biol. Rep.* 9: 104-126; Clark et al. (1989) *J. Biol. Chem.* 264: 17544-17550; Della-Cioppa et al. (1987)

*Plant Physiol.* 84: 965-968; Romer et al. (1993) *Biochem. Biophys. Res. Commun.* 196: 1414-1421; and Shah et al. (1986) *Science* 233: 478-481.

Methods for transformation of chloroplasts are known in the art. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

In specific embodiments, the MRP sequences of the invention can be provided to a plant using a variety of transient transformation methods. Such transient transformation methods include, but are not limited to, the introduction of the MRP protein or variants and fragments thereof directly into the plant or the introduction of an MRP transcript into the plant. Such methods include, for example, microinjection or particle bombardment. See, for example, Crossway et al. (1986) *Mol. Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the MRP polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma # P3143).

Thus, transgenic plants having low phytic acid content and high levels of bioavailable phosphorus can be generated by reducing or inhibiting MRP gene expression in a plant. For example, the transgenic plant can contain a transgene comprising an inverted repeat of Lpa1 that suppresses endogenous Lpa1 gene expression. In this manner, transgenic plants having the low phytic acid phenotype of lpa1 mutant plants can be generated. The transgenic plant can contain an MRP suppressor sequence alone or an MRP suppressor sequence can be "stacked" with one or more polynucleotides of interest, including, for example, one or more polynucleotides that can affect phytic acid levels or that provide another desirable phenotype to the transgenic plant. For example, such a transgene can be "stacked" with similar constructs involving one or more additional inositol phosphate kinase genes such as ITPK-5 (inositol 1,3,4-trisphosphate 5/6 kinase; e.g., SEQ ID NO: 65; see also WO 03/027243), IPPK (inositol polyphosphate kinase; e.g., SEQ ID NO: 64; see also WO 02/049324), and/or a myo-inositol-1 phosphate synthase gene (milps; see U.S. Pat. Nos. 6,197,561 and 6,291,224; e.g., milps-3 (SEQ ID NO: 25)). With such "stacked" transgenes, even greater reduction in phytic acid content of a plant can be achieved, thereby making more phosphorus bioavailable.

Thus, in certain embodiments the nucleic acid sequences of the present invention can be "stacked" with any combination of nucleic acids of interest in order to create plants with a desired phenotype. By "stacked" or "stacking" is intended that a plant of interest contains one or more nucleic acids collectively comprising multiple nucleotide sequences so that the transcription and/or expression of multiple genes are altered in the plant. For example, antisense nucleic acids of the present invention may be stacked with other nucleic acids which comprise a sense or antisense nucleotide sequence of at least one of ITPK-5 (e.g., SEQ ID NO: 65) and/or inositol polyphosphate kinase (IPPK; e.g., SEQ ID NO: 64), or other genes implicated in phytic acid metabolic pathways such as Lpa3 or myo-inositol kinase (see, e.g., copending application entitled, "Plant Myo-Inositol Kinase Polynucleotides and Methods of Use, Appl. No. 60/573,000, filed May 20, 2004; SEQ ID NO: 68); Lpa2 (see U.S. Pat. Nos. 5,689,054 and 6,111,168); myo-inositol 1-phosphate synthase (milps; e.g., SEQ ID NO: 25), myo-inositol monophosphatase (IMP) (see WO 99/05298 and U.S. application Ser. No. 10/042,465, filed Jan. 9, 2002); IP2K (e.g., SEQ ID NO: 67); and the like. The addition of such nucleic acids could enhance the reduction of phytic acid and InsP intermediates, thereby providing a plant with more bioavailable phosphate and/or reduced phytate. The nucleic acids of the present invention can also be stacked with any other gene or combination of genes to produce plants with a variety of desired trait combinations. For example, in some embodiments, a phytase gene (e.g., SEQ ID NO: 66) is stacked with an lpa1 mutant so that phytase is expressed at high levels in the transgenic plant. Phytase genes are known in the art. See, for example, Maugenest et al. (1999) *Plant Mol. Biol.* 39: 503-514; Maugenest et al. (1997) *Biochem. J.* 322: 511-517; WO 200183763; WO200200890.

An MRP polynucleotide also can be stacked with any other polynucleotide(s) to produce plants having a variety of desired trait combinations including, for example, traits desirable for animal feed such as high oil genes (see, e.g., U.S. Pat. No. 6,232,529, which is incorporated herein by reference); balanced amino acids (e.g., hordothionins; see U.S. Pat. Nos. 5,990,389; 5,885,801; 5,885,802; and 5,703,409, each of which is incorporated herein by reference); barley high lysine (Williamson et al. (1987) *Eur. J. Biochem.* 165: 99-106 and WO 98/20122); high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123); increased digestibility (e.g., modified storage proteins) and thioredoxins (U.S. Pat. No. 7,009,087).

An MRP polynucleotide also can be stacked with one or more polynucleotides encoding a desirable trait such as a polynucleotide that confers, for example, insect, disease or herbicide resistance (e.g., *Bacillus thuringiensis* toxic proteins; U.S. Pat. Nos. 5,366,892; 5,747,450; 5,737,514; 5,723, 756; 5,593,881; Geiser et al. (1986) *Gene* 48: 109); lectins (Van Damme et al. (1994) *Plant Mol. Biol.* 24: 825); fumonisin detoxification genes (U.S. Pat. No. 5,792,931); avirulence and disease resistance genes (Jones et al. (1994) *Science* 266: 789; Martin et al. (1993) *Science* 262: 1432; Mindrinos et al. (1994) *Cell* 78: 1089); acetolactate synthase mutants that lead to herbicide resistance such as the S4 and/or Hra mutations; inhibitors of glutamine synthase such as phosphinothricin or basta (e.g., the bar gene); and glyphosate (e.g., the EPSPS gene and the GAT gene; see, for example, U.S. Publication No. 20040082770 and WO 03/092360). Additional polynucleotides that can be stacked with a MRP polynucleotide include, for example, those encoding traits desirable for processing or process products such as modified oils (e.g., fatty acid desaturase genes (U.S. Pat. No. 5,952,544;

WO 94/11516); modified starches (e.g., ADPG pyrophosphorylases, starch synthases, starch branching enzymes, and starch debranching enzymes); and polymers or bioplastics (e.g., U.S. Pat. No. 5,602,321). An MRP polynucleotide of the invention also can be stacked with one or more polynucleotides that provide desirable agronomic traits such as male sterility (e.g., U.S. Pat. No. 5,583,210), stalk strength, flowering time, or transformation technology traits such as cell cycle regulation or gene targeting (e.g., WO 99/61619; WO 00/17364; WO 99/25821). Other desirable traits that are known in the art include high oil content; increased digestibility; balanced amino acid content; and high energy content. Such traits may refer to properties of both seed and non-seed plant tissues, or to food or feed prepared from plants or seeds having such traits; such food or feed will have improved quality.

These stacked combinations can be created by any method including but not limited to cross breeding plants by any conventional or TopCross methodology, or genetic transformation. In this regard, it is understood that transformed plants of the invention include a plant that contains a sequence of the invention that was introduced into that plant via breeding of a transformed ancestor plant. If traits are stacked by genetically transforming the plants, the nucleic acids of interest can be combined at any time and in any order. More generally, where any method requires more than one step to be performed, it is understood that steps may be performed in any order that accomplishes the desired end result. For example, a transgenic plant comprising one or more desired traits can be used as the target to introduce further traits by subsequent transformation. The traits can be introduced simultaneously in a co-transformation protocol with the polynucleotides of interest provided by any combination of cassettes suitable for transformation. For example, if two sequences will be introduced, the two sequences can be contained in separate cassettes (trans) or contained on the same transformation cassette (cis). Transcription and/or expression of the sequences can be driven by the same promoter or by different promoters. In certain cases, it may be desirable to introduce a cassette that will suppress the expression of the polynucleotide of interest. This may be combined with any combination of other cassettes to generate the desired combination of traits in the plant. Alternatively, traits may be stacked by transforming different plants to obtain those traits; the transformed plants may then be crossed together and progeny may be selected which contains all of the desired traits.

Stacking may also be performed with fragments of a particular gene or nucleic acid. In such embodiments, a plants is transformed with at least one fragment and the resulting transformed plant is crossed with another transformed plant; progeny of this cross may then be selected which contain the fragment in addition to other transgenes, including, for example, other fragments. These fragments may then be recombined or otherwise reassembled within the progeny plant, for example, using site-specific recombination systems known in the art. Such stacking techniques could be used to provide any property associated with fragments, including, for example, hairpin RNA (hpRNA) interference or intron-containing hairpin RNA (ihpRNA) interference.

It is understood that in some embodiments the nucleic acids to be stacked with MRP can also be designed to reduce or eliminate the expression of a particular protein, as described in detail herein for MRP. Thus, the methods described herein with regard to the reduction or elimination of expression of MRP are equally applicable to other nucleic acids and nucleotide sequences of interest, such as, for example, IPPK, ITPK-5, and milps, examples of which are known in the art and which are expected to exist in most varieties of plants. Accordingly, the descriptions herein of MRP fragments, variants, and other nucleic acids and nucleotide sequences apply equally to other nucleic acids and nucleotide sequences of interest such as milps (e.g., SEQ ID NO: 25), IPPK (e.g., SEQ ID NO: 64), ITPK-5 (e.g., SEQ ID NO: 65), IP2K (e.g., SEQ ID NO:67), and Lpa3 or MIK (myo-inositol kinase; e.g., SEQ ID NO: 68). For example, an antisense construct could be designed for milps comprising a nucleotide sequence that shared 90% sequence identity to the complement of SEQ ID NO: 25 or was at least a 19-nucleotide fragment of the complement of SEQ ID NO: 25.

Transformation protocols as well as protocols for introducing polypeptides or polynucleotides into plants may vary depending on the type of plant or plant cell, i.e., monocot or dicot, targeted for transformation. Suitable methods of introducing polypeptides or polynucleotides into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3: 2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6: 923-926); and Lec1 transformation (WO 00/28058). Also see Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6: 559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91: 440-444 (maize); Fromm et al. (1990) *Biotechnology* 8: 833-839 (maize); Hooykaas-Van Slogteren et al. (1984) *Nature (London)* 311: 763-764; Bowen et al., U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5: 81-84. These plants may then be grown and either pollinated with the same transformed strain or different strains; the resulting progeny having the desired phenotypic characteristic can then be identified. Two or more generations may be grown to ensure that the desired phenotypic characteristic is stably maintained and inherited and then seeds harvested to ensure that stable transformants exhibiting the desired phenotypic characteristic have been achieved. In this manner, the present invention provides transformed seed (also referred to as "transgenic seed") having a nucleotide construct of the invention, for example, a cassette of the invention, stably incorporated into their genome.

As used herein, the term "plant" includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art, including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or that a polypeptide is introduced into a plant.

Thus, it is recognized that methods of the present invention do not depend on the incorporation of an entire nucleotide construct into the genome, only that the plant or cell thereof is altered as a result of the introduction of a nucleotide construct or polypeptide into a cell. In one embodiment of the invention, the genome may be altered following the introduction of a nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

In other embodiments, the polynucleotides of the invention may be introduced into plants by contacting plants with a virus or viral nucleic acids. Generally, such methods involve incorporating a nucleotide construct of the invention within a viral DNA or RNA molecule. It is recognized that an MRP of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191; 5,889,190; 5,866,785; 5,589,367; 5,316,931, and Porta et al. (1996) *Molecular Biotechnology* 5: 209-221; herein incorporated by reference.

The use of the term polynucleotides herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The promoter nucleotide sequences and methods disclosed herein are useful in regulating expression of any heterologous nucleotide sequence in a host plant in order to vary the phenotype of a plant. Because the Lpa1 promoter provides weak constitutive expression of operably linked coding regions, the Lpa1 promoter finds particular use in altering gene expression in various tissues.

Various changes in phenotype are of interest including modifying the fatty acid composition in seeds, altering the amino acid content of seeds, altering a seed's pathogen defense mechanism, and the like. These results can be achieved by providing expression of heterologous products or increased expression of endogenous products in embryos. Alternatively, the results can be achieved by providing for a reduction of expression of one or more endogenous products, particularly enzymes or cofactors in the seed. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered by genetic engineering in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165: 99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502); corn (Pedersen et al. (1986) *J. Biol. Chem.* 261: 6279; Kirihara et al. (1988) *Gene* 71: 359); and rice (Musumura et al. (1989) *Plant Mol. Biol.* 12: 123). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48: 109, and the like.

Genes encoding disease resistance traits include detoxification genes, such as against fumonisin (U.S. Pat. No. 5,792,931); avirulence (avr) and disease resistance (R) genes (Jones et al. (1994) *Science* 266: 789; Martin et al. (1993) *Science* 262: 1432; and Mindrinos et al. (1994) *Cell* 78: 1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron. Other genes include kinases and those encoding compounds toxic to either male or female gametophytic development.

The quality of grain is reflected in traits such as, for example, levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170: 5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Some chemicals can inhibit MRP protein transport activity. For example, the sulfonylurea glibenclamide can inhibit the glucuronide transport activity of *Arabidopsis AtMRP*5 and can affect its function in guard cells (Gaedeke et al. (2001) *EMBO J.* 20: 1875-1887; Lee et al. (2004) *Plant Physiol.* 134: 528-538). It is expected that glibenclamide would also inhibit maize MRP3 transport activity and thus would produce a low phytic acid phenotype.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

EXPERIMENTAL

Example 1

Identification and Characterization of Maize Low Phytic Acid (Lpa) Mutant Plants A collection of indexed mutagenized F2 families derived from several Mu active stocks (Bensen et al. (1995) *Plant Cell* 7: 75-84) was screened for seeds having high inorganic phosphate content using a rapid $P_i$ assay as described below. Candidates identified as producing high-$P_i$ seed were crossed with suitable maize and the progeny examined to confirm the mutations and to determine whether the mutations were allelic to the previously identified lpa1 mutant (referred to herein as "lpa1-1"; see U.S. Pat. No. 5,689,054; Raboy et al. (2000) *Plant Physiol.* 124: 355-68). Several of these lpa lines were allelic to the earlier-identified lpa1 mutant, and these Mu-insertion alleles of the lpa1 mutant were used to clone the gene responsible for the lpa1 mutation. Segregation populations were created by crossing heterozygous line PV03 57 C-05 (carrying Mu-tagged lpa1) with homozygous line GP24L3 (carrying EMS allele lpa1-1). F1 plants were self-pollinated to produce F2 seeds. The phenotype of F1 plants was determined by analyzing F2 seed Pi and phytic acid. Genomic DNA was extracted from leaves of individual F1 plants and used for PCR analysis as further described in Example° 2.

Inorganic Phosphate (Pi) Assay

A rapid test was used to assay inorganic phosphate content in kernels. Individual kernels were placed in a 25-well plastic tray and crushed at 2000 psi using a hydraulic press. Two milliliters of 1N $H_2SO_4$ was added to each sample. The samples were incubated at room temperature for two hours, after which four milliliters of 0.42% ammonium molybdate-1N $H_2SO_4$:10% ascorbic acid (6:1) was added to each sample. Increased $P_i$ content was signaled by the development of blue color within about 20 minutes. Positive controls included lpa2 mutant kernels, and negative controls included wild-type kernels.

Determination of Phytic Acid and Inorganic Phosphate Content

Dry, mature seeds were assayed for phytic acid and $P_i$ content using modifications of the methods described by Haug and Lantzsch ((1983) *J. Sci. Food Agric.* 34: 1423-1426, entitled "Sensitive method for the rapid determination of phytate in cereals and cereal products") and Chen et al. ((1956) *Anal. Chem.* 28: 1756-1758, entitled "Microdetermination of phosphorus"). Single kernels were ground using a Geno/Grinder2000™ grinder (Sepx CertiPrep®, Metuchen, N.J.). Samples of 25 to 35 mg were placed into 1.5 ml Eppendorf® tubes and 1 ml of 0.4 N HCl was added to the tubes, which were then shaken on a gyratory shaker at room temperature for 3.5 hours. The tubes were then centrifuged at 3,900 g for 15 minutes. Supernatants were transferred into fresh tubes and used for both phytic acid and $P_i$ determinations; measurements were performed in duplicate.

For the phytic acid assay, 35 µl of each extract was placed into wells of a 96-well microtiter plate and then 35 µl of distilled $H_2O$ and 140 µl of 0.02% ammonium iron (III) sulphate-0.2 N HCl were added to each sample. The microtiter plate was covered with a rubber lid and heated in a thermal cycler at 99° C. for 30 minutes, then cooled to 4° C. and kept on an ice water bath for 15 minutes, and then left at room temperature for 20 minutes. The plate was then sealed with sticky foil and centrifuged at 3,900 g at 24° C. for 30 minutes. Eighty µl of each supernatant was placed into wells of a fresh 96-well plate. For absorbance measurements, 120 µl of 1% 2,2'-bipyridine-1% thioglycolic acid solution (10 g 2,2'-bipyridine (Merck Art. 3098), 10 ml thioglycolic acid (Merck Art. 300) in ddw to 1 liter) was added to each well and absorbance was recorded at 519 nm using a VERSAmax™ microplate reader (Molecular Devices®, Sunnyvale, Calif.). Phytic acid content is presented as phytic acid phosphorus (PAP). Authentic phytic acid (Sigma®, P-7660) served as a standard. This phytic acid assay also measured $InsP_5$ and $InsP_4$ present in the samples.

Phytic acid was also assayed according to modifications of the methods described by Latta & Eskin (1980) (*J. Agric Food Chem.* 28: 1313-1315) and Vaintraub & Lapteva (1988) (*Analytical Biochemistry* 175: 227-230). For this assay, 25 µl of extract was placed into wells of a 96-well microtiter plate; then 275 µl of a solution of 36.3 mM NaOH and 100 µl of Wade reagent (0.3% sulfosalicylic acid in 0.03% $FeCl_3.6H_2O$) was added to each well. The samples were mixed and centrifuged at 39,000 g at 24° C. for 10 minutes. An aliquot of supernatant (200 µl) from each well was transferred into a new 96-well plate, and absorbance was recorded at 500 nm using a VERSAmax™ microplate reader (Molecular Devices®, Sunnyvale, Calif.).

To determine $P_i$, 200 µl of each extract was placed into wells of a 96 well microtiter plate. 100 µl of 30% aqueous trichloroacetic acid was then added to each sample and the plates were shaken and then centrifuged at 3,900 g for 10 minutes. Fifty µl of each supernatant was transferred into a fresh plate and 100 µl of 0.42% ammonium molybdate-1N $H_2SO_4$: 10% ascorbic acid (7:1) was added to each sample. The plates were incubated at 37° C. for 30 minutes and then absorbance was measured at 800 nm. Potassium phosphate was used as a standard. $P_i$ content was presented as inorganic phosphate phosphorus.

Determination of Seed Myo-Inositol

Myo-inositol was quantified in dry, mature seeds and excised embryos. Tissue was ground as described above and mixed thoroughly. 100 milligram samples were placed into 7 ml scintillation vials and 1 ml of 50% aqueous ethanol was added to each sample. The vials were then shaken on a gyratory shaker at room temperature for 1 hour. Extracts were decanted through a 0.45 µm nylon syringe filter attached to a 1 ml syringe barrel. Residues were re-extracted with 1 ml fresh 50% aqueous ethanol and the second extracts were filtered as before. The two filtrates were combined in a 10×75 mm glass tube and evaporated to dryness in a SpeedVac® microcentrifuge (Savant). The myo-inositol derivative was produced by redissolving the residues in 50 µl of pyridine and 50 µl of trimethylsilyl-imidazole:trimethylchlorosilane (100: 1) (Tacke and Casper (1996) *J. AOAC Int.* 79: 472-475). Precipitate appearing at this stage indicates that the silylation reaction did not work properly. The tubes were capped and incubated at 60° C. for 15 minutes. One milliliter of 2,2,4-trimethylpentane and 0.5 milliliters of distilled water were added to each sample. The samples were then vortexed and centrifuged at 1,000 g for 5 minutes. The upper organic layers were transferred with Pasteur pipettes into 2 milliliter glass autosampler vials and crimp capped.

Myo-inositol was quantified as a hexa-trimethylsilyl ether derivative using an Agilent Technologies® model 5890 gas chromatograph coupled with an Agilent Technologies® model 5972 mass spectrometer. Measurements were performed in triplicate. One μl samples were introduced in the splitless mode onto a 30 m×0.25 mm i.d.×0.25 μm film thickness 5MS column (Agilent Technologies®). The initial oven temperature of 70° C. was held for 2 minutes, then increased at 25° C. per minute to 170° C., then increased at 5° C. per minute to 215° C., and finally increased at 25° C. per minute to 250° C. and then held for 5 minutes. The inlet and transfer line temperatures were 250° C. Helium at a constant flow of 1 ml per minute was used as the carrier gas. Electron impact mass spectra from m/z 50-560 were acquired at −70 eV after a 5-minute solvent delay. The myo-inositol derivative was well resolved from other peaks in the total ion chromatograms. Authentic myo-inositol standards in aqueous solutions were dried, derivatized, and analyzed at the same time. Regression coefficients of four-point calibration curves were typically 0.999-1.000.

Determination of Seed Inositol Phosphates

The presence of significant amounts of inositol phosphates in mature seeds was determined by HPLC according to the Dionex Application Note AN65, "Analysis of inositol phosphates" (Dionex Corporation®, Sunnyvale, Calif.). Tissue was ground and mixed as described above. 500 mg samples were placed into 20 ml scintillation vials and 5 ml of 0.4 M HCl was added to the samples. The samples were shaken on a gyratory shaker at room temperature for 2 hours and then allowed to sit at 4° C. overnight. Extracts were centrifuged at 1,000 g for 10 min and filtered through a 0.45 μm nylon syringe filter attached to a 5 ml syringe barrel. Just prior to HPLC analysis, 600 μl aliquots of each sample were clarified by passage through a 0.22 μm centrifugal filter. A Dionex Corporation® DX 500 HPLC with a Dionex Corporation® model AS3500 autosampler was used. 25 μl samples were introduced onto a Dionex Corporation® 4×250 mm OmniPac™ PAX-100 column; Dionex Corporation® 4×50 mm OmniPac™ PAX-100 guard and ATC-1 anion trap columns also were used. Inositol phosphates were eluted at 1 ml/min with the following mobile phase gradient: 68% A (distilled water)/30% B (200 mM NaOH) for 4.0 min; 39% A/59% B at 4.1 through 15.0 min; return to initial conditions at 15.1 min. The mobile phase contained 2% C (50% aqueous isopropanol) at all times to maintain column performance. A Dionex Corporation® conductivity detector module II was used with a Dionex Corporation® ASRS-Ultra II anion self-regenerating suppressor set up in the external water mode and operated with a current of 300 mA. Although quantitative standards were available, $InsP_3$, $InsP_4$ and $InsP_5$ were partially but clearly resolved from each other and $InsP_6$.

The results of the above assays demonstrated that the lpa1 mutant maize plants have a phenotype of reduced phytic acid and increased $P_i$ in seeds, but lpa1 seeds do not accumulate inositol phosphate intermediates.

Example 2

Isolation and Characterization of Maize MRP3 (Lpa1) Gene

Initially, a PCR-based method was used in an effort to clone the lpa1 gene, but this effort was unsuccessful. However, a Mu-insertion site in a transcriptional activator gene was identified, and co-segregation analysis indicated that this Mu-insertion site was very closely linked to the Lpa1 locus. This marker, designated "TAP," was used for map-based cloning of the Lpa1 gene.

The PCR protocol used to identify the TAP marker is known as SAIFF: Selected Amplification of Insertion Flanking Fragments. First, genomic DNA was prepared from 5-8 plants of individual lines which were $Mu^+$ and $Mu^-$. The genomic DNA was digested with BfaI or MseI, neither of which cuts the Mu TIR (Terminal Inverted Repeat). The restriction ends generated by BfaI and MseI are the same and are compatible with the Mse/Bfa adaptor.

10×RL buffer: 2.5 μl
BSA: 0.25 μl
DNA: 0.3-0.5 μg
Enzymes: 1 μl
Water: bring to 25 μl This mixture was incubated at 37° C. for 3 to 6 hours and then denatured at 65° C. for 20 minutes. Adaptors were then ligated to the digested DNA by adding 5 μl of adaptor mixture to each reaction:

100 mM rATP: 0.3 μl
10×RL buffer: 0.5 μl
40 uM Adaptor: 1 μl
T4 ligase: 1 μl (3 U/μl)
Water: bring to 5 μl This mixture was then incubated at 4° C. overnight. The ligation reaction was purified with a PCR Purification Kit (Qiagen®) to remove excess adaptors, and the reaction was brought to a final volume of 50 μl in water or elution buffer.

Control PCR was performed to check the digestion and ligation. Either regular Taq enzyme or another non-hot start DNA polymerase was used for the control PCR. 1 μl of the purified ligation reaction was used as the template in a 10 μl PCR reaction. The primer used was the adaptor primer (MspExt18 or the nested MseInt18 primer). DMSO was added to the mixture to a final level of 5%. The PCR conditions were 94° C. 2 min; 35 cycles of 94° C. 30 sec, 55° C. 30 sec, and 72° C. 2 min 30 sec; and a final extension at 72° C. for 7 min. The reaction was then run on a 1% agarose gel and the amplification reaction visualized. Non-specific adaptor-to-adaptor amplification should occur, and there should be a nice smear on the gel ranging in size from 300 bp to 3 kb.

1 μl of the purified ligation reaction was then used as the template in a 10 μl PCR reaction using Hot Start™ DNA polymerase (Qiagen®). Primers MuExt22D and MspExt18 were added to a final concentration of 0.3-0.5 μM. DMSO was added to a final level of 5%. PCR conditions were 95° C. 15 min, 20 cycles of 94° C. 30 sec, 55° C. 30 sec, and 72° C. 2 min 30 sec, followed by a final extension at 72° C. for 7 min. The reaction was then diluted 1:10 with water.

Nested ($2^{nd}$ round) PCR was performed with Ex Taq DNA polymerase, but any robust enzyme could be used. 1 μl of the Mu+ and Mu− pools was used as template in a 10 μl reaction. The primers were MuInt19 and Adaptor nested primers (+2 selective primers, 0.3-0.5 μM final concentration). DMSO was added to a final level of 5%. "Touchdown" PCR conditions were: 95° C. 2 min, 11 cycles of 94° C. 30 sec, (65° C.-0.8° C./cycle) for 30 sec, and 72° C. 2 min 30 sec, followed by 24 cycles of 94° C. 30 sec, 56° C. 30 sec, and 72° C. 2 min 30 sec, with a final extension at 72° C. for 7 min. PCR reactions were electrophoresed on a 1.5% agarose gel and examined to identify bands which were present in the $Mu^+$ pool but absent in the Mu− pool.

The second-round (nested) PCR was then repeated using as template first round PCR reactions from individual plants to confirm the co-segregation. DNA fragments that were present in all Mu+ individuals and absent in all Mu– individuals were isolated from the gel and purified. The purified DNA was cloned into a vector such as TOPO TA or pGEM-T Easy according to the manufacturer's instructions (Invitrogen™, Carlsbad, Calif.; Promega®, Madison, Wis.).

Clones were screened with PCR to identify correctly-cloned inserts for each fragment of interest. White colonies (8) were selected and resuspended in 40 µl water; the remainder of the colony was streaked on selective media (LB+Amp) for later recovery. 1 µl of the resuspended colonies were used as the template in a 10 µl PCR reaction. PCR conditions were the same as described above for nested PCR, and one positive clone was selected for each fragment.

Cultures of bacteria carrying the selected clone were grown in liquid selective media (LB+Amp). Plasmid minipreps were performed using a Spin Column Miniprep Kit (Qiagen®). The final volume was brought to 50 µl with elution buffer, and the minipreps were checked by digesting 2 µl of plasmid DNA with EcoRI. The DNA was then sequenced to confirm that each plasmid contained the MuTIR (53 bp including the MuInt19 site). The sequence of the fragment was then used to design a fragment-specific primer to pair with MuInt19 or MuExt22D, and co-segregation analysis was performed using PCR on DNA from all individuals in the segregation population.

BfaI and MseI share the same adaptor:

```
MseI/BfaI adaptor-lower:
5'-TACTCAGGACTCATCGACCGT-3'      (SEQ ID NO: 26)

MseI/BfaI adaptor-upper:
5'-GTGAACGGTCGATGAGTCCTGAG-3'    (SEQ ID NO: 27)
```

Adaptors were made by mixing these two oligonucleotides, denaturing at 95° C. for 5 minutes, and then cooling the mixture down slowly to room temperature. The adaptor is designed in such a way that the original restriction sites are not restored after the ligation.

```
Adaptor Ext 18 primer (MspExt18):
5'-GTGAACGGTCGATGAGTC-3'    (SEQ ID NO: 28)

MseI/BfaI adp Int18 primer (MseInt18):
5'-GTCGATGAGTCCTGAGTA-3'    (SEQ ID NO: 29)
```

BfaI+2 selective primers (16):

```
BfaIntGAA:  GATGAGTCCTGAGTAGAA  (SEQ ID NO: 30)
BfaIntGAC:  GATGAGTCCTGAGTAGAC  (SEQ ID NO: 31)
BfaIntGAG:  GATGAGTCCTGAGTAGAG  (SEQ ID NO: 32)
BfaIntGAT:  GATGAGTCCTGAGTAGAT  (SEQ ID NO: 33)
BfaIntGCA:  GATGAGTCCTGAGTAGCA  (SEQ ID NO: 34)
BfaIntGCC:  GATGAGTCCTGAGTAGCC  (SEQ ID NO: 35)
BfaIntGCG:  GATGAGTCCTGAGTAGCG  (SEQ ID NO: 36)
BfaIntGCT:  GATGAGTCCTGAGTAGCT  (SEQ ID NO: 37)
BfaIntGGA:  GATGAGTCCTGAGTAGGA  (SEQ ID NO: 38)
BfaIntGGC:  GATGAGTCCTGAGTAGGC  (SEQ ID NO: 39)
BfaIntGGG:  GATGAGTCCTGAGTAGGG  (SEQ ID NO: 40)
BfaIntGGT:  GATGAGTCCTGAGTAGGT  (SEQ ID NO: 41)
BfaIntGTA:  GATGAGTCCTGAGTAGTA  (SEQ ID NO: 42)
BfaIntGTC:  GATGAGTCCTGAGTAGTC  (SEQ ID NO: 43)
BfaIntGTG:  GATGAGTCCTGAGTAGTG  (SEQ ID NO: 44)
BfaIntGTT:  GATGAGTCCTGAGTAGTT  (SEQ ID NO: 45)
```

MseI+2 selective primers (16):

```
MseIntAAA:  CGATGAGTCCTGAGTAAAA  (SEQ ID NO: 46)
MseIntAAC:  CGATGAGTCCTGAGTAAAC  (SEQ ID NO: 47)
MseIntAAG:  CGATGAGTCCTGAGTAAAG  (SEQ ID NO: 48)
MseIntAAT:  CGATGAGTCCTGAGTAAAT  (SEQ ID NO: 49)
MseIntACA:  CGATGAGTCCTGAGTAACA  (SEQ ID NO: 50)
MseIntACC:  GATGAGTCCTGAGTAACC   (SEQ ID NO: 51)
MseIntACG:  GATGAGTCCTGAGTAACG   (SEQ ID NO: 52)
MseIntACT:  GATGAGTCCTGAGTAACT   (SEQ ID NO: 53)
MseIntAGA:  CGATGAGTCCTGAGTAAGA  (SEQ ID NO: 54)
MseIntAGC:  GATGAGTCCTGAGTAAGC   (SEQ ID NO: 55)
MseIntAGG:  GATGAGTCCTGAGTAAGG   (SEQ ID NO: 56)
MseIntAGT:  CGATGAGTCCTGAGTAAGT  (SEQ ID NO: 57)
MseIntATA:  CGATGAGTCCTGAGTAATA  (SEQ ID NO: 58)
MseIntATC:  GATGAGTCCTGAGTAATC   (SEQ ID NO: 59)
MseIntATG:  GATGAGTCCTGAGTAATG   (SEQ ID NO: 60)
MseIntATT:  CGATGAGTCCTGAGTAATT  (SEQ ID NO: 61)
```

10×RL Buffer:
100 mM Tris-HCl, pH 7.5
100 mM MgOAc,
500 mM KOAc,
50 mM DTT

Map-based cloning requires a high-resolution genetic map and a physical map around the locus of interest. Using the TAP marker, which was closely linked to the Lpa1 locus, the inventors identified a BAC contig containing about 120 BAC clones from a proprietary BAC library. PCR markers were developed based on BAC-end sequences and EST sequences, and the segregating populations of individuals described above were also used for genetic mapping. Individual F1 seeds were phenotyped by measuring Pi and phytic acid content. DNA was extracted from the individual F1 seeds with the Qiagen® Genomic DNA Purification Kit. Individuals were genotyped using PCR carried out according to the instructions of the Expand High Fidelity PCR system (Roche®). 792 individuals were analyzed to construct a fine map around the Lpa1 locus.

Based on the genetic map and the BAC physical map, the inventors identified two over-lapping BACs which cover the Lpa1 locus. The two BACs, b149a.i9 and b156a.m1, were sequenced. Open reading frames in each BAC were identified by using the Fgenesh computer program and BLAST searching against maize EST databases. BAC b149a.i9 is 140 kb in length and has several ORFs predicted by Fgenesh. Only two ORFs were found to have corresponding ESTs. One of the ORFs encodes an MRP ABC transporter protein. Gene-specific primers were synthesized from these two ORFs and used to search for the Mu insertion in the lpa1 mutant Mu-insertion alleles. A Mu insertion was found in the MRP ABC transporter gene in lpa1 allele PV03 56 C-05. A Mu insertion was also found in the same gene for eight other lpa1 alleles. Mu is inserted in Exon 1 at nucleotide 585 in Mu82978.17; at nucleotide 874 in PV03 57 C-3; and in Exon 11 at nucleotide 6069 in Mu82911.08. The remaining 6 alleles all have the same Mu insertion site as Mu82978.17. The MRP gene was also sequenced from four lpa1 EMS alleles. In two alleles (91286 and 94580), a stop codon was introduced in place of codons encoding R and Q at amino acids 371 and 595, respectively. In allele 91281, E was changed to L at amino acid 680, while in the original lpa1-1 allele, A was mutated to V at amino acid 1432.

The maize MRP ABC transporter gene was designated ZmMRP3 (Zea mays multidrug resistance-associated protein 3), or Lpa1 (low phytic acid). The MRP group of the ABC transporter family includes many proteins which are involved in diverse cellular responses. MRPs can transport a great range of substances. Some of the MRPs also have regulatory activity on other transporters or channel proteins. This maize MRP (ZmMRP3) is the first MRP shown to play a role in phytic acid metabolism and cellular function, and provides a new way in which phytic acid and available phosphorus content of plant seeds may be manipulated. Previously, the phytic acid biosynthesis pathway was altered by manipulating genes encoding the enzymes that convert glucose 6-P to phytic acid. In contrast, while the invention is not bound by a particular mechanism of operation, MRP is a transporter and/or transporter regulator. Thus, altering MRP expression and/or functionality in transgenic plants would be expected to have minimal effects on InsP intermediates of phytic acid biosynthesis pathway.

During the course of this study, the inventors determined that knockout lpa1 alleles are lethal when they are homozygous. Because the Lpa1 gene has now been cloned and further characterized as disclosed herein, it is now possible to make transgenic plants with Lpa1 expression constructs under tight control. An advantage of using Lpa1 is that it could be used to develop the low phytic acid trait without changing the composition of myo-inositol phosphate intermediates. In addition, a suppression of Lpa1 expression that was limited to suppression in developing embryos could produce transgenic plants having low phytic acid and high available phosphorus in seeds with minimal impact on agronomic performance.

Thus, SEQ ID NO:1 sets forth the genomic sequence of ZmMRP3 (Lpa1), SEQ ID NO:2 sets forth the deduced cDNA sequence, and SEQ ID NO: 3 sets forth the deduced amino acid sequence of the ZmMRP3 (Lpa1) protein. The Lpa1 protein contains 1510 amino acids and has a calculated molecular weight of about 166.8 kiloDaltons and a pI of about 8.44.

Zm-MRP3 Protein Structure

The Lpa1 polypeptide was identified as an ABC transporter, as it contains consensus features of the ABC transporter family of proteins. ABC transporters are a large family of proteins found in bacteria, fungi, plants and animals. In coupling to ATP hydrolysis, the ABC transporter transports a great variety of substrates across the plasma membrane and various intracellular membranes. Among the substrates known to be transported by ABC transporters are sugars, amino acids, inorganic acids, lipids, peptides, heavy metal ions, glutathione conjugates, alkaloids, and secondary metabolites.

The member of the ABC superfamily can be divided into several subfamilies based on phylogenic pathways and structural features. The names used to define the subfamilies are historic and related to the function of drug resistance, although many members are not involved in drug transport. The three best characterized subfamilies are the pleiotropic drug resistance protein (PDR), multidrug resistance protein (MDR), and multidrug resistance-associated protein (MRP). The maize Lpa1 is a MRP ABC transporter. Previously, two MRP genes, ZmMRP1 and ZmMRP2, have been cloned from maize and their function is not known. The Lpa1 gene differs from those two ZmMRPs and thus was designated ZmMRP3.

FIG. 1A and FIG. 1B show a comparison of the Lpa1 polypeptide with Pfam consensus sequences for the ABC transporter ("ABC_tran"; Pfam Accession No. PF00005; SEQ ID NO: 62) and the ABC transporter transmembrane region ("ABC_membrane"; Pfam Accession No. PF00664; SEQ ID NO: 63). All ABC proteins consist of one or two copies of a modular structure which has two basic structural elements: an integral transmembrane domain (TMD) and a cytosolic ATP-binding domain (also known as nucleotide binding fold, or NBF). The NBF is involved in binding ATP and it contains a Walker A box, an ABC signature motif, and a Walker B box. The Walker A and B boxes also are found in other nucleotide-binding proteins, such as P-, F- and V-ATPase, G-proteins and adenylate kinase. The ABC signature motif, however, is unique to the NBFs of ABC transporters.

The members of the MRP subfamily of ABC transporters have two copies of the modular structure (see FIG. 1). Maize ZmMRP3 contains about 10 transmembrane spans in the first copy and 4 in the second copy. Two ATP-binding domains of ZmMRP3 are located at amino acids 631-843 and amino acids 1267-1450, respectively. Within the ATP-binding domains, a Walker A box is at amino acids 664-672 (GVIGSGKSS; SEQ ID NO: 18) and amino acids 1301-1309 (GRTGSGKST; SEQ ID NO: 19), an ABC signature motif is at amino acids 754-765 (LSGGQKQRVQLA; SEQ ID NO: 20) and amino acids 1404-1415 (WSVGQRQLIALG; SEQ ID NO: 21), and a Walker B box is at amino acids 774-779 (IYLLDD; SEQ ID NO: 22) and amino acids 1424-1428 (ILVLD; SEQ ID NO: 23). The second ATP-binding domain of ZmMRP3 is followed by a C1 domain with a motif of IAHRI (SEQ ID NO: 24) from amino acids 1458-1462.

The MRP gene was amplified from different maize lines by PCR and sequenced. This revealed a variant Lpa1 polypeptide (SEQ ID NO: 5) which differs from Lpa1 at positions 3, 17, and 61. This variant polypeptide is encoded by the cDNA set forth in SEQ ID NO: 4.

Example 3

Identification of Lpa1 Homologs in Other Plants

Database searches identified similar proteins from other plants which were not previously known to have a role in phytic acid metabolism as discussed herein. Accordingly, the invention additionally provides Lpa1 plant proteins and proteins comprising Lpa1 consensus sequences and domains as well as polynucleotides encoding them.

The maize MRP3 (Lpa1) gene is located on the short arm of chromosome 1 and consists of 11 exons and 10 introns. It is well known that there is significant conservation of gene content and gene order among the genomes of the plant family Gramineae. Previously, extensive studies have been focused on comparison of rice and maize gene linkage blocks and a comparative map established. Using the Lpa1 locus and its surrounding sequences, the inventors found the corresponding region in rice on chromosome 3 and identified an MRP gene in this region. Although twelve rice MRP genes had been annotated previously (Jasinski et al. (2003) *Plant Physiol.* 131: 1169-77), this annotation did not include this MRP on chromosome 3, which we designated OsMRP13 (SEQ ID NO: 6). OsMRP13 has the same number of exons and introns as the maize Lpa1 gene ZmMRP3 and encodes a protein of 1505 amino acids (SEQ ID NO: 7). The maize MzMRP3 and rice OsMRP13 genes share 83% nucleotide sequence identity and the encoded proteins share 91% amino acid sequence identity (see FIGS. 4 and 5). The two genes also share similar structures (see FIG. 2). The inventors conducted a Lynx™ study to determine the expression patterns of the rice gene. Lynx™ gene expression profiling technology utilizes massively parallel signature sequence (MPSS; see Brenner et al. (2000) *Nature Biotechnology* 18: 630-634; Brenner et al. (2000) *Proc. Nat'l. Acad. Sci. USA* 97: 1665-1670). MPSS generates 17-mer sequence tags of millions of cDNA molecules, which are cloned on microbeads. The technique provides an unprecedented depth and sensitivity of mRNA detection, including messages expressed at very low levels. The Lynx™ database search revealed that the rice gene OsMRP13 is expressed in developing seeds but has lower levels of expression in other tissues. It is very likely that the rice OsMRP13 has the same function as the maize Lpa1 gene in phytic acid metabolism in developing seeds.

*Arabidopsis* has 14 known MRP genes (AtMRP15 is a pseudogene). The inventors discovered that AtMRP5 has the same exon/intron organization as the maize ZmMRP3 gene, and that the sizes of corresponding exons and introns also are similar. The maize ZmMRP3 and *Arabidopsis* AtMRP5 share 62% nucleotide sequence identity and 67% amino acid sequence identity. Among the 14 known *Arabidopsis* MRPs, AtMRP5 shares the highest level of sequence identity with ZmMRP3. A Lynx™ study was performed on AtMRP5 and confirmed that AtMRP5 is expressed in *Arabidopsis* seeds. It remains to be determined whether *Arabidopsis* AtMRP5 has the same function as maize ZmMRP3 in phytic acid metabolism.

A soybean homolog of maize ZmMRP3 also was identified by searching a soybean EST database. The inventors conducted a Lynx™ study to characterize the expression of the soybean gene (corresponding to the sequence set forth in SEQ ID NO: 10). The Lynx™ study revealed that the soybean gene is expressed in developing seeds but has lower levels of expression in other tissues. A study of EST distribution in various plant tissues also indicated that the soybean gene expression is seed-preferred.

Example 4

Stacking Lpa1 with Other Inositol Phosphate Kinase Genes

By "stacking" (i.e., transforming a plant with) constructs designed to reduce or eliminate the expression of Lpa1 and other proteins, it is expected that the reduction of phytic acid and increase in available phosphorus will be enhanced in comparison to plants transformed with constructs designed to reduce or eliminate the expression of Lpa1 alone. Accordingly, expression cassettes are prepared making use of inverted repeat constructs known as Inverted Repeats Without Terminators, or "IRNTs." The first and second portion of such constructs self-hybridize to produce a hairpin structure which can suppress expression of the relevant endogenous gene. Each expression cassette contains an IRNT ("Lpa1 IRNT") that can suppress endogenous Lpa1 gene expression. This Lpa1 IRNT includes two portions of an Lpa1 inverted repeat surrounding the Adh1 gene intron. Other expression cassettes contain an additional IRNT that can suppress expression of IPPK, ITPK-5, myo-inositol kinase (MIK), IP2K, phytase, and MI1PS3, respectively. "Glb1" indicates the globulin 1 promoter, and "Ole" indicates the oleosin promoter. Each expression cassette is provided in a plasmid which contains additional useful features for transformation and expression in plants. Lpa1 constructs can also be stacked with constructs designed to increase the expression of other proteins, such as, for example, phytase.

The plasmids are inserted into *Agrobacterium* vectors and used to transform maize cells. Sample protocols for creation of *Agrobacterium* strains harboring a plasmid are described, for example, in Lin (1995) in *Methods in Molecular Biology*, ed. Nickoloff, J. A. (Humana Press, Totowa, N.J.). Successful transformation can be verified by restriction analysis of the plasmid after transformation back into *E. coli* DH5α cells. The *Agrobacterium* is used to transform a host plant such as maize, and the resulting transgenic plants are screened for transformation and for phytic acid phenotype as described in detail above.

In some embodiments, the Lpa1 gene is mutated and the mutated Lpa1 gene is over-expressed in order to generate transgenic plants with dominant phenotype of reduced Lpa1 activity. For example, the mutation found in EMS-generated allele lpa1-1 is A1432V (i.e., the alanine at position 1432 is changed to valine). This mutation can be introduced into a polynucleotide by PCR-based mutagenesis in which a primer is synthesized with an altered nucleotide corresponding to the desired change. The resulting PCR product is then ligated with other fragments to make a full-length mutated Lpa1 gene carrying the lpa1-1 mutation. A transformation construct consisting of the mutated Lpa1 gene driven by the oleosin promoter could be used to produce transgenic plants having the dominant phenotype of reduced Lpa1 activity; these plants would yield grain with reduced phytate and increased available phosphorus.

Total knockout of the Lpa1 gene (for example, in Mutator-insertion alleles) is lethal. It is believed that the lethality of an Lpa1 knockout could be rescued by overexpressing phytase in a plant lacking Lpa1 activity.

Plants with Lpa1 constructs or mutations can then be crossed with plants containing other constructs to obtain progeny containing multiple constructs. Thus, for example, a plant with an Lpa1 construct can be crossed with a plant containing an Lpa3 construct; progeny containing both the Lpa1 and the Lpa3 construct may then be obtained.

Example 5

Production of Lpa1 Transgenic Plants Using *Agrobacterium*-mediated Transformation For *Agrobacterium*-mediated transformation of maize with an Lpa1 construct of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the Lpa1 construct to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period, an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Bombardment and Culture Media

Bombardment medium (560Y) comprises 4.0 g/l N6 basal salts (Sigma® C-1416), 1.0 ml/l Eriksson's Vitamin Mix (1000× Sigma®-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite™ (added after bringing to volume with D-I $H_2O$); and 8.5 mg/l silver nitrate (added after sterilizing the medium and cooling to room temperature). Selection medium (560R) comprises 4.0 g/l N6 basal salts (Sigma® C-1416), 1.0 ml/l Eriksson's Vitamin Mix (1000× Sigma®-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite™ (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (Gibco® 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite™ (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (Gibco® 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l Bacto-agar (added after bringing to volume with polished D-I $H_2O$), sterilized and cooled to 60° C.

Example 6

Production of Lpa1 Transgenic Plants Using Soybean Embryo Transformation

Soybean embryos are bombarded with a plasmid containing an Lpa1 construct as follows. To induce somatic embryos, cotyledons 3-5 mm in length dissected from surface-sterilized, immature seeds of the soybean cultivar A2872 are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker at 150 rpm at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (*London*) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313: 810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the Lpa1 construct operably linked to the CaMV 35S promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm Petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Production of Lpa1 Transgenic Plants Using *Brassica napus* Seed Transformation

*Brassica napus* seeds are transformed using a transformation and regeneration protocol modified from Mehra-Palta et al. (1991), "Genetic Transformation of *Brassica napus* and *Brassica rapa*," in *Proc. 8th GCIRC Congr.*, ed. McGregor (University Extension Press, Saskatoon, Sask., Canada), pp. 1108-1115 and Stewart et al. (1996), "Rapid DNA Extraction From Plants," in *Fingerprinting Methods Based on Arbitrarily Primed PCR*, Micheli and Bova, eds. (Springer, Berlin), pp. 25-28. See Cardoza and Stewart (2003) *Plant Cell Rep.* 21: 599-604.

Seeds are surface-sterilized for 5 minutes with 10% sodium hypochlorite with 0.1% Tween™ added as a surfactant, rinsed for one minute with 95% ethanol, and then washed thoroughly with sterile distilled water. Seeds are germinated on MS basal medium (Murashige and Skoog (1962) *Physiol. Plant* 15: 473-497) containing 20 g/liter sucrose and 2 g/liter Gelrite™. Hypocotyls are excised from 8- to 10-day-old seedlings, cut into 1-cm pieces, and preconditioned for 72 hours on MS medium supplemented with 1 mg/liter 2,4-D (2,4-dichlorophenoxy acetic acid) and containing 30 g/liter sucrose and 2 g/liter Gelrite™.

*Agrobacterium* containing a plasmid comprising an Lpa1 construct of the invention is grown overnight in liquid LB medium to an $OD_{600}$ of 0.8, pelleted by centrifugation, and resuspended in liquid callus induction medium containing acetosyringone at a final concentration of 0.05 mM. *Agrobacterium* is then cocultivated with the preconditioned hypocotyl segments for 48 hours on MS medium with 1 mg/liter 2,4-D. After the cocultivation period, explants are transferred to MS medium containing 1 mg/liter 2,4-D, 400 mg/liter timentin, and 200 mg/liter kanamycin to select for transformed cells. After 2 weeks, in order to promote organogenesis, the explants are transferred to MS medium containing 4 mg/liter BAP (6-benzylaminopurine), 2 mg/liter zeatin, 5 mg/liter silver nitrate, antibiotics selective for the transformation construct, 30 g/liter sucrose, and 2 g/liter Gelrite™. After an additional 2 weeks, in order to promote shoot development, tissue is transferred to MS medium containing 3 mg/liter BAP, 2 mg/liter zeatin, antibiotics, 30 g/liter sucrose, and 2 g/liter Gelrite™. Shoots that develop are transferred for elongation to MS medium containing 0.05 mg/liter BAP, 30 g/liter sucrose, antibiotics, and 3 g/liter Gelrite™. Elongated shoots are then transferred to root development medium containing half-strength MS salts, 10 mg/liter sucrose, 3 g/liter Gelrite™, 5 mg/liter IBA (indole-3-butyric acid), and antibiotics. All cultures are maintained at 25° C.+/−2° C. in a 16-hour light/8-hour dark photoperiod regime with light supplied by cool white daylight fluorescent lights. The rooted shoots are transferred to soil and grown under the same photoperiod regime at 20° C. in a plant growth chamber.

Transformation of plants with the Lpa1 construct is confirmed using PCR of DNA extracted from putative transgenic plants.

Example 8

Variants of Lpa1

A. Variant Nucleotide Sequences of Lpa1 (SEQ ID NO: 2) that do not Alter the Encoded Amino Acid Sequence The Lpa1 nucleotide sequence set forth in SEQ ID NO: 2 is used to generate variant nucleotide sequences having the nucleotide sequence of the open reading frame with about 70%, 76%, 81%, 86%, 92%, and 97% nucleotide sequence identity when compared to the starting unaltered ORF nucleotide sequence of SEQ ID NO: 2. In some embodiments, these functional variants are generated using a standard codon table. In these embodiments, while the nucleotide sequence of the variant is altered, the amino acid sequence encoded by the open reading frame does not change.

B. Variant Amino Acid Sequences of Lpa1

Variant amino acid sequences of Lpa1 are generated. In this example, one amino acid is altered. Specifically, the open reading frame set forth in SEQ ID NO: 2 is reviewed to determined the appropriate amino acid alteration. The selection of the amino acid to change is made by consulting the protein alignment (with the other homologs or orthologs and other gene family members from various species). See FIGS. 1, 4, and 5. An amino acid is selected that is deemed not to be under high selection pressure (not highly conserved) and which is rather easily substituted by an amino acid with similar chemical characteristics (i.e., similar functional side-chain). Using the alignments set forth in FIGS. 1, 4, and 5, an appropriate amino acid can be changed. Variants having about 70%, 75%, 80%, 85%, 90%, 95%, and 97% nucleic acid sequence identity to SEQ ID NO: 2 are generated using this method.

C. Additional Variant Amino Acid Sequences of Lpa1

In this example, artificial protein sequences are created having about 80%, 85%, 90%, 95%, and 97% identity relative to the reference protein sequence. This latter effort requires identifying conserved and variable regions from the alignments set forth in FIGS. 1, 4, and 5 and then the judicious application of an amino acid substitutions table. These parts will be discussed in more detail below.

Largely, the determination of which amino acid sequences are altered is made based on the conserved regions among MRPs. See FIGS. 1, 4, and 5. It is recognized that conservative substitutions can be made in the conserved regions below without altering function. In addition, one of skill will understand that functional variants of the Lpa1 sequence of the invention can have minor non-conserved amino acid alterations in the conserved domain.

Artificial protein sequences are then created that are different from the original in the intervals of 80-85%, 85-90%, 90-95%, and 95-100% identity. Midpoints of these intervals are targeted, with liberal latitude of plus or minus 1%, 2%, or 3%, for example. The amino acids substitutions will be effected by a custom Perl script. The substitution table is provided below in Table 1.

TABLE 1

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal, then leucine, and so on down the list until the desired target of percent change is reached. Interim number substitutions can be made so as not to cause reversal of changes. The list is ordered 1-17, so start with as many isoleucine changes as needed before leucine, and so on down to methionine. Clearly, many amino acids will in this manner not need to be changed. Changes between L, I, and V will involve a 50:50 substitution of the two alternate optimal substitutions.

The variant amino acid sequences are written as output. Perl script is used to calculate the percent identities. Using this procedure, variants of Lpa1 are generated having about 80%, 85%, 90%, and 95% amino acid identity to the starting unaltered ORF nucleotide sequence of SEQ ID NO: 2.

Example 9

Pedigree Breeding

Pedigree breeding starts with the crossing of two genotypes, such as a transformed (i.e., transgenic) inbred line and one other elite inbred line having one or more desirable characteristics that is lacking or which complements the first transgenic inbred line. If the two original parents do not provide all the desired characteristics, other sources can be included in the breeding population. In the pedigree method, superior segregating plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F5, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify a transgenic inbred line and a hybrid that is made using the transgenic inbred line. Backcrossing can be used to transfer one or more specifically desirable traits from one line, the donor parent, to an inbred called the recurrent parent, which has overall good agronomic characteristics yet lacks that desirable trait or traits.

Therefore, an embodiment of this invention is a method of making a backcross conversion of a maize transgenic inbred line containing an Lpa1 construct, comprising the steps of crossing a plant of an elite maize inbred line with a donor plant comprising a mutant gene or transgene conferring a desired trait, selecting an F1 progeny plant comprising the mutant gene or transgene conferring the desired trait, and backcrossing the selected F1 progeny plant to a plant of the elite maize inbred line. This method may further comprise the step of obtaining a molecular marker profile of the elite maize inbred line and using the molecular marker profile to select for a progeny plant with the desired trait and the molecular marker profile of the maize elite inbred line. In the same manner, this method may be used to produce an F1 hybrid seed by adding a final step of crossing the desired trait conversion of the elite maize inbred line with a different maize plant to make F1 hybrid maize seed comprising a mutant gene or transgene conferring the desired trait.

Recurrent Selection and Mass Selection

Recurrent selection is a method used in a plant breeding program to improve a population of plants. The method entails individual plants cross-pollinating with each other to form progeny. The progeny are grown and superior progeny are selected by any number of selection methods, which include individual plant, half-sib progeny, full-sib progeny, selfed progeny and topeross yield evaluation. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self-pollination, directed pollination could be used as part of the breeding program.

Mutation Breeding

Mutation breeding is one of many methods that could be used to introduce new traits into a particular maize inbred line. Mutations that occur spontaneously or are artificially induced can be useful sources of variability for a plant breeder. The goal of artificial mutagenesis is to increase the rate of mutation for a desired characteristic. Mutation rates can be increased by many different means. Such means include: temperature; long-term seed storage; tissue culture conditions; radiation such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); genetic means such as transposable elements or DNA damage repair mutations; chemical mutagens (such as base analogues (5-bromo-uracil); and related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in Fehr (1993) "Principals of Cultivar Development" (Macmillan Publishing Company), the disclosure of which is incorporated herein by reference. In addition, mutations created in other lines may be used to produce a backcross conversion of a transgenic elite line that comprises such mutation.

Example 10

Gene Silencing with the Lpa1 Promoter

The promoter of a target gene (e.g., Lpa1) is inactivated by introducing into a plant an expression cassette comprising a promoter and an inverted repeat of fragments of the Lpa1 promoter. For example, an expression cassette may be created that comprises the Ole promoter operably linked to an inverted repeat comprising fragments of the Lpa1 promoter that are approximately 200 bp in length and that are separated by the Adh1 intron. The Lpa1 promoter fragments may be selected from a portion of the promoter which is rich in CpG islands, such as, for example, the 3' portion of the Lpa1 promoter. The sequence of the Lpa1 promoter is set forth in nucleotides 1-3134 of SEQ ID NO: 1. The expression cassette is used to transform a plant, which is then assayed for lack of expression of the Lpa1 gene. While the invention is not bound by any particular mechanism of operation, the method is thought to produce a small RNA molecule which recognizes the native promoter of the target gene and leads to methylation and inactivation (i.e., gene silencing) of the native promoter. Consequently, the gene associated with the promoter is not expressed. This trait is heritable and cosegregates with the transgenic construct.

Example 11

Construction of an Lpa1 Silencing Plasmid Driven by KT13

An expression cassette was prepared making use of an inverted repeat construct known as Inverted Repeats Without Terminators, or "IRNTs." The first and second portion of such a construct hybridize to each other to produce a hairpin structure which can suppress expression of the corresponding endogenous gene (e.g., Lpa1). In this Lpa1 IRNT, the first and second portions are separated by a "spacer" portion.

To make the spacer DNA, a polynucleotide fragment encoding part of the soybean Fad2-1 and soybean Fad2-2 proteins (Heppard et al. (1996) Plant Physiol. 110: 311-9) was produced as follows. First, a recombinant DNA fragment ("KSFad2-hybrid", set forth in SEQ ID NO: 72) was produced that contained a polynucleotide fragment of about 890 nucleotides comprising about 470 nucleotides from the soybean Fad2-2 gene and about 420 nucleotides from the soybean Fad2-1 gene. This KSFad2-hybrid recombinant DNA fragment was constructed by PCR amplification as follows. A DNA fragment of approximately 0.47 kb was obtained by PCR amplification using primers KS1 (SEQ ID NO: 73) and KS2 (SEQ ID NO: 74) from a template of genomic DNA purified from leaves of *Glycine max* cv. Jack. An approximately 0.42 kb DNA fragment was obtained from the same template by PCR amplification using primers KS3 (SEQ ID NO: 75) and KS4 (SEQ ID NO: 76). The 0.47 kb DNA fragment and 0.42 kb DNA fragment were gel-purified using GeneClean® (Qbiogene, Irvine Calif.), and then were mixed together and used as a template for PCR amplification with primers KS1 and KS4 to yield an approximately 890 bp fragment ("KSFad2-hybrid", set forth in SEQ ID NO: 72) that was cloned into the commercially available plasmid pGEM-T Easy (Promega, Madison, Wis.).

The KSFad2 hybrid fragment was then modified to contain additional restriction enzyme recognition sites, as follows. The KSFad2 hybrid fragment named "KSFad2-hybrid" was re-amplified by standard PCR methods using Pfu Turbo DNA polymerase (Stratagene®, La Jolla, Calif.), a plasmid containing KSFad2-hybrid as DNA template, and the following primer sets. The oligonucleotide primers (SEQ ID NO: 77 and SEQ ID NO: 78) were designed to add a BsiWI restriction endonuclease to the 5' end of the amplified fragment and to add an AvrII site to its 3' end. The resulting DNA "spacer" sequence comprising about 470 nucleotides from the soybean Fad2-2 gene and 418 nucleotides from the soybean Fad2-1 is shown in SEQ ID NO: 79.

To prepare the first and second portions of the inverted repeat constructs, a polynucleotide fragment encoding part of the soybean Lpa1 protein (Lpa1, SEQ ID NO: 10) was amplified by standard PCR methods using Pfu Turbo® DNA polymerase (Stratagene®, La Jolla, Calif.) and the following primer sets. Lpa1 oligonucleotide primers (SEQ ID NO: 69 and SEQ ID NO: 70) were designed to add NotI and SalI restriction endonuclease sites at the 5' end of the amplified fragment and BsiWI and AvrII restriction endonuclease sites at the 3' end of the amplified fragment as well as a stop codon (TAA) at its 3' end. The DNA sequence comprising the 556 bp polynucleotide from soybean Lpa1 is set forth in SEQ ID NO: 71.

Preparation of Expression Cassette

An expression cassette was constructed comprising the Lpa1 "IRNTs" operably linked to the strong seed-specific promoter KTI3 (Jofuku et al. (1989) *Plant Cell* 1: 1079-1093).

A plasmid derived from pKS121 was used to construct the expression cassette. Plasmid pKS121 was described in PCT Pub. No. WO 02/00904; this plasmid contains the KTI3 promoter/NotI/Kti3 3' terminator fragment. For use in the present expression cassette, the plasmid pKS121 was engineered to contain a second hygromycin phosphotransferase gene with a 35S-CaMV promoter. The plasmid was then digested with the restriction enzymes NotI and SalI and the digest was run on a 0.8% TAE-agarose gel to isolate and purify a 7350 bp DNA fragment using the Qiagen® gel extraction kit.

In order to insert the inverted repeat constructs and the spacer region into this plasmid, several polynucleotide fragments were prepared. Aliquots of the polynucleotide fragment comprising the 556 bp polynucleotide from soybean Lpa1 (SEQ ID NO: 71) were digested with two separate sets of restriction enzymes. First, an aliquot of the amplified Lpa1 fragment was digested with NotI and BsiWI and run on a 0.8% TAE-agarose gel to isolate a 566 bp DNA fragment, which was purified using the Qiagen® gel extraction kit. A separate aliquot of the amplified Lpa1 fragment was digested with SalI and AvrII and run on a 0.8% TAE-agarose gel to isolate a 579 bp DNA fragment, which was also purified using the Qiagen® gel extraction kit. Furthermore, the amplified polynucleotide comprising the DNA "spacer" sequence (SEQ ID NO: 79) was digested with BsiWI and AvrII, run on a 0.8% TAE-agarose gel and a 901 bp DNA fragment was purified using the Qiagen® gel extraction kit.

To assemble the expression cassette comprising the Lpa1 "IRNTs" operably linked to the strong seed-specific promoter KTI3, all four isolated and purified fragments described above were ligated together. The ligation mixture was transformed into *E. coli* and transformed colonies were selected on hygromycin. Hygromycin-resistant colonies were selected and grown overnight in LB media with appropriate antibiotic selection. Proper construction of the expression cassette was confirmed by isolating DNA from these bacterial cultures using a Qiagen® miniprep kit according to the manufacturer's protocol and then analyzing with appropriate restriction digests.

Example 12

Production of High $P_i$ Lpa1 Transgenic Soybean Somatic Embryos

The expression cassettes comprising the Lpa1 "IRNTs" operably linked to the strong seed-specific promoter KTI3

(described in Example 11) was transformed into soybean embryogenic suspension cultures using the protocol described in Example 6. Individual immature soybean embryos were then dried down by transferring them into an empty small Petri dish that was seated on top of a 10-cm Petri dish containing some agar gel to allow slow dry down. This process is intended to mimic the last stages of soybean seed development, and dried-down embryos are capable of producing plants when transferred to soil or soil-less media. Storage products produced by embryos at this stage are similar in composition to storage products produced by zygotic embryos at a similar stage of development and most importantly the storage product profile is predictive of plants derived from a somatic embryo line (see PCT Pub. No. WO 94/11516).

Determination Inorganic Phosphate Content

Somatic soybean embryos were assayed for $P_i$ (inorganic phosphate) content using modifications of Chen et al. ((1956) *Anal. Chem.* 28: 1756-1758). Single embryos were weighed and placed into 1.2 ml deep-well tubes of a 96 well rack (Corning® Incorporated). Metal balls were then added to the tubes and the samples were ground using a Geno/Grinder2000™ grinder (Sepx CertiPrep®, Metuchen, N.J.). Then 150 µl water was added to each tube and the rack was shaken for 5 minutes and centrifuged at 3,000 g for 5 minutes. The pellet was resuspended and the complete slurry was transferred (without the metal balls) to a new set of into 1.2 ml deep-well tubes of a 96 well rack. The original tubes (still containing the metal balls) were washed with an additional 150 µl water and then shaken for 5 minutes and centrifuged at 2,500 g for 5 minutes. This solution was then pooled with the complete slurry in the new tubes, and 75 µl of 2N HCl was added to each tube. The tubes were incubated for 2 hours at room temperature. Thereafter, 188 µl of 30% aqueous trichloroacetic acid was added to each sample, and the samples were mixed and centrifuged at 2,500 g for 10 minutes. The supernatants were transferred into fresh tubes and used for $P_i$ determinations; measurements were performed in duplicate.

To determine $P_i$, 100 µl of each supernatant was placed into a well of a 96 well microtiter plate and 100 µl of a mixture of 0.42% ammonium molybdate-1N $H_2SO_4$: 10% ascorbic acid (7:1) was added to each sample. The plates were incubated at 37° C. for 30 minutes and absorbance was measured at 800 nm; sodium phosphate ($NaH_2PO_4$) was used as a standard. Table 2 shows data comparing the $P_i$ content of transgenic soybean lines transformed with pJMS33 (described in Example 11) to wild type somatic embryos. Multiple events were generated expressing the Lpa1 IRNT described in Example 11. Ten out of twenty lines analyzed (50%) showed an increased $P_i$ content when compared to wild-type somatic embryos, ranging from 3.5-fold higher than wild type to nearly 8-fold higher than wild type.

TABLE 2

$P_i$ content of somatic soybean embryos from different transgenic events expressing the Lpa1 IRNT (as % of wild type (wt) content)

| Event | $P_i$ (% of wt) |
|---|---|
| Wild type embryo | 100 |
| 4-3 | 755 |
| 3-1 | 464 |
| 4-2 | 350 |
| 7-7 | 432 |
| 1-2 | 496 |
| 7-1 | 520 |
| 8-2 | 759 |

TABLE 2-continued $P_i$ content of somatic soybean embryos from different transgenic events expressing the Lpa1 IRNT (as % of wild type (wt) content)

| Event | $P_i$ (% of wt) |
|---|---|
| 7-6 | 381 |
| 4-1 | 543 |
| 8-3 | 478 |

Example 13

Transgenic Maize Seeds have Reduced Phytic Acid and Increased $P_i$ Content

Two expression cassettes were constructed to provide cosuppression of an MRP. These expression cassettes (designated plasmids P36 and P94) were made using MRP polynucleotide fragments. Each construct contained an inverted repeat of an MRP polynucleotide such that the first and second portions self-hybridized to produce a hairpin structure that can suppress expression of the relevant endogenous gene (e.g., maize Lpa1). Between the two fragments of the inverted repeat was an intron that helped to form the loop portion in the hairpin structure. Transcription was driven by the oleosin promoter in plasmid P36 and by the Glb1 promoter in plasmid P94; neither construct had a terminator. In both plasmids P36 and P94, the intron used was the Adh1 intron (GenBank Accession No. X04050), although other introns may also be used.

The plasmids were used to produce transgenic maize using protocols described in Example 1. Transgenic T1 seeds were screened for elevated $P_i$ content using a rapid $P_i$ assay, and quantitative analysis of phytic acid and $P_i$ were also performed. The results of these assays demonstrated that cosuppression of MRP expression resulted in a decrease in phytic acid content and an increase in $P_i$ in the transgenic seeds (see Table 3).

TABLE 3

Maize plants transformed with MRP expression constructs produced transgenic seeds with reduced phytic acid and increased $P_i$ content.

| Plasmid #/ Event | Wt K $P_i$ (mg/g) | CS K $P_i$ (mg/g) | Wt K PAP (mg/g) | CS K PAP (mg/g) | PA reduction |
|---|---|---|---|---|---|
| Plasmid 36 | | | | | |
| 1 | 0.31 | 1.17 | 2.76 | 0.72 | 74% |
| 2 | 0.18 | 1.05 | 2.75 | 0.73 | 74% |
| 3 | 0.27 | 0.99 | 2.53 | 0.99 | 61% |
| 4 | 0.26 | 1.21 | 2.43 | 0.84 | 66% |
| 5 | 0.43 | 1.12 | 2.15 | 0.85 | 60% |
| 6 | 0.31 | 1.20 | 2.41 | 0.79 | 67% |
| 7 | 0.34 | 1.06 | 2.59 | 0.61 | 77% |
| 8 | 0.26 | 1.15 | 2.60 | 0.57 | 78% |
| 9 | 0.21 | 1.09 | 2.61 | 0.70 | 73% |
| 10 | 0.31 | 1.26 | 2.55 | 0.82 | 68% |
| 11 | 0.19 | 1.08 | 2.46 | 0.66 | 73% |
| 12 | 0.32 | 1.09 | 2.50 | 0.78 | 69% |
| Plasmid 94 | | | | | |
| 1 | 0.14 | 1.01 | 3.47 | 2.29 | 34% |
| 2 | 0.12 | 1.37 | 3.10 | 1.12 | 64% |
| 3 | 0.16 | 1.44 | 3.09 | 1.00 | 68% |
| 4 | 0.10 | 1.20 | 3.44 | 1.75 | 49% |
| 5 | 0.24 | 1.25 | 3.04 | 1.53 | 50% |
| 6 | 0.24 | 1.47 | 2.67 | 0.98 | 63% |

TABLE 3-continued

Maize plants transformed with MRP expression constructs produced transgenic seeds with reduced phytic acid and increased $P_i$ content.

| Plasmid #/ Event | Wt K $P_i$ (mg/g) | CS K $P_i$ (mg/g) | Wt K PAP (mg/g) | CS K PAP (mg/g) | PA reduction |
|---|---|---|---|---|---|
| 7 | 0.21 | 1.46 | 2.98 | 1.11 | 63% |
| 8 | 0.18 | 1.17 | 3.00 | 1.76 | 41% |

Wt K = wild-type kernels in a segregation ear;
CS K = cosuppression kernels in a segregation ear;
$P_i$ = inorganic phosphate phosphorus;
PAP = phytic acid phosphorus;
PA = phytic acid As indicated in the table legend, "Wt K" were kernels in a segregation ear without the MRP transgene and "CS K" were the kernels in the same segregation ear that did contain the MRP transgene. The PAP values in Table 3 were measured according to modifications of the methods described by Latta & Eskin (1980) *J. Agric Food Chem.* 28: 1313-1315 and Vaintraub & Lapteva (1988) *Analytical Biochemistry* 175: 227-230; see Example 1 for detail.

Example 14

Production of Transgenic *Sorghum*

The promoter construct prepared in Example 10 is used to transform sorghum according to the teachings of U.S. Pat. No. 6,369,298. Briefly, a culture of *Agrobacterium* is transformed with a vector comprising an expression cassette containing the promoter construct prepared in Example 10. The vector also comprises a T-DNA region into which the promoter construct is inserted. General molecular techniques used in the invention are provided, for example, by Sambrook et al. (eds.) *Molecular Cloning: A Laboratory Manual,* 1989, Cold Spring Harbor Laboratory Press, Cold Spring Harbor, N.Y.

Immature sorghum embryos are obtained from the fertilized reproductive organs of a mature sorghum plant. Immature embryos are aseptically isolated from the developing kernel at about 5 days to about 12 days after pollination and held in sterile medium until use; generally, the embryos are about 0.8 to about 1.5 mm in size.

The *Agrobacterium*-mediated transformation process of the invention can be broken into several steps. The basic steps include: an infection step (step 1); a co-cultivation step (step 2); an optional resting step (step 3); a selection step (step 4); and a regeneration step (step 5). In the infection step, the embryos are isolated and the cells contacted with the suspension of *Agrobacterium*.

The concentration of *Agrobacterium* used in the infection step and co-cultivation step can affect the transformation frequency. Very high concentrations of *Agrobacterium* may damage the tissue to be transformed, such as the immature embryos, and result in a reduced callus response. The concentration of *Agrobacterium* used will vary depending on the *Agrobacterium* strain utilized, the tissue being transformed, the sorghum genotype being transformed, and the like. Generally a concentration range of about $0.5 \times 10^9$ cfu/ml to $1 \times 10^9$ cfu/ml will be used.

The embryos are incubated with the suspension of *Agrobacterium* about 5 minutes to about 8 minutes. This incubation or infection step takes place in a liquid solution that includes the major inorganic salts and vitamins of N6 medium (referred to as "N6 salts," or medium containing about 463.0 mg/l ammonium sulfate; about 1.6 mg/l boric acid; about 125 mg/l calcium chloride anhydrous; about 37.25 mg/l $Na_2$-EDTA; about 27.8 mg/l ferrous sulfate.$7H_2O$; about 90.37 mg/l magnesium sulfate; about 3.33 mg/l manganese sulfate $H_2O$; about 0.8 mg/l potassium iodide; about 2,830 mg/l potassium nitrate; about 400 mg/l potassium phosphate monobasic; and about 1.5 mg/l zinc sulfate.$7H_2O$.

In addition, the media in the infection step generally excludes $AgNO_3$. $AgNO_3$ is generally included in the co-cultivation, resting (when used) and selection steps when N6 media is used. In the co-cultivation step, the immature embryos are co-cultivated with the *Agrobacterium* on a solid medium. The embryos are positioned axis-down on the solid medium and the medium can include $AgNO_3$ at a range of about 0.85 to 8.5 mg/l. The embryos are co-cultivated with the *Agrobacterium* for about 3-10 days.

Following the co-cultivation step, the transformed cells may be subjected to an optional resting step. Where no resting step is used, an extended co-cultivation step may utilized to provide a period of culture time prior to the addition of a selective agent. For the resting step, the transformed cells are transferred to a second medium containing an antibiotic capable of inhibiting the growth of *Agrobacterium*. This resting phase is performed in the absence of any selective pressures on the plant cells to permit preferential initiation and growth of callus from the transformed cells containing the heterologous nucleic acid. The antibiotic added to inhibit *Agrobacterium* growth may be any suitable antibiotic; such antibiotics are known in the art and include Cefotaxime, timetin, vancomycin, carbenicillin, and the like. Concentrations of the antibiotic will vary according to what is standard for each antibiotic, and those of ordinary skill in the art will recognize this and be able to optimize the antibiotic concentration for a particular transformation protocol without undue experimentation. The resting phase cultures are preferably allowed to rest in the dark at 28° C. for about 5 to about 8 days. Any of the media known in the art can be utilized for the resting step.

Following the co-cultivation step, or following the resting step, where it is used, the transformed plant cells are exposed to selective pressure to select for those cells that have received and are expressing polypeptide from the heterologous nucleic acid introduced by *Agrobacterium*. Where the cells are embryos, the embryos are transferred to plates with solid medium that includes both an antibiotic to inhibit growth of the *Agrobacterium* and a selection agent. The agent used to select for transformants will select for preferential growth of explants containing at least one selectable marker insert positioned within the superbinary vector and delivered by the *Agrobacterium*. Generally, any of the media known in the art suitable for the culture of sorghum can be used in the selection step, such as media containing N6 salts or MS salts. During selection, the embryos are cultured until callus formation is observed. Typically, calli grown on selection medium are allowed to grow to a size of about 1.5 to about 2 cm in diameter.

After the calli have reached the appropriate size, the calli are cultured on regeneration medium in the dark for several weeks to allow the somatic embryos to mature, generally about 1 to 3 weeks. Preferred regeneration media includes media containing MS salts. The calli are then cultured on rooting medium in a light/dark cycle until shoots and roots develop. Methods for plant regeneration are known in the art (see, e.g., Kamo et al. (1985) Bot. Gaz. 146(3): 327-334; West et al. (1993) Plant Cell 5:1361-1369; and Duncan et al. (1985) *Planta* 165: 322-332).

Small plantlets are then transferred to tubes containing rooting medium and allowed to grow and develop more roots for approximately another week. The plants are then transplanted to soil mixture in pots in the greenhouse.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim(s).

That which is claimed:

1. An expression cassette comprising a nucleic acid molecule which comprises a promoter that drives expression in a plant cell and is operably linked to:
   a) a first nucleotide sequence having the nucleotide sequence as set forth in SEQ ID NO: 71;
   b) a spacer nucleotide sequence; and
   c) a second nucleotide sequence that is fully complementary to the first nucleotide sequence;
   wherein a), b) and c) are arranged in a 5' to 3' direction, respectively; and wherein expression of said nucleic acid molecule in a soybean plant transformed with said expression cassette results in a hairpin RNA structure which decreases the expression of an endogenous multidrug resistance-associated protein (MRP) in said soybean plant and thereby reducing phytate levels of said transformed soybean plant compared to a control soybean plant lacking said expression cassette.

2. A soybean plant stably transformed with a heterologous nucleic acid molecule which comprises a promoter active in said soybean plant and is operably linked to:
   a) a first nucleotide sequence having at least 500 contiguous nucleotides of the nucleotide sequence as set forth in SEQ ID NO: 10;
   b) a spacer nucleotide sequence; and
   c) a second nucleotide sequence that is fully complementary to the first nucleotide sequence;
   wherein a), b) and c) are arranged in a 5' to 3' direction, respectively; and wherein expression of said nucleic acid molecule in said soybean plant results in a hairpin RNA structure which decreases the expression of an endogenous multidrug resistance-associated protein (MRP) in said transformed soybean plant and thereby reducing phytate levels of said transformed soybean plant compared to a control soybean plant lacking said heterologous nucleic acid molecule.

3. The soybean plant of claim 2, wherein said first nucleotide sequence is the nucleotide sequence as set forth in SEQ ID NO: 71.

4. A transformed seed obtained from the soybean plant of claim 2, and wherein said seed comprises said heterologous nucleic acid molecule.

5. A transformed seed obtained from the soybean plant of claim 3, and wherein said seed comprises said heterologous nucleic acid molecule.

6. A method of producing a transformed soybean plant having reduced levels of phytate, said method comprising the steps of:
   i) transforming soybean plant cells with an expression cassette comprising a nucleic acid molecule which comprises a promoter that drives expression in a plant cell and is operably linked to:
      a) a first nucleotide sequence having at least 500 contiguous nucleotides of the nucleotide sequence as set forth in SEQ ID NO: 10;

b) a spacer nucleotide sequence; and
c) a second nucleotide sequence that is fully complementary to the first nucleotide sequence;
wherein a), b) and c) are arranged in a 5' to 3' direction, respectively; and
ii) regenerating a transformed soybean plant from the transformed soybean plant cells of step i);
and wherein expression of said nucleic acid molecule in the transformed soybean plant of step ii) results in a hairpin RNA structure which decreases the expression of an endogenous multidrug resistance-associated protein (MRP) in the transformed soybean plant of step ii) and thereby reducing phytate levels in the transformed soybean plant compared to a control soybean plant lacking said expression cassette.

7. The method of claim 6, wherein said first nucleotide sequence is set forth in SEQ ID NO: 71.

* * * * *